United States Patent
Black et al.

(10) Patent No.: US 9,272,030 B2
(45) Date of Patent: Mar. 1, 2016

(54) USE OF TAU TO MONITOR IMMUNOTHERAPY

(75) Inventors: Ronald Black, Audubon, PA (US); Jack Steven Jacobsen, Ramsey, NJ (US); Lioudmila Tchistiakova, Andover, MA (US); Angela Widom, Acton, MA (US); Davinder Gill, Andover, MA (US); Lars Ekman, La Jolla, CA (US); Ivan Lieberburg, Berkeley, CA (US); Michael Grundman, San Diego, CA (US); James Callaway, San Diego, CA (US); Keith M. Gregg, Goodyear, AZ (US); Wagner Zago, San Mateo, CA (US); Manuel J. Buttini, Belvaux (LU); Gene G. Kinney, Berlingame, CA (US)

(73) Assignees: JANSSEN SCIENCES IRELAND UC (IE); WYETH LLC, Madison, NJ (US)

( * ) Notice: Subject to any disclaimer, the term of this patent is extended or adjusted under 35 U.S.C. 154(b) by 37 days.

(21) Appl. No.: 13/642,845

(22) PCT Filed: Apr. 22, 2011

(86) PCT No.: PCT/US2011/033649
§ 371 (c)(1),
(2), (4) Date: Apr. 8, 2013

(87) PCT Pub. No.: WO2011/133919
PCT Pub. Date: Oct. 27, 2011

(65) Prior Publication Data
US 2013/0209453 A1 Aug. 15, 2013
US 2015/0118223 A9 Apr. 30, 2015

Related U.S. Application Data

(63) Continuation-in-part of application No. 12/738,396, filed as application No. PCT/US2008/080382 on Oct. 17, 2008.

(60) Provisional application No. 60/999,423, filed on Oct. 17, 2007, provisional application No. 61/083,827, filed on Jul. 25, 2008, provisional application No. 61/327,062, filed on Apr. 22, 2010, provisional application No. 61/450,619, filed on Mar. 8, 2011.

(51) Int. Cl.
*C07K 16/18* (2006.01)
*A61K 39/00* (2006.01)
*A61K 39/395* (2006.01)

(52) U.S. Cl.
CPC ............ *A61K 39/3955* (2013.01); *C07K 16/18* (2013.01); *A61K 2039/505* (2013.01); *A61K 2039/545* (2013.01); *A61K 2039/55* (2013.01); *C07K 2317/24* (2013.01); *C07K 2317/34* (2013.01)

(58) Field of Classification Search
None
See application file for complete search history.

(56) References Cited

U.S. PATENT DOCUMENTS

2009/0155256 A1* 6/2009 Black et al. ............... 424/133.1
2013/0209453 A1 8/2013 Black et al.

FOREIGN PATENT DOCUMENTS

| WO | WO 2009/052439 A2 | 4/2009 | |
|----|----|----|----|
| WO | WO 2011/133919 A1 | 4/2009 | |
| WO | WO 2009052439 | * 4/2009 | ............. A61K 39/00 |

OTHER PUBLICATIONS

Jensen et al. 1995 "increased cerebrospinal fluid tau in patients with Alzheimer's disease" Neurosci lett 186(2-3):189-91 (abstract only).*
Stefani et al. 2009 "CSF biomarkers, impairment of cerebral hemodynamics and degree of cognitive decline in Alzheimer's and mixed dementia" J neurol sci 283(1-2):109-15 (abstract only).*
Visser et al. 2009 "prevalence and prognostic value of csf markers of alzheiemr's disease pathology in patients with subjective cognitive impairment of mild cognitive impairment in the DESCRIPA study: a prospective cohort study" Lancet Neurol 8(7):619-27 (abstract only).*
Rafii 2009 "Recent developmets in Alzheimer's disease therapeutics" BMC medicine 7:7.*
Bayer, et al., "Evaluation of the safety and innumogenicity of synthetic Aβ42 (AN1792) in patients with AD," *Neurology*, 64:94-102, (2005).
EP 11 77 2806 Supplementary European Search Report mailed Aug. 28, 2013.
Gilman, et al., "Clinical Effects of Abeta Immunization (AN1792) in Patients with AD in an Interrupted Trial," *Neurology*, vol. 64, No. 9, pp. 1553-1562 (2005).
Greenberg, et al., "Alzheimer disease's double-edged vaccine," *Nature Medicine*, vol. 9, No. 4 pp. 389-390 (2003).
Hampel, et al., "Measurement of Phosphorylated Tau Epitopes in the Differential Diagnosis of Alzheimer Disease," *Arch Gen Psychiatry*, 61(1):95-102 (2004).
Jensen et al., "Increased cerebrospinal fluid tau in patients with Alzheimer's disease," *Neurosci Lett*, 186(2-3): 189-91 abstract only (1995).
PCT/US2011/033649 International Preliminary Report on Patentability and Written Opinion issued Oct. 23, 2012.
PCT/US2011/033649 International Search Report and Written Opinion mailed Aug. 26, 2011.
Ray, "Wyeth Study Finds Alzheimer's Drug Works in ApoE4 Non Carriers," Poster 2008, [Retrived from the Internet Jun. 16, 2011: >URL: http://elan2006.blogspot.com/2008/07elan-wyeth-study-finds-alzheimers-drug-html>.

(Continued)

*Primary Examiner* — Gregory S Emch
*Assistant Examiner* — Adam M Weidner
(74) *Attorney, Agent, or Firm* — Alston & Bird LLP

(57) ABSTRACT

The invention provides methods of immunotherapy of Alzheimer's and similar diseases in which the regime administered is monitored by measuring levels of tau.

16 Claims, 25 Drawing Sheets

(56) References Cited

OTHER PUBLICATIONS

Robert, et al., "Engineered antibody intervention strategies for Alzheimer's disease and related demenitias by targeting amyloid and toxic oligomers," *Protein Eng Des Sel.*, 22(3):199-2008 (2009).

Salloway, et al., "A phase 2 multiple ascending dose trial of bapineuzumab in mild to moderate Alzheimer disease," *Neurology*, vol. 73, No. 24, pp. 2061-2070 (2009).

Stefani et al., "CSF biomarkers, Impairment of cerebral hemodynamics and degree of cognitive decline in Alzheimer's and mixed dementia," *J Neurol Sci.*, 283(102):109-15 (2009).

Sudol, et al., "Generating differentially targeted amyloid-beta specific intrabodies as a passive vaccination strategy for Alzheimer's disease," *Molecular Therapy: The Journal of the American Society of Gene Therapy*, vol. 17, No. 12, pp. 2031-2040 (2009).

Visser et al., "Prevalence and prognostic value of CSF markers of Alzheimer's disease pathology in patients with subjective cognitive impairment or mild cognitive impairment in the DESCRIPA study: a prospective cohort study," *Lancet Neurol*, (7):619-27, (2009).

Zhao et al., "Macrophage-Mediated Degradation of beta-Amyloid via an Apolipoprotein E Isoforrn-Dependent Mechanism," *J Neurosci.*, 29(11):3603-3612 (2009).

\* cited by examiner

SEQUENCE LISTING

```
<160> NUMBER OF SEQ ID NOS: 99

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30
```

Asp Gly Lys Thr Tyr Leu Asn Trp Leu Leu Gln Lys Pro Gly Gln Ser
            35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Tyr Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

```
Thr His Phe Pro Arg Thr Phe Gly Gln Gly Thr Lys Val Glu Ile Lys
            100                 105                 110
```

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115
```

<210> SEQ ID NO 6
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 7
<211> LENGTH: 449
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

Glu Val Gln Leu Val Glu Ser Gly Gly Gly Leu Val Gln Pro Gly Gly
1 5 10 15

Ser Leu Arg Leu Ser Cys Ala Gly Ser Gly Phe Thr Phe Ser Asn Tyr
20 25 30

Gly Met Ser Trp Val Arg Gln Ala Pro Gly Lys Gly Leu Glu Trp Val
35 40 45

Ala Ser Ile Arg Ser Gly Gly Arg Thr Tyr Tyr Ser Asp Asn Val
50 55 60

Lys Gly Arg Phe Thr Ile Ser Arg Glu Asn Ala Lys Asn Ser Leu Tyr
65 70 75 80

Leu Gln Met Asn Ser Leu Arg Ala Glu Asp Thr Ala Val Tyr Tyr Cys
85 90 95

Val Arg Tyr Asp His Tyr Ser Gly Ser Ser Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Ile His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Lys Lys Val Glu Ala Glu Asp Leu Gly Ile Tyr Tyr Cys Phe Gln Gly
                85                  90                  95

Ser His Val Pro Leu Thr Phe Gly Ala Gly Thr Lys Leu Glu Leu Glu
            100                 105                 110

<210> SEQ ID NO 9
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ala Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30
```

```
Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
 50                  55                  60

Leu Lys Ser Arg Leu Thr Ile Ser Lys Asp Thr Ser Arg Lys Gln Val
 65                  70                  75                  80

Phe Leu Lys Ile Thr Ser Val Asp Pro Ala Asp Thr Ala Thr Tyr Tyr
                 85                  90                  95

Cys Val Arg Arg Pro Ile Thr Pro Val Leu Val Asp Ala Met Asp Tyr
            100                 105                 110

Trp Gly Gln Gly Thr Ser Val Thr Val Ser Ser
        115                 120

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ser
                 85                  90                  95

Ser His Val Pro Leu Thr Phe Gly Gly Gly Thr Lys Leu Glu Ile Lys
            100                 105                 110

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Ser Leu Ser Thr Ser
             20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
 50                  55                  60

Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95
```

Cys Ala Arg Arg Thr Thr Thr Ala Asp Tyr Phe Ala Tyr Trp Gly Gln
                100                 105                 110

Gly Thr Thr Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
        115                 120

<210> SEQ ID NO 14
<211> LENGTH: 120

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Asp Lys Tyr Tyr Asn Pro Ser
    50                  55                  60

Leu Lys Ser Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Arg
```

```
1               5                   10                  15
Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
            85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
            85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
```

```
                    50                  55                  60

Leu Lys Ser Arg Leu Thr Ile Ser Lys Asp Thr Ser Lys Asn Thr Leu
 65                  70                  75                  80

Tyr Leu Gln Met Asn Ser Leu Arg Ala Glu Asp Thr Ala Val Tyr Tyr
                    85                  90                  95

Cys Ala Arg Arg Thr Thr Thr Ala Asp Tyr Phe Ala Tyr Trp Gly Gln
                   100                 105                 110

Gly Thr Thr Val Thr Val Ser Ser
            115                 120

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
 50                  55                  60

Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                    85                  90                  95

Cys Ala Arg Arg Thr Thr Thr Ala Asp Tyr Phe Ala Tyr Trp Gly Gln
                   100                 105                 110

Gly Thr Thr Val Thr Val Ser Ser
            115                 120

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
 50                  55                  60

Leu Lys Ser Arg Phe Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                    85                  90                  95

Cys Ala Arg Arg Thr Thr Thr Ala Asp Tyr Phe Ala Tyr Trp Gly Gln
```

```
                100                 105                 110

Gly Thr Thr Val Thr Val Ser Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
        115                 120

<210> SEQ ID NO 22
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
        115                 120

<210> SEQ ID NO 23
<211> LENGTH: 120
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Val Val Gln Pro Gly Arg
1               5                   10                  15

-continued

```
Ser Leu Arg Leu Ser Cys Ala Phe Ser Gly Phe Thr Leu Ser Thr Ser
         20                  25                  30

Gly Met Ser Val Gly Trp Ile Arg Gln Ala Pro Gly Lys Gly Leu Glu
         35                  40                  45

Trp Val Ala His Ile Trp Trp Asp Asp Lys Tyr Tyr Asn Pro Ser
 50                  55                  60

Leu Lys Ser Arg Phe Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
         20                  25                  30

Gly Met Ser Val Gly Trp Ile Arg Gln Ala Pro Gly Lys Gly Leu Glu
         35                  40                  45

Trp Val Ala His Ile Trp Trp Asp Asp Lys Tyr Tyr Asn Pro Ser
 50                  55                  60

Leu Lys Ser Arg Leu Thr Ile Ser Lys Asp Thr Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
         20                  25                  30

Gly Met Ser Val Gly Trp Ile Arg Gln Ala Pro Gly Lys Gly Leu Glu
         35                  40                  45

Trp Leu Ala His Ile Trp Trp Asp Asp Lys Tyr Tyr Asn Pro Ser
 50                  55                  60
```

```
Leu Lys Ser Arg Phe Thr Ile Ser Lys Asp Thr Ser Lys Asn Thr Leu
 65                  70                  75                  80

Tyr Leu Gln Met Asn Ser Leu Arg Ala Glu Asp Thr Ala Val Tyr Tyr
             85                   90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 28
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Asp Lys Tyr Tyr Asn Pro Ser
     50                  55                  60

Leu Lys Ser Arg Phe Thr Ile Ser Lys Asp Thr Ser Lys Asn Thr Leu
 65                  70                  75                  80

Tyr Leu Gln Met Asn Ser Leu Arg Ala Glu Asp Thr Ala Val Tyr Tyr
             85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
            20                  25                  30

Gly Met Ser Val Gly Trp Val Arg Gln Ala Pro Gly Lys Gly Leu Glu
        35                  40                  45

Trp Leu Ala His Ile Trp Trp Asp Asp Asp Lys Tyr Tyr Asn Pro Ser
     50                  55                  60

Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
             85                  90                  95

Cys Ala Arg Arg Thr Thr Thr Ala Asp Tyr Phe Ala Tyr Trp Gly Gln
            100                 105                 110
```

```
Gly Thr Thr Val Thr Val Ser Ser
        115                 120

<210> SEQ ID NO 30
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 32
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 32

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Asn
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Glu Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Asn Val Asp Thr Ala Asp Thr Ala Thr Tyr Tyr
                85                  90                  95

Cys Ala Arg Arg Arg Ile Ile Tyr Asp Val Glu Asp Tyr Phe Asp Tyr
            100                 105                 110

Trp Gly Gln Gly Thr Thr Leu Thr Val Ser Ser
        115                 120
```

<210> SEQ ID NO 33
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (14)..(14)
<223> OTHER INFORMATION: Thr or Ser
<220> FEATURE:
<221> NAME/KEY: MOD_RES
<222> LOCATION: (15)..(15)
<223> OTHER INFORMATION: Leu or Pro
<220> FEATURE:
<221> NAME/KEY: MOD_RES
<222> LOCATION: (30)..(30)
<223> OTHER INFORMATION: Ile or Val
<220> FEATURE:
<221> NAME/KEY: MOD_RES
<222> LOCATION: (50)..(50)
<223> OTHER INFORMATION: Arg, Gln or Lys
<220> FEATURE:
<221> NAME/KEY: MOD_RES
<222> LOCATION: (88)..(88)
<223> OTHER INFORMATION: Val or Leu
<220> FEATURE:
<221> NAME/KEY: MOD_RES
<222> LOCATION: (105)..(105)
<223> OTHER INFORMATION: Gln or Gly
<220> FEATURE:
<221> NAME/KEY: MOD_RES
<222> LOCATION: (108)..(108)
<223> OTHER INFORMATION: Lys or Arg
<220> FEATURE:
<221> NAME/KEY: MOD_RES
<222> LOCATION: (109)..(109)
<223> OTHER INFORMATION: Val or Leu

<400> SEQUENCE: 33

Asp Xaa Val Met Thr Gln Xaa Pro Leu Ser Leu Pro Val Xaa Xaa Gly

```
            1               5                  10                 15
Gln Pro Ala Ser Ile Ser Cys Arg Ser Ser Gln Ser Leu Xaa Tyr Ser
            20                 25                 30

Asp Gly Asn Ala Tyr Leu His Trp Phe Leu Gln Lys Pro Gly Gln Ser
            35                 40                 45

Pro Xaa Leu Leu Ile Tyr Lys Val Ser Asn Arg Phe Ser Gly Val Pro
    50                 55                 60

Asp Arg Phe Ser Gly Ser Gly Ser Gly Thr Asp Phe Thr Leu Lys Ile
65                  70                 75                  80

Ser Arg Val Glu Ala Glu Asp Xaa Gly Val Tyr Tyr Cys Ser Gln Ser
                85                 90                 95

Thr His Val Pro Trp Thr Phe Gly Xaa Gly Thr Xaa Xaa Glu Ile Lys
                100                105                110

Arg
```

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (7)..(7)
<223> OTHER INFORMATION: Ser or Leu
<220> FEATURE:
<221> NAME/KEY: MOD_RES
<222> LOCATION: (46)..(46)
<223> OTHER INFORMATION: Glu, Val, Asp or Ser
<220> FEATURE:
<221> NAME/KEY: MOD_RES
<222> LOCATION: (63)..(63)
<223> OTHER INFORMATION: Thr or Ser
<220> FEATURE:
<221> NAME/KEY: MOD_RES
<222> LOCATION: (75)..(75)
<223> OTHER INFORMATION: Ala, Ser, Val or Thr
<220> FEATURE:
<221> NAME/KEY: MOD_RES
<222> LOCATION: (76)..(76)
<223> OTHER INFORMATION: Lys or Arg
<220> FEATURE:
<221> NAME/KEY: MOD_RES
<222> LOCATION: (89)..(89)
<223> OTHER INFORMATION: Glu or Asp
<220> FEATURE:
<221> NAME/KEY: MOD_RES
<222> LOCATION: (107)..(107)
<223> OTHER INFORMATION: Leu or Thr

<400> SEQUENCE: 34

```
Xaa Val Gln Leu Val Glu Xaa Gly Gly Gly Leu Val Gln Pro Gly Gly
1               5                  10                 15

Ser Leu Arg Leu Ser Cys Ala Ala Ser Gly Phe Thr Phe Ser Arg Tyr
            20                 25                 30

Ser Met Ser Trp Val Arg Gln Ala Pro Gly Lys Gly Leu Xaa Leu Val
            35                 40                 45

Ala Gln Ile Asn Ser Val Gly Asn Ser Thr Tyr Tyr Pro Asp Xaa Val
    50                 55                 60

Lys Gly Arg Phe Thr Ile Ser Arg Asp Asn Xaa Xaa Asn Thr Leu Tyr
65                  70                 75                  80
```

```
Leu Gln Met Asn Ser Leu Arg Ala Xaa Asp Thr Ala Val Tyr Tyr Cys
                 85                  90                  95

Ala Ser Gly Asp Tyr Trp Gly Gln Gly Thr Xaa Val Thr Val Ser Ser
            100                 105                 110

<210> SEQ ID NO 35
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 36
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Ala Arg Tyr Gln Ala Pro Gly Lys Gly Leu Glu
        35                  40                  45
```

```
Leu Val Ala Gln Ile Asn Ser Val Gly Asn Ser Thr Tyr Tyr Pro Asp
         50                  55                  60

Thr Val Lys Gly Arg Phe Thr Ile Ser Arg Asp Asn Ala Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Ser Gly Asp Tyr Trp Gly Gln Gly Thr Leu Val Thr Val
                 100                 105                 110

Ser Ser Ala Ser Thr Lys Gly Pro Ser Val Phe Pro Leu Ala Pro Ser
         115                 120                 125

Ser Lys Ser Thr Ser Gly Gly Thr Ala Ala Leu Gly Cys Leu Val Lys
     130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                 165                 170                 175

Tyr Ser Leu Ser Ser Val Val Thr Val Pro Ser Ser Ser Leu Gly
             180                 185                 190

Thr Gln Thr Tyr Ile Cys Asn Val Asn His Lys Pro Ser Asn Thr Lys
         195                 200                 205

Val Asp Lys Lys Val Glu Pro Lys Ser Cys Asp Lys Thr His Thr Cys
     210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                 245                 250                 255

Val Thr Cys Val Val Val Asp Val Ser His Glu Asp Pro Glu Val Lys
             260                 265                 270

Phe Asn Trp Tyr Val Asp Gly Val Glu Val His Asn Ala Lys Thr Lys
         275                 280                 285

Pro Arg Glu Glu Gln Tyr Asn Ser Thr Tyr Arg Val Val Ser Val Leu
     290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                 325                 330                 335

Ala Lys Gly Gln Pro Ala Arg Tyr Glu Pro Gln Val Tyr Thr Leu Pro
             340                 345                 350

Pro Ser Arg Asp Glu Leu Thr Lys Asn Gln Val Ser Leu Thr Cys Leu
         355                 360                 365

Val Lys Gly Phe Tyr Pro Ser Asp Ile Ala Val Glu Trp Glu Ser Asn
     370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                 405                 410                 415

Trp Gln Gln Gly Asn Val Phe Ser Cys Ser Val Met His Glu Ala Leu
             420                 425                 430

His Asn His Tyr Thr Gln Lys Ser Leu Ser Leu Ser Pro Gly Lys
         435                 440                 445

<210> SEQ ID NO 37
<211> LENGTH: 112
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Val Pro Leu Thr Phe Gly Gln Gly Thr Lys Leu Glu Ile Lys
            100                 105                 110

<210> SEQ ID NO 38
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Ser Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser
        115                 120

<210> SEQ ID NO 39
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Thr Leu Lys Glu Ser Gly Pro Ala Leu Val Lys Pro Thr Gln
1               5                   10                  15

Thr Leu Thr Leu Thr Cys Thr Leu Ser Gly Phe Ser Leu Ser Thr Ser
```

```
                    20                  25                  30
Gly Met Gly Val Gly Trp Ile Arg Gln Pro Gly Lys Ala Leu Glu
                35                  40                  45

Trp Leu Ala His Ile Trp Trp Asp Asp Lys Ser Tyr Asn Pro Ser
 50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gln Leu Gly Leu Arg Ser Ile Asp Ala Met Asp Tyr
                100                 105                 110

Trp Gly Gln Gly Thr Thr Val Thr Val Ser
                115                 120

<210> SEQ ID NO 40
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Lys Leu Pro Val Arg Leu Leu Val Leu Met Phe Trp Ile Pro Gly
1               5                   10                  15

Ser Ser Ser Asp Val Met Met Thr Gln Thr Pro Leu Ser Leu Pro Val
                20                  25                  30

Ser Leu Gly Asp Gln Ala Ser Ile Ser Cys Arg Ser Ser Gln Ser Leu
                35                  40                  45

Val His Ser Asn Gly Asn Thr Tyr Leu Glu Trp Tyr Met Gln Lys Pro
            50                  55                  60

Gly Gln Ser Pro Met Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Ser Val Glu Ala Glu Asp Leu Gly Val Phe Tyr Cys
                100                 105                 110

Phe Gln Gly Ser Arg Val Pro Leu Thr Phe Gly Ala Gly Thr Lys Leu
                115                 120                 125

Glu Leu Lys Arg
            130

<210> SEQ ID NO 41
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
                20                  25                  30

Pro Ser Gln Thr Leu Ser Leu Thr Cys Ser Phe Ser Gly Phe Ser Leu
                35                  40                  45

Ser Thr Ser Gly Met Gly Val Ser Trp Ile Arg Gln Pro Ser Gly Lys
```

```
                        50                  55                  60

Gly Leu Glu Trp Leu Ala His Ile Tyr Trp Asp Asp Lys Arg Tyr
 65                  70                  75                  80

Asn Pro Ser Leu Lys Ser Arg Leu Thr Ile Ser Lys Asp Thr Ser Arg
                    85                  90                  95

Asn Gln Val Phe Leu Lys Ile Thr Ser Val Asp Thr Asp Thr Ala
                100                 105                 110

Thr Tyr Tyr Cys Thr Arg Ser Ser Gly Ser Ile Val Ile Ala Thr Gly
                115                 120                 125

Phe Ala Tyr Trp Gly Gln Gly Thr Leu Val Thr Val Ser Ala
                130                 135                 140

<210> SEQ ID NO 42
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Asp Phe Gln Val Gln Ile Phe Ser Phe Leu Leu Ile Ser Ala Ser
 1               5                  10                  15

Val Ile Ile Ser Arg Gly Gln Ile Val Leu Thr Gln Ser Pro Ala Ile
                20                  25                  30

Met Ser Ala Ser Pro Gly Glu Lys Val Thr Met Thr Cys Ser Ala Ser
            35                  40                  45

Ser Ser Val Ser Tyr Met His Trp Tyr Gln Gln Lys Ser Gly Thr Ser
        50                  55                  60

Pro Lys Arg Trp Ile Tyr Asp Ser Ser Arg Leu Ala Ser Gly Val Pro
 65                  70                  75                  80

Ser Arg Phe Ser Gly Gly Ser Gly Thr Ser Tyr Ser Pro Thr Ile
                85                  90                  95

Ser Asn Met Glu Ala Glu Asp Ala Ala Thr Tyr Phe Cys Gln Asn Trp
                100                 105                 110

Arg Ser Ser Pro Thr Phe Gly Ala Gly Thr Lys Leu Glu Leu Lys Arg
                115                 120                 125

<210> SEQ ID NO 43
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Glu Trp Thr Trp Val Phe Leu Phe Leu Leu Ser Val Thr Ala Gly
 1               5                  10                  15

Val His Ser Gln Val Gln Leu Gln Gln Ser Gly Pro Glu Leu Met Lys
                20                  25                  30

Pro Gly Ala Ser Val Lys Ile Ser Cys Lys Ala Thr Gly Tyr Thr Phe
            35                  40                  45

Ser Thr Ser Trp Ile Glu Trp Ile Lys Gln Arg Pro Gly His Gly Leu
        50                  55                  60

Glu Trp Ile Gly Glu Val Leu Pro Gly Ser Gly Lys Ser Asn His Asn
 65                  70                  75                  80

Ala Asn Phe Lys Gly Arg Ala Thr Phe Thr Ala Asp Thr Ala Ser Asn
```

```
                    85                  90                  95
Thr Ala Tyr Met Gln Leu Ser Ser Leu Thr Ser Glu Asp Ser Ala Val
                100                 105                 110

Tyr Tyr Cys Ala Arg Glu Gly Ser Asn Asn Asn Ala Leu Ala Tyr Trp
        115                 120                 125

Gly Gln Gly Thr Leu Val Thr Val Ser Ala
    130                 135
```

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Asp Ile Gln Met Thr Gln Ser Pro Ser Leu Ser Ala Ser Val Gly
1               5                   10                  15

Asp Arg Val Thr Ile Thr Cys Ser Ala Ser Gln Gly Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Arg Lys Leu Pro Tyr
                85                  90                  95

Thr Phe Gly Gly Gly Thr Lys Val Glu Ile Lys Arg
            100                 105
```

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Glu Val Gln Leu Val Glu Ser Gly Gly Gly Leu Val Gln Pro Gly Gly
1               5                   10                  15

Ser Leu Arg Leu Ser Cys Ala Ser Gly Phe Asp Phe Ser Arg Tyr
            20                  25                  30

Trp Met Asn Trp Val Arg Gln Ala Pro Gly Lys Gly Leu Glu Trp Val
            35                  40                  45

Ser Glu Ile Asn Pro Asp Ser Ser Thr Ile Asn Tyr Thr Pro Ser Leu
    50                  55                  60

Lys Asp Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp Gly Gln Gly Thr Thr Leu Thr Val Ser
            100                 105                 110

Ser
```

<210> SEQ ID NO 46

<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Asp Phe Ser Arg Tyr
            20                  25                  30

Trp Met Asn Trp Ile Arg Gln Pro Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Arg Val Thr Ile Ser Lys Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Met Gly Tyr Trp Gly Gln Gly Thr Leu Val Thr Val Ser
            100                 105                 110

Ser

<210> SEQ ID NO 47
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Asp Met Arg Val Pro Ala Gln Leu Leu Gly Leu Leu Met Leu Trp
1               5                   10                  15

Val Ser Gly Ser Ser Gly Asp Val Val Met Thr Gln Ser Pro Leu Ser
            20                  25                  30

Leu Pro Val Thr Pro Gly Glu Pro Ala Ser Ile Ser Cys Lys Ser Ser
        35                  40                  45

Gln Ser Leu Leu Asp Ser Asp Gly Lys Thr Tyr Leu Asn Trp Leu Leu
    50                  55                  60

Gln Lys Pro Gly Gln Ser Pro Gln Arg Leu Ile Tyr Leu Val Ser Lys
65                  70                  75                  80

Leu Asp Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Trp Gln Gly Thr His Phe Pro Arg Thr Phe Gly Gln Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 48
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 49
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atggacatgc gcgtgcccgc ccagctgctg ggcctgctga tgctgtgggt gtccggctcc      60
tccggcgacg tggtgatgac ccagtccccc ctgtccctgc ccgtgacccc cggcgagccc     120

-continued

```
gcctccatct cctgcaagtc ctcccagtcc ctgctggact ccgacggcaa gacctacctg    180
aactggctgc tgcagaagcc cggccagtcc ccccagcgcc tgatctacct ggtgtccaag    240
ctggactccg gcgtgcccga ccgcttctcc ggctccggct ccggcaccga cttcaccctg    300
aagatctccc gcgtggaggc cgaggacgtg ggcgtgtact actgctggca gggcacccac    360
ttcccccgca ccttcggcca gggcaccaag gtggagatca agcgtactgt ggctgcacca    420
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgttag    726
```

<210> SEQ ID NO 50
<211> LENGTH: 330
<212> TYPE: PRT
<213> ORGANISM: Homo sapiens

<400> SEQUENCE: 50

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Leu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 51
<211> LENGTH: 329
<212> TYPE: PRT
<213> ORGANISM: Homo sapiens

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Leu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 52
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Gly Arg Thr Tyr Tyr Ser
65                  70                  75                  80

Asp Asn Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Val Arg Tyr Asp His Tyr Ser Gly Ser Ser Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Ala Leu
                245                 250                 255

Gly Ala Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

```
Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 53
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Gly Arg Thr Tyr Tyr Ser
65                  70                  75                  80

Asp Asn Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Val Arg Tyr Asp His Tyr Ser Gly Ser Ser Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
```

```
                    210                 215                 220
His Lys Pro Ser Asn Thr Lys Val Asp Lys Val Glu Pro Lys Ser
225                 230                 235                 240

Cys Asp Lys Thr His Thr Cys Pro Pro Cys Pro Ala Pro Glu Ala Leu
                245                 250                 255

Gly Ala Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly
465

<210> SEQ ID NO 54
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Val Arg Tyr Asp His Tyr Ser Gly Ser Ser Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130             135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Leu Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 55
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Leu Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

Ala Leu His Asn His Tyr Thr Gln Lys Ser Leu Ser Leu Ser Pro Gly
           420                 425                 430
435                 440                 445

<210> SEQ ID NO 56
<211> LENGTH: 327
<212> TYPE: PRT
<213> ORGANISM: Homo sapiens

<400> SEQUENCE: 56

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 57
<211> LENGTH: 326

<212> TYPE: PRT
<213> ORGANISM: Homo sapiens

<400> SEQUENCE: 57

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 58
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Arg Thr Tyr Tyr Ser
65                  70                  75                  80

Asp Asn Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
                100                 105                 110

Tyr Tyr Cys Val Arg Tyr Asp His Tyr Ser Gly Ser Ser Asp Tyr Trp
            115                 120                 125

Gly Gln Gly Thr Leu Val Thr Val Ser Ser Ala Ser Thr Lys Gly Pro
            130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Lys Thr Tyr Thr Cys Asn Val Asp
            210                 215                 220

His Lys Pro Ser Asn Thr Lys Val Asp Lys Arg Val Glu Ser Lys Tyr
225                 230                 235                 240

Gly Pro Pro Cys Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser Gln Glu Asp
            275                 280                 285

Pro Glu Val Gln Phe Asn Trp Tyr Val Asp Gly Val Glu Val His Asn
            290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Arg Leu Thr Val Asp Lys
```

```
                    420                 425                 430
Ser Arg Trp Gln Glu Gly Asn Val Phe Ser Cys Ser Val Met His Glu
            435                 440                 445
Ala Leu His Asn His Tyr Thr Gln Lys Ser Leu Ser Leu Ser Leu Gly
        450                 455                 460
Lys
465

<210> SEQ ID NO 59
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Glu Phe Gly Leu Ser Trp Leu Phe Leu Val Ala Ile Leu Lys Gly
1               5                   10                  15
Val Gln Cys Glu Val Gln Leu Leu Glu Ser Gly Gly Gly Leu Val Gln
            20                  25                  30
Pro Gly Gly Ser Leu Arg Leu Ser Cys Ala Ala Ser Gly Phe Thr Phe
        35                  40                  45
Ser Asn Tyr Gly Met Ser Trp Val Arg Gln Ala Pro Gly Lys Gly Leu
    50                  55                  60
Glu Trp Val Ala Ser Ile Arg Ser Gly Gly Gly Arg Thr Tyr Tyr Ser
65                  70                  75                  80
Asp Asn Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Val Arg Tyr Asp His Tyr Ser Gly Ser Ser Asp Tyr Trp
        115                 120                 125
Gly Gln Gly Thr Leu Val Thr Val Ser Ser Ala Ser Thr Lys Gly Pro
    130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
        195                 200                 205
Val Pro Ser Ser Ser Leu Gly Thr Lys Thr Tyr Thr Cys Asn Val Asp
    210                 215                 220
His Lys Pro Ser Asn Thr Lys Val Asp Lys Arg Val Glu Ser Lys Tyr
225                 230                 235                 240
Gly Pro Pro Cys Pro Pro Cys Pro Ala Pro Glu Phe Leu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser Gln Glu Asp
        275                 280                 285
Pro Glu Val Gln Phe Asn Trp Tyr Val Asp Gly Val Glu Val His Asn
    290                 295                 300
```

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
    450                 455                 460

<210> SEQ ID NO 60
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
            210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 61
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe

```
            115                 120                 125
Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 62
<211> LENGTH: 330
<212> TYPE: PRT
<213> ORGANISM: Homo sapiens

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
           50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Ala Ala Gly Ala Pro Ser Val Phe Leu Phe Pro Pro
             115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 63
<211> LENGTH: 329
<212> TYPE: PRT
<213> ORGANISM: Homo sapiens

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

```
Lys Val Glu Pro Lys Ser Cys Asp Lys Thr His Thr Cys Pro Pro Cys
                100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 64
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Gly Arg Thr Tyr Tyr Ser
65                  70                  75                  80

Asp Asn Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Val Arg Tyr Asp His Tyr Ser Gly Ser Ser Asp Tyr Trp
```

```
                    115                 120                 125
Gly Gln Gly Thr Leu Val Thr Val Ser Ser Ala Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Ala Ala
                245                 250                 255

Gly Ala Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 65
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65
```

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Arg Thr Tyr Tyr Ser
65                  70                  75                  80

Asp Asn Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Val Arg Tyr Asp His Tyr Ser Gly Ser Ser Asp Tyr Trp
            115                 120                 125

Gly Gln Gly Thr Leu Val Thr Val Ser Ser Ala Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Ala Ala
                245                 250                 255

Gly Ala Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
```

```
                420             425             430
Val Asp Lys Ser Arg Trp Gln Gln Gly Asn Val Phe Ser Cys Ser Val
            435             440             445

Met His Glu Ala Leu His Asn His Tyr Thr Gln Lys Ser Leu Ser Leu
450             455             460

Ser Pro Gly
465

<210> SEQ ID NO 66
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300
```

-continued

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 67
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Gly Met Ser Trp Val Arg Gln Ala Pro Gly Lys Gly Leu Glu Trp Val
            35                  40                  45

Ala Ser Ile Arg Ser Gly Gly Gly Arg Thr Tyr Tyr Ser Asp Asn Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

<210> SEQ ID NO 68
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
atggagtttg gctgagctg cttttttctt gtggctattt taaaaggtgt ccagtgtgag        60
gtgcagctgc tggagtccgg cggcggcctg gtgcagcccg gcggctccct gcgcctgtcc       120
tgcgccgcct ccggcttcac cttctccaac tacggcatgt cctgggtgcg ccaggccccc       180
ggcaagggcc tggagtgggt ggcctccatc cgctccggcg gcggccgcac ctactactcc       240
gacaacgtga agggccgctt caccatctcc cgcgacaact ccaagaacac cctgtacctg       300
cagatgaact ccctgcgcgc cgaggacacc gccgtgtact actgcgtgcg ctacgaccac       360
tactccggct cctccgacta ctggggccag ggcaccctgg tgaccgtgtc ctccgcgtcg       420
accaagggcc catcggtctt ccccctggca ccctcctcca agagcacctc tgggggcaca       480
gcggccctgg gctgcctggt caaggactac ttccccgaac cggtgacggt gtcgtggaac       540
tcaggcgccc tgaccagcgg cgtgcacacc ttcccggctg tcctacagtc ctcaggactc       600
tactccctca gcagcgtggt gaccgtgccc tccagcagct gggcaccca gacctacatc        660 tgcaacgtga atcacaagcc cagcaacacc aaggtggaca gaaagttga gcccaaatct        720

```
tgtgacaaaa ctcacacatg cccaccgtgc ccagcacctg aagccgctgg ggcaccgtca      780
gtcttcctct tccccccaaa acccaaggac accctcatga tctcccggac ccctgaggtc      840
acatgcgtgg tggtggacgt gagccacgaa gaccctgagg tcaagttcaa ctggtacgtg      900
gacggcgtgg aggtgcataa tgccaagaca aagccgcggg aggagcagta caacagcacg      960
taccgtgtgg tcagcgtcct caccgtcctg caccaggact ggctgaatgg caaggagtac     1020
aagtgcaagg tctccaacaa agccctccca gcccccatcg agaaaaccat ctccaaagcc     1080
aaagggcagc cccgagaacc acaggtgtac accctgcccc catcccggga ggagatgacc     1140
aagaaccagg tcagcctgac ctgcctggtc aaaggcttct atcccagcga catcgccgtg     1200
gagtgggaga gcaatgggca gccggagaac aactacaaga ccacgcctcc cgtgctggac     1260
tccgacggct ccttcttcct ctatagcaag ctcaccgtgg acaagagcag gtggcagcag     1320
gggaacgtct tctcatgctc cgtgatgcat gaggctctgc acaaccacta cacgcagaag     1380
agcctctccc tgtccccggg taaatga                                         1407

<210> SEQ ID NO 69
<211> LENGTH: 449
<212> TYPE: PRT
<213> ORGANISM: Homo sapiens

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

-continued

```
                245                 250                 255
Arg Thr Pro Glu Val Thr Cys Val Val Asp Val Ser His Glu Asp
            260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
                355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Lys

<210> SEQ ID NO 70
<211> LENGTH: 448
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
                20                  25                  30
Gly Met Ser Trp Val Arg Gln Ala Pro Gly Lys Gly Leu Glu Trp Val
            35                  40                  45
Ala Ser Ile Arg Ser Gly Gly Gly Arg Thr Tyr Tyr Ser Asp Asn Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Val Arg Tyr Asp His Tyr Ser Gly Ser Ser Asp Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
```

165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 71
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Val Glu Ile Lys
            100                 105                 110

Arg

<210> SEQ ID NO 72
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 73
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Ile His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 74
```

<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Val Arg Arg Pro Ile Thr Pro Val Leu Val Asp Ala Met Asp Tyr
            100                 105                 110

Trp Gly Gln Gly Thr Leu Val Thr Val Ser Ser
        115                 120

<210> SEQ ID NO 75
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Ile Val Met Thr Gln Ser Pro Leu Ser Leu Pro Val Thr Pro Gly
1               5                   10                  15

Glu Pro Ala Ser Ile Ser Cys Arg Val Ser Gln Ser Leu Leu His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Arg His Val Pro Tyr Thr Phe Gly Gly Gly Thr Lys Val Glu Ile Lys
            100                 105                 110

<210> SEQ ID NO 76
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Asp Asn
            20                  25                  30

Gly Met Ala Trp Val Arg Gln Ala Pro Gly Lys Gly Leu Glu Trp Val
        35                  40                  45

Ser Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser
        115

<210> SEQ ID NO 77
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asp Asn
            20                  25                  30

Gly Met Ala Trp Val Arg Gln Ala Pro Gly Lys Gly Leu Glu Trp Val
        35                  40                  45

Ser Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser
        115

<210> SEQ ID NO 78
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Gly Met Ala Trp Val Arg Gln Ala Pro Gly Lys Gly Leu Glu Trp Ile
        35                  40                  45

Ser Phe Ile Ser Asn Leu Ala Tyr Ser Ile Asp Tyr Ala Asp Thr Val
    50                  55                  60
```

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser
        115

<210> SEQ ID NO 79
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Tyr Thr Glu Ala Tyr
            20                  25                  30

Tyr Ile His Trp Val Arg Gln Ala Pro Gly Gln Gly Leu Glu Trp Met
            35                  40                  45

Gly Arg Ile Asp Pro Ala Thr Gly Asn Thr Lys Tyr Ala Pro Arg Leu
    50                  55                  60

Gln Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Leu Tyr Ser Leu Pro Val Tyr Trp Gly Gln Gly Thr Thr Val
            100                 105                 110

Thr Val Ser Ser
        115

<210> SEQ ID NO 80
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asp Ala Lys Thr Tyr Leu Asn Trp Phe Gln Gln Arg Pro Gly Gln Ser
            35                  40                  45

Pro Arg Arg Leu Ile Tyr Gln Ile Ser Arg Leu Asp Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
            85                  90                  95

Thr His Tyr Pro Val Leu Phe Gly Gln Gly Thr Arg Leu Glu Ile Lys
            100                 105                 110

Arg Thr

<210> SEQ ID NO 81
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Ala Ile His Trp Val Arg Gln Ala Pro Gly Gln Gly Leu Glu Trp Met
        35                  40                  45

Gly Phe Thr Ser Pro Tyr Ser Gly Val Ser Asn Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Phe Asp Asn Tyr Asp Arg Gly Tyr Val Arg Asp Tyr Trp Gly
            100                 105                 110

Gln Gly Thr Leu Val
        115

<210> SEQ ID NO 82
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Asp
            20                  25                  30

Arg Ile Ser Phe Leu Asn Trp Tyr Gln Gln Lys Pro Gly Gln Pro Pro
        35                  40                  45

Lys Leu Leu Ile Tyr Ala Ala Thr Lys Gln Gly Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Phe Pro Trp Ser Phe Gly Gly Gly Thr Lys Val Glu Ile Lys Arg
            100                 105                 110

Thr Val

<210> SEQ ID NO 83
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Arg Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Ser Tyr Asn Pro Ser
50                  55                  60

Leu Lys Ser Gln Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Asn Tyr Tyr Tyr Asp Asp Tyr Phe Ala Tyr Trp Gly
            100                 105                 110

Gln Gly Thr Leu Val Thr Val Ser Ser
        115                 120

<210> SEQ ID NO 84
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Ala Gly Thr Lys Leu Glu Ile Lys
            100                 105                 110

<210> SEQ ID NO 85
<211> LENGTH: 9
<212> TYPE: PRT
<213> ORGANISM: Homo sapiens

<400> SEQUENCE: 85

Ala Glu Phe Arg His Asp Ser Gly Tyr
1               5

<210> SEQ ID NO 86
<211> LENGTH: 6
<212> TYPE: PRT
<213> ORGANISM: Homo sapiens

<400> SEQUENCE: 86

Ala Glu Phe Arg His Asp
1               5

```
1               5

<210> SEQ ID NO 87
<211> LENGTH: 7
<212> TYPE: PRT
<213> ORGANISM: Homo sapiens

<400> SEQUENCE: 87

Glu Phe Arg His Asp Ser Gly
1               5

<210> SEQ ID NO 88
<211> LENGTH: 5
<212> TYPE: PRT
<213> ORGANISM: Homo sapiens

<400> SEQUENCE: 88

Glu Phe Arg His Asp
1               5

<210> SEQ ID NO 89
<211> LENGTH: 16
<212> TYPE: PRT
<213> ORGANISM: Homo sapiens

<400> SEQUENCE: 89

Tyr Glu Val His His Gln Lys Leu Val Phe Phe Ala Glu Asp Val Gly
1               5                   10                  15

<210> SEQ ID NO 90
<211> LENGTH: 4
<212> TYPE: PRT
<213> ORGANISM: Homo sapiens

<400> SEQUENCE: 90

Val Phe Phe Ala
1

<210> SEQ ID NO 91
<211> LENGTH: 9
<212> TYPE: PRT
<213> ORGANISM: Homo sapiens

<400> SEQUENCE: 91

Gln Lys Leu Phe Phe Ala Glu Asp Val
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Leu Val Phe Phe Ala Gly Asp Val
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag
```

<400> SEQUENCE: 93

His His His His His
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ala Glu Phe Arg
1               5

<210> SEQ ID NO 95
<211> LENGTH: 110
<212> TYPE: PRT
<213> ORGANISM: Homo sapiens

<400> SEQUENCE: 95

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 96
<211> LENGTH: 109
<212> TYPE: PRT
<213> ORGANISM: Homo sapiens

<400> SEQUENCE: 96

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
                100                 105

-continued

```
<210> SEQ ID NO 97
<211> LENGTH: 110
<212> TYPE: PRT
<213> ORGANISM: Homo sapiens

<400> SEQUENCE: 97

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 98
<211> LENGTH: 107
<212> TYPE: PRT
<213> ORGANISM: Mus sp.

<400> SEQUENCE: 98

Val Pro Glu Val Ser Ser Val Phe Ile Phe Pro Pro Lys Pro Lys Asp
1               5                   10                  15

Val Leu Thr Ile Thr Leu Thr Pro Lys Val Thr Cys Val Val Val Asp
            20                  25                  30

Ile Ser Lys Asp Asp Pro Glu Val Gln Phe Ser Trp Phe Val Asp Asp
        35                  40                  45

Val Glu Val His Thr Ala Gln Thr Gln Pro Arg Glu Glu Gln Phe Asn
    50                  55                  60

Ser Thr Phe Arg Ser Val Ser Glu Leu Pro Ile Met His Gln Asp Trp
65                  70                  75                  80

Leu Asn Gly Lys Glu Phe Lys Cys Arg Val Asn Ser Ala Ala Phe Pro
                85                  90                  95

Ala Pro Ile Glu Lys Thr Ile Ser Lys Thr Lys
            100                 105

<210> SEQ ID NO 99
<211> LENGTH: 110
<212> TYPE: PRT
<213> ORGANISM: Mus sp.

<400> SEQUENCE: 99

Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
65                  70                  75                  80
```

```
Gln Asp Trp Met Ser Gly Lys Glu Phe Lys Cys Lys Val Asn Asn Lys
                85                  90                  95

Asp Leu Pro Ala Pro Ile Glu Arg Thr Ile Ser Lys Pro Lys
                100                 105                 110
```

USE OF TAU TO MONITOR IMMUNOTHERAPY

CROSS-REFERENCE TO RELATED APPLICATION

This application is a U.S. National Phase application under 35 U.S.C 371 of PCT/US2011/033649 filed Apr. 22, 2011, which claims priority from U.S. Application No. 61/327,062, filed Apr. 22, 2010 and U.S. Application No. 61/450,619, filed Mar. 8, 2011, each of which is incorporated by reference in its entirety for all purposes. This application is also a continuation in part of U.S. application Ser. No. 12/738,396, filed Jun. 24, 2010, the US national phase of International Application No. PCT/US2008/080382, filed Oct. 17, 2008, which claims priority from related to U.S. Application No. 60/999,423, filed Oct. 17, 2007, U.S. Application No. 61/083,827 filed Jul. 25, 2008. Each of the above applications is incorporated by reference in its entirety for all purposes.

REFERENCE TO A SEQUENCE LISTING

The Sequence Listing written in file Sequence Listing for 057436-404683.txt is 164,718 bytes and was created on Apr. 22, 2011. The information contained in this file is hereby incorporated by reference.

BACKGROUND OF THE INVENTION

I. General

Alzheimer's disease (AD) is a progressive disease resulting in senile dementia. See generally Selkoe, *TINS* 16:403 (1993); Hardy et al., WO 92/13069; Selkoe, *J. Neuropathol. Exp. Neurol.* 53:438 (1994); Duff et al., *Nature* 373:476 (1995); Games et al., *Nature* 373:523 (1995). Broadly speaking, the disease falls into two categories: late onset, which occurs in old age (65+ years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropile up to 150 μm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed Aβ or β-amyloid peptide. Aβ peptide is a 4-kDa internal fragment of 39-43 amino acids of a larger transmembrane glycoprotein named amyloid precursor protein (APP). As a result of proteolytic processing of APP by different secretase enzymes, Aβ is primarily found in both a short form, 40 amino acids in length, and a long form, ranging from 42-43 amino acids in length. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The physical symptoms associated with this type of neural deterioration characterize Alzheimer's disease.

Several mutations within the APP protein have been correlated with the presence of Alzheimer's disease. See, e.g., Goate et al., *Nature* 349:704 (1991) (valine[717] to isoleucine); Chartier Harlan et al., *Nature* 353:844 (1991)) (valine[717] to glycine); Murrell et al., *Science* 254:97 (1991) (valine[717] to phenylalanine); Mullan et al., *Nature Genet.* 1:345 (1992) (a double mutation changing lysine[595]-methionme[596] to aspargme[595]-leucine[596]). Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the prescnilin genes, PS1 and PS2, are thought indirectly to affect processing of APP to generate increased amounts of long form Aβ (see Hardy, *TINS* 20: 154 (1997)).

Apolipoprotein E (ApoE) encodes a cholesterol-processing protein. The gene, which maps to 19q13.2, has three allelic variants: ApoE4, ApoE3, and ApoE2. The frequency of the apoE4 version of the gene in the general population varies, but is always less than 30% and frequently 8%-15%. ApoE3 is the most common form and ApoE2 is the least common. Persons with one E4 allele usually have about a two to three fold increased risk of developing Alzheimer's disease. Persons with two E4 alleles (usually around 1% of the population) have about a nine-fold increase in risk. Nonetheless, even persons with two E4 alleles do not always get Alzheimer's disease. At least one E4 allele is found in about 40% of patients with late-onset Alzheimer's disease. Genetic screening for E4 has not been routinely performed, because it has not been known how to use this information for a therapeutic regime.

Tau is a well-known human protein that can exist in phosphorylated form (see, e.g., Goedert Proc. Natl. Acad. Sci. U.S.A. 85:4051-4055 (1988); Goedert, EMBO J. 8:393-399 (1989); Lee, Neuron 2:1615-1624 (1989); Goedert, Neuron 3:519-526 (1989); Andreadis, Biochemistry 31:10626-10633 (1992). Total tau (t-tau, i.e., phosphorylated and unphosphorylated forms) and phospho-tau (p-tau, i.e., phorphorylated tau) are released by the brain in response to neuronal injury and neurodegeneration and have been reported to occur at increased levels in the CSF of Alzheimer's patients relative to the general population (Jack et al., Lancet Neurol 9: 119-28 (2010)).

SUMMARY OF THE CLAIMED INVENTION

The invention provides a method of treating Alzheimer's disease, comprising administering to a patient having zero ApoE4 alleles ("ApoE4 non-carrier patient") and Alzheimer's disease, an effective regime of an antibody that specifically binds to an N-terminal epitope of Aβ. Optionally, the antibody specifically binds to an epitope within residues 1-7 of Aβ, or an epitope within residues 1-5 of Aβ, or an epitope within residues 3-7 of Aβ. Optionally, the dosage of the antibody within a range of about 0.15 mg/kg to about 2 mg/kg is administered by intravenous infusion. Optionally, the dosage is administered every 4 to 16 weeks. Optionally, the dosage is administered every 10 to 14 weeks. Optionally, the dosage is administered every 13 weeks. Optionally, the dosage is about 0.5 mg/kg to about 1 mg/kg. Optionally, the dosage is about 0.5 mg/kg to 2 mg/kg. Optionally, the dosage is about 2 mg/kg. Optionally, the antibody is bapineuzumab. Optionally, the method also involves monitoring for vasogenic edema, and optionally administering a corticosteroid to the patient to treat vasogenic edema detected by the monitoring.

The invention also provides a method of reducing cognitive decline in a patient having zero ApoE4 alleles ("ApoE4 non-carrier patient"), comprising administering to the patient an antibody that specifically binds to an N-terminal epitope of Aβ in a regime effective to reduce the cognitive decline of the patient relative to a control patient to whom the antibody is not administered; wherein: the ApoE4 non-carrier patient and control patient have been diagnosed with mild to moderate Alzheimer's disease; and the cognitive decline is measured by ADAS-COG, NTB, MMSE or CDR-SB. Optionally, the antibody is administered by intravenous infusion at a dosage within a range of about 0.15 mg/kg to about 2 mg/kg. Optionally, the antibody is bapineuzumab. Optionally, the dosage is about 0.5 mg/kg and the cognitive decline is measured by ADAS-COG. Optionally, the dosage is about 2 mg/kg and the cognitive decline is measured by ADAS-COG. Optionally, the cognitive decline is measured by NTB. Optionally, the dosage is 0.5 mg/kg. Optionally, the dosage is about 0.5 mg/kg and the cognitive decline is measured by CDR. Optionally, the dosage is about 0.5 mg/kg and the cognitive decline is measured by MMSE. Optionally, the dosage is about 2 mg/kg and the cognitive decline is measured by MMSE.

The invention also provides a method of reducing brain volume decline in a patient having zero ApoE4 alleles ("ApoE4 non-carrier patient"), comprising administering to the ApoE4 non-carrier patient an antibody that specifically binds to an N-terminal epitope of Aβ in a regime effective to reduce the brain volume decline of the ApoE4 non-carrier patient relative to a control patient to whom the antibody is not administered; wherein the ApoE4 non-carrier patient and control patient have been diagnosed with mild to moderate Alzheimer's disease. Optionally, the antibody is administered by intravenous infusion at a dosage within a range of about 0.15 mg/kg to about 2 mg/kg. Optionally, the antibody is bapineuzumab. Optionally, the dosage is about 0.5 mg/kg. Optionally, the dosage is about 2 mg/kg. Optionally, the brain volume decline is measured by MRI.

The invention also provides a method of treating Alzheimer's disease, comprising administering to an ApoE4 non-carrier patient an antibody that specifically recognizes the N-terminal region of Aβ in a regime effective to maintain a mean serum concentration of the antibody in the range of about 0.1 μg/ml to about 60 μg/ml. Optionally, the range is about 0.4 jug/ml to about 20 μg/ml. Optionally, the range is about 1 μg/ml to about 5 μg/ml. Optionally, the maximum serum concentration of the antibody in the patient less than about 28 μg antibody/ml serum. Optionally, the maximum serum concentration is within a range of about 4-18 μg antibody/ml serum. Optionally, the antibody is bapineuzumab.

The invention also provides a method of treating Alzheimer's disease, comprising administering to an ApoE4 non-carrier patient an antibody that specifically recognizes the N-terminal region of Aβ in a regime effective to achieve a mean plasma Aβ concentration of at least 450 pg/ml. Optionally, the mean plasma Aβ concentration is in the range of about 600 pg/ml to about 3000 pg/ml. Optionally, the mean plasma Aβ concentration is in the range of about 700 pg/ml to about 2000 pg/ml. Optionally, the mean plasma Aβ concentration is in the range of about 700 pg/ml to about 2000 pg/ml. Optionally, the mean plasma Aβ concentration is in the range of about 800 pg/ml to about 1000 pg/ml.

The invention also provides a method of treating Alzheimer's disease, comprising subcutaneously administering to a patient having the disease and one or two copies of an ApoE4 allele an effective regime of an antibody that binds to an N-terminal epitope of Aβ. Optionally, the method further comprises monitoring for vasogenic edema. Optionally, the antibody is administered at a dose of 0.01-0.6 mg/kg and a frequency of between weekly and monthly. Optionally, the antibody is administered at a dose of 0.05-0.5 mg/kg. Optionally, the antibody is administered at a dose of 0.05-0.25 mg/kg. Optionally, the antibody is administered at a dose of 0.015-0.2 mg/kg weekly to biweekly. Optionally, the antibody is administered at a dose of 0.05-0.15 mg/kg weekly to biweekly. Optionally, the antibody is administered at a dose of 0.05-0.07 mg/kg weekly. Optionally, the antibody is administered at a dose of 0.06 mg/kg weekly. Optionally, the antibody is administered at a dose of 0.1 to 0.15 mg/kg biweekly. Optionally, the antibody is administered at a dose of 0.1 to 0.3 mg/kg monthly. Optionally, the antibody is administered at a dose of 0.2 mg/kg monthly. Optionally, the antibody is administered at a dose of 1-40 mg and a frequency of between weekly and monthly. Optionally, the antibody is administered at a dose of 5-25 mg. Optionally, the antibody is administered at a dose of 2.5-15 mg. Optionally, the antibody is administered at a dose of 1-12 mg weekly to biweekly. Optionally, the antibody is administered at a dose of 2.5-10 mg weekly to biweekly. Optionally, the antibody is administered at a dose of 2.5-5 mg weekly. Optionally, the antibody is administered at a dose of 4-5 mg weekly. Optionally, the antibody is administered at a dose of 7-10 mg biweekly. Optionally, the method further comprises monitoring for vasogenic edema.

The invention further comprises a method of treating Alzheimer's disease, comprising administering to a patient having the disease and one or two ApoE4 alleles an effective regime of an antibody that binds to an N-terminal epitope of Aβ; administering a corticosteroid to the patient to treat vasogenic edema arising from the administration of the antibody. Optionally, the method further comprises monitoring the patient for vasogenic edema. Optionally, the dose or frequency of administration of the antibody is reduced or eliminated during the vasogenic edema relative to the dose or frequency before the vasogenic edema. Optionally, the dose or frequency of administration of the antibody is increased after resolution of the vasogenic edema relative to the dose or frequency either before or during the vasogenic edema.

The invention further comprises a method of treating or effecting prophylaxis in a population of patients of an amyloidogenic disease characterized by amyloid deposits of Aβ in the brain, comprising: administering different regimes to different patients in the population depending on which allelic forms of ApoE are present in the patients; wherein at least one of the regimes comprises administering an agent that is an antibody to Aβ or an agent that induces an antibody to Aβ on administration to a patient. Optionally, the different regimes each comprise administering an agent that is an antibody to Aβ or an agent that induces an antibody to Aβ on administration to a patient; and the dose of the agent and/or the frequency of administration of the agent and/or the capacity of the agent to induce a clearing response to amyloid deposits and/or the mean serum concentration of the agent or antibodies induced by the agent and/or the maximum serum concentration of the agent or antibodies induced by the agent is reduced and/or the time of initiation of treatment relative to disease progression is earlier in (a) patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4 allele.

Optionally, a first regime comprises administering an agent that is an antibody to Aβ or an agent that induces an antibody to Aβ on administration to a patient and a second regime lacks an antibody to Aβ or an agent that induces an antibody to Aβ and the first regime is administered to patients having zero copies of an ApoE4 allele and the second regime is administered to patients having one or two copies of an ApoE4 allele. Optionally, a first regime comprises administering a first antibody to Aβ and the second regime comprises administering a second antibody to Aβ and the second antibody has reduced binding to an Fcγ receptor or C1q relative to the first antibody, and the first antibody is administered to patients having zero copies of an ApoE4 allele and the second antibody is administered to patients having one or two copies of an ApoE4 allele. Optionally, the second antibody has one or more mutations in the constant region that reduce binding to the Fcγ receptor and/or C1q, the mutations not being present in the first antibody. Optionally, the one or more mutations is/are at position(s) in a heavy chain constant region selected from the group consisting of positions 234, 235, 236 and 237 (EU numbering). Optionally, the one or more mutations are mutations at positions 234, 235 and 237. Optionally, the one or more mutations are L234A, L235A and G237A. Optionally, the isotype of the constant region is human IgG1. Optionally, the isotype of the constant region is human IgG2 or IgG4. Optionally, the first antibody is bapineuzumab and the second antibody is an L234A, L235A, G237A variant of bapineuzumab. Optionally, a first regime comprises administering a first antibody to Aβ and a second regime comprises administering a second antibody to Aβ, the first antibody being of human IgG1 isotype and the second antibody of human IgG4 isotype, and the first antibody is administered to patients having zero copies of an ApoE4 allele and the second antibody is administered to patients having one or two copies of an ApoE4 allele.

In some methods, the disease is Alzheimer's disease. Some methods further comprise determining which alleles of ApoE are present in the patient.

Optionally, the different regimes differ in dose of the agent administered. Optionally, the different regimes differ in frequency of the agent administered. Optionally, the different regimes differ in the type of agent administered.

Optionally, the dose of the agent and/or the frequency of administration of the agent and/or the capacity of the agent to induce a clearing response to amyloid deposits is reduced in (a) patients having two ApoE4 alleles relative to patients having one ApoE4 allele; and/or (b) patients having one copy of an ApoE4 allele relative to patients having zero copies of an ApoE4 allele, and/or (c) patients having two copies of an ApoE4 allele relative to patients having one copy of an ApoE4 allele. Optionally, the dose of the agent and/or the frequency of administration of the agent and/or the capacity of the agent to induce a clearing response to amyloid deposits is reduced in patients having one or two ApoE4 alleles relative to patients having zero ApoE4 alleles of an ApoE4 allele. Optionally, patients in the population having one or two ApoE4 alleles are administered a dose of 0.15-1 mg/kg, and patients in the population having zero ApoE4 alleles are administered a dose of 0.5-2 mg/kg of an antibody specifically binding within residues 1-11 of Aβ. Optionally, the patients in the population having one or two ApoE4 alleles are administered a lower dosage of agent than patients having zero ApoE4 alleles until vasogenic edema has appeared and resolved, and the same dosage of agent thereafter.

Optionally, the patients in the population having one or two ApoE4 alleles are administered a lower frequency of the agent than the patients having zero ApoE4 alleles until vasogenic edema has appeared and resolved, and the same dosage of agent thereafter. Optionally, the patients in the population having one or two ApoE4 alleles are administered an antibody with reduced capacity to induce a clearing response to amyloid deposits relative to bapineuzumab.

Optionally, the method further comprises monitoring at least some of the patients in the population for vasogenic edema. Optionally, the monitoring is performed by MRI. Optionally, patients in the population with zero ApoE4 alleles are not monitored by MRI. Optionally, the agent is an antibody binding to an epitope within residues 1-11 of Aβ. Optionally, the antibody has human IgG1 isotype. Optionally, the antibody is bapineuzumab. Optionally, the agent is an antibody having reduced capacity to induce a clearing response to amyloid deposits relative to bapineuzumab. Optionally, the antibody is an L234A, L235A, G237A variant of bapineuzumab.

Optionally, wherein patients with one or two ApoE4 alleles are administered 1-3 doses of humanized 266 antibody following by subsequent doses of bapineuzumab and patients with zero ApoE4 alleles are administered the same total number of doses but all with bapineuzumab. In some methods, the antibody is a humanized 266 antibody. Optionally, patients with one or two ApoE4 alleles are administered humanized 266 and patients with zero ApoE4 alleles are administered bapineuzumab.

The invention further provides a method of monitoring a population of patients undergoing treatment or prophylaxis for a disease characterized by amyloid deposits of Aβ in the brain with an agent that is an antibody to Aβ or an agent that induces an antibody to Aβ, the method comprising: performing different monitoring regimes in different patients in the population for vasogenic edema, wherein the frequency of monitoring is greater for (a) patients having two copies of ApoE4 relative to patients having zero copies of ApoE4 and/or (b) patients having one copy of an ApoE4 allele relative to patients having zero copies of an ApoE4 allele, and/or (c) patients having two copies of an ApoE4 allele relative to patients having one copy of an ApoE4 allele. Optionally, the disease is Alzheimer's disease. Optionally, the method further comprises determining which allelic forms of ApoE are present in each patient in the population. Optionally, the monitoring is by brain imaging. Optionally, the monitoring is by MRI. Optionally, patients having one ApoE4 allele are monitored more frequently than patients having zero ApoE4 alleles. Optionally, patients having two ApoE4 alleles are monitored more frequently than patients having one ApoE4 allele. Optionally, patients having one ApoE4 allele are monitored more frequently than patients having zero ApoE4 alleles. Optionally, patients having zero ApoE4 alleles are not monitored by MRI for vasogenic edema.

The invention further provides a method of treating or effecting prophylaxis of a patient for a disease characterized by amyloid deposits of Aβ in the brain, comprising administering to a patient with at least one ApoE4 allele an agent that is an antibody to an epitope within residue 1-11 of Aβ or an agent that induces such an antibody to Aβ, and monitoring the patient for vasogenic edema by MRI. Optionally, the agent is bapineuzumab. Optionally, the agent is an L234A, L235A, G237A variant of bapineuzumab.

The invention further provides a method of treating or effecting prophylaxis of a disease characterized by amyloid deposits of Aβ in the brain in a patient having at least one ApoE4 allele, comprising administering a first regime to the patient before vasogenic edema appears, and a second regime after vasogenic edema has resolved; wherein the first and second regimes each comprise administering an agent that is an antibody to Aβ or an agent that induces an antibody to Aβ on administration to a patient; and the dose of the agent and/or the frequency of administration of the agent and/or the capacity of the agent to clear amyloid deposits is reduced in the first regime relative to the second regime. Optionally, the disease is Alzheimer's disease. Optionally, the patient has one or two ApoE4 alleles. Optionally, the first and second regimes each comprises administering an antibody that specifically binds to an epitope within residues 1-11 of Aβ to the patient, and the antibody is administered at a dose of 0.15-1 mg/kg before vasogenic edema appears and 0.5-2 mg/kg after vasogenic edema has resolved. Optionally, the antibody is bapineuzumab. Optionally, the antibody is a L234A, L235A, G237A variant of bapincuzumab.

The invention further provides a method of treating or effecting prophylaxis of Alzheimer's disease in a patient, comprising administering to the patient an antibody that specifically binds to an epitope within residues 1-11 of Aβ to a patient having one or two ApoE4 alleles, wherein the antibody is administered in a regime in which 0.15-1 mg/kg of antibody is administered quarterly by intravenous administration, or at a dose frequency and route of administration that generates an equivalent average serum concentration or area under the curve. Optionally, the antibody is bapineuzumab. Optionally the dose is 0.5 mg/kg.

The invention further provides a method of treating or effecting prophylaxis of Alzheimer's disease in a patient, comprising administering to the patient an antibody that specifically binds to an epitope within residues 1-11 of Aβ to a patient having zero ApoE4 alleles, wherein the dose of the antibody is 0.5-2 mg/kg administered quarterly by intravenous administration, or a dose frequency and route of administration that generates an equivalent serum concentration or area under the curve. Optionally, the antibody is an L234A, L235A, G237A variant of bapineuzumab.

The invention further provides a method of treating or effecting prophylaxis of Alzheimer's disease in a population of patients, comprising administering an antibody that specifically binds to an epitope within residues 1-11 of Aβ to the patients, wherein the antibody is administered at a dose of 0.15-1 mg/kg in patients of the population having one or two ApoE4 alleles and a dose of 0.5-2.5 mg/kg in patients of the population having zero ApoE4 alleles, and the mean dose is higher in the patients having zero ApoE4 alleles. Optionally, the antibody is bapineuzumab. Optionally, the antibody is an L234A, L235A, G237A variant of bapineuzumab. Optionally, the dose is 0.5 mg/kg in patients of the population having one or two ApoE4 alleles and 2 mg/kg in patients of the population having zero ApoE4 alleles.

The invention further provides a use of a measurement of ApoE4 copy number is selecting from different regimes for treatment or prophylaxis of a disease characterized by amyloid deposits in the brain in the patient wherein the different regimes each comprise administering an agent that is an antibody to Aβ or an agent that induces an antibody to Aβ on administration to a patient, and the dose of the agent and/or the frequency of administration of the agent and/or the capacity of the agent to induce a clearing response to amyloid deposits and/or the mean scrum concentration of the agent or antibodies induced by the agent and/or the maximum scrum concentration of the agent or antibodies induced by the agent is reduced and/or the time of initiation of treatment relative to disease progression is earlier in a regime administered to (a) patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4.

The invention further provides a method of selecting a regime for treatment or prophylaxis of a disease characterized by amyloid deposits in the brain of a patient, the method comprising determining the number of ApoE4 alleles present in a patient; selecting from different regimes based on the number of ApoE4 alleles present, wherein the different regimes each comprise administering an agent that is an antibody to Aβ or an agent that induces an antibody to Aβ on administration to a patient, and the dose of the agent and/or the frequency of administration of the agent and/or the capacity of the agent to induce a clearing response to amyloid deposits and/or the mean serum concentration of the agent or antibodies induced by the agent and/or the maximum serum concentration of the agent or antibodies induced by the agent is reduced and/or the time of initiation of treatment relative to disease progression is earlier in (a) patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4.

The invention further provides a use of a measurement of ApoE4 copy number in the manufacture of a medicament to treat Alzheimer's disease, wherein the medicament comprises an antibody to Aβ or an agent that induces an antibody to Aβ.

The invention further provides a use of at least one agent that is an antibody to Aβ or an agent that induces an antibody to Aβ on administration to a patient in the manufacture of a medicament for the treatment or prophylaxis of a disease characterized by amyloid deposits in the brain of a patient by different regimes depending on the number of ApoE4 alleles in the patient, wherein the different regimes comprise administering an agent to a patient and the dose of the agent and/or the frequency of administration of the agent and/or the capacity of the agent to induce a clearing response to amyloid deposits and/or the mean serum concentration of the agent or antibodies induced by the agent and/or the maximum scrum concentration of the agent or antibodies induced by the agent is reduced and/or the time of initiation of treatment relative to disease progression is earlier in (a) patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4.

The invention further provides a method of treating or effecting prophylaxis in a population of patients of an amyloidogenic disease characterized by amyloid deposits of Aβ in the brain, comprising: administering different regimes to different patients in the population depending on which allelic forms of ApoE are present in the patients; wherein the different regimes each comprise administering an agent that is an antibody to Aβ or an agent that induces an antibody to Aβ on administration to a patient; and the mean serum concentration of the agent or antibodies induced by the agent and/or the maximum concentration of the agent or antibodies induced by the agent is reduced in patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4.

The invention further provides a method of treating or effecting prophylaxis in a population of patients of an amyloidogenic disease characterized by amyloid deposits of Aβ in the brain, comprising: determining the ApoE4 status of the patient; administering different regimes to different patients in the population depending on which allelic forms of ApoE are present in the patients; wherein the different regimes each comprise administering an agent that is an antibody to Aβ or an agent that induces an antibody to Aβ on administration to a patient; and the dose of the agent and/or the frequency of administration of the agent and/or the capacity of the agent to induce a clearing response to amyloid deposits and/or the mean serum concentration of the agent or antibodies induced by the agent and/or the maximum serum concentration of the agent or antibodies induced by the agent is reduced and/or the time of initiation of treatment relative to disease progression is earlier in (a) patients having two copies of an ApoE4 allele relative to patients having zero copies of an ApoE4 allele, and/or (b) patients having one copy of an ApoE4 allele relative to patients having zero copies of an ApoE4 allele, and/or (c) patients having two copies of an ApoE4 allele relative to patients having one copy of an ApoE4.

The invention further provides a humanized form of a 10D5 antibody comprising a human heavy chain constant region with L234A, L235A and G237A mutations, wherein positions are numbered by the EU numbering system. Optionally, the isotype is human IgG1, IgG2 or IgG4, preferably IgG1. The 10D5 hybridoma was deposited with the ATCC on Apr. 8, 2003 and assigned accession number PTA-5129. The ATCC is located at 10801 University Blvd., Manassas, Va. 20110.

The invention further provides a humanized form of a 12A11 antibody comprising a humanized light chain variable region of SEQ ID NO: 10 and a humanized heavy chain variable region of SEQ ID NO: 11 and a human heavy chain constant region with L234A, L235A and G237A mutations, wherein positions are numbered by the EU numbering system. Optionally, the isotype is human IgG1, IgG2 or IgG4, preferably IgG1.

The invention further provides a humanized form of a 3D6 antibody comprising a human heavy chain constant region with L234A, L235A and G237A mutations, wherein positions are numbered by the EU numbering system. The 3D6 hybridoma was deposited with the ATCC on Apr. 8, 2003 and assigned accession number PTA-5130. The ATCC is located at 10801 University Blvd., Manassas, Va. 20110. Optionally, the isotype is human IgG1, IgG2 or IgG4, preferably IgG1. The 3D6 hybridoma was deposited with the ATCC on Apr. 8, 2003.

The invention further provides an isolated humanized antibody comprising a mature light chain variable region sequence of SEQ ID NO: 2 and a mature heavy chain variable region sequence of SEQ ID NO: 3, and a human heavy chain constant region of IgG isotype with L234A, L235A, and G237A mutations, wherein positions are numbered by the EU numbering system. Optionally, the isotype is human IgG1 isotype.

The invention further provides an isolated humanized form of a 12B4 antibody, wherein the 12B4 antibody is characterized by a mature light chain variable region sequence of SEQ ID NO: 31 and a mature heavy chain variable region sequence of SEQ ID NO: 32, and a human heavy chain constant region of IgG isotype with L234A, L235A, and G237A mutations, wherein positions are numbered by the EU numbering system. Optionally, the isotype is human IgG1 isotype.

The invention further provides a method of treating or effecting prophylaxis of a disease characterized by Aβ deposits in the brain of patient comprising administering an effective regime of a humanized antibody to the patient; wherein the humanized antibody comprises a mature light chain variable region sequence of SEQ ID NO: 2 and a mature heavy chain variable region sequence of SEQ ID NO: 3, and a human heavy chain constant of IgG1 isotype with L234A, L235A, and G237A mutations, wherein position are numbered by the EU numbering system. Optionally, the patient has at least one ApoE4 allele. Optionally the dose is 0.15-1 mg/kg. Optionally, the dose is 0.15-2 mg/kg. Optionally, the method further comprises monitoring the patient by MRI for vasogenic edema. Optionally, the method is for treating a population of the patients and the regime administered to different patients in the population does not depend on the number of ApoE4 alleles present in a patient.

The invention further provides a method of effecting prophylaxis of a disease characterized by deposits of Aβ deposits in the brain of a patient comprising administering an effective regime of an agent that is an antibody to Aβ or an agent that induces an antibody to Aβ on administration to a patient, wherein the patient has at least one ApoE4 allele. Optionally, the patient has two ApoE4 alleles. Optionally, the patient is asymptomatic. Optionally, the patient has a mini-mental test score of 27 or higher. Optionally, the patient has a mini-mental test score of 20-26. Optionally, the patient is at least sixty years of age. Optionally, the method further comprises determining the number of ApoE4 alleles in the patient.

The invention further provides a method of treating or effecting prophylaxis of a disease characterized by amyloid deposits of Aβ in the brain in a patient comprising administering a first regime comprise administering an agent that is an antibody to Aβ or an agent that induces an antibody to Aβ to the patient; monitoring the patient for vasogenic edema; maintaining the first regime if vasogenic edema does not appear; and administering a second regime to the patient if vasogenic edema does appear, wherein the second regime is a reduced dose of the agent and/or a reduced frequency of the agent, and/or a different agent with reduced capacity to bind an Fcγ receptor and/or C1q or is a lack of antibody to Aβ or an agent that induces an antibody to Aβ; wherein the second regime is maintained at least for the duration of the vasogenic edema. Optionally, the agent in the first regime is an antibody that specifically binds to an epitope within residues 1-11 of Aβ. Optionally, the first regime comprises administering a first antibody to Aβ and the second regime comprises administering a second antibody to Aβ with reduced capacity to find to an Fcγ receptor and or C1q relative to the first antibody. Optionally, the first antibody is bapineuzumab and the second antibody is an L234A, L235A, G237A variant of bapincuzumab.

The invention further provides a method of treating or effecting prophylaxis of Alzheimer's disease in a patient population, comprising administering an antibody that specifically binds to an epitope within residues 1-11 of Aβ and has mutations in the constant region that reduce binding to an Fcγ receptor and or C1q to the patient, wherein the antibody is administered at the same dose and/or frequency to each patient regardless of the number of ApoE4 alleles in the patient. Optionally, the antibody is an L234A, L235A, and G237A variant of bapineuzumab. Optionally, the method further comprises a step of monitoring the patient for vasogenic edema.

The invention further provides a method of treating or effecting prophylaxis of Alzheimer's disease in a patient population, comprising administering an agent that is an antibody to Aβ or which induces an antibody to Aβ on administration to some of the patients in the population, wherein patients in the population having zero ApoE4 alleles receive the agent and patients in the population having two ApoE4 alleles do not receive the agent. Optionally, patients in the population having one ApoE4 allele do not receive the agent. Optionally, the antibody is administered by intravenous infusion at a dosage within a range of about 0.15 mg/kg to about 2 mg/kg. Optionally, the antibody is bapineuzumab. Optionally, the dosage is about 0.5 mg/kg. Optionally, the dosage is about 2 mg/kg. Optionally, the brain volume decline is measured by MRI.

The invention further provides a method of determining a regime for bapineuzumab administration, comprising providing instructions to a healthcare professional that assists the healthcare professional determine a regime of bapineuzumab to administer to a patient having zero copies of an ApoE4 allele. Optionally, the regime is characterized by administering bapineuzumab at a dose of 0.5-2 mg/kg. Optionally, the regime is characterized by administering 0.5-2 mg/kg of bapineuzumab quarterly by intravenous administration, or at a dose frequency and route of administration that generates an equivalent average serum concentration or area under the curve. Optionally, the regime further comprises monitoring the patient for vasogenic edema. Optionally, the monitoring regime is different than the monitoring regime for a patient having or two copies of an ApoE4 allele. Optionally, the method further comprises the step of determining the number of ApoE4 alleles present in a patient. Optionally, the method further comprises providing bapineuzumab to a healthcare professional. Optionally, the instructions and bapincuzumab are provided in combination. Optionally, the regime further comprises monitoring at the patient for vasogenic edema. Optionally, the monitoring is performed by MRI. Optionally, the monitoring is by brain imaging.

The invention further provides a method of determining a regime for bapineuzumab administration comprising providing instructions to a healthcare professional that assists the healthcare professional determine a regime of bapineuzumab to administer to a patient having one or two copies of an ApoE4 allele. Optionally, the regime is characterized by administering bapineuzumab at a dose of 0.15-1 mg/kg. Optionally, the regime is characterized by administering bapineuzumab at a dose of 0.15-1 mg/kg quarterly by intravenous administration, or at a dose frequency and route of administration that generates an equivalent average serum concentration or area under the curve. Optionally, the determined regime comprises a first and a second regime, wherein the first regime is administered to the patient before vasogenic edema appears, and the second regime after vasogenic edema has resolved; and wherein the first and second regimes each comprise administering bapineuzumab; wherein the first regime differs relative to the second regime in at least one of (i)-(ii) below: (i) the dose of the bapineuzumab is reduced; (ii) the frequency of administration of the bapineuzumab is reduced. Optionally, the regime further comprises monitoring the patient for vasogenic edema. Optionally, the monitoring regime is different than the monitoring regime for a patient having or two copies of an ApoE4 allele. Optionally, the method further comprises the step of determining the number of ApoE4 alleles present in a patient. Optionally, the method further comprises providing bapineuzumab to a healthcare professional. Optionally, the instructions and bapineuzumab are provided in combination. Optionally, the regime further comprises monitoring at the patient for vasogenic edema. Optionally, the monitoring is performed by MRI. Optionally, the monitoring is by brain imaging. Optionally, the monitoring regime is different than the monitoring regime for a patient having zero copies of an ApoE4 allele. Optionally, the frequency of monitoring is greater for: (a) patients having two copies of the ApoE4 allele relative to patients having zero copies of an ApoE4 allele; (b) patients having one copy of an ApoE4 allele relative to patients having zero copies of an ApoE4 allele; and/or (c) patients having two copies of an ApoE4 allele relative to patients having one copy of an ApoE4 allele.

The invention further provides a kit for determining a regime for bapineuzumab administration comprising instructions to a healthcare professional that assist the healthcare professional determine which regime of bapincuzumab to administer to a patient having zero copies of an ApoE4 allele. Optionally, the instructions specify a regime characterized by administering bapincuzumab at a dose of 0.5-2 mg/kg. Optionally, the instructions specify administering 0.5-2 mg/kg of bapineuzumab quarterly by intravenous administration, or at a dose frequency and route of administration that generates an equivalent average serum concentration or area under the curve. Optionally, the instructions specify monitoring the patient for vasogenic edema. Optionally, the instructions specify that the monitoring regime is different that the monitoring regime for a patient having one or two copies of an ApoE4 allele. Optionally, the instructions specify that the determined regime comprises a first and a second regime, wherein the first regime is administered to the patient before vasogenic edema appears, and the second regime after vasogenic edema has resolved; and wherein the first and second regimes each comprise administering bapineuzumab; wherein the first regime differs relative to the second regime in at least one of (i)-(ii) below: (i) the dose of the bapineuzumab is reduced; (ii) the frequency of administration of the bapineuzumab is reduced. Optionally, the instructions specify determining the number of ApoE4 alleles present in a patient. Optionally, the kit further comprises bapineuzumab. Optionally, the instructions specify monitoring at the patient for vasogenic edema. Optionally, the instructions specify the monitoring is performed by MRI. Optionally, the instructions specify the monitoring is by brain imaging.

The invention further provides a kit for determining a regime for bapineuzumab administration comprising instructions to a healthcare professional that assist the healthcare professional determine which regime of bapineuzumab to administer to a patient having one or two copies of an ApoE4 allele. Optionally, the instructions specify administering bapineuzumab at a dose of 0.15-1 mg/kg. Optionally, the instructions specify administering bapineuzumab at a dose of 0.15-1 mg/kg quarterly by intravenous administration, or at a dose frequency and route of administration that generates an equivalent average serum concentration or area under the curve. Optionally, the instructions specify that the determined regime comprises a first and a second regime, wherein the first regime is administered to the patient before vasogenic edema appears, and the second regime after vasogenic edema has resolved; and wherein the first and second regimes each comprise administering bapineuzumab; wherein the first regime differs relative to the second regime in at least one of (i)-(ii) below: (i) the dose of the bapineuzumab is reduced; (ii) the frequency of administration of the bapineuzumab is reduced. Optionally, the instructions specify determining the number of ApoE4 alleles present in a patient. Optionally, the kit further comprises bapincuzumab. Optionally, the instructions specify monitoring at the patient for vasogenic edema.

Optionally, the instructions specify the monitoring is performed by MRI. Optionally, the instructions specify the monitoring is by brain imaging. Optionally, the instructions specify the monitoring regime is different that the monitoring regime for a patient having zero copies of an ApoE4 allele. Optionally, the instructions specify that the frequency of monitoring is greater for: (a) patients having two copies of the ApoE4 allele relative to patients having zero copies of an ApoE4 allele; (b) patients having one copy of an ApoE4 allele relative to patients having zero copies of an ApoE4 allele; and/or (c) patients having two copies of an ApoE4 allele relative to patients having one copy of an ApoE4 allele.

The invention further provides a method for improving the safety of bapineuzumab in patients having one or two ApoE4 alleles, comprising advising the physician to administer a lower dose of bapineuzumab to a patient having one or two ApoE alleles relative to that of a patient having zero ApoE alleles.

The invention further provides a method for improving the safety of bapineuzumab in patients having one or two ApoE4 alleles, comprising advising the physician to monitor the patient by MRI more frequently than a patient having one or two ApoE alleles relative to that of a patient having zero ApoE alleles.

The invention further provides an isolated antibody comprising a human heavy chain constant region of isotype IgG1, wherein amino acids at positions 234, 235, and 237 (EU numbering) are each alanine. Optionally, no other amino acid from positions 230-240 or 315-325 in the human heavy chain constant region is occupied by an amino acid not naturally found at that position in a human IgG1 constant region. Optionally, no amino acid in the human heavy chain constant region other than positions 234, 235 and 237 is occupied by an amino acid not naturally found at that position in a human IgG1 constant region. Optionally, the human heavy chain constant region comprise CH1, hinge, CH2 and CH3 regions. Optionally, the human heavy chain constant region has an amino acid sequence comprising SEQ ID NO:66 or SEQ ID NO:67 or an allotype of either of these sequences. Optionally, the human heavy chain constant region has an amino acid sequence comprising SEQ ID NO:66 or SEQ ID NO:67. Optionally, the antibody is a fully human antibody. Optionally, the antibody is a humanized antibody. Optionally, the antibody is chimeric antibody.

Any of the above-described methods can be practiced with a further step of determining CSF levels of phopho or total tau before and after initiating a treatment regime (e.g., administering an antibody). Although a particular regime can be shown to achieve a statistically significant benefit across a patient population, the response in individually patients may vary. A reduction in the CSF level of phospho or total tau after initiating the regime relative to the level before initiating the regime in a particular patient provides an indication the regime is effective in that patient. Likewise, any of the above described kits can contain additional reagents for measuring total or phospho tau. Such reagents can include antibody pairs specifically binding to different epitopes on the intended analyte (total or phospho tau).

Thus, the invention provides methods of treating Alzheimer's disease, comprising: administering to a patient having zero ApoE4 alleles ("ApoE4 non-carrier patient") and Alzheimer's disease, a regime of an antibody that specifically binds to an N-terminal epitope of Aβ; and determining CSF levels of phopho or total tau before and after initiating the regime, a reduction after initiating the regime providing an indication the regime is effective in the patient. The invention further provides methods of treating Alzheimer's disease, comprising: administering to a patient having the disease and one or two ApoE4 alleles a regime of an antibody that binds to an N-terminal epitope of Aβ; administering a corticosteroid to the patient to treat vasogenic edema arising from the administration of the antibody; and determining CSF levels of phopho or total tau before and after initiating the regime, a reduction after initiating the regime providing an indication the regime is effective in the patient.

The invention further provides methods of treating or effecting prophylaxis in a population of patients of an amyloidogenic disease characterized by amyloid deposits of Aβ in the brain, comprising: administering different regimes to different patients in the population depending on which allelic forms of ApoE are present in the patients; wherein at least one of the regimes comprises administering an antibody to Aβ to a patient. A response to treatment of patients receiving the antibody to Aβ is monitored by determining CSF levels of phopho or total tau before and after initiating a regime involving administration of the antibody, a reduction after initiating the regime in a patient providing an indication the regime is effective in the patient.

The invention further provides methods of treating or effecting prophylaxis of a disease characterized by amyloid deposits of Aβ in the brain in a patient having at least one ApoE4 allele, comprising administering a first regime to the patient before vasogenic edema appears, and a second regime after vasogenic edema has resolved. The first and second regimes each comprise administering an antibody to Aβ; wherein the first regime differs relative to the second regime in at least of (i)-(iii) below: (i) the dose of the antibody is reduced; (ii) the frequency of administration of the antibody is reduced; (iii) the capacity of the antibody to clear amyloid deposits is reduced; and determining CSF levels of phopho or total tau before and after initiating the first or second regime, wherein a reduction after initiating the first or second regime provides an indication the regime is effective in the patient.

The invention further provides methods of treating or effecting prophylaxis of Alzheimer's disease in a patient, comprising administering to the patient an antibody that specifically binds to an epitope within residues 1-11 of Aβ to a patient having one or two ApoE4 alleles, wherein the antibody is administered in a regime in which 0.15-1 mg/kg of antibody is administered quarterly by intravenous administration, or at a dose frequency and route of administration that generates an equivalent average serum concentration or area under the curve; and determining CSF levels of phopho or total tau before and after initiating the regime, a reduction after initiating the regime providing an indication the regime is effective in the patient. The invention further provides methods treating or effecting prophylaxis of Alzheimer's disease in a population of patients, comprising: administering an antibody that specifically binds to an epitope within residues 1-11 of Aβ to the patients, wherein the antibody is administered at a dose of 0.15-1 mg/kg in patients of the population having one or two ApoE4 alleles and a dose of 0.5-2.5 mg/kg in patients of the population having zero ApoE4 alleles, and the mean dose is higher in the patients having zero ApoE4 alleles; and determining CSF levels of phopho or total tau before and after initiating the regime, a reduction after initiating the regime in a patient providing an indication the regime is effective in the patient.

The invention further provides methods of treating or effecting prophylaxis of Alzheimer's disease in a patient population, comprising: administering an antibody that specifically binds to an epitope within residues 1-11 of Aβ and has mutations in the constant region that reduce binding to an Fcγ receptor and/or C1q to the patient, wherein the antibody is administered at the same dose and/or frequency to each patient regardless of the number of ApoE4 alleles in the patient; and determining CSF levels of phopho or total tau before and after initiating the regime in patients of the population, a reduction after initiating the regime in a patient providing an indication the regime is effective in the patient.

The invention further provides methods of treating or effecting prophylaxis of Alzheimer's disease in a patient population, comprising administering an antibody to Aβ to some of the patients in the population, wherein patients in the population having zero ApoE4 alleles receive the antibody and patients in the population having two ApoE4 alleles do not receive the antibody; and determining CSF levels of phopho or total tau before and after initiating administration of the antibody in patients in the population receiving the antibody, a reduction after initiating administration of the antibody in a patient providing an indication that administration of the antibody is effective in the patient.

The invention further provides methods of treating or effecting prophylaxis of a disease characterized by Aβ deposits in the brain of patient comprising administering a regime of a humanized antibody to the patient; wherein the humanized antibody comprises a mature light chain variable region sequence of SEQ ID NO:2 and a mature heavy chain variable region sequence of SEQ ID NO:3, and a human heavy chain constant of IgG1 isotype with L234A, L235A, and G237A mutations, wherein position are numbered by the EU numbering system; and determining CSF levels of phopho or total tau before and after initiating the regime, a reduction indicating after initiating the regime indicating the regime is effective in the patient.

The invention provides methods of monitoring a patient being administered a regime of an antibody to Aβ. The methods involve determining CSF levels of total or phospho tau in a body fluid of the patient before and 6-18 months after initiation of the regime, wherein the determining indicates a reduced level of total or phospho tau at 6-18 months compared to the level before initiating of the regime. In some methods, the determining after initiation of the regime is performed 11-13 months after initiating the regime. In some methods, the reduction in level is 30-150 pg/ml CSF for total tau or 2-15 pg/ml phospho tau. In some methods, the determining is performed on a plurality of occasions at a frequency between 6-18 months after initiating the regime. In some methods, the patient continues to receive the regime after the determining.

The invention further provides methods of monitoring a patient being administered a regime of an antibody to Aβ. The methods involve determining levels of total or phospho-tau in a body fluid of the patient before and after initiation of the regime, wherein the regime of the patient is adjusted responsive to the relative levels of total or phospho tau before and after initiation of the regime. In some methods, the determining indicates the level of total or phospho tau is the same or increased after initiation of treatment and the patient receives an increased dose or frequency of the antibody after the determining. In some methods, the determining indicates the level of total or phospho tau is the same or increased and the regime of an antibody to Aβ is discontinued after the determining. In some methods, the regime is adjusted without regard to measured levels of other biomarkers or cognitive indexes, if any. In some methods, the regime is adjusted without regard to measured levels of biomarker FFDG, BBSI, VBSI, or CSF Aβ42, if any. In some methods, the regime is adjusted without regard to measured levels of other biomarkers or cognitive values, if any, except for brain amyloid levels.

The invention further provides methods of monitoring treatment of a population of patients being administered a regime of an antibody to Aβ, comprising determining levels of total or phospho tau in a body fluid of the patients before and after initiation of the regime. A lower proportion of patients determined to have reduced levels of total or phospho tau after initiation of the regime thereafter receive a different regime than patients having the same or increased levels of total or phospho tau after initiation of the regime.

The invention provides a method of inhibiting soluble Aβ-induced synaptotoxicity, comprising administering to a subject, a regime of an antibody that specifically binds to an N-terminal epitope of Aβ. Optionally, the method inhibits soluble Aγ-induced synaptic loss. Optionally, the method inhibits soluble Aβ-induced AMPAR internalization. Optionally, the method inhibits soluble Aβ-induced spine density loss. Optionally, the method inhibits soluble Aβ binding to synapses. Optionally, the method inhibits soluble Aβ-induced tau phosphorylation. Optionally, the dosage of the antibody within a range of about 0.15 mg/kg to about 2 mg/kg is administered by intravenous infusion. Optionally, the dosage is administered every 4 to 16 weeks. Optionally, the dosage is administered every 10 to 14 weeks. Optionally, the dosage is administered every 13 weeks. Optionally, the dosage is about 0.5 mg/kg to about 1 mg/kg. Optionally, the dosage is about 0.5 mg/kg to 2 mg/kg. Optionally, the dosage is about 2 mg/kg. Optionally, the antibody specifically binds to an epitope within residues 1-7 of Aβ, or an epitope within residues 1-5 of Aβ, or an epitope within residues 3-7 of Aβ. Optionally, the antibody is a humanized form of a mouse 3D6 antibody (ATCC accession number PTA-5130), and optionally positions 234, 235 and 237 in the heavy chain constant region are occupied by Ala, Ala and Ala respectively, wherein positions are numbered by the EU numbering system. Optionally, the antibody is bapincuzumab. Optionally, the subject is suspected of, or already suffering Alzheimer's disease. Optionally, the subject is asymptomatic but has a known genetic risk of Alzheimer's disease.

The invention further provides a method of screening an agent to determine whether the agent has activity useful in treating Alzheimer's disease. Optionally, the method comprises contacting the agent with a transgenic nonhuman animal disposed to develop a characteristic of Alzheimer's disease; and determining whether the agent inhibits soluble Aβ-induced synaptotoxicity relative to a control transgenic nonhuman animal. Optionally, the method comprises contacting the agent with a tissue sample from a brain of a patient with Alzheimer's disease or a transgenic nonhuman animal having characteristic Alzheimer's disease's pathology; and determining whether the agent inhibits soluble Aβ-induced synaptotoxicity relative to a control tissue sample. Optionally, the agent is an antibody that specifically binds to an N-terminal epitope of Aβ. Optionally, the agent inhibits soluble Aβ-induced synaptic loss. Optionally, the agent inhibits soluble Aβ-induced AMPAR internalization. Optionally, the agent inhibits soluble Aβ-induced spine density loss. Optionally, the agent inhibits soluble Aβ binding to synapses. Optionally, the agent inhibits soluble Aβ-induced tau phosphorylation.

Statistical differences were determined by ANOVA; ***P<0.001 with respect to Aβ-only group. Scale bar, 10 μm.

Figure 32:
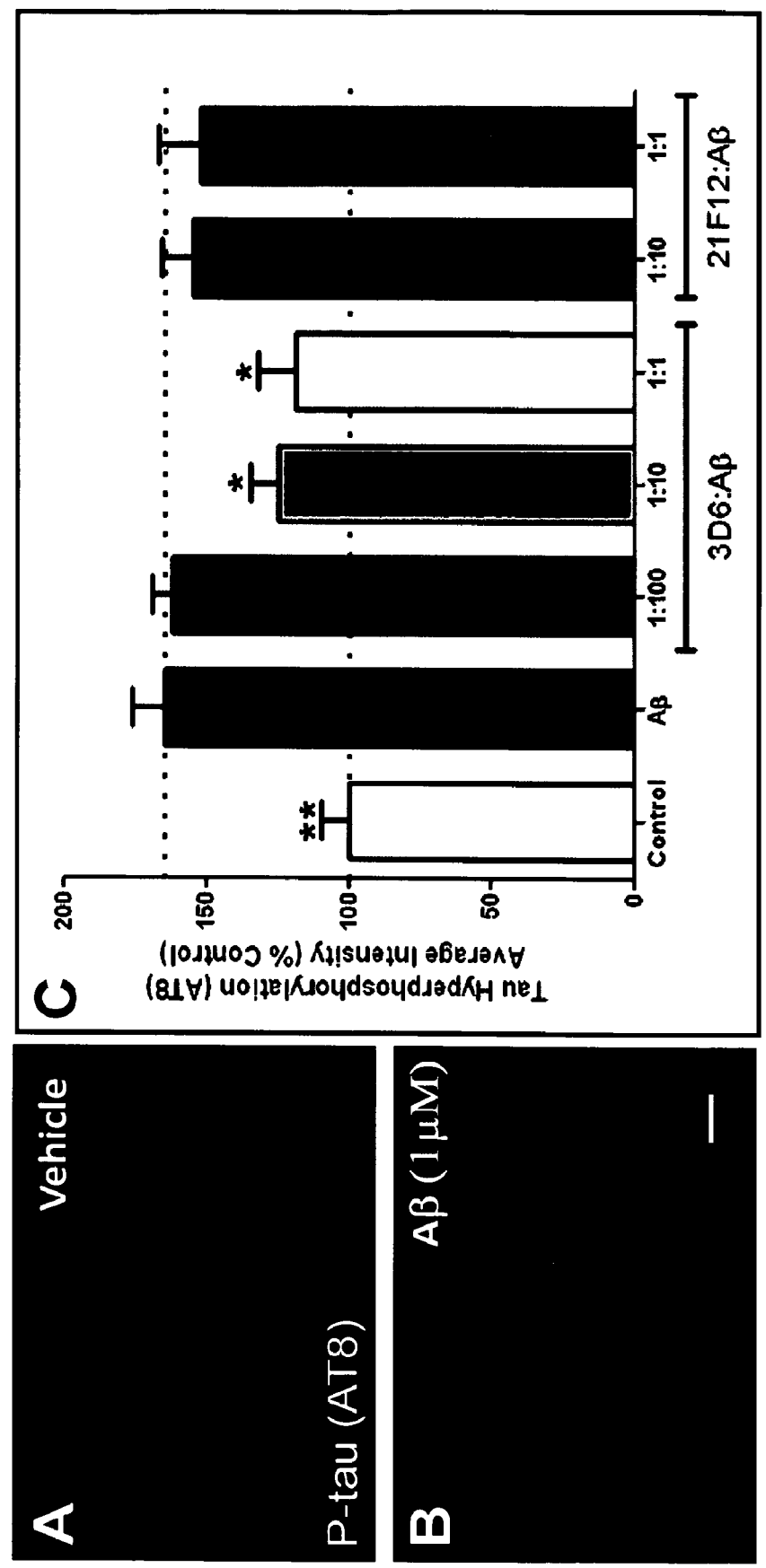

FIG. 32 show 3D6 mAb blocks the Aβ-induced tau hyperphosphorylation. (A, B) Representative images showing soluble Aβ-induced (1 μM, 8 h) tau hyperphosphorylation, visualized by staining with AT8 antibody. (C) Quantification of tau hyperphosphorylation in neurons treated with soluble Aβ in the presence or not of anti-Aβ mAbs. 3D6, but not 21F12 shows a concentration-dependent blockage of the soluble Aβ effects. The data were normalized by control levels (vehicle control) and values represent the means±SEMs of results from 25 optical fields (>2 neurons/field), pooled from 5 independent experiments/cultures. Statistical differences were determined by ANOVA; ***P<0.001 with respect to Aβ-only group. Scale bar, 10 μm.

Figure 33:
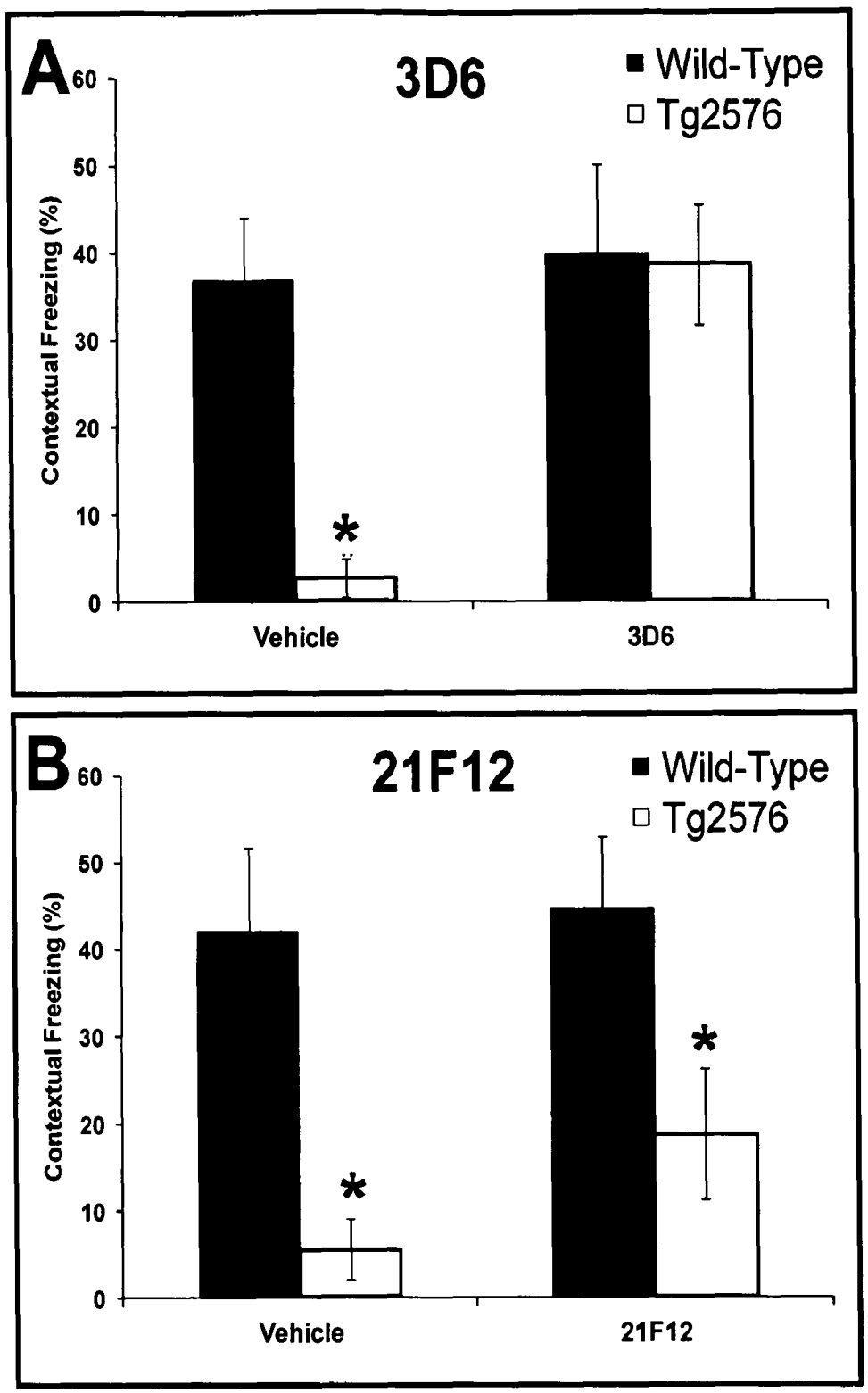

FIG. 33 shows passive immunization with 3D6 mAb acutely reverses the Aβ-related behavioral deficits in Tg2576 mouse. Effects of passive immunotherapy with 3D6 and 21F12 (both 30 mg/kg) 24 h prior to training. (A) 3D6 restores the freezing behavior of Tg2576 to the levels exhibited by vehicle-treated wild-type. (B) 21F12, on the other hand, shows no effects. Neither 3D6 nor 21F12 affect the freezing behavior in wild type animals. The values represent the means±SEMs of results from N=8-12 animals/genotype/treatment. Statistical differences were determined by ANOVA; *P<0.05 with respect to wild type groups.

Figure 34:
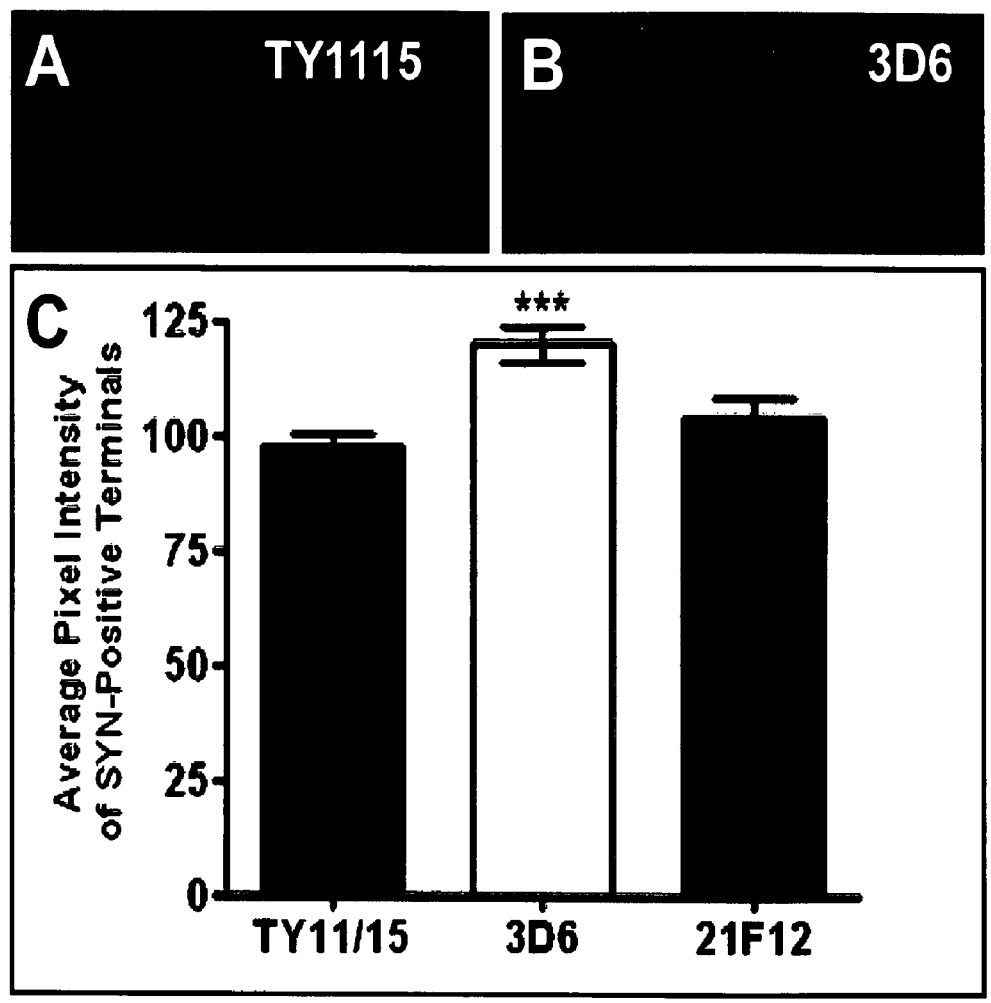

FIG. 34 shows passive Aβ immunizations with 3D6 prevented synaptophysin loss in the frontal neocortex of PDAPP mice. Effects of passive immunotherapy with anti-Aβ mAbs (3 mg/kg/week for 6 months) on neocortical synaptophysin levels. (A,B) Representative images showing synaptophysin levels in control-(TY1115) and 3D6-treated animals. (C) Significant improvements of synapsophysin levels over controls were found after passive immunization with 3D6, but not 21F12. Values represent the means±SEMs of results from N=18-20 animals (4 optical fields/animal), Statistical differences were determined by ANOVA; ***P<0.001 with respect to TY1115 group.

DEFINITIONS

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains. The term "domain" refers to a globular region of a heavy or light chain polypeptide comprising peptide loops (e.g., comprising 3 to 4 peptide loops) stabilized, for example, by pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains). "Constant" domains on the heavy chain are referred to interchangeably as "heavy chain constant regions", "heavy chain constant domains", "CH" regions or "CH" domains). A heavy chain constant region is also commonly understood to refer collectively to the domains present in a full length constant region, which are CH1, hinge, CH2, and CH3 domains in the case of antibodies of IgG isotype. "Variable" domains on the light chain are referred to interchangeably as "light chain variable regions", "light chain variable domains", "VL" regions or "VL" domains). "Variable" domains on the heavy chain are referred to interchangeably as "heavy chain constant regions," "heavy chain constant domains," "CH" regions or "CH" domains).

The term "region" refers to a part or portion of an antibody chain and includes constant or variable domains as defined herein, as well as more discrete parts or portions of said domains. For example, light chain variable domains or regions include "complementarity determining regions" or "CDRs" interspersed among "framework regions" or "FRs", as defined herein.

References to an antibody or immunoglobulin include intact antibodies and binding fragments thereof. Typically, fragments compete with the intact antibody from which they were derived for specific binding to an antigen. Fragments include separate heavy and light chains, Fab, Fab' F(ab')2, Fabc, and Fv. Separate chains include NANOBODIES™ (i.e., the isolated VH fragment of the heavy chain of antibodies from camels or llamas, optionally humanized) Isolated VH fragments can also be obtained from other sources, such as human antibodies. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. (See, e.g., Songsivilai & Lachmann, Clin. Exp. Immunol. 79:315-321 (1990); Kostelny et al., J. Immunol. 148, 1547-1553 (1992).)

"Specific binding" of an antibody means that the antibody exhibits appreciable affinity for antigen or a preferred epitope and, preferably, does not exhibit significant cross reactivity. Appreciable or preferred binding includes binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$. An antibody that "does not exhibit significant cross reactivity" is one that will not appreciably bind to an undesirable entity (e.g., an undesirable proteinaceous entity). For example, an antibody that specifically binds to Aβ will appreciably bind Aβ but will not significantly react with non-Aβ proteins or peptides (e.g., non-Aβ proteins or peptides included in plaques). An antibody specific for a preferred epitope will, for example, not significantly cross react with remote epitopes on the same protein or peptide. Specific binding can be determined according to any art-recognized means for determining such binding. Preferably, specific binding is determined according to Scatchard analysis and/or competitive binding assays.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region (also known as variable region framework) substantially from a human immunoglobulin or antibody and complementarity determining regions (CDRs) (e.g., at least one CDR, preferably two CDRs, more preferably three CDRs) substantially from a non-human immunoglobulin or antibody (e.g., rodent, and optionally, mouse), and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region (also known as a variable region framework) substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80-90% (e.g., at least 90%), preferably 90-95%, more preferably 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

An "antigen" is an entity (e.g., a proteinaceous entity or peptide) to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labelled assay, solid phase direct labelled sandwich assay (see Harlow and Lane, *Antibodies: A Laboratory Manual*, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labelled RIA (Moldenhauer et al., *Scand. J. Immunol.* 32:77 (1990). Typically, such an assay involves the use of purified antigen bound to a solid surface or cells bearing either of these, an unlabelled test immunoglobulin and a labelled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

Figure 1:
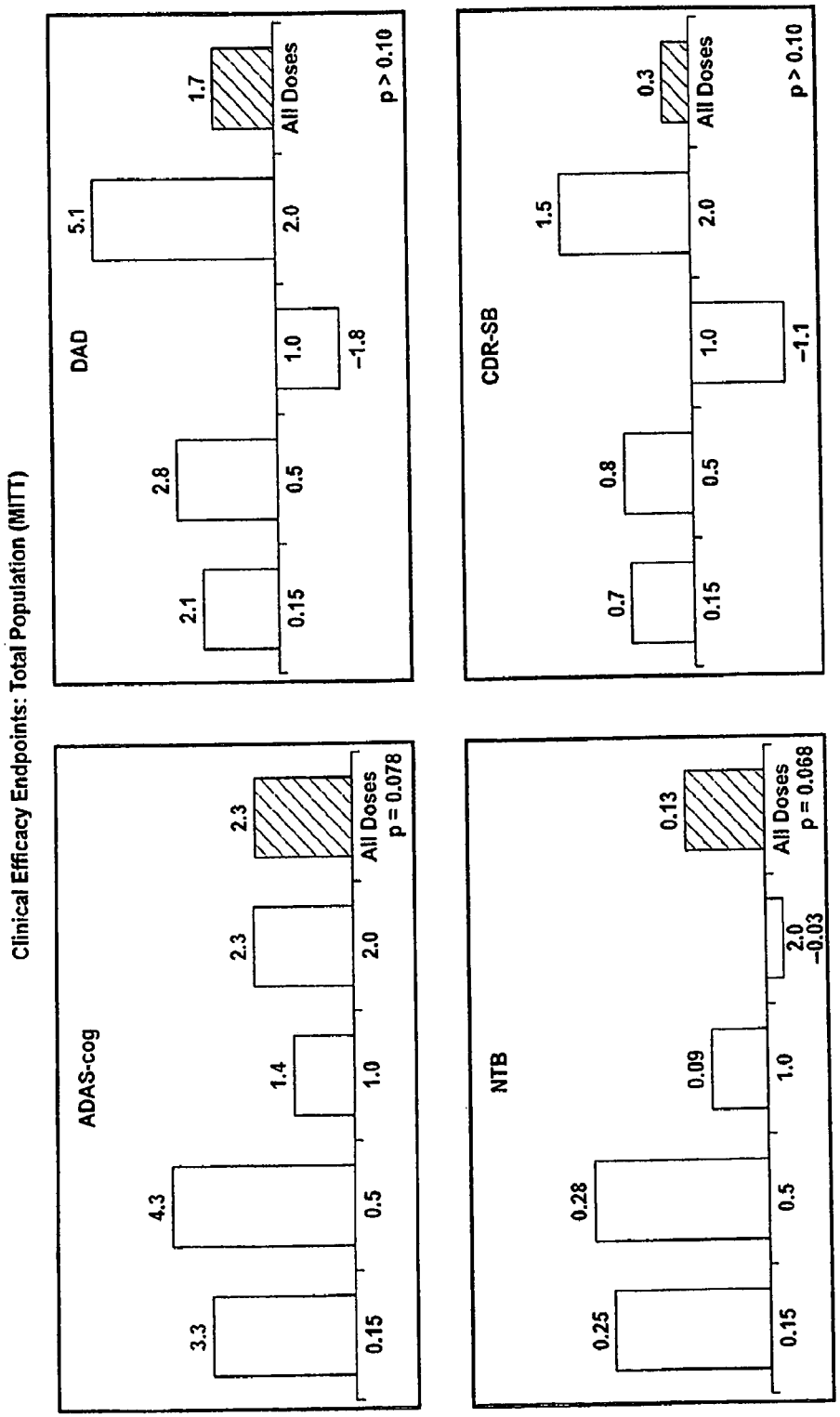
FIG. 1 shows changes in ADAS-Cog, DAD, NTB and CDR-SB in treated patients relative to placebo patients using a repeated measures statistical model without assumption of linearity. Bars above zero indicate improvement relative to placebo. MITT=modified intent to treat.

Exemplary epitopes or antigenic determinants can be found within the human amyloid precursor protein (APP), but are preferably found within the Aβ peptide of APP. Multiple isoforms of APP exist, for example APP$^{695}$, APP$^{751}$ and APP$^{770}$. Amino acids within APP are assigned numbers according to the sequence of the APP$^{770}$ isoform (see e.g., GenBank Accession No. P05067). The sequences of Aβ peptides and their relationship to the APP precursor are illustrated by FIG. 1 of Hardy et al., TINS 20, 155-158 (1997). For example, Aβ2 has the sequence:

H$_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-OH (SEQ ID NO: 1).

Unless otherwise apparent from the context, reference to Aβ also includes natural allelic variations of the above sequence, particularly those associated with hereditary disease, such as the Arctic mutation, E693G, APP 770 numbering. Aβ41, Aβ40 and Aβ39 differ from Aβ42 by the omission of A1a, Ala-Ile, and Ala-Ile-Val respectively from the C-terminal end. Aβ43 differs from Aβ42 by the presence of a threonine residue at the C-terminus. Preferred epitopes or antigenic determinants, as described herein, are located within the N-terminus of the Aβ peptide and include residues within amino acids 1-11 of Aβ, preferably from residues 1-10, 1-3, 1-4, 1-5, 1-6, 1-7 or 3-7 of Aβ42. Additional preferred epitopes or antigenic determinants include residues 2-4, 5, 6, 7 or 8 of Aβ, residues 3-5, 6, 7, 8 or 9 of Aβ, or residues 4-7, 8, 9 or 10 of Aβ42. Other preferred epitopes occur within central or C-terminal regions as described below.

An N-terminal epitope of Aβ means an epitope with residues 1-11. An epitope within a C-terminal region means an epitope within residues 29-43, and an epitope within a central regions means an epitope with residues 12-28

"Soluble" or "dissociated" Aβ refers to non-aggregating or disaggregated Aβ polypeptide.

"Insoluble" Aβ refers to aggregating Aβ polypeptide, for example, Aβ held together by noncovalent bonds. Aβ (e.g., Aβ42) is believed to aggregate, at least in part, due to the presence of hydrophobic residues at the C-terminus of the peptide (part of the transmembrane domain of APP). One method to prepare soluble Aβ is to dissolve lyophilized peptide in neat DMSO with sonication. The resulting solution is centrifuged to remove any insoluble particulates.

The term "Fc region" refers to a C-terminal region of an IgG antibody, in particular, the C-terminal region of the heavy chain(s) of said IgG antibody. Although the boundaries of the Fc region of an IgG heavy chain can vary slightly, a Fc region is typically defined as spanning from about amino acid residue Cys226 to the carboxyl-terminus of an IgG heavy chain(s).

The term "effector function" refers to an activity that resides in the Fc region of an antibody (e.g., an IgG antibody) and includes, for example, the ability of the antibody to bind effector molecules such as complement and/or Fc receptors, which can control several immune functions of the antibody such as effector cell activity, lysis, complement-mediated activity, antibody clearance, and antibody half-life. Effector function can also be influenced by mutations in the hinge region.

The term "effector molecule" refers to a molecule that is capable of binding to the Fc region of an antibody (e.g., an IgG antibody) including a complement protein or a Fc receptor.

The term "effector cell" refers to a cell capable of binding to the Fc portion of an antibody (e.g., an IgG antibody) typically via an Fc receptor expressed on the surface of the effector cell including, but not limited to, lymphocytes, e.g., antigen presenting cells and T cells.

The term "Kabat numbering" unless otherwise stated, is defined as the numbering of the residues as in Kabat et al. (Sequences of Proteins of Immunological Interest, 5th Ed. Public Health Service, National Institutes of Health, Bethesda, Md. (1991)), incorporated herein by reference.

The term "Fc receptor" or "FcR" refers to a receptor that binds to the Fc region of an antibody. Typical Fc receptors which bind to an Fc region of an antibody (e.g., an IgG antibody) include, but are not limited to, receptors of the FcγRI, FcγRII, and FcγRIII subclasses, including allelic variants and alternatively spliced forms of these receptors. Fc receptors are reviewed in Ravetch and Kinet, Annu. Rev. Immunol 9:457-92 (1991); Capel et al., Immunomethods 4:25-34 (1994); and de Haas et al., J. Lab. Clin. Med. 126: 330-41 (1995).

The term "adjuvant" refers to a compound that when administered in conjunction with an antigen augments and/or redirects the immune response to the antigen, but when administered alone does not generate an immune response to the antigen. Adjuvants can augment an immune response by several mechanisms including lymphocyte recruitment, stimulation of B and/or T cells, and stimulation of macrophages.

The area under the curve (AUC) is the area under the curve in a plot of concentration of drug in plasma against time. In an individual patient, the area under the curve represents the area under the curve based on that patient. In a population of patients, the area under the curve represents the mean area under the curve for a comparable time interval of different patients in the population.

The mean serum concentration in an individual patient represents the mean concentration of an antibody (or induced antibodies for an active agent) over a period of time. The mean serum concentration in a population of patients represents the mean of the mean serum concentrations of the individual patients over comparable periods of time.

The maximum serum concentration in an individual patient represents the maximum concentration of an antibody (or induced antibodies for an active agent) during a course of treatment. The maximum serum concentration in a population of individuals represents the mean of maximum concentrations of the antibody or induces antibodies between individuals in the population.

For brevity, the term "ApoE4 carrier" is sometimes used to refer to patients having one or two ApoE4 alleles and "ApoE4 noncarrier", ApoE4 non-carrier" or "non-ApoE4 carrier" to refer to patients having zero ApoE4 alleles.

DETAILED DESCRIPTION OF THE INVENTION

1. General

The invention provides methods of immunotherapy of Alzheimer's and similar diseases in which the regime administered to a patient depends on the ApoE genotype of the patient. The methods are based in part on (1) the observation that certain immunotherapy regimes lead to higher instances in the appearance of vasogenic edema (VE) in patients having an ApoE4 allele (E4) than in patients lacking an E4 allele, and more frequently still in patients having two E4 alleles, and/or (2) the initial observation of differential efficacy in ApoE4 carrier patients compared to ApoE4 non-carrier patients or patients receiving at least six doses compared to patients receiving less than six doses. The results also show that frequency of cases of vasogenic edema increases with dose frequency and amount.

Although practice of the invention is not dependent on an understanding of mechanism, it is hypothesized that the association of the vasogenic edema with an ApoE4 genotype may stem from a greater deposition of Aβ deposits and hence induction of a greater clearing response when antibodies bind to the deposits. Clearing of amyloid deposits may lead to vasogenic edema by any or all of several mechanisms. Removal of amyloid from blood vessel walls (vascular amyloid) may cause leakiness of blood vessels; more amyloid in perivascular space may cause slower drainage of interstitial fluid, and/or net increased flow of amyloid from intravascular compartment to brain parenchyma may lead to osmotic gradients. Although vasogenic edema effect is usually asymptomatic and reversible and does not preclude further treatment, it is desirable nevertheless to adjust the therapeutic regime to reduce the risk of vasogenic edema occurring.

The invention thus provides methods in which the immunotherapy regime is varied, for example to adjust the phagocytic response, depending on the ApoE status of the patient. Although the phagocytic response is useful in clearing amyloid deposits, the response, can optionally be controlled to avoid vasogenic edema. In general, patients having two E4 alleles, who are most susceptible to the vasogenic edema are administered either a lower dose or a lower frequency of the same agent as patients with zero E4 alleles, or are administered a different agent that is less prone to induce a phagocytic response or receive the agent through an alternate mode of administration, such as, for example, subcutaneous administration. Patients with one E4 allele can be treated the same as either patients with zero or two E4 alleles or a treatment can be customized for them in which the dose and/or frequency of administration is intermediate between that administered to patients with zero or two ApoE4 alleles.

The present data show that an N-terminal specific antibody to Aβ inhibits soluble Aβ binding to synapses and therefore soluble-Aβ induced synaptotoxicity whereas an C-terminal specific antibody to Aβ was ineffective. The present invention therefore provides methods of inhibiting soluble Aβ-induced synaptotoxicity such as synaptic loss, AMPAR internalization, spine density loss, and tau phosphorylation. Additionally, phospho-tau in tissues samples can be used as a marker for soluble-Aβ induced synaptotoxicity.

II. APOE

Human ApoE has the UniProtKB/Swiss-Prot entry accession number PO2649. The E2, E3, and E4 variants are described in *Genomics* 3:373-379 (1988), *J. Biol. Chem.* 259: 5495-5499 (1984); and *Proc. Natl. Acad. Sci. U.S.A.* 82:3445-3449 (1985). Association of the E4 form with late onset Alzheimer's disease has been reported by e.g., Corder, *Science* 261, 921-3 (1993); Farrer, JAMA, 278, 1349-56 (1997); and Saunders, *Neurology* 43, 1467-72 (1993). The allelic forms present in any individual can be determined by many conventional techniques, such as direct sequencing, use of GeneChip® arrays or the like, allele-specific probes, single-base extension methods, allelic specific extension. Allelic forms can also be determined at the protein level by ELISA using antibodies specific for different allelic expression products. Kits for genetic and immunological analysis are commercially available (e.g., Innogenetics, Inc.; Graceful Earth, Inc.). Determination of allelic forms are usually made in vitro, that is, on samples removed and never returned to a patient.

III. Different Strategies for Treating or Monitoring Depending on ApoE

A. Different Treatment Regimes

Some immunotherapy regimes for immunotherapy of Alzheimer's and other diseases have been associated with vasogenic edema (VE) in the brain of some patients. Generally, the incidence of VE is greater in ApoE4 carriers than in ApoeE4 non-carriers and in patients receiving higher doses of certain agents in certain immunotherapy regimes. VE has been observed on magnetic resonance imaging (MRI) as high signal intensities on the fluid-attenuated inversion recovery (FLAIR) sequence involving cerebral abnormalities and gyral swelling. VE generally is observed after the first or second administration of the immunotherapeutic agent, although it has been observed after the third or fourth administration. Most patients with VE discovered on MRI are asymptomatic. VE is heterogeneous on presentation, and MRI findings in a particular patient may vary over time. The gyral swelling and to some extent, the larger magnetic resonance (MR) changes seen on FLAIR differentiate VE from the commonly observed white matter changes seen on FLAIR in both normal elderly and Alzheimer's disease patients (Hentschel et al., 2005; de Leeuw et al. 2001).

Vasogenic edema (VE) is characterized by an increase in extracellular fluid volume due to increased permeability of brain capillary endothelial cells to macromolecular serum proteins (e.g., albumin). VE may be the result of increased brain capillary permeability. Clinical symptoms observed in patients with VE, when existent, are varied and to date have been largely mild in nature. Of the cases of VE observed on regularly scheduled MRI, the majority of patients are asymptomatic. Clinical observations associated with the symptomatic cases of VE have included altered mental states (e.g., increased confusion, lethargy, disorientation, and hallucinations), vomiting, headache, gait difficulties, visual disturbances, fatigue, irritability, ataxia, decreased appetite, and diarrhea.

As summarized above, the invention provides different treatment regimes depending on whether a patient has zero, one or two E4 alleles. Thus, in a population of treated individuals, those having zero E4 alleles can be treated differently from those having two alleles. Those having one E4 allele can be treated differently (in an intermediate fashion) to those with either zero or two E4 alleles or can be grouped with individuals having zero or two the E4 allele in any of the regimes that follow. It follows that individuals having one E4 allele can be treated differently than individuals with zero alleles and/or that individual with two ApoE4 alleles can be treated differently than individuals with one ApoE4 allele. Ongoing experience with some immunotherapeutic agents suggests that VE is more likely to occur at doses greater than 5 mg/kg (see PCT/US07/09499).

In some methods, ApoE4 status is the only genetic marker determining different treatment regimes in different patients. In other methods, differential treatment regimes can be based on ApoE4 in combination with other genetic markers associated with Alzheimer's disease susceptibility or resistance.

A population of treated individuals optionally has sufficient total number of patients and sufficient numbers of sub-populations with different numbers of ApoE4 alleles that an association between different treatment regimes and different ApoE4 alleles can be seen relative to a random assignment of the different regimes with a statistical confidence of at least 95%. For example, the treated population can consist of at least 100, 500 or 1000 individuals of who 10-70% and more typically 30-50% have at least one an ApoE4 allele. A treated population can also (i.e., optionally) be recognized as the total population treated with a particular drug produced by a particular manufacturer.

In some methods, as discussed in greater detail below, individuals having zero ApoE4 alleles are administered an agent in a regime designed to achieve efficacy as assessed from one or more clinical endpoints, such as, for example, cognitive measures (e.g., ADAS-cog, NTB, DAD, MMSE, CDR-SB, NPI), biomarkers (e.g., CSF tau), and brain volume (e.g., BBSI, VBSI), as well as other parameters, such as, for example desirable safety, pharmacokinetics and pharmacodynamics. In some methods, one or two E4 alleles are administered a reduced dose and/or frequency of the same agent as individuals with zero E4 alleles. A goal of such method is to deliver a reduced mean serum concentration of the agent over a period of time (reduced area under the curve) and/or to reduce the maximum peak concentration. This can be accomplished for example, by reducing the dose and administering at the same frequency, or reducing the frequency and administering at the same dose or administering at reduced dose and frequency. If the dose is reduced but the frequency kept constant, the dose is usually reduced between 10-90%, often about 30-75 or 40-60%. If the frequency is reduced, but the dose kept constant, then the frequency is typically reduced between two and five fold. Sometimes, the frequency is reduced by simply omitting an occasional dose or two consecutive doses from the regime administered to patients with zero ApoE4 alleles. Such doses can for example be omitted during the period a patient is experiencing vasogenic edema.

In other methods, individual having one or two E4 alleles are administered a reduce dose of the agent at an increased frequency relative to individuals having zero E4 alleles. For, example, the dose can be halved and the frequency doubled. In such methods, the total drug delivered to the two subpopulations over time (i.e., area under the curve) can be the same within experimental error, but the maximum plasma concentration is lower in individuals having two E4 alleles. For example, in patients having one or two E4 alleles the maximum serum concentration of antibody is preferably below 14 µg/ml and for patients having zero alleles, the maximum serum concentration of antibody is preferably below 28 µg/ml.

In other methods, treatment is administered at different stages relative to disease progression depending on ApoE4 status. In such methods, treatment is administered earlier in patients having two ApoE4 alleles relative to patients having zero ApoE4 alleles or in patients having one ApoE4 allele relative to patients having zero ApoE4 alleles and/or in patients having two ApoE4 alleles relative to patients having one ApoE4 allele. Disease progression can be measured by e.g., the MMSE scale on which a score of 27 to 20 is considered normal, and 20-26 considered mild Alzheimer's. Thus, for example, the mean MMSE score of non-ApoE4 carriers on commencement of treatment can be higher than that of ApoE4 carriers (patients with one or two ApoE4 alleles). Optionally, treatment of ApoE4 carriers can be begun prophylactically before clinical symptoms are evident. Such patients can be identified by screening populations for ApoE4 status. Treatment can be commenced on detecting such status or subsequently when the patient reaches a certain age (e.g., 55, 60 or 65 years) when there is a high risk of Alzheimer's developing. Although understanding of mechanism is not required for practice of such methods, it is believed that early treatment of ApoE4 carriers may be beneficial because the ApoE4 allele reduces capacity to repair neuronal damage, and/or because deposition of Aβ is greater in such patients.

In some methods, treatment is administered by a different route in patients having zero ApoE4 alleles and patients having one ApoE4 allele and/or patients having two ApoE4 alleles. For example, treatment can be administered intravenously in patients having zero ApoE4 alleles and subcutaneously in patients having one or two alleles. The dosage is typically greater and/or frequency of administration less in such non-ApoE4 carrier patients relative to ApoE4 carrier patients.

In some methods, a positive response to treatment (i.e., inhibition of cognitive decline or inhibition of decline in brain volume) takes longer to develop in ApoE4 carriers than non-carriers. The greater time may reflect reduced capacity for neuronal repair and/or greater amyloid burden in such patients; and/or use of a less potent treatment regime. In such methods, treatment can be administered for at least one year and optionally at least 2, 3 or 4 years before ceasing treatment for lack of effect. In some methods, treatment is administered for at least six quarterly administrations.

As noted, agents are sometimes provided with a label contraindicating use in ApoE4 carriers. Such agents can be used in methods of treatment in which only non-ApoE4 carriers receive an agent of the invention (i.e., an antibody that binds to Aβ or an agent that induces such an antibody). In such methods ApoE4 carriers do not receive an antibody that binds to Aβ or an agent that induces such an antibody but can receive other treatments such memantine.

Methods in which dose and/or frequency of administration are reduced depending on ApoE4 are most useful for agents that initiate a clearing response against amyloid deposits. In general, such agents are antibodies binding to an epitope within Aβ1-11, and which have an Fc region, or fragments of Aβ that induce such antibodies (i.e., contain an epitope within Aβ1-11). Antibodies binding to epitopes within central or C-terminal regions of Aβ usually bind predominantly to soluble forms of Aβ rather than amyloid deposits, and thus initiate little, if any clearing response against amyloid deposits, particularly dense or vascular deposits.

Examples of suitable dosages ranges and frequencies for administration are provided below. Different dosages and/or frequencies of administration for patients with different E4 status can be selected from within such ranges of dose and frequency. For example, patients with one or two E4 alleles can be administered a dose of 0.1 to 1 mg/kg antibody by intravenous infusion every thirteen weeks, and patients with zero E4 alleles can be administered a dose of 1 to 2 mg/kg every thirteen weeks. Optionally, patients with two E4 alleles are administered a dose of 0.15 to 0.5 mg/kg, patients with one E4 allele are administered a dose of 0.15 to 1 mg/kg (e.g., 0.5 to 1 mg/kg) and patients with zero E4 alleles are administered a dose of 0.15-2 mg/kg (e.g., 1-2 mg/kg) every thirteen weeks. In a preferred regime, patients with one or two E4 alleles are administered a dose of 0.5 mg/kg of an antibody binding to an epitope within residues 1-11 of Aβ (e.g., bapineuzumab) and patients with zero E4 alleles a dose of 2 mg/kg. The doses are administered intravenously at quarterly intervals until vasogenic edema appears (if it does). After vasogenic edema appears, the next dose is missed and thereafter, patients return to the quarterly dosing schedule at a lower dose of 0.15 mg/kg. If vasogenic edema appears again treatment can be terminated. Patients with zero E4 alleles are administered a dose of 0.5-2 mg/kg, with individually patients with zero E4 alleles optionally receiving doses of 0.5 mg/kg, 1.0 mg/kg, 1.5 mg/kg and 2.0 mg/kg.

As another example, patients with two E4 alleles are given a first dose of 0.5 mg/kg, and subsequent doses of 1 mg/kg. Alternatively, patients with two E4 alleles are given a first dose of 0.5 mg/kg, second and third doses of 1 mg/kg and subsequent doses of 2.0 mg/kg.

As another example, patients with zero E4 alleles can be administered a dose of 0.015-0.2 mg/kg antibody subcutaneously once per week and patients with two E4 alleles can be administered the same dose every two weeks. Equivalent regimes to any of the above can be devised by varying either the amount or frequency or route of administration to deliver the same area under the curve (i.e., mean dose integrated with time) of antibody to the serum.

In some methods, patients with one or two E4 alleles are administered agent to achieve a lower mean serum concentration of antibody over time than patients with zero E4 alleles. The lower mean serum concentration is maintained over a period of at least one or threes month, and usually three months to one year, or indefinitely. The mean serum concentration of all such patients is preferably within the range 2-7 µg antibody/ml serum with that for patients with one or two E4 alleles being lower than that for patients with zero E4 alleles. For example patients with zero E4 alleles can be administered to achieve a mean serum concentration of antibody within a range of 4.5-7 pg antibody/ml and patients with one or two E4 alleles can be administered agent to achieve a mean serum concentration in the range of 2-4.5 pg antibody/ml.

In such methods, individuals within any subpopulation defined by presence of two, one or zero E4 alleles are usually administered the same regime. However, the regime can also be customized for individuals within a subpopulation. In this case, the mean dose and/or frequency and/or average serum concentration and/or maximum concentration of agent or antibodies induced by the agent in a subpopulation of individuals with two E4 alleles is lower than that of individuals having zero E4 alleles.

In some methods, a different agent is administered to individuals with two E4 alleles than individuals with zero E4 alleles. The different agents usually differ in their capacity to induce a clearing response against amyloid deposits (i.e., preexisting deposits). Such a capacity can be tested, for example, in an ex vivo clearing assay as described by U.S. Pat. No. 6,750,324. In brief, an antibody and microglial cells are incubated with an amyloid deposit from a diseased Alzheimer's patient or transgenic mouse model, and the clearing reaction is monitored using a labelled antibody to Aβ. Clearing capacity of active agents can be similarly tested using sera induced by the active agent as a source of antibody for the assay. Clearing capacity of both passive and active agents can also be evaluated in a transgenic mouse model as also described U.S. Pat. No. 6,750,324 or in a human patient by MRI monitoring. Optionally, the clearing response is measured in an assay that distinguishes between compact and diffuse amyloid deposits. Differences in clearing capacity of some antibodies are more evident or only evident when the comparison is made with respect to clearing capacity of compact amyloid deposits. Optionally, the clearing response is evaluated from a reduction in clearing of vascular amyloid of a mutated antibody relative to an isotype matched otherwise-identical antibody. Vascular amyloid clearing can be assessed by a statistical significant difference between populations of animal models or human patients treated with a mutated antibody and an otherwise-identical isotype-matched antibody without the mutations.

Additionally or alternatively to assays measuring a clearing response, some antibodies suitable for use in the methods of the invention can be recognized by reduced binding to C1q and/or to Fcγ receptor(s). Capacity to bind C1q and/or an Fcγ receptor can be reduced by mutations near the hinge region of a heavy chain as discussed in more detail below. Reduced capacity can be determined, for example, by comparing a mutated antibody with an isotype matched otherwise identical antibody lacking the mutation(s) present in the mutated antibody (i.e., having residues from a wild type human constant region (e.g., bapineuzumab vs. AAB-003), or by comparing otherwise identical antibodies having different isotypes (e.g., human IgG1 versus human IgG4).

Some antibodies having reduced capacity to bind C1q and/or Fcγ receptor(s) reduce micro-hemorrhaging relative to isotype matched controls but retain at least some activity in inhibiting cognitive decline and/or clearing amyloid deposits. In some antibodies, reduced amyloid clearing capacity is mainly associated with reduced clearing capacity of vascular amyloid and/or compact amyloid deposits and not with diffuse amyloid deposits. Such antibodies offer a potentially improved efficacy:side-effects profile, particularly for use in ApoE4 carriers.

Antibodies having reduced binding to C1q and/or an Fcγ receptor can be used in differential methods of treatment as described above. For example, an antibody with reduced binding to C1q and/or and Fcγ receptor can be administered to patients having one or two ApoE4 alleles and an otherwise identical antibody without the mutation(s) to patients with zero ApoE4 alleles. Alternatively, an antibody with reduced binding to C1q and/or an Fcγ receptor can be administered to patients irrespective of the number of ApoE4 alleles.

Antibodies with constant regions mutated to reduce C1q and/or Fcγ receptor binding are sometimes administered at higher dosages than otherwise identical antibodies without the mutation. For some such antibodies, the dosage can be adjusted upward to achieve an equivalent therapeutic effect with reduced side effects.

Clearing capacity is affected both by the epitope specificity of an antibody (or antibodies induced by a fragment for active administration) and on the presence of, and type of effector function of the antibody, in particular by the capacity of the Fc region if present to bind to Fcγ receptors. Although clearing amyloid deposits is one useful mechanism of action, agents that lack the capacity to clear deposits can be useful by other mechanisms, such as binding to soluble Aβ and/or soluble oligomeric forms of Aβ. Such binding may reduce toxicity of such species and/or inhibit their aggregating to form deposits among other possible mechanisms.

Agents with a propensity to induce such a clearing response include antibodies binding to an epitope within residues 1-11 and particularly 1-7 of Aβ, particularly such antibodies having a human IgG1 isotype, which interacts most strongly with Fcγ receptors. Fragments of Aβ that contain epitopes within residues 1-11 and particularly 1-7 are similarly effective in inducing a clearing response. Optionally, agents which initiate a clearing response, can be provided with a label contraindicating use to patients with one or two ApoE4 alleles. Agents with less or no propensity to induce a clearing response include antibodies to Aβ that have isotypes other than human IgG1, antibodies that lack an Fc region (e.g., Fab fragments, Fv fragments, or Nanobodies), or antibodies with Fc regions mutated by genetic engineering to reduce interactions with Fcγ receptors. Such agents also include antibodies that specifically bind to an epitope within a region of Aβ other than residues 1-11, (i.e., to a mid-epitope or C-terminal epitope, as described above) and antibodies that specifically bind to soluble or oligomeric forms of Aβ without binding to amyloid deposits. Such agents also include fragments of Aβ that lack epitopes within residues 1-11 of Aβ. In such methods, individuals having two E4 alleles are administered an agent with a lower tendency to induce a phagocytic clearing response than individuals having zero alleles. For example, individuals having zero E4 alleles can be administered an antibody binding to an epitope within residues 1-11 of Aβ and having human IgG1 isotype and individuals having two E4 alleles can be administered the same antibody except that the antibody is a Fab fragment or has an isotype other than human IgG1 or has an engineered Fc region to reduce binding to Fcγ receptors. The agent administered to individuals having two E4 alleles can also be an antibody to a mid or C-terminal epitope of Aβ or a fragment of Aβ from a mid or C-terminal region (i.e., lacking an epitope from within Aβ1-11).

In some methods, patients with two E4 alleles are administered an antibody having an epitope within a mid or C-terminal regions for one or more initial doses and an antibody having an epitope within an N-terminal region for subsequent doses. Such an antibody can be a humanized 266 antibody, a humanized 2H6 antibody, a deglycosylated humanized 2H6 antibody or RN1219. Such an antibody can also be a humanized antibody that specifically binds to an epitope within Aβ28-40 or Aβ33-40. The initial doses preferably consist of 1, 2 or 3 doses. Patients having zero alleles can be administered an antibody having an epitope within an N-terminal region.

The different regimes administered to different patients depending on their E4 status can be maintained indefinitely. However, such is not usually necessary. It has been found that the vasogenic edema side effect associated with the E4 allele usually occurs by the third dose, if at all. Thus, once patients have received about 2-3 doses of treatment, patients having one or two ApoE4 alleles who have not developed vasogenic edema probably will not develop it, and can thereafter, if desired, be treated by the same regime as patients having zero E4 alleles. Likewise patients with one or two ApoE4 alleles who do develop vasogenic edema notwithstanding the present differential treatment regime usually resolve this condition and can thereafter, if desired, be treated in similar fashion to patients having zero E4 alleles. Optionally, the dose is titrated up after recovering from vasogenic edema to that used for non-carriers.

Vasogenic edema typically resolves of its own accord. However, resolution can be facilitated if desired by administration of a corticosteroid.

Agents can be packaged with labels indicating differential treatment procedures dependent on ApoE4 status consistent with any of the above regimes or combinations thereof.

B. Different Monitoring Regimes

Alternatively or additionally, the invention provides different monitoring regimes for patients depending on their E4 status. Vasogenic edema is an increase in brain volume from leakage of plasma into the interstitial space. Once extravasated, fluid is retained outside the vasculature, mostly in the white matter of the brain. Vasogenic edema can be monitored by brain imaging particularly by MRI, Positron Emission Tomography (PET Imaging) or Fluid Attenuated Inversion Recovery (FLAIR) sequence imaging (See *Pediatric Neurology*, 20(3):241-243; *AJNR*, 26:825-830; *NEJM*, 334(8):494-500; *Pediatr Nephrol*, 18:1161-1166; *Internal Medicine Journal*, 35:83-90; *JNNP*, 68:790-791; *AJNR*, 23:1038-1048; *Pak J Med Sci*, 21(2):149-154 and, *AJNR*, 21:1199-1209). Vasogenic edema presents with a high signal intensity in white matter. The vasogenic edema observed is often asymptomatic but can also be accompanied by headache, nausea, vomiting, confusion, seizures, visual abnormalities, altered mental functioning, ataxia, frontal symptoms, parietal symptoms, stupor, and focal neurological signs.

According to the present methods, patients with two E4 alleles can be subjected to brain imaging more frequently than patients having zero E4 alleles. For example, patients with two copies of E4 can be imaged before beginning treatment and quarterly thereafter, whereas patients with zero E4 alleles can be imaged before beginning treatment and annually or biannually thereafter. Alternatively, brain imaging can be omitted altogether in patients having zero E4 alleles. Patients having one E4 allele can be imaged with intermediate frequency between patients having zero and two E4 alleles, or can be grouped with patients having either zero or two E4 alleles. It follows that patients with one E4 allele can be monitored differently (e.g., more frequently) than patients with zero E4 alleles and patients with two E4 alleles can be monitored differently (e.g., more frequently) than patients with one E4 allele.

In patients developing vasogenic edema, monitoring can be continued during the vasogenic edema and for about a year after symptoms resolve. Thereafter, assuming no neurologic findings, monitoring can optionally be performed six monthly or annually.

Agents can be packaged with labels indicating differential monitoring procedures dependent on ApoE4 status consistent with any of the above regimes or combinations thereof.

C. Universal Treatment or Monitoring Regimes

Although ApoE4 carriers and non-carriers can have different responses to treatment as discussed above, and some treatment regimes that are safe and effective in ApoE4 carriers are also safe and effective, although not necessarily optimal, in non-ApoE4 carriers and can be used in both types of patients without regard to ApoE status of the patients. In some such regimes, the agent is an antibody that binds to an N-terminal epitope of Aβ having mutation(s) in its constant region that reduce binding to an Fcγ receptor and/or C1q. AAB-003 is an example of such an antibody. In other regimes, the dose and/or frequency and/or the maximal serum concentration and/or mean serum concentration of an administered or induced antibody are constrained within limits as described in PCT/US2007/009499 and further summarized below to reduce the risk of vasogenic edema.

IV. Agents

A. Antibodies

A variety of antibodies to Aβ have been described in the patent and scientific literature for use in immunotherapy of Alzheimer's disease, some of which are in clinical trials (see, e.g., U.S. Pat. No. 6,750,324). Such antibodies can specifically bind to an N-terminal epitope, a mid (i.e., central)-epitope or a C-terminal epitope as defined above. Some antibodies are N-terminal specific (i.e., such antibodies specifically bind to the N-terminus of Aβ without binding to APP). As noted above antibodies binding to epitopes within residues 1-10, 1-3, 1-4, 1-5, 1-6, 1-7 or 3-7 of Aβ42 or within residues 2-4, 5, 6, 7 or 8 of Aβ, or within residues 3-5, 6, 7, 8 or 9 of Aβ, or within residues 4-7, 8, 9 or 10 of Aβ42 can be used. Some antibodies are C-terminal specific (i.e., specifically bind to a C-terminus of Aβ without binding to APP) Antibodies can be polyclonal or monoclonal. Polyclonal sera typically contain mixed populations of antibodies specifically binding to several epitopes along the length of APP. However, polyclonal sera can be specific to a particular segment of Aβ such as Aβ1-11) without specifically binding to other segments of Aβ. Preferred antibodies are chimeric, humanized (including veneered antibodies) (see Queen et al., *Proc. Natl. Acad. Sci. USA* 86:10029-10033 (1989) and WO 90/07861, U.S. Pat. No. 5,693,762, U.S. Pat. No. 5,693,761, U.S. Pat. No. 5,585,089, U.S. Pat. No. 5,530,101 and Winter, U.S. Pat. No. 5,225,539), or human (Lonberg et al., WO 93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547-1553 (1994), *Nature Biotechnology* 14, 826 (1996), Kucherlapati, WO 91/10741 (1991)) EP1481008, Bleck, Bioprocessing Journal 1 (September/October 2005), US 2004132066, US 2005008625, WO 04/072266, WO 05/065348, WO 05/069970, and WO 06/055778.

3D6 antibody, 10D5 and variants thereof are examples of antibodies that can be used. Both are described in US 20030165496, US 20040087777, WO 02/46237, and WO 04/080419, WO 02/088306 and WO 02/088307. 10D5 antibodies are also described in US 20050142131. Additional 3D6 antibodies are described in US 20060198851 and PCT/US05/45614. 3D6 is a monoclonal antibody (mAb) that specifically binds to an N-terminal epitope located in the human β-amyloid peptide, specifically, residues 1-5. By comparison, 10D5 is a mAb that specifically binds to an N-terminal epitope located in the human β-amyloid peptide, specifically, residues 3-6. A cell line producing the 3D6 monoclonal antibody (RB96 3D6.32.2.4) was deposited with the American Type Culture Collection (ATCC), Manassas, Va. 20108, USA on Apr. 8, 2003 under the terms of the Budapest Treaty and assigned accession number PTA-5130. A cell line producing the 10D5 monoclonal antibody (RB44 10D5.19.21) was deposited with the ATCC on Apr. 8, 2003 under the terms of the Budapest Treaty and assigned accession number PTA-5129.

Bapincuzumab (International Non-Proprietary Name designated by the World Health Organization) means a humanized 3D6 antibody comprising a light chain having a mature variable region having the amino acid sequence designated SEQ ID NO: 2 and a heavy chain having a mature variable region having the amino acid sequence designated SEQ ID NO: 3. (The heavy and light chain constant regions of the antibody designated bapineuzumab by WHO are human IgG1 and human kappa respectively.) A humanized light chain including variable and constant regions is designated SEQ ID NO: 48 below, and a humanized heavy chain including variable and constant regions is designated SEQ ID NO: 66 or 67 (SEQ ID NO: 66 having an additional C-terminal lysine relative to SEQ ID NO: 67).

```
Humanized 3D6 Light Chain Variable Region
                                                                            (SEQ ID NO: 2)
Asp Val Val Met Thr Gln Ser Pro Leu Ser Leu Pro Val Thr Pro Gly Glu Pro Ala Ser Ile Ser Cys Lys Ser Ser Gln Ser Leu Leu Asp Ser Asp Gly Lys Thr Tyr Leu Asn Trp Leu Leu Gln Lys Pro Gly Gln Ser Pro Gln Arg Leu Ile Tyr Leu Val Ser Lys Leu Asp Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Trp Gln Gly Thr His Phe Pro Arg Thr Phe Gly Gln Gly Thr Lys Val Glu Ile Lys Humanized 3D6 Heavy Chain Variable Region
                                                                            (SEQ ID NO: 3)
Glu Val Gln Leu Leu Glu Ser Gly Gly Gly Leu Val Gln Pro Gly Gly Ser Leu Arg Leu Ser Cys Ala Ala Ser Gly Phe Thr Phe Ser Asn Tyr Gly Met Ser Trp Val Arg Gln Ala Pro Gly Lys Gly Leu Glu Trp Val Ala Ser Ile Arg Ser Gly Gly Gly Arg Thr Tyr Tyr Ser Asp Asn Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Val Arg Tyr Asp His Tyr Ser Gly Ser Ser Asp Tyr Trp Gly Gln Gly Thr Leu Val Thr Val Ser Ser
```

A second version of humanized 3D6 antibody comprising a light chain having a mature variable region having the amino acid sequence designated SEQ ID NO: 4 and a heavy chain having a mature variable region having the amino acid sequence designated SEQ ID NO: 5 is shown below.

```
Humanized 3D6 Light Chain Variable Region
                                                                            (SEQ ID NO: 4)
Tyr Val Val Met Thr Gln Ser Pro Leu Ser Leu Pro Val Thr Pro Gly Glu Pro Ala Ser Ile Ser Cys Lys Ser Ser Gln Ser Leu Leu Asp Ser Asp Gly Lys Thr Tyr Leu Asn Trp Leu Leu Gln Lys Pro Gly Gln Ser Pro Gln Arg Leu Ile Tyr Leu Val Ser Lys Leu Asp Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Trp Gln Gly Thr His Phe Pro Arg Thr Phe Gly Gln Gly Thr Lys Val Glu Ile Lys Humanized 3D6 Heavy Chain Variable Region
                                                                            (SEQ ID NO: 5)
Glu Val Gln Leu Leu Glu Ser Gly Gly Gly Leu Val Gln Pro Gly Gly Ser Leu Arg Leu Ser Cys Ala Ala Ser Gly Phe Thr Phe Ser Asn Tyr Gly Met Ser Trp Val Arg Gln Ala Pro Gly Lys Gly Leu Glu Trp Val Ala Ser Ile Arg Ser Gly Gly Gly Arg Thr Tyr Tyr Ser Asp Asn Val Lys Gly Arg Phe Thr Ile Ser Arg Asp Asn Ala Lys Asn Ser Leu Tyr Leu Gln Met Asn Ser Leu Arg Ala Glu Asp Thr Ala Leu Tyr Tyr Cys Val Arg Tyr Asp His Tyr Ser Gly Ser Ser Asp Tyr Trp Gly Gln Gly Thr Leu Val Thr Val Ser Ser
```

A third version of humanized 3D6 antibody comprising a light chain having the amino acid sequence designated SEQ ID NO: 6 and a heavy chain having the amino acid sequence designated SEQ ID NO: 7 is described in US 2005/0090648 A1 published on Apr. 28, 2005 issued as U.S. Pat. No. 7,318,923, which is incorporated herein by reference for all purposes.

```
Humanized 3D6 Light Chain
                                                                          (SEQ ID NO: 6)
Asp Val Val Met Thr Gln Ser Pro Leu Ser Leu Pro Val Thr Leu Gly Gln Pro Ala Ser Ile Ser Cys Lys Ser Ser Gln Ser Leu Leu Asp Ser Asp Gly Lys Thr Tyr Leu Asn Trp Leu Gln Gln Arg Pro Gly Gln Ser Pro Arg Arg Leu Ile Tyr Leu Val Ser Lys Leu Asp Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Trp Gln Gly Thr His Phe Pro Arg Thr Phe Gly Gly Gly Thr Lys Val Glu Ile Lys Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys Humanized 3D6 Heavy Chain
                                                                          (SEQ ID NO: 7)
Glu Val Gln Leu Val Glu Ser Gly Gly Gly Leu Val Gln Pro Gly Gly Ser Leu Arg Leu Ser Cys Ala Gly Ser Gly Phe Thr Phe Ser Asn Tyr Gly Met Ser Trp Val Arg Gln Ala Pro Gly Lys Gly Leu Glu Trp Val Ala Ser Ile Arg Ser Gly Gly Gly Arg Thr Tyr Tyr Ser Asp Asn Val Lys Gly Arg Phe Thr Ile Ser Arg Glu Asn Ala Lys Asn Ser Leu Tyr Leu Gln Met Asn Ser Leu Arg Ala Glu Asp Thr Ala Val Tyr Tyr Cys Val Arg Tyr Asp His Tyr Ser Gly Ser Ser Asp Tyr Trp Gly Gln Gly Thr Leu Val Thr Val Ser Ser Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys.
```

A version of humanized 10D5 antibody comprising a light chain having a mature variable region having the amino acid sequence designated SEQ ID NO: 8 and a heavy chain having a mature variable region having the amino acid sequence designated SEQ ID NO: 9 is shown below.

```
Humanized 10D5 Light Chain Variable Region
                                                                              (SEQ ID NO: 8)
Asp Val Leu Met Thr Gln Thr Pro Leu Ser Leu Pro Val Ser Leu Gly Asp Gln Ala Ser Ile Ser Cys Arg Ser Ser Gln Asn Ile Ile His Ser Asn Gly Asn Thr Tyr Leu Glu Trp Tyr Leu Gln Lys Pro Gly Gln Ser Pro Lys Leu Leu Ile Tyr Lys Val Ser Asn Arg Phe Ser Gly Val Pro Asp Arg Phe Ser Gly Ser Gly Ser Gly Thr Asp Phe Thr Leu Lys Ile Lys Lys Val Glu Ala Glu Asp Leu Gly Ile Tyr Tyr Cys Phe Gln Gly Ser His Val Pro Leu Thr Phe Gly Ala Gly Thr Lys Leu Glu Leu Glu Humanized 10D5 Heavy Chain Variable Region
                                                                              (SEQ ID NO: 9)
Gln Ala Thr Leu Lys Glu Ser Gly Pro Gly Ile Leu Gln Ser Ser Gln Thr Leu Ser Leu Thr Cys Ser Phe Ser Gly Phe Ser Leu Ser Thr Ser Gly Met Gly Val Ser Trp Ile Arg Gln Pro Ser Gly Lys Gly Leu Glu Trp Leu Ala His Ile Tyr Trp Asp Asp Lys Arg Tyr Asn Pro Ser Leu Lys Ser Arg Leu Thr Ile Ser Lys Asp Thr Ser Arg Lys Gln Val Phe Leu Lys Ile Thr Ser Val Asp Pro Ala Asp Thr Ala Thr Tyr Tyr Cys Val Arg Arg Pro Ile Thr Pro Val Leu Val Asp Ala Met Asp Tyr Trp Gly Gln Gly Thr Ser Val Thr Val Ser Ser
```

12A11 or a chimeric or humanized or nanobody form thereof is a preferred antibody. The 12A11 antibody or a variant thereof, is described in US 20050118651, US 20060198851, WO 04/108895, and WO 06/066089, all of which are incorporated by reference in their entirety herein for all purposes.

12A11 is a mAb that specifically binds to an N-terminal epitope located in the human β-amyloid peptide, specifically, residues 3-7. A cell line producing the 12A11 monoclonal antibody was deposited at the ATCC (American Type Culture Collection, 10801 University Boulevard, Manassas, Va. 20110-2209) on Dec. 12, 2005 and assigned ATCC accession number PTA-7271.

A preferred version of the humanized 12A11 antibody is version 1 comprising a light chain having the amino acid sequence designated SEQ ID NO: 10 and a heavy chain having the amino acid sequence designated SEQ ID NO: 11. Version 1 of humanized 12A11 is described in US 20050118651 A1 published on Jun. 2, 2005, which is incorporated herein by reference for all purposes.

```
Humanized 12A11 Light Chain
                                                                              (SEQ ID NO: 10)
Asp Val Val Met Thr Gln Ser Pro Leu Ser Leu Pro Val Thr Pro Gly Glu Pro Ala Ser Ile Ser Cys Arg Ser Ser Gln Ser Ile Val His Ser Asn Gly Asn Thr Tyr Leu Glu Trp Tyr Leu Gln Lys Pro Gly Gln Ser Pro Gln Leu Leu Ile Tyr Lys Val Ser Asn Arg Phe Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Phe Gln Ser Ser His Val Pro Leu Thr Phe Gly Gln Gly Thr Lys Leu Glu Ile Lys Humanized 12A11 Heavy Chain Variable Region (version 1)
                                                                              (SEQ ID NO: 11)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A second version of the humanized 12A11 antibody comprising a light chain having the amino acid sequence designated SEQ ID NO: 10 and a heavy chain having the amino acid sequence designated SEQ ID NO: 12 (version 2) is described in US 20050118651 A1 published on Jun. 2, 2005, which is incorporated herein by reference for all purposes.

```
Humanized 12A11 Heavy Chain Variable Region (version 2)
                                                                                    (SEQ ID NO: 12)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A third version of the humanized 12A11 antibody comprising a light chain having the amino acid sequence designated SEQ ID NO: 10 and a heavy chain having the amino acid sequence designated SEQ ID NO: 13 (version 2.1) is described in US 20050118651 A1 published on Jun. 2, 2005, which is incorporated herein by reference for all purposes.

```
Humanized 12A11 Heavy Chain Variable Region (version 2.1)
                                                                                    (SEQ ID NO: 13)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Asn Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A fourth version of the humanized 12A11 antibody comprising a light chain having the amino acid sequence designated SEQ ID NO: 10 and a heavy chain having the amino acid sequence designated SEQ ID NO: 14 (version 3) is described in WO 02/088306 published on Jun. 2, 2005, which is incorporated herein by reference for all purposes.

```
Humanized 12A11 Heavy Chain Variable Region (version 3)
                                                                                    (SEQ ID NO: 14)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A fifth version of the humanized 12A11 antibody comprising a light chain having the amino acid sequence designated SEQ ID NO: 10 and a heavy chain having the amino acid sequence designated SEQ ID NO: 15 (version 4.1) is described in US 20050118651 A1 published on Jun. 2, 2005, which is incorporated herein by reference for all purposes.

```
Humanized 12A11 Heavy Chain Variable Region (version 4.1)
                                                                              (SEQ ID NO: 15)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A sixth version of the humanized 12A11 antibody comprising a light chain having the amino acid sequence designated SEQ ID NO: 10 and a heavy chain having the amino acid sequence designated SEQ ID NO: 16 (version 4.2) is described in US 20050118651 A1 published on Jun. 2, 2005, which is incorporated herein by reference for all purposes.

```
Humanized 12A11 Heavy Chain Variable Region (version 4.2)
                                                                              (SEQ ID NO: 16)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

An seventh version of the humanized 12A11 antibody comprising a light chain having the amino acid sequence designated SEQ ID NO: 10 and a heavy chain having the amino acid sequence designated SEQ ID NO: 17 (version 4.3) is described in US 20050118651 A1 published on Jun. 2, 2005, which is incorporated herein by reference for all purposes.

```
Humanized 12A11 Heavy Chain Variable Region (version 4.3)
                                                                              (SEQ ID NO: 17)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A eighth version of the humanized 12A11 antibody comprising a light chain having the amino acid sequence designated SEQ ID NO: 10 and a heavy chain having the amino acid sequence designated SEQ ID NO: 18 (version 4.4) is described in US 20050118651 A1 published on Jun. 2, 2005, which is incorporated herein by reference for all purposes.

```
Humanized 12A11 Heavy Chain Variable Region (version 4.4)
                                                                            (SEQ ID NO: 18)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A ninth version of the humanized 12A11 antibody comprising a light chain having the amino acid sequence designated SEQ ID NO: 10 and a heavy chain having the amino acid sequence designated SEQ ID NO: 19 (version 5.1) is described in US 20050118651 A1 published on Jun. 2, 2005, which is incorporated herein by reference for all purposes.

```
Humanized 12A11 Heavy Chain Variable Region (version 5.1)
                                                                            (SEQ ID NO: 19)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A tenth version of the humanized 12A11 antibody comprising a light chain having the amino acid sequence designated SEQ ID NO: 10 and a heavy chain having the amino acid sequence designated SEQ ID NO: 20 (version 5.2) is described in US 20050118651 A1 published on Jun. 2, 2005, which is incorporated herein by reference for all purposes.

```
Humanized 12A11 Heavy Chain Variable Region (version 5.2)
                                                                            (SEQ ID NO: 20)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

An eleventh version of the humanized 12A11 antibody comprising a light chain having the amino acid sequence designated SEQ ID NO: 10 and a heavy chain having the amino acid sequence designated SEQ ID NO: 21 (version 5.3) is described in US 20050118651 A1 published on Jun. 2, 2005, which is incorporated herein by reference for all purposes.

```
Humanized 12A11 Heavy Chain Variable Region (version 5.3)
                                                                            (SEQ ID NO: 21)
Gln Val Gln Leu Val Glu Ser Gly Gly Gly Val Val Gln Pro Gly Arg Ser Leu Arg Leu Ser
```

-continued

```
Cys Ala Phe Ser Gly Phe Thr Leu Ser Thr Ser Gly Met Ser Val Gly Trp Ile Arg Gln Ala

Pro Gly Lys Gly Leu Glu Trp Leu Ala His Ile Trp Trp Asp Asp Lys Tyr Tyr Asn Pro

Ser Leu Lys Ser Arg Leu Thr Ile Ser Lys Asp Thr Ser Lys Asn Thr Leu Tyr Leu Gln Met

Asn Ser Leu Arg Ala Glu Asp Thr Ala Val Tyr Tyr Cys Ala Arg Arg Thr Thr Thr Ala

Asp Tyr Phe Ala Tyr Trp Gly Gln Gly Thr Thr Val Thr Val Ser Ser Val
```

A twelfth version of the humanized 12A11 antibody comprising a light chain having the amino acid sequence designated SEQ ID NO: 10 and a heavy chain having the amino acid sequence designated SEQ ID NO: 22 (version 5.4) is described in US 20050118651 A1 published on Jun. 2, 2005, which is incorporated herein by reference for all purposes.

```
Humanized 12A11 Heavy Chain Variable Region (version 5.4)
                                                                     (SEQ ID NO: 22)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Lys Tyr Tyr Asn Pro Ser Leu Lys Ser Arg Phe Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser Val
```

A thirteenth version of the humanized 12A11 antibody comprising a light chain having the amino acid sequence designated SEQ ID NO: 10 and a heavy chain having the amino acid sequence designated SEQ ID NO: 23 (version 5.5) is described in US 20050118651 A1 published on Jun. 2, 2005, which is incorporated herein by reference for all purposes.

```
Humanized 12A11 Heavy Chain Variable Region (version 5.5)
                                                                     (SEQ ID NO: 23)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Lys Tyr Tyr Asn Pro Ser Leu Lys Ser Arg Leu Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A fourteenth version of the humanized 12A11 antibody comprising a light chain having the amino acid sequence designated SEQ ID NO: 10 and a heavy chain having the amino acid sequence designated SEQ ID NO: 24 (version 5.6) is described in US 20050118651 A1 published on Jun. 2, 2005, which is incorporated herein by reference for all purposes.

```
Humanized 12A11 Heavy Chain Variable Region (version 5.6)
                                                                     (SEQ ID NO: 24)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Lys Tyr Tyr Asn Pro Ser Leu Lys Ser Arg Phe Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A fifteenth version of the humanized 12A11 antibody comprising a light chain having the amino acid sequence designated SEQ ID NO: 10 and a heavy chain having the amino acid sequence designated SEQ ID NO: 25 (version 6.1) is described in US 20050118651 A1 published on Jun. 2, 2005, which is incorporated herein by reference for all purposes.

```
Humanized 12A11 Heavy Chain Variable Region (version 6.1)                                            (SEQ ID NO: 25)

Gln Val Gln Leu Val Glu Ser Gly Gly Gly Val Val Gln Pro Gly Arg Ser Leu Arg Leu Ser

Cys Ala Phe Ser Gly Phe Thr Leu Ser Thr Ser Gly Met Ser Val Gly Trp Ile Arg Gln Ala

Pro Gly Lys Gly Leu Glu Trp Val Ala His Ile Trp Trp Asp Asp Asp Lys Tyr Tyr Asn Pro

Ser Leu Lys Ser Arg Phe Thr Ile Ser Lys Asp Thr Ser Lys Asn Thr Val Tyr Leu Gln Met

Asn Ser Leu Arg Ala Glu Asp Thr Ala Val Tyr Tyr Cys Ala Arg Arg Thr Thr Thr Ala

Asp Tyr Phe Ala Tyr Trp Gly Gln Gly Thr Thr Val Thr Val Ser Ser
```

A sixteenth version of the humanized 12A11 antibody comprising a light chain having the amino acid sequence designated SEQ ID NO: 10 and a heavy chain having the amino acid sequence designated SEQ ID NO: 26 (version 6.2) is described in US 20050118651 A1 published on Jun. 2, 2005, which is incorporated herein by reference for all purposes.

```
Humanized 12A11 Heavy Chain Variable Region (version 6.2)                                            (SEQ ID NO: 26)

Gln Val Gln Leu Val Glu Ser Gly Gly Gly Val Val Gln Pro Gly Arg Ser Leu Arg Leu Ser

Cys Ala Phe Ser Gly Phe Thr Leu Ser Thr Ser Gly Met Ser Val Gly Trp Ile Arg Gln Ala

Pro Gly Lys Gly Leu Glu Trp Val Ala His Ile Trp Trp Asp Asp Asp Lys Tyr Tyr Asn Pro

Ser Leu Lys Ser Arg Leu Thr Ile Ser Lys Asp Thr Ser Lys Asn Thr Leu Tyr Leu Gln Met

Asn Ser Leu Arg Ala Glu Asp Thr Ala Val Tyr Tyr Cys Ala Arg Arg Thr Thr Thr Ala

Asp Tyr Phe Ala Tyr Trp Gly Gln Gly Thr Thr Val Thr Val Ser Ser
```

A seventeenth version of the humanized 12A11 antibody comprising a light chain having the amino acid sequence designated SEQ ID NO: 10 and a heavy chain having the amino acid sequence designated SEQ ID NO: 27 (version 6.3) is described in US 20050118651 A1 published on Jun. 2, 2005, which is incorporated herein by reference for all purposes.

```
Humanized 12A11 Heavy Chain Variable Region (version 6.3)                                            (SEQ ID NO: 27)

Gln Val Gln Leu Val Glu Ser Gly Gly Gly Val Val Gln Pro Gly Arg Ser Leu Arg Leu Ser

Cys Ala Phe Ser Gly Phe Thr Leu Ser Thr Ser Gly Met Ser Val Gly Trp Ile Arg Gln Ala

Pro Gly Lys Gly Leu Glu Trp Leu Ala His Ile Trp Trp Asp Asp Asp Lys Tyr Tyr Asn Pro

Ser Leu Lys Ser Arg Phe Thr Ile Ser Lys Asp Thr Ser Lys Asn Thr Leu Tyr Leu Gln Met

Asn Ser Leu Arg Ala Glu Asp Thr Ala Val Tyr Tyr Cys Ala Arg Arg Thr Thr Thr Ala

Asp Tyr Phe Ala Tyr Trp Gly Gln Gly Thr Thr Val Thr Val Ser Ser
```

A eighteenth version of the humanized 12A11 antibody comprising a light chain having the amino acid sequence designated SEQ ID NO: 10 and a heavy chain having the amino acid sequence designated SEQ ID NO: 28 (version 6.4) is described in US 20050118651 A1 published on Jun. 2, 2005, which is incorporated herein by reference for all purposes.

```
Humanized 12A11 Heavy Chain Variable Region (version 6.4)
                                                                                    (SEQ ID NO: 28)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Val Ala His Ile Trp Trp Asp Asp Asp Lys Tyr Tyr Asn Pro Ser Leu Lys Ser Arg Phe Thr Ile Ser Lys Asp Thr Ser Lys Asn Thr Leu Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A nineteenth version of the humanized 12A11 antibody comprising a light chain having the amino acid sequence designated SEQ ID NO: 10 and a heavy chain having the amino acid sequence designated SEQ ID NO: 29 (version 7) is described in US 20050118651 A1 published on Jun. 2, 2005, which is incorporated herein by reference for all purposes.

```
Humanized 12A11 Heavy Chain Variable Region (version 7)
                                                                                    (SEQ ID NO: 29)
Gln Val Gln Leu Val Glu Ser Gly Gly Gly Val Val Gln Pro Gly Arg Ser Leu Arg Leu Ser Cys Ala Phe Ser Gly Phe Thr Leu Ser Thr Ser Gly Met Ser Val Gly Trp Val Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Thr Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

A twentieth version of the humanized 12A11 antibody comprising a light chain having the amino acid sequence designated SEQ ID NO: 10 and a heavy chain having the amino acid sequence designated SEQ ID NO: 30 (version 8) is described in US 20050118651 A1 published on Jun. 2, 2005, which is incorporated herein by reference for all purposes.

```
Humanized 12A11 Heavy Chain Variable Region (version 8)
                                                                                    (SEQ ID NO: 30)
Gln Val Gln Leu Val Glu Ser Gly Gly Gly Val Val Gln Pro Gly Arg Ser Leu Arg Leu Ser Cys Ala Phe Ser Gly Phe Ser Leu Ser Thr Ser Gly Met Ser Val Gly Trp Ile Arg Gln Ala Pro Gly Lys Gly Leu Glu Trp Leu Ala His Ile Trp Trp Asp Asp Asp Lys Tyr Tyr Asn Pro Ser Leu Lys Ser Arg Leu Thr Ile Ser Lys Asp Asn Ser Lys Asn Thr Val Tyr Leu Gln Met Asn Ser Leu Arg Ala Glu Asp Thr Ala Val Tyr Tyr Cys Ala Arg Arg Thr Thr Thr Ala Asp Tyr Phe Ala Tyr Trp Gly Gln Gly Thr Thr Val Thr Val Ser Ser
```

Other exemplary antibodies include 12B4 antibody or variant thereof, as described in US 20040082762A1 and WO 03/077858. 12B4 is a mAb that specifically binds to an N-terminal epitope located in the human β-amyloid peptide, specifically, residues 3-7. The light (SEQ ID NO: 31) and heavy chain (SEQ ID NO: 32) of 12B4 have the following variable regions (not including signal sequences).

```
                                                                                    (Seq ID NO: 31)
Asp Val Leu Met Thr Gln Thr Pro Leu Ser Leu Pro Val Ser Leu Gly Asp Gln Ala Ser Ile

Ser Cys Arg Ser Ser Gln Asn Ile Val His Ser Asn Gly Asn Thr Tyr Leu Glu Trp Tyr Leu
```

-continued

```
Gln Lys Pro Gly Gln Ser Pro Lys Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Leu Gly Val Tyr Tyr Cys Phe Gln Gly Ser His Val Pro Leu Thr Phe Gly Ala

Gly Thr Lys Leu Glu Leu Lys
```

(SEQ ID NO: 32)
```
Gln Val Thr Leu Lys Glu Ser Gly Pro Gly Ile Leu Gln Pro Ser Gln Thr Leu Ser Leu Thr

Cys Ser Phe Ser Gly Phe Ser Leu Ser Thr Asn Gly Met Gly Val Ser Trp Ile Arg Gln Pro

Ser Gly Lys Gly Leu Glu Trp Leu Ala His Ile Tyr Trp Asp Glu Asp Lys Arg Tyr Asn Pro

Ser Leu Lys Ser Arg Leu Thr Ile Ser Lys Asp Thr Ser Asn Asn Gln Val Phe Leu Lys Ile

Thr Asn Val Asp Thr Ala Asp Thr Ala Thr Tyr Tyr Cys Ala Arg Arg Arg Ile Ile Tyr Asp

Val Glu Asp Tyr Phe Asp Tyr Trp Gly Gln Gly Thr Thr Leu Thr Val Ser Ser
```

Other exemplary antibodies are 6C6 antibody, or a variant thereof, as described in a US 20060165682 and WO 06/06604. 6C6 is a mAb that specifically binds to an N-terminal epitope located in the human β-amyloid peptide, specifically, residues 3-7. A cell line producing the antibody 6C6 was deposited on Nov. 1, 2005, with the ATCC under the terms of the Budapest Treaty and assigned accession number PTA-7200.

Other exemplary antibodies are 2H3 antibody and variants thereof as described in US 20060257396. 2113 is a mAb that specifically binds to an N-terminal epitope located in the human β-amyloid peptide, specifically, residues 2-7. A cell line producing the antibody 2H3 was deposited on Dec. 13, 2005, with the ATCC under the terms of the Budapest Treaty and assigned accession number PTA-7267.

Other exemplary antibodies include 3A3 and variants thereof as described in US 20060257396. 3A3 is a mAb that specifically binds to an N-terminal epitope located in the human β-amyloid peptide, specifically, residues 3-7. A cell line producing the antibody 3A3 was deposited on Dec. 13, 2005, with the ATCC under the terms of the Budapest Treaty and assigned accession number PTA-7269.

Other exemplary antibodies are 2B1, 1C2 or 9G8. Cell lines producing the antibodies 2B1, 1C2 and 9G8 were deposited on Nov. 1, 2005, with the ATCC under the terms of the Budapest Treaty and were assigned accession numbers PTA-7202, PTA-7199 and PTA-7201, respectively.

Another exemplary antibody is a humanized 266 antibody or variant thereof. The 266 antibody binds to an epitope between residues 13-28 of Aβ. A cell line producing the antibody 266 antibody was deposited on Jul. 20, 2004 with the ATCC under the terms of the Budapest Treaty and assigned accession number PTA-6123. Humanized forms of the 266 antibody are described in US 20040265308, US 20040241164, WO 03/016467, and U.S. Pat. No. 7,195,761. The light (SEQ ID NO: 33) and heavy chain (SEQ ID NO: 34) of the 266 antibody have the following variable region sequences (not including signal sequences).

(SEQ ID NO: 33)
```
Asp Xaa Val Met Thr Gln Xaa Pro Leu Ser Leu Pro Val Xaa Xaa Gly Gln Pro Ala Ser Ile

Ser Cys Arg Ser Ser Gln Ser Leu Xaa Tyr Ser Asp Gly Asn Ala Tyr Leu His Trp Phe Leu

Gln Lys Pro Gly Gln Ser Pro Xaa Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Xaa Gly Val Tyr Tyr Cys Ser Gln Ser Thr His Val Pro Trp Thr Phe Gly Xaa

Gly Thr Xaa Xaa Glu Ile Lys Arg
``` wherein: Xaa at position 2 is Val or Ile; Xaa at position 7 is Ser or Thr; Xaa at position 14 is Thr or Ser; Xaa at position 15 is Leu or Pro; Xaa at position 30 is Ile or Val; Xaa at position 50 is Arg, Gln, or Lys; Xaa at position 88 is Val or Leu; Xaa at position 105 is Gln or Gly; Xaa at position 108 is Lys or Arg; and Xaa at position 109 is Val or Leu; and (SEQ ID NO: 34)
```
Xaa Val Gln Leu Val Glu Xaa Gly Gly Gly Leu Val Gln Pro Gly Gly Ser Leu Arg Leu Ser Cys Ala Ala Ser Gly Phe Thr Phe Ser Arg Tyr Ser Met Ser Trp Val Arg Gln Ala Pro Gly Lys Gly Leu Xaa Leu Val Ala Gln Ile Asn Ser Val Gly Asn Ser Thr Tyr Tyr Pro Asp Xaa Val Lys Gly Arg Phe Thr Ile Ser Arg Asp Asn Xaa Xaa Asn Thr Leu Tyr Leu Gln Met Asn Ser Leu Arg Ala Xaa Asp Thr Ala Val Tyr Tyr Cys Ala Ser Gly Asp Tyr Trp Gly Gln Gly Thr Xaa Val Thr Val Ser Ser
``` wherein: Xaa at position 1 is Glu or Gln; Xaa at position 7 is Ser or Leu; Xaa at position 46 is Glu, Val, Asp, or Scr; Xaa at position 63 is Thr or Scr; Xaa at position 75 is Ala, Scr, Val or Thr; Xaa at position 76 is Lys or Arg; Xaa at position 89 is Glu or Asp; and Xaa at position 107 is Leu or Thr.

An exemplary humanized 266 antibody comprises the following light chain (SEQ ID NO: 35) and heavy chain (SEQ ID NO: 36) sequences (not including signal sequences).

The antibody can also be 15C11 or a humanized form thereof (see US 20060165682), which specifically binds to an epitope within Aβ15-24.

The antibody can also be a humanized form of 20C2 or a variant thereof. Such antibodies are described, e.g., in US 2007081998. The core linear epitope for 20C2 corresponds to amino acid residues 3-8 of Aβ1-42, with a conformational epitope that is dependent upon elements from within residues

```
                                                                           (SEQ ID NO: 35)
Asp Val Val Met Thr Gln Ser Pro Leu Ser Leu Pro Val Thr Leu Gly Gln Pro Ala Ser Ile

Ser Cys Arg Ser Ser Gln Ser Leu Ile Tyr Ser Asp Gly Asn Ala Tyr Leu His Trp Phe Leu

Gln Lys Pro Gly Gln Ser Pro Arg Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Ser Gln Ser Thr His Val Pro Trp Thr Phe Gly Gln

Gly Thr Lys Val Glu Ile Lys Arg Thr Val Ala Ala Pro Ser Val Phe Ile Phe Pro Pro Ser

Asp Glu Gln Leu Lys Ser Gly Thr Ala Ser Val Val Cys Leu Leu Asn Asn Phe Tyr Pro

Arg Glu Ala Lys Val Gln Trp Lys Val Asp Asn Ala Leu Gln Ser Gly Asn Ser Gln Glu

Ser Val Thr Glu Gln Asp Ser Lys Asp Ser Thr Tyr Ser Leu Ser Ser Thr Leu Thr Leu Ser

Lys Ala Asp Tyr Glu Lys His Lys Val Tyr Ala Cys Glu Val Thr His Gln Gly Leu Ser Ser

Pro Val Thr Lys Ser Phe Asn Arg Gly Glu Cys (SEQ ID NO: 36)
Glu Val Gln Leu Val Glu Ser Gly Gly Gly Leu Val Gln Pro Gly Gly Ser Leu Arg Leu Ser

Cys Ala Ala Ser Gly Phe Thr Phe Ser Arg Tyr Ser Met Ser Trp Val Ary Gln Ala Pro Gly

Lys Gly Leu Glu Leu Val Ala Gln Ile Asn Ser Val Gly Asn Ser Thr Tyr Tyr Pro Asp Thr

Val Lys Gly Arg Phe Thr Ile Ser Arg Asp Asn Ala Lys Asn Thr Leu Tyr Leu Gln Met

Asn Ser Leu Arg Ala Glu Asp Thr Ala Val Tyr Tyr Cys Ala Ser Gly Asp Tyr Trp Gly

Gln Gly Thr Leu Val Thr Val Ser Ser Ala Ser Thr Lys Gly Pro Ser Val Phe Pro Leu Ala

Pro Ser Ser Lys Ser Thr Ser Gly Gly Thr Ala Ala Leu Gly Cys Leu Val Lys Asp Tyr Phe

Pro Glu Pro Val Thr Val Ser Trp Asn Ser Gly Ala Leu Thr Ser Gly Val His Thr Phe Pro

Ala Val Leu Gln Ser Ser Gly Leu Tyr Ser Leu Ser Ser Va Val Thr Val Pro Ser Ser Ser

Leu Gly Thr Gln Thr Tyr Ile Cys Asn Val Asn His Lys Pro Ser Asn Thr Lys Val Asp Lys

Lys Val Glu Pro Lys Ser Cys Asp Lys Thr His Thr Cys Pro Pro Cys Pro Ala Pro Glu Leu

Leu Gly Gly Pro Ser Val Phe Leu Phe Pro Pro Lys Pro Lys Asp Thr Leu Met Ile Ser Arg

Thr Pro Glu Val Thr Cys Val Val Val Asp Val Ser His Glu Asp Pro Glu Val Lys Phe Asn

Trp Tyr Val Asp Gly Val Glu Val His Asn Ala Lys Thr Lys Pro Arg Glu Glu Gln Tyr

Asn Ser Thr Tyr Arg Val Val Ser Val Leu Thr Val Leu His Gln Asp Trp Leu Asn Gly

Lys Glu Tyr Lys Cys Lys Val Ser Asn Lys Ala Leu Pro Ala Pro Ile Glu Lys Thr Ile Ser

Lys Ala Lys Gly Gln Pro Ary Glu Pro Gln Val Tyr Thr Leu Pro Pro Ser Arg Asp Glu Leu

Thr Lys Asn Gln Val Ser Leu Thr Cys Leu Val Lys Gly Phe Tyr Pro Ser Asp Ile Ala Val

Glu Trp Glu Ser Asn Gly Gln Pro Glu Asn Asn Tyr Lys Thr Thr Pro Pro Val Leu Asp

Ser Asp Gly Ser Phe Phe Leu Tyr Ser Lys Leu Thr Val Asp Lys Ser Arg Trp Gln Gln Gly

Asn Val Phe Ser Cys Ser Val Met His Glu Ala Leu His Asn His Tyr Thr Gln Lys Ser Leu

Ser Leu Ser Pro Gly Lys
```

17-42 of Aβ. The light (SEQ ID NO: 37) and heavy chain (SEQ ID NO: 38) of humanized 20C2 antibody (version 1) have the following variable region sequences (not including signal sequences).

```
                                                                    (SEQ ID NO: 37)
Asp Val Val Met Thr Gln Ser Pro Leu Ser Leu Pro Val Thr Pro Gly Glu Pro Ala Ser Ile

Ser Cys Arg Ser Ser Gln Ser Ile Leu His Ser Asn Gly Asn Thr Tyr Leu Glu Trp Tyr Leu

Gln Lys Pro Gly Gln Ser Pro Gln Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Gly Ser Leu Val Pro Leu Thr Phe Gly

Gln Gly Thr Lys Leu Glu Ile Lys (SEQ ID NO: 38)
Gln Val Thr Leu Lys Glu Ser Gly Pro Ala Leu Val Lys Pro Thr Gln Thr Leu Thr Leu Thr

Cys Thr Phe Ser Gly Phe Ser Leu Ser Thr Ser Gly Met Gly Val Gly Trp Ile Arg Gln Pro

Pro Gly Lys Ala Leu Glu Trp Leu Ala His Ile Tip Tip Asp Asp Asp Lys Ser Tyr Asn Pro

Ser Leu Lys Ser Arg Leu Thr Ile Ser Lys Asp Thr Ser Lys Asn Gln Val Val Leu Thr Met

Thr Asn Met Asp Pro Val Asp Thr Ala Thr Tyr Tyr Cys Ala Arg Arg Gln Leu Gly Leu

Arg Ser Ile Asp Ala Met Asp Tyr Tip Gly Gln Gly Thr Thr Val Thr Val Ser Ser
```

An additional humanized 20C2 antibody (version 2) comprises the light chain variable region sequence of SEQ ID NO: 37 and the heavy chain variable region sequence of SEQ ID NO: 39 (not including signal sequence).

```
                                                                    (SEQ ID NO: 39)
Gln Val Thr Leu Lys Glu Ser Gly Pro Ala Leu Val Lys Pro Thr Gln Thr Leu Thr Leu Thr

Cys Thr Leu Ser Gly Phe Ser Leu Ser Thr Ser Gly Met Gly Val Gly Trp Ile Arg Gln Pro

Pro Gly Lys Ala Leu Glu Trp Leu Ala His Ile Trp Trp Asp Asp Asp Lys Ser Tyr Asn Pro

Ser Leu Lys Ser Arg Leu Thr Ile Ser Lys Asp Thr Ser Lys Asn Gln Val Val Leu Thr Met

Thr Asn Met Asp Pro Val Asp Thr Ala Thr Tyr Tyr Cys Ala Arg Arg Gln Leu Gly Leu

Arg Ser Ile Asp Ala Met Asp Tyr Trp Gly Gln Gly Thr Thr Val Thr Val Ser
```

Another antibody that can be used according to the invention is C705 or a variant thereof, which binds an epitope comprising amino acids 7-12 of the Aβ peptide, as described in WO 05/028511. The C705 antibody comprises the light chain variable region sequence of SEQ ID NO: 40 and heavy chain variable region of SEQ ID NO: 41, signal sequence underlined.

```
                                                                    (SEQ ID NO: 40)
    Met Lys Leu Pro Val Arg Leu Leu Val Leu Met Phe Trp Ile Pro Gly Ser Ser Ser Asp Val

Met Met Thr Gln Thr Pro Leu Ser Leu Pro Val Ser Leu Gly Asp Gln Ala Ser Ile Ser Cys

Arg Ser Ser Gln Ser Leu Val His Ser Asn Gly Asn Thr Tyr Leu Glu Trp Tyr Met Gln Lys

Pro Gly Gln Ser Pro Met Leu Leu Ile Tyr Lys Val Ser Asn Arg Phe Ser Gly Val Pro Asp

Arg Phe Ser Gly Ser Gly Ser Gly Thr Asp Phe Thr Leu Lys Ile Ser Ser Val Glu Ala Glu

Asp Leu Gly Val Phe Tyr Cys Phe Gln Gly Ser Arg Val Pro Leu Thr Phe Gly Ala Gly

Thr Lys Leu Glu Leu Lys Arg (SEQ ID NO: 41)
    Met Asp Arg Leu Thr Ser Ser Phe Leu Leu Leu Ile Val Pro Ala Tyr Val Leu Ser Gln Val

Thr Leu Lys Glu Ser Gly Pro Gly Ile Leu Gln Pro Ser Gln Thr Leu Ser Leu Thr Cys Ser

Phe Ser Gly Phe Ser Leu Ser Thr Ser Gly Met Gly Val Ser Trp Ile Arg Gln Pro Ser Gly

Lys Gly Leu Glu Trp Leu Ala His Ile Tyr Trp Asp Asp Asp Lys Arg Tyr Asn Pro Ser
```

-continued

```
Leu Lys Ser Arg Leu Thr Ile Ser Lys Asp Thr Ser Arg Asn Gln Val Phe Leu Lys Ile Thr

Ser Val Asp Thr Thr Asp Thr Ala Thr Tyr Tyr Cys Thr Arg Ser Ser Gly Ser Ile Val Ile

Ala Thr Gly Phe Ala Tyr Trp Gly Gln Gly Thr Leu Val Thr Val Ser Ala
```

Another antibody that can be used according to the invention is C706 or a variant thereof, which binds to an epitope comprising amino acids 6-11 of the Aβ peptide, as described in WO 05/028511. The C706 antibody comprises the light chain variable region sequence of SEQ ID NO: 42, and the heavy chain variable region sequence of SEQ ID NO: 43. Signal sequences are underlined.

(SEQ ID NO: 42)
```
Met Asp Phe Gln Val Gln Ile Phe Ser Phe Leu Leu Ile Ser Ala Ser Val Ile Ile Ser Arg

Gly Gln Ile Val Leu Thr Gln Ser Pro Ala Ile Met Ser Ala Ser Pro Gly Glu Lys Val Thr

Met Thr Cys Ser Ala Ser Ser Ser Val Ser Tyr Met His Trp Tyr Gln Gln Lys Ser Gly Thr

Ser Pro Lys Arg Trp Ile Tyr Asp Ser Ser Arg Leu Ala Ser Gly Val Pro Ser Arg Phe Ser

Gly Gly Gly Ser Gly Thr Ser Tyr Ser Pro Thr Ile Ser Asn Met Glu Ala Glu Asp Ala Ala

Thr Tyr Phe Cys Gln Asn Trp Arg Ser Ser Pro Thr Phe Gly Ala Gly Thr Lys Leu Glu

Leu Lys Arg
```

(SEQ ID NO: 43)
```
Met Glu Trp Thr Trp Val Phe Leu Phe Leu Leu Ser Val Thr Ala Gly Val His Ser Gln Val

Gln Leu Gln Gln Ser Gly Pro Glu Leu Met Lys Pro Gly Ala Ser Val Lys Ile Ser Cys Lys

Ala Thr Gly Tyr Thr Phe Ser Thr Ser Trp Ile Glu Trp Ile Lys Gln Arg Pro Gly His Gly

Leu Glu Trp Ile Gly Glu Val Leu Pro Gly Ser Gly Lys Ser Asn His Asn Ala Asn Phe Lys

Gly Arg Ala Thr Phe Thr Ala Asp Thr Ala Ser Asn Thr Ala Tyr Met Gln Leu Ser Ser Leu

Thr Ser Glu Asp Ser Ala Val Tyr Tyr Cys Ala Arg Glu Gly Ser Asn Asn Asn Ala Leu

Ala Tyr Trp Gly Gln Gly Thr Leu Val Thr Val Ser Ala
```

Other antibodies that can be used according to the invention include humanized 2286 antibodies and variants thereof. These antibodies recognize an epitope comprising amino acids 28-40 of the Aβ peptide, as described in US 20070160616. A humanized 2286 antibody (version 1) comprises the light chain variable region of SEQ ID NO: 44 and the heavy chain variable region of SEQ ID NO: 45 (not including signal sequences).

(SEQ ID NO: 44)
DIQMTQSPSSLSASVGDRVTITCSASQGISNYLNWYQQKPGKAPKLLIYY

TSSLHSGVPSRFSGSGSGTDFTFTISSLQPEDIATYYCQQYRKLPYTFGG

GTKVEIKR (SEQ ID NO: 45)
EVQLVESGGGLVQPGGSLRLSCAASGFDFSRYWMNWVRQAPGKGLEWVSE

INPDSSTINYTPSLKDRFTISRDNAKNTLYLQMNSLRAEDTAVYYCARQM

GYWGQGTTLTVSS

Another version of humanized 2286 comprises the light chain variable region of SEQ ID NO: 44 and the heavy chain variable region of SEQ ID NO: 46 (not including signal sequences).

(SEQ ID NO: 46)
QVQLQESGPGLVKPSETLSLTCTVSGFDFSRYWMNWIRQPPGKGLEWIGE

INPDSSTINYTPSLKDRVTISKDTSKNQFSLKLSSVTAADTAVYYCARQM

GYWGQGTLVTVSS

Additional antibodies that can be used according to the invention are a fourth version of humanized 3D6 and a second version of humanized 10D5, as disclosed in U.S. Pat. Nos. 7,318,923 and 7,320,790, respectively. These antibodies bind to the N-terminus of the Aβ peptide, as explained above. The humanized 3D6 (version 4) comprises the light chain variable region sequence of SEQ ID NO: 71 and the heavy chain variable region sequence of SEQ ID NO: 72.

```
                                                             (SEQ ID NO: 71)
Asp Val Val Met Thr Gln Ser Pro Leu Ser Leu Pro Val Thr Leu Gly Gln Pro Ala Ser Ile

Ser Cys Lys Ser Ser Gln Ser Leu Leu Asp Ser Asp Gly Lys Thr Tyr Leu Asn Trp Leu

Gln Gln Arg Pro Gly Gln Ser Pro Arg Arg Leu Ile Tyr Leu Val Ser Lys Leu Asp Ser Gly

Val Pro Asp Arg Phe Ser Gly Ser Gly Ser Gly Thr Asp Phe Thr Leu Lys Ile Ser Arg Val

Glu Ala Glu Asp Val Gly Val Tyr Tyr Cys Trp Gln Gly Thr His Phe Pro Arg Thr Phe

Gly Gly Gly Thr Lys Val Glu Ile Lys Arg (SEQ ID NO: 72)
Glu Val Gln Leu Val Glu Ser Gly Gly Gly Leu Val Gln Pro Gly Gly Ser Leu Arg Leu Ser

Cys Ala Gly Ser Gly Phe Thr Phe Ser Asn Tyr Gly Met Ser Trp Val Arg Gln Ala Pro Gly

Lys Gly Leu Glu Trp Val Ala Ser Ile Arg Ser Gly Gly Gly Arg Thr Tyr Tyr Ser Asp Asn

Val Lys Gly Arg Phe Thr Ile Ser Arg Glu Asn Ala Lys Asn Ser Leu Tyr Leu Gln Met

Asn Ser Leu Arg Ala Glu Asp Thr Ala Val Tyr Tyr Cys Val Arg Tyr Asp His Tyr Ser

Gly Ser Ser Asp Tyr Trp Gly Gln Gly Thr Leu Val Thr Val Ser Ser
```

The humanized 10D5 antibody (version 2) comprises the light chain variable region sequence of SEQ ID NO: 73 and the heavy chain variable region sequence of SEQ ID NO: 74.

```
                                                             (SEQ ID NO: 73)
Asp Val Val Met Thr Gln Ser Pro Leu Ser Leu Pro Val Thr Leu Gly Gln Pro Ala Ser Ile

Ser Cys Arg Ser Ser Gln Asn Ile Ile His Ser Asn Gly Asn Thr Tyr Leu Glu Trp Tyr Leu

Gln Lys Pro Gly Gln Ser Pro Arg Leu Leu Ile Tyr Lys Val Ser Asn Arg Phe Ser Gly Val

Pro Asp Arg Phe Ser Gly Ser Gly Ser Gly Thr Asp Phe Thr Leu Lys Ile Ser Arg Val Glu

Ala Glu Asp Val Gly Val Tyr Tyr Cys Phe Gln Gly Ser His Val Pro Leu Thr Phe Gly Gly

Gly Thr Lys Val Glu Ile Lys Arg (SEQ ID NO: 74)
Gln Val Thr Leu Lys Glu Ser Gly Pro Val Leu Val Lys Pro Thr Glu Thr Leu Thr Leu Thr

Cys Thr Phe Ser Gly Phe Ser Leu Ser Thr Ser Gly Met Gly Val Ser Trp Ile Arg Gln Pro

Pro Gly Lys Ala Leu Glu Trp Leu Ala His Ile Tyr Trp Asp Asp Lys Arg Tyr Asn Pro

Ser Leu Lys Ser Arg Leu Thr Ile Ser Lys Asp Thr Ser Lys Ser Gln Val Val Leu Thr Met

Thr Asn Met Asp Pro Val Asp Thr Ala Thr Tyr Tyr Cys Val Arg Arg Pro Ile Thr Pro Val

Leu Val Asp Ala Met Asp Tyr Trp Gly Gln Gly Thr Leu Val Thr Val Ser Ser
```

Another exemplary antibody is humanized 2E7, as disclosed in WO 07/113,172. The 2E7 antibody binds residues 1-12 of Aβ peptide, but not 2-13, or longer variants of the peptide. Humanized 2E7 antibody (version 1) comprises light chain variable region sequence of SEQ ID NO: 75 and heavy chain variable region sequence of SEQ ID NO: 76.

```
                                                  (SEQ ID NO: 75)
DIVMTQSPLSLPVTPCEPASISCRVSQSLLHSNGYTYLHWYLQKPGQSPQ

LLIYKVSNRFSGVPDRFSGSGSGTDFTLKISRVEAEDVGVYYCSQTRHVP

YTEGGGTKVEIK
```

```
                                                  (SEQ ID NO: 76)
EVQLVESGGGLVQPGGSLRLSCAASGFTFSDNGMAWVRQAPGKGLEWVSF

ISNLAYSIDYADTVTGRFTISRDNAKNSLYLQMNSLRAEDTAVYYCVSGT

WFAYWGQGTLVTVSS
```

A second version of humanized 2E7 antibody comprises the light chain variable region of SEQ ID NO: 75 and the heavy chain variable region sequence of SEQ ID NO: 77 (see, e.g., WO 07/113,172).

```
                                                  (SEQ ID NO: 77)
EVQLVESGGGLVQPGGSLRLSCAVSGFTFSDNGMAWVRQAPGKGLEWVSFI

SNLAYSIDYADTVTGRFTISRDNAKNSLYLQMNSLRAEDTAVYYCVSGTWF

AYWGQGTLVTVSS
```

Humanized 2E7 antibody (version 3) comprises the light chain variable region sequence of SEQ ID NO: 75 and the heavy chain variable region sequence of SEQ ID NO: 78 (see, e.g., WO 07/113,172).

(SEQ ID NO: 78)
EVQLVESGGGLVQPGGSLRLSCAASGFTFSDNGMAWVRQAPGKGLEWISFI

SNLAYSIDYADTVTGRFTISRDNAKNSLYLQMNSLRAEDTAVYYCVSGTWF

AYWGQGTLVTVSS

An additional antibody that can be used according to the invention includes humanized 9TL antibody (ATCC accession numbers PTA-6124 and PTA-6125), as described in WO 06/036291. The heavy and light chain variable regions, without signal sequences, are shown as SEQ ID NO: 79 and SEQ ID NO: 80, respectively.

(SEQ ID NO: 79)
QVQLVQSGAEVKKPGASVKVSCKASGYYTEAYYIHWVRQAPGQGLEWMGRI

DPATGNTKYAPRLQDRVTMTRDTSTSTVYMELSSLRSEDTAVYYCASLYSL

PVYWGQGTTVTVSS (SEQ ID NO: 80)
DVVMTQSPLSLPVTLGQPASISCKSSQSLLYSDAKTYLNWFQQRPGQSPRR

LIYQISRLDPGVPDRFSGSGSGTDFTLKISRVEAEDVGVYYCLQGTHYPVL

FGQGTRLEIKRT

Humanized versions of the 6G antibody can also be used according to the invention. The heavy and light chain variable regions, without signal sequences, are shown as SEQ ID NOs:81 and 82, respectively.

(SEQ ID NO: 81)
QVQLVQSGAEVKKPGASVKVSCKASGYTFTTYAIHWVRQAPGQGLEWMGFT

SPYSGVSNYNQKFKGRVTMTRDTSTSTVYMELSSLRSEDTAVYYCARFDNY

DRGYVRDYWGQGTLV (SEQ ID NO: 82)
DIVMTQSPDSLAVSLGERATINCRASESVDNDRISFLNWYQQKPGQPPKLL

IYAATKQGTGVPDRFSGSGSGTDFTLTISSLQAEDVAVYYCQQSKEFPWSF

GGGTKVEIKRTV

Additional antibodies that can be used according to the invention are humanized versions of the 2.1 antibody, as described in WO 06/081171. These antibodies rely on the CDRs of the murine 2.1 antibody and substitute residues from the human VKII A19/JK4 light chain variable framework region. The heavy chain variable framework region used for substitution is roughly based on VH 2-70. An exemplary humanized 2.1 antibody comprises the heavy and light chain variable regions, without signal sequences, shown as SEQ ID NOs: 83 and 84, respectively.

(SEQ ID NO: 83)
QVTLKESGPALVKPTQTLTLTCTFSGFSLRTSGMGVGWIRQPPGKALEWLA

HIWWDDDKSYNPSLKSQLTISKDTSKNQVVLTMTNMDPVDTATYYCARRNY

YYDDYFAYWGQGTLVTVSS (SEQ ID NO: 84)
DVLMTQSPLSLPVTLGQPASISCRSSQSIVHSNGNTYLEWYLQRPGQSPKL

LIYKVSNRFSGVPDRFSGSGSGTDFTLKISRVEAEDVGVYYCFQGSHVPLI

FGAGTKLEIK

Other antibodies that can be used according to the invention include CW1181 and CW1185 antibodies. These antibodies specifically bind to two regions of the Aβ peptide, as described in WO 03/070760 and US 20050196399. The first region comprises AEFRHDSGY (SEQ ID NO: 85) or a fragment thereof (e.g., AEFRHD (SEQ ID NO: 86), or EFRHDSG (SEQ ID NO: 87), EFRHD (SEQ ID NO: 88)) and second region comprises the amino acid sequence YEVHHQKLVFFAEDVG (SEQ ID NO: 89) or a fragment thereof (e.g., VFFA (SEQ ID NO: 90), or QKLFFAEDV (SEQ ID NO: 91)).

An additional antibody that can be used according to the invention is the monoclonal NAB61 antibody. NAB61 binds Aβ1-11, but does not bind to full length APP or C99, as disclosed in WO 07/062,088. Similarly, the monoclonal 82E1 antibody can be used according to the invention. 82E1 binds the N-terminus of the Aβ peptide, but not full length APP, as disclosed in US 20080025988.

Other antibodies of the invention are anti-ADDL antibodies. Such antibodies have been generated and selected for the ability to bind ADDLs specifically, without binding to Aβ monomer or amyloid fibrils. See e.g., WO 04/031400.

Other antibodies that can be used include (i) the catalytic antibody ABP 102 (Abzyme, from Abiogen Pharma); (ii) ACI-01 Ab7 C2 (AC Immune Genentech); (iii) AZD-3102 (AstraZeneca/Dyax); (iv) IVIg (Gammagard S/D Immune Globulin Intravenous (Human), from Baxter Bioscience); (v) BAN 2401 (BioArctic Neuroscience AB/Eisai Co. Ltd.; (vi) R1450 (Hoffman-La Roche/MorphoSys); (vii) LY2062430 (Eli Lilly); (viii) h3D6 (Eli Lilly); (ix) ACU-5A5 (a ADDL mAb from Merck/Acumen); α-amyloidspheroid (ASPD) antibody (Mitsubishi Pharma Corp.); (xi) the antibody derived from PBMCs of an AN1792 patient (Neurimmune Therapeutics AG); (xii) BC05 (Takeda); (xiii) the CEN701-CEN706 antibodies (Centocor/Johnson & Johnson); and (xiv) PF-04360365 (also called RN-1219 (h2286), from Pfizer/Rinat Neurosciences). Each of these antibodies can be used according to any of the methods of the invention.

The ABP 102 antibody cleaves aggregated Aβ as described, e.g., in U.S. Pat. No. 6,387,674 and WO 99/06536. The ACI-01 Ab7 C2 antibody binds the Aβ peptide between residues 10-20 and is described in US 20070166311. The IVIg Gammagard SD Immune Globulin antibody is described, e.g., on the Baxter Bioscience website at Baxter.com. The BAN 2401 antibody is a humanized antibody that binds Aβ protofibrils, and is described, e.g., in WO 05/123775. The human R-1450 HuCAL antibody has a dual 266/3D6 epitope. The humanized LY2062430 antibody (IgG) binds the Aβ peptide between residues 16-23, and is described, e.g., in U.S. Pat. No. 7,195,761. The humanized h3D6 antibody binds the Aβ peptide at residues 1-5, and is described, e.g., in U.S. Pat. No. 7,318,923. The BC05 antibody binds a C terminal Aβ epitope, as described by Asami-Odaka et al. (2005) Neurodegenerative Diseases 2:36-43. The CEN701-CEN706 antibodies are described, e.g., in WO 05/028511. The humanized PF-04360365 antibody binds the Aβ peptide between residues 28-40 and is described, e.g., in WO 04/032868.

Any of the antibodies or antibody fragments described herein can be designed or prepared using standard methods, as disclosed, e.g., in US 20040038304, US 20070020685, US 200601660184, US 20060134098, US 20050255552, US 20050130266, US 2004025363, US 20040038317, US 20030157579, and U.S. Pat. No. 7,335,478.

Any of the antibodies described above can be produced with different isotypes or mutant isotypes to control the extent of binding to different Fcγ receptors. Antibodies lacking an Fc region (e.g., Fab fragments) lack binding to Fcγ receptors. Selection of isotype also affects binding to Fcγ receptors. The respective affinities of various human IgG isotypes for the three Fcγ receptors, FcγRI, FcγRII, and FcγRIII, have been determined. (See Ravetch & Kinet, Annu. Rev. Immunol. 9, 457 (1991)). FcγRI is a high affinity receptor that binds to IgGs in monomeric form, and the latter two are low affinity receptors that bind IgGs only in multimeric form. In general, both IgG1 and IgG3 have significant binding activity to all three receptors, IgG4 to FcγRI, and IgG2 to only one type of FcγRII called IIa$_{LR}$ (see Parren et al., J. Immunol. 148, 695 (1992). Therefore, human isotype IgG1 is usually selected for stronger binding to Fcγ receptors is desired, and IgG2 is usually selected for weaker binding.

Mutations on, adjacent, or close to sites in the hinge link region (e.g., replacing residues 234, 235, 236 and/or 237 with another residue) in all of the isotypes reduce affinity for Fcγ receptors, particularly FcγRI receptor (see, e.g., U.S. Pat. No. 6,624,821). Optionally, positions 234, 236 and/or 237 are substituted with alanine and position 235 with glutamine. (See, e.g., U.S. Pat. No. 5,624,821.) Position 236 is missing in the human IgG2 isotype. Exemplary segments of amino acids for positions 234, 235 and 237 for human IgG2 are Ala Ala Gly, Val Ala Ala, Ala Ala Ala, Val Glu Ala, and Ala Glu Ala. A preferred combination of mutants is L234A, L235A, and G237A for human isotype IgG1. A particular preferred antibody is bapineuzumab having human isotype IgG and these three mutations of the Fc region. Other substitutions that decrease binding to Fcγ receptors are an E233P mutation (particularly in mouse IgG1) and D265A (particularly in mouse IgG2a). Other examples of mutations and combinations of mutations reducing Fc and/or C1q binding are described in the Examples (E318A/K320A/R322A (particularly in mouse IgG1), L235A/E318A/K320A/K322A (particularly in mouse IgG2a). Similarly, residue 241 (Ser) in human IgG4 can be replaced, e.g., with proline to disrupt Fc binding.

Additional mutations can be made to the constant region to modulate effector activity. For example, mutations can be made to the IgG2a constant region at A330S, P331S, or both. For IgG4, mutations can be made at E233P, F234V and L235A, with G236 deleted, or any combination thereof. IgG4 can also have one or both of the following mutations S228P and L235E. The use of disrupted constant region sequences to modulate effector function is further described, e.g., in WO 06/118,959 and WO 06/036291.

Additional mutations can be made to the constant region of human IgG to modulate effector activity (see, e.g., WO 06/03291). These include the following substitutions: (i) A327G, A330S, P331S; (ii) E233P, L234V, L235A, G236 deleted; (iii) E233P, L234V, L235A; (iv) E233P, L234V, L235A, G236 deleted, A327G, A330S, P331S; and (v) E233P, L234V, L235A, A327G, A330S, P331S to human IgG1.

The affinity of an antibody for the FcR can be altered by mutating certain residues of the heavy chain constant region. For example, disruption of the glycosylation site of human IgG1 can reduce FcR binding, and thus effector function, of the antibody (see, e.g., WO 06/036291). The tripeptide sequences NXS, NXT, and NXC, where X is any amino acid other than proline, are the enzymatic recognition sites for glycosylation of the N residue. Disruption of any of the tripeptide amino acids, particularly in the CH2 region of IgG, will prevent glycosylation at that site. For example, mutation of N297 of human IgG1 prevents glycosylation and reduces FcR binding to the antibody.

The sequences of several exemplary humanized 3D6 antibodies and their components parts are shown below. Human constant regions show allotypic variation and isoallallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes. The allotype of the IgG1 constant region shown below is 3D6 (AAB-001) is G1mz which has Glu at position 356 and Met at position 358. The allotype of the kappa constant region shown below is Km3, which has an Ala at position 153 and a Val at position 191. A different allotye Km(1) has Val and Leu at positions 153 and 191 respectively. Allotypic variants are reviewed by J Immunogen 3: 357-362 (1976) and Loghem. Monogr Allergy 19: 40-51 (1986). Other allotypic and isoallotypic variants of the illustrated constant regions are included. Also included are constant regions having any permutation of residues occupying polymorphic positions in natural allotypes. Examples of other heavy chain IgG1 allotypes include: G1m (f), G1m(a) and G1m(x). G1m(f) differs from G1m(z) in that it has an Arg instead of a Lys at position 214. G1m(a) has amino acids Arg, Asp, Glu, Leu at positions 355-358.

Humanized 3D6 Full Length Light Chain (signal sequence underlined) (bapineuzumab and AAB-003)

(SEQ ID NO: 47)
MDMRVPAQLLGLLMLWVSGSSGDVVMTQSPLSLPVTPGEPASISCKSSQSL

LDSDGKTYLNWLLQKPGQSPQRLIYLVSKLDSGVPDRFSGSGSGTDFTLKI

SRVEAEDVGVYYCWQGTHFPRTFGQGTKVEIKRTVAAPSVFIFPPSDEQLK

SGTASVVCLLNNFYPREAKVQWKVDNALQSGNSQESVTEQDSKDSTYSLSS

TLTLSKADYEKHKVYACEVTHQGLSSPVTKSFNRGEC

Humanized 3D6 Full Length Light Chain, Not Including Signal Sequence (bapineuzumab and AAB-003)

(SEQ ID NO: 48)
DVVMTQSPLSLPVTPGEPASISCKSSQSLLDSDGKTYLNWLLQKPGQSPQR

LIYLVSKLDSGVPDRFSGSGSGTDFTLKISRVEAEDVGVYYCWQGTHFPRT

FGQGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC

DNA encoding humanized 3D6 Light Chain Coding Sequence (signal sequence underlined) (bapineuzumab and AAB-003)

(SEQ ID NO: 49)
ATGGACATGCGCGTGCCCGCCCAGCTGCTGGGCCTGCTGATGCTGTGGGTG

TCCGGCTCCTCCGGCGACGTGGTGATGACCCAGTCCCCCCTGTCCCTGCCC

GTGACCCCCGGCGAGCCCGCCTCCATCTCCTGCAAGTCCTCCCAGTCCCTG

```
CTGGACTCCGACGGCAAGACCTACCTGAACTGGCTGCTGCAGAAGCCCGGC

CAGTCCCCCCAGCGCCTGATCTACCTGGTGTCCAAGCTGGACTCCGGCGTG

CCCGACCGCTTCTCCGGCTCCGGCTCCGGCACCGACTTCACCCTGAAGATC

TCCCGCGTGGAGGCCGAGGACGTGGGCGTGTACTACTGCTGGCAGGGCACC

CACTTCCCCCGCACCTTCGGCCAGGGCACCAAGGTGGAGATCAAGCGTACT

GTGGCTGCACCATCTGTCTTCATCTTCCCGCCATCTGATGAGCAGTTGAAA

TCTGGAACTGCCTCTGTTGTGTGCCTGCTGAATAACTTCTATCCCAGAGAG

GCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGC

ACCCTGACGCTGAGCAAAGCAGACTACGAGAAACACAAAGTCTACGCCTGC

GAAGTCACCCATCAGGGCCTGAGCTCGCCCGTCACAAAGAGCTTCAACAGG

GGAGAGTGTTAG
```

Human Heavy Chain Constant Region, IgG1 Isotype, L234A/G237A

```
                                        (SEQ ID NO: 50)
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPEALGAPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNVF

SCSVMHEALHNHYTQKSLSLSPGK
```

The C-terminal K residue can be absent, as indicated below.

```
                                        (SEQ ID NO: 51)
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPEALGAPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNVF

SCSVMHEALHNHYTQKSLSLSPG.
```

Humanized 3D6 Full Length Heavy Chain (IgG1 Isotype, L234A/G237A) including signal sequence (underlined)

```
                                        (SEQ ID NO: 52)
MEFGLSWLFLVAILKGVQCEVQLLESGGGLVQPGGSLRLSCAASGFTFSNY

GMSWVRQAPGKGLEWVASIRSGGGRTYYSDNVKGRFTISRDNSKNTLYLQM

NSLRAEDTAVYYCVRYDHYSGSSDYWGQGTLVTVSSASTKGPSVFPLAPSS

KSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPEA

LGAPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHYTQ

KSLSLSPGK
```

The C-terminal K residue can be absent, as indicated below.

```
                                        (SEQ ID NO: 53)
MEFGLSWLFLVAILKGVQCEVQLLESGGGLVQPGGSLRLSCAASGFTFSNY

GMSWVRQAPGKGLEWVASIRSGGGRTYYSDNVKGRFTISRDNSKNTLYLQM

NSLRAEDTAVYYCVRYDHYSGSSDYWGQGTLVTVSSASTKGPSVFPLAPSS

KSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPEA

LGAPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHYTQ

KSLSLSPG.
```

Humanized 3D6 Full Length Heavy Chain Not Including Signal Sequence (IgG1 Isotype, L234A/G237A)

```
                                        (SEQ ID NO: 54)
EVQLLESGGGLVQPGGSLRLSCAASGFTFSNYGMSWVRQAPGKGLEWVASI

RSGGGRTYYSDNVKGRFTISRDNSKNTLYLQMNSLRAEDTAVYYCVRYDHY

SGSSDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKKVEPKSCDKTHTCPPCPAPEALGAPSVFLFPPKPKDTLMI

SRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFL

YSKLTVDKSRWQQGNVFSCSVMHEALHNHYTQKSLSLSPGK
```

The C-terminal K residue can be absent, as indicated below.

```
                                        (SEQ ID NO: 55)
EVQLLESGGGLVQPGGSLRLSCAASGFTESNYGMSWVRQAPGKGLEWVASI

RSGGGRTYYSDNVKGRFTISRDNSKNTLYLQMNSLRAEDTAVYYCVRYDHY

SGSSDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKKVEPKSCDKTHTCPPCPAPEALGAPSVFLFPPKPKDTLMI

SRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSR
```

EEMTKNQVSLICLVKGFYPSDIAVEWESNGQPENNYKTTPPVLDSDGSFFL
YSKLTVDKSRWQQGNVFSCSVMHEALHNHYTQKSLSLSPG.

Human Heavy Chain Constant Region, IgG4 Isotype, S241P (Kabat numbering); S228P (EU numbering)

(SEQ ID NO: 56)
ASTKGPSVFPLAPCSRSTSESTAALGCLVKDYFPEPVTVSWNSGALTSGVH
TFPAVLQSSGLYSLSSVVTVPSSSLGTKTYTCNVDHKPSNTKVDKRVESKY
GPPCPPCPAPEFLGGPSVFLFPPKPKDTLMISRTPEVTCVVVDVSQEDPEV
QFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCS
VMHEALHNHYTQKSLSLSLGK

The C-terminal K residue can be absent, as indicated below.

(SEQ ID NO: 57)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLG

Humanized 3D6 Full Length Heavy Chain (IgG4 Isotype, S241P), Including Signal Sequence (underlined)

(SEQ ID NO: 58)
<u>MEFGLSWLFLVAILKGVQC</u>EVQLLESGGGLVQPGGSLRLSCAASGFTFSN
YGMSWVRQAPGKGLEWVASIRSGGGRTYYSDNVKGRFTISRDNSKNTLYL
QMNSLRAEDTAVYYCVRYDHYSGSSDYWGQGTLVTVSSASTKGPSVFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFLGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLGK

The C-terminal K residue can be absent, as indicated below.

(SEQ ID NO: 59)
<u>MEFGLSWLFLVAILKGVQC</u>EVQLLESGGGLVQPGGSLRLSCAASGFTFSN
YGMSWVRQAPGKGLEWVASIRSGGGRTYYSDNVKGRFTISRDNSKNTLYL
QMNSLRAEDTAVYYCVRYDHYSGSSDYWGQGTLVTVSSASTKGPSVFPLA
PCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAP
EFLGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEAL
HNHYTQKSLSLSLG.

Humanized 3D6 Heavy Chain, Not Including Signal Sequence (IgG4 Isotype, S241P)

(SEQ ID NO: 60)
EVQLLESGGGLVQPGGSLRLSCAASGFTFSNYGMSWVRQAPGKGLEWVAS
IRSGGGRTYYSDNVKGRFTISRDNSKNTLYLQMNSLRAEDTAVYYCVRYD
HYSGSSDYWGQGTLVTVSSASTKGPSVFPLAPCSRSTSESTAALGCLVKD
YFPEPVTVSWNSGALTSGVHTFPAVLQSSGLYSLSSVVTVPSSSLGTKTY
TCNVDHKPSNTKVDKRVESKYGPPCPPCPAPEFLGGPSVFLFPPKPKDTL
MISRTPEVTCVVVDVSQEDPEVQFNWYVDGVEVHNAKTKPREEQFNSTYR
VVSVLTVLHQDWLNGKEYKCKVSNKGLPSSIEKTISKAKGQPREPQVYTL
PPSQEEMTKNQVSLICLVKGFYPSDIAVEWESNGQPENNYKTTPPVLDSD
GSFFLYSRLTVDKSRWQEGNVFSCSVMHEALHNHYTQKSLSLSLGK

The C-terminal K residue can be absent, as indicated below.

(SEQ ID NO: 61)
EVQLLESGGGLVQPGGSLRLSCAASGFTFSNYGMSWVRQAPGKGLEWVAS
IRSGGGRTYYSDNVKGRFTISRDNSKNTLYLQMNSLRAEDTAVYYCVRYD
HYSGSSDYWGQGTLVTVSSASTKGPSVFPLAPCSRSTSESTAALGCLVKD
YFPEPVTVSWNSGALTSGVHTFPAVLQSSGLYSLSSVVTVPSSSLGTKTY
TCNVDHKPSNTKVDKRVESKYGPPCPPCPAPEFLGGPSVFLFPPKPKDTL
MISRTPEVTCVVVDVSQEDPEVQFNWYVDGVEVHNAKTKPREEQFNSTYR
VVSVLTVLHQDWLNGKEYKCKVSNKGLPSSIEKTISKAKGQPREPQVYTL
PPSQEEMTKNQVSLICLVKGFYPSDIAVEWESNGQPENNYKTTPPVLDSD
GSFFLYSRLTVDKSRWQEGNVFSCSVMHEALHNHYTQKSLSLSLG.

Human Heavy Chain Constant Region, IgG1 Isotype (AAB-003), L234A/L235A/G237A (SEQ ID NO: 62)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPEAAGAPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

The C-terminal K residue can be absent, as indicated below.

(SEQ ID NO: 63)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGAPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPG.

Humanized 3D6 Full Length Heavy Chain Including Signal Sequence (IgG1 isotype, L234A/L235A/G237A): AAB-003

(SEQ ID NO: 64)
<u>MEFGLSWLFLVAILKGVQC</u>EVQLLESGGGLVQPGGSLRLSCAASGFTFSN

YGMSWVRQAPGKGLEWVASIRSGGGRTYYSDNVKGRFTISRDNSKNTLYL

QMNSLRAEDTAVYYCVRYDHYSGSSDYWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPEAAGAPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

The C-terminal K residue can be absent, as indicated below.

(SEQ ID NO: 65)
<u>MEFGLSWLFLVAILKGVQC</u>EVQLLESGGGLVQPGGSLRLSCAASGFTFSN

YGMSWVRQAPGKGLEWVASIRSGGGRTYYSDNVKGRFTISRDNSKNTLYL

QMNSLRAEDTAVYYCVRYDHYSGSSDYWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPEAAGAPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPG.

Humanized 3D6 Heavy Chain, Not Including Signal Sequence (IgG1 isotype, L234A/L235A/G237A): AAB-003

(SEQ ID NO: 66)
EVQLLESGGGLVQPGGSLRLSCAASGFTFSNYGMSWVRQAPGKGLEWVAS

IRSGGGRTYYSDNVKGRFTISRDNSKNTLYLQMNSLRAEDTAVYYCVRYD

HYSGSSDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGAPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

The C-terminal K residue can be absent, as indicated below.

(SEQ ID NO: 67)
EVQLLESGGGLVQPGGSLRLSCAASGFTFSNYGMSWVRQAPGKGLEWVAS

IRSGGGRTYYSDNVKGRFTISRDNSKNTLYLQMNSLRAEDTAVYYCVRYD

HYSGSSDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGAPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPG.

DNA encoding humanized 3D6 Heavy Chain Coding Region including Signal Sequence (underlined) (IgG1 isotype, L234A/L235A/G237A): AAB-003

(SEQ ID NO: 68)
<u>ATGGAGTTTGGGCTGAGCTGGCTTTTTCTTGTGGCTATTTTAAAAGGTGT</u>

<u>CCAGTGT</u>GAGGTGCAGCTGCTGGAGTCCGGCGGCGGCCTGGTGCAGCCCG

GCGGCTCCCTGCGCCTGTCCTGCGCCGCCTCCGGCTTCACCTTCTCCAAC

TACGGCATGTCCTGGGTGCGCCAGGCCCCCGGCAAGGGCCTGGAGTGGGT

GGCCTCCATCCGCTCCGGCGGCGGCCGCACCTACTACTCCGACAACGTGA

AGGGCCGCTTCACCATCTCCCGCGACAACTCCAAGAACACCCTGTACCTG

CAGATGAACTCCCTGCGCGCCGAGGACACCGCCGTGTACTACTGCGTGCG

CTACGACCACTACTCCGGCTCCTCCGACTACTGGGGCCAGGGCACCCTGG

TGACCGTGTCCTCCGCGTCGACCAAGGGCCCATCGGTCTTCCCCCTGGCA

CCCTCCTCCAAGAGCACCTCTGGGGGCACAGCGGCCCTGGGCTGCCTGGT

CAAGGACTACTTCCCCGAACCGGTGACGGTGTCGTGGAACTCAGGCGCCC

TGACCAGCGGCGTGCACACCTTCCCGGCTGTCCTACAGTCCTCAGGACTC

TACTCCCTCAGCAGCGTGGTGACCGTGCCCTCCAGCAGCTTGGGCACCCA

GACCTACATCTGCAACGTGAATCACAAGCCCAGCAACACCAAGGTGGACA

AGAAAGTTGAGCCCAAATCTTGTGACAAAACTCACACATGCCCACCGTGC

CCAGCACCTGAAGCCGCTGGGGCACCGTCAGTCTTCCTCTTCCCCCCAAA

-continued

```
ACCCAAGGACACCCTCATGATCTCCCGGACCCCTGAGGTCACATGCGTGG

TGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

GCCCCCATCGAGAAAACCATCTCCAAAGCCAAAGGGCAGCCCCGAGAACC

ACAGGTGTACACCCTGCCCCCATCCCGGGAGGAGATGACCAAGAACCAGG

TCAGCCTGACCTGCCTGGTCAAAGGCTTCTATCCCAGCGACATCGCCGTG

GAGTGGGAGAGCAATGGGCAGCCGGAGAACAACTACAAGACCACGCCTCC

CGTGCTGGACTCCGACGGCTCCTTCTTCCTCTATAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCCCCGGG

TAAATGA
```

Full-length heavy chain of bapineuzumab, not including signal sequence, IgG1 isotype, no Fc mutations (SEQ ID NO: 69)
```
EVQLLESGGGLVQPGGSLRLSCAASGFTFSNYGMSWVRQAPGKGLEWVAS

IRSGGGRTYYSDNVKGRFTISRDNSKNTLYLQMNSLRAEDTAVYYCVRYD

HYSGSSDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVICVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLICLVKGFYPSDIAVEWESNGQPENNYKTTPPVL

DSDGSFFLYSKLTVDKSRWQQGNVFSCSVMHEALHNHYTQKSLSLSPGK
```

The C-terminal K residue can be absent, as indicated below.

(SEQ ID NO: 70)
```
EVQLLESGGGLVQPGGSLRLSCAASGFTFSNYGMSWVRQAPGKGLEWVAS

IRSGGGRTYYSDNVKGRFTISRDNSKNTLYLQMNSLRAEDTAVYYCVRYD

HYSGSSDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPG
```

In some antibodies, positions 234, 235, and 237 of a human IgG heavy chain constant region can be AAA respectively, LLA respectively, LAG respectively, ALG respectively, AAG respectively, ALA respectively, or LAA respectively. As shown above, AAB-003 is an L234A, L235A, and G237A variant of bapineuzumab (i.e., having identical amino acid sequences to bapineuzumab except for the L234A, L235A, and G237A mutations, alanine (A) being the variant amino acid). Like bapineuzumab, AAB-003 has a full-length human kappa light chain constant region and a full-length human IgG1 heavy chain constant region (in either bapineuzumab or AAB-003, a C-terminal lysine residue is sometimes cleaved intracellularly and is sometimes missing from the final product).

Although the three mutations in AAB-003 are close to the hinge region rather than the complement binding region, AAB-003 has reduced binding to both Fcγ receptors and to C1q, relative to bapineuzumab. Thus, the AAB-003 antibody has reduced capacity to induce both phagocytosis and the complement cascade. Furthermore, AAB-003 displays less binding to human FcγRII than an otherwise identical antibody with fewer than the three mutations present in AAB-003 (e.g., one with substitutions at residues 234 and 237), indicating that all three mutations in the AAB-003 Fc region contribute to reducing effector function. Mutation of the heavy chain constant region to reduce interaction with Fcγ receptor(s) and or C1q can reduce microhemorrhaging in a mouse model without eliminating useful activities. Microhemorraghing in mice is one factor that may contribute to vasogenic edema occurring in humans. Antibodies bearing such mutations retain the ability to inhibit cognitive decline as well as ability to clear amyloid deposits.

Similarly heavy chain constant region mutants can also be combined with the variable region sequences described above, e.g., for humanized 12A11 and 12B4 antibodies. The following table shows exemplary combinations of heavy chain variable regions and heavy chain constant regions with mutation(s) for antibodies described above. The heavy chains shown in the table for a particular antibody e.g., 12A11, can be paired with any of the light chain variable regions described above for that antibody linked to a light chain constant region (e.g., a human kappa light chain constant region as follows:

(SEQ ID NO: 85)
```
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
``` or an allotype or isoallotype thereof.

TABLE 1

Correlation of Full Length Heavy Chain SEQ ID NOS with Respective Variable and Constant Region SEQ ID NOS

| Antibody | Heavy Chain Variable region | Heavy Chain Constant region |
|---|---|---|
| 10D5 (version 1) | 9 | 50 |
| | 9 | 51 |
| | 9 | 56 |
| | 9 | 57 |
| | 9 | 62 |
| | 9 | 63 |
| 12B4 | 32 | 50 |
| | 32 | 51 |
| | 32 | 56 |
| | 32 | 57 |
| | 32 | 62 |
| | 32 | 63 |
| 12A11 (version 1) | 11 | 50 |
| | 11 | 51 |
| | 11 | 56 |
| | 11 | 57 |

TABLE 1-continued

Correlation of Full Length Heavy Chain SEQ ID NOS with Respective Variable and Constant Region SEQ ID NOS

| Antibody | Heavy Chain Variable region | Heavy Chain Constant region |
|---|---|---|
|  | 11 | 62 |
|  | 11 | 63 |
| 12A11 (version 2) | 12 | 50 |
|  | 12 | 51 |
|  | 12 | 56 |
|  | 12 | 57 |
|  | 12 | 62 |
|  | 12 | 63 |
| 12A11 (version 2.1) | 13 | 50 |
|  | 13 | 51 |
|  | 13 | 56 |
|  | 13 | 57 |
|  | 13 | 62 |
|  | 13 | 63 |
| 12A11 (version 3) | 14 | 50 |
|  | 14 | 51 |
|  | 14 | 56 |
|  | 14 | 57 |
|  | 14 | 62 |
|  | 14 | 63 |
| 12A11 (version 4.1) | 15 | 50 |
|  | 15 | 51 |
|  | 15 | 56 |
|  | 15 | 57 |
|  | 15 | 62 |
|  | 15 | 63 |
| 12A11 (version 4.2) | 16 | 50 |
|  | 16 | 51 |
|  | 16 | 56 |
|  | 16 | 57 |
|  | 16 | 62 |
|  | 16 | 63 |
| 12A11 (version 4.3) | 17 | 50 |
|  | 17 | 51 |
|  | 17 | 56 |
|  | 17 | 57 |
|  | 17 | 62 |
|  | 17 | 63 |
| 12A11 (version 4.4) | 18 | 50 |
|  | 18 | 51 |
|  | 18 | 56 |
|  | 18 | 57 |
|  | 18 | 62 |
|  | 18 | 63 |
| 12A11 (version 5.1) | 19 | 50 |
|  | 19 | 51 |
|  | 19 | 56 |
|  | 19 | 57 |
|  | 19 | 62 |
|  | 19 | 63 |
| 12A11 (version 5.2) | 20 | 50 |
|  | 20 | 51 |
|  | 20 | 56 |
|  | 20 | 57 |
|  | 20 | 62 |
|  | 20 | 63 |
| 12A11 (version 5.3) | 21 | 50 |
|  | 21 | 51 |
|  | 21 | 56 |
|  | 21 | 57 |
|  | 21 | 62 |
|  | 21 | 63 |
| 12A11 (version 5.4) | 22 | 50 |
|  | 22 | 51 |
|  | 22 | 56 |
|  | 22 | 57 |
|  | 22 | 62 |
|  | 22 | 63 |
| 12A11 (version 5.5) | 23 | 50 |
|  | 23 | 51 |
|  | 23 | 56 |
|  | 23 | 57 |
|  | 23 | 62 |
|  | 23 | 63 |
| 12A11 (version 5.6) | 24 | 50 |
|  | 24 | 51 |
|  | 24 | 56 |
|  | 24 | 57 |
|  | 24 | 62 |
|  | 24 | 63 |
| 12A11 (version 6.1) | 25 | 50 |
|  | 25 | 51 |
|  | 25 | 56 |
|  | 25 | 57 |
|  | 25 | 62 |
|  | 25 | 63 |
| 12A11 (version 6.2) | 26 | 50 |
|  | 26 | 51 |
|  | 26 | 56 |
|  | 26 | 57 |
|  | 26 | 62 |
|  | 26 | 63 |
| 12A11 (version 6.3) | 27 | 50 |
|  | 27 | 51 |
|  | 27 | 56 |
|  | 27 | 57 |
|  | 27 | 62 |
|  | 27 | 63 |
| 12A11 (version 6.4) | 28 | 50 |
|  | 28 | 51 |
|  | 28 | 56 |
|  | 28 | 57 |
|  | 28 | 62 |
|  | 28 | 63 |
| 12A11 (version 7) | 29 | 50 |
|  | 29 | 51 |
|  | 29 | 56 |
|  | 29 | 57 |
|  | 29 | 62 |
|  | 29 | 63 |
| 12A11 (version 8) | 30 | 50 |
|  | 30 | 51 |
|  | 30 | 56 |
|  | 30 | 57 |
|  | 30 | 62 |
|  | 30 | 63 |
| 12B4 | 32 | 50 |
|  | 32 | 51 |
|  | 32 | 56 |
|  | 32 | 57 |
|  | 32 | 62 |
|  | 32 | 63 |
| 266 | 34 | 50 |
|  | 34 | 51 |
|  | 34 | 56 |
|  | 34 | 57 |
|  | 34 | 62 |
|  | 34 | 63 |
| 20C2 (version 1) | 38 | 50 |
|  | 38 | 51 |
|  | 38 | 56 |
|  | 38 | 57 |
|  | 38 | 62 |
|  | 38 | 63 |
| 20C2 (version 2) | 39 | 50 |
|  | 39 | 51 |
|  | 39 | 56 |
|  | 39 | 57 |
|  | 39 | 62 |
|  | 39 | 63 |
| C705 | 41 | 50 |
|  | 41 | 51 |
|  | 41 | 56 |
|  | 41 | 57 |
|  | 41 | 62 |
|  | 41 | 63 |
| C706 | 43 | 50 |
|  | 43 | 51 |

TABLE 1-continued

Correlation of Full Length Heavy Chain SEQ ID NOS with Respective Variable and Constant Region SEQ ID NOS

| Antibody | Heavy Chain Variable region | Heavy Chain Constant region |
|---|---|---|
|  | 43 | 56 |
|  | 43 | 57 |
|  | 43 | 62 |
|  | 43 | 63 |
| 2286 (version 1) | 45 | 50 |
|  | 45 | 51 |
|  | 45 | 56 |
|  | 45 | 57 |
|  | 45 | 62 |
|  | 45 | 63 |
| 2286 (version 2) | 46 | 50 |
|  | 46 | 51 |
|  | 46 | 56 |
|  | 46 | 57 |
|  | 46 | 62 |
|  | 46 | 63 |
| 3D6 (version 4) | 72 | 50 |
|  | 72 | 51 |
|  | 72 | 56 |
|  | 72 | 57 |
|  | 72 | 62 |
|  | 72 | 63 |
| 10D6 (version 2) | 74 | 50 |
|  | 74 | 51 |
|  | 74 | 56 |
|  | 74 | 57 |
|  | 74 | 62 |
|  | 74 | 63 |
| 2E7 (version 1) | 76 | 50 |
|  | 76 | 51 |
|  | 76 | 56 |
|  | 76 | 57 |
|  | 76 | 62 |
|  | 76 | 63 |
| 2E7 (version 2) | 77 | 50 |
|  | 77 | 51 |
|  | 77 | 56 |
|  | 77 | 57 |
|  | 77 | 62 |
|  | 77 | 63 |
| 2E7 (version 3) | 78 | 50 |
|  | 78 | 51 |
|  | 78 | 56 |
|  | 78 | 57 |
|  | 78 | 62 |
|  | 78 | 63 |
| 9TL | 79 | 50 |
|  | 79 | 51 |
|  | 79 | 56 |
|  | 79 | 57 |
|  | 79 | 62 |
|  | 79 | 63 |
| 6G | 81 | 50 |
|  | 81 | 51 |
|  | 81 | 56 |
|  | 81 | 57 |
|  | 81 | 62 |
|  | 81 | 63 |
| 2.1 | 82 | 50 |
|  | 82 | 51 |
|  | 82 | 56 |
|  | 82 | 57 |
|  | 82 | 62 |
|  | 82 | 63 |

Amino acids in the constant region are numbered by alignment with the human antibody EU (see Cunningham et al., *J. Biol. Chem.*, 9, 3161 (1970)). That is, the heavy and light chains of an antibody are aligned with the heavy and light chains of EU to maximize amino acid sequence identity and each amino acid in the antibody is assigned the same number as the corresponding amino acid in EU. The EU numbering system is conventional (see generally, Kabat et al., *Sequences of Protein of Immunological Interest*, NIH Publication No. 91-3242, US Department of Health and Human Services (1991)).

The affinity of an antibody for complement component C1q can be altered by mutating at least one of the amino acid residues 318, 320, and 322 of the heavy chain to a residue having a different side chain. Other suitable alterations for altering, e.g., reducing or abolishing, specific C1q-binding to an antibody include changing any one of residues 318 (Glu), 320 (Lys) and 322 (Lys), to Ala. C1q binding activity can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. In addition, it is also be possible to use such polar non-ionic residues as Ser, Thr, Cys, and Met in place of residues 320 and 322, but not 318, to abolish C1q binding activity. Replacement of the 318 (Glu) residue by a polar residue may modify but not abolish C1q binding activity. Replacing residue 297 (Asn) with Ala results in removal of lytic activity while only slightly reducing (about three fold weaker) affinity for C1q. This alteration destroys the glycosylation site and the presence of carbohydrate that is required for complement activation. Any other substitution at this site also destroys the glycosylation site.

Additional mutations that can affect C1q binding to the constant region of human IgG1 include those described, e.g., in WO 06/036291. In this case, at least one of the following substitutions can be made to reduce C1q binding: D270A, K322A, P329A, and P311 S. Each of these mutations, including those at residues 297, 318, and 320 can be made individually or in combination.

Antibodies with heavy chain constant region mutations that reduce binding to Fcγ receptor(s) and/or C1q can be used in any of the methods of the invention. Preferably, such antibodies have reduced binding relative to an otherwise identical antibody lacking the mutation of at least 50% to at least one Fcγ receptor and/or to C1q.

B. Aβ Fragments

Numerous fragments of Aβ have been now been described in the scientific and patent literature as agents for active immunotherapy (see, e.g., U.S. Pat. No. 6,750,324, US 20040213800; US 20070134762). In general, fragments including an epitope within residues 1-11 of Aβ induce antibodies that bind Fcγ receptors and induce a clearing response against amyloid deposits, whereas fragments lacking an epitope within residues 1-11 of Aβ induce antibodies that bind preferentially or exclusively to soluble forms of Aβ rather than plaques and induces little if any clearing response against amyloid deposits.

Preferred fragment for inducing antibodies that bind to amyloid deposits and induce a clearing response are N-terminal fragments beginning at residues 1-3 of Aβ and ending at residues 7-11 of Aβ. Exemplary N-terminal fragments include Aβ1-5, 1-6, 1-7, 1-10, 3-7, 1-3, and 1-4 with 1-7 being particularly preferred. A class of exemplary fragments includes fragments beginning at a residue between 1-3 (inclusive) and ending at a residue between 7-11 (inclusive).

Preferred fragments for inducing antibodies to soluble Aβ, which induce little, if any, clearing response against amyloid deposits include Aβ15-21, Aβ16-22, Aβ17-23, Aβ18-24, Aβ19-25, A315-22, Aβ16-23, Aβ17-24, Aβ18-25, Aβ15-23, Aβ16-24, A317-25, Aβ18-26, Aβ15-24, Aβ16-25, and Aβ15-25. Aβ16-23 is particularly preferred meaning s a fragment including residues 16-23 of Aβ and lacking other residues of Aβ. Also preferred are C-terminal fragments of Aβ42 or 43 of 5-10 and preferably 7-10 contiguous amino acids. Analogous C-terminal fragments of Aβ40, or 39 can also be used. These fragments can generate an antibody response that includes end-specific antibodies. Fragments preferably lack T-cell epitopes that would induce T-cells against Aβ. Generally, T-cell epitopes are greater than 10 contiguous amino acids. Therefore, preferred fragments of Aβ are of size 5-10 or preferably 7-10 contiguous amino acids; i.e., sufficient length to generate an antibody response without generating a T-cell response. Absence of T-cell epitopes is preferred because these epitopes are not needed for immunogenic activity of fragments, and may cause an undesired inflammatory response in a subset of patients.

Agents to induce antibodies to Aβ that can be used in the methods of the invention also include (i) ACI-24 (AC Immune); (ii) Affitopes AD02 and AD02 (Affiris GmbH); (iii) Arctic Immunotherapeutic KLVFFAGDV (SEQ ID NO: 92) (BioArctic Neuroscience/Eisai); (iv) Aβ1-15-K-K-Aβ1-15 (Brigham & Women's Hospital); (v) β-Vaxm and Recall-Vax™ (Intellect Neurosciences); (vi) K6-Aβ1-30 (Intellect Neurosciences/NYU); (vii) V-950 (Merck); (viii) CAD106 (Novartis/Cytos); (ix) Aβ DCtag™ nanoparticle adjuvant (Prana Biotechnology/PRIMABioMed); (x) PX106 (also 2Aβ1-11-PADRE, from Pharmexa/Lundbeck); (xi) Aβ4-10 conjugated to a T cell epitope (U. Toronto); and (xii) p3102 and p3075 (United Biomedical).

ACI-24 is an Aβ1-15 liposome construct with Aβ1-15-K-K-16C palmitic acid inserted into a liposomal bilayer. These compounds are described in US 2004/0242845, WO 05/081872, US 2007/0281006, and US 2006/0073158. Affitopes AD01 and AD02 are mimotopes from the N-terminus of Aβ, as described in WO 06/005707. The Arctic Immunotherapeutic is derived from Aβ22 of E692G, as described in US 20020162129 and US 20070248606. Aβ1-15-K-K-Aβ1-15 represents two linked N-terminal Aβ fragments, as described in WO 05/012330 and WO 02/0123553. β-Vax™, Recall-Vax™ and K6-Aβ1-30 are Aβ fragments linked to a T cell epitope, as described in WO 01/42306. V-950 is an 8-mer Aβ peptide linked to a multivalent linear peptide with at least one spacer and a multivalent branched multiple antigen peptide, as described in WO 06/121656. CAD106 is a Qβ carrier (an RNA VLP) linked to an N-terminal Aβ peptide, as described in WO 04/016282. The Aβ DCtag™ nanoparticle adjuvant is described, e.g., in WO 02/00245. PX106 is a Aβ1-11 peptide linked to a T cell epitope called a "pan DR epitope peptide (PADRE)," as described in U.S. Pat. No. 7,135,181. p3102 and p3075 are Aβ1-14 peptides linked by a spacer to a T cell epitope (e.g., measles epitope), as described in US 20030068325 US 20040247612, U.S. Pat. No. 6,906,169, and WO 02/096350.

Fragments are usually natural Aβ peptides but can include unnatural amino acids or modifications of N or C terminal amino acids at a one, two, five, ten or even all positions. For example, the natural aspartic acid residue at position 1 and/or 7 of Aβ can be replaced with isoaspartic acid. Examples of unnatural amino acids are D, alpha, alpha-disubstituted amino acids, N-alkyl amino acids, lactic acid, 4-hydroxyproline, γ-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, omega-N-methylarginine, β-alanine, ornithine, norleucine, norvaline, hydroxyproline, thyroxine, γ-amino butyric acid, homoserine, citrulline, and isoaspartic acid. Some therapeutic agents of the invention are all-D peptides, e.g., all-D Aβ or all-D Aβ fragment, and all-D peptide analogs. Fragments can be screened for prophylactic or therapeutic efficacy in transgenic animal models in comparison with untreated or placebo controls.

Fragments are typically conjugated to carrier molecules, which provide a T-cell epitope, and thus promote an immune response against the fragment conjugated to the carrier. A single agent can be linked to a single carrier, multiple copies of an agent can be linked to multiple copies of a carrier, which are in turn linked to each other, multiple copies of an agent can be linked to a single copy of a carrier, or a single copy of an agent can be linked to multiple copies of a carrier, or different carriers. Suitable carriers include serum albumins, keyhole limpet hemocyanin, immunoglobulin molecules, thyroglobulin, ovalbumin, tetanus toxoid, or a toxoid from other pathogenic bacteria, such as diphtheria (e.g., CRM197), E. coli, cholera, or H. pylori, or an attenuated toxin derivative. T cell epitopes are also suitable carrier molecules. Some conjugates can be formed by linking agents of the invention to an immunostimulatory polymer molecule (e.g., tripalmitoyl-5-glycerine cysteine ($Pam_3Cys$), mannan (a mannose polymer), or glucan (a β1→2 polymer)), cytokines (e.g., IL-1, IL-1 alpha and β peptides, IL-2, γ-INF, IL-10, GM-CSF), and chemokines (e.g., MIP1-α and β, and RANTES) Immunogenic agents can also be linked to peptides that enhance transport across tissues, as described in O'Mahony, WO 97/17613 and WO 97/17614. Immunogens may be linked to the carries with or with out spacers amino acids (e.g., gly-gly).

Additional carriers include virus-like particles. Virus-like particles (VLPs), also called pseudovirions or virus-derived particles, represent subunit structures composed of multiple copies of a viral capsid and/or envelope protein capable of self assembly into VLPs of defined spherical symmetry in vivo. (Powilleit, et al., (2007) *PLoS ONE* 2 (5):e415.) These particles have been found to be useful as antigen delivery systems. VLPs can be produced and readily purified in large quantities and due to their particulate nature and high molecular weights. VLPs induce an immune response without additional application of an adjuvant. (Ulrich et al., (1996) *Intervirology* 39:126-132.) Exemplary chimeric particles useful as VLP antigen delivery systems include those based on hepatitis B virus, human immunodeficiency virus (HIV), yeast retrotransposon Ty, yeast totivirus L-A, parvovirus, influenza virus, Norwalk virus, rotavirus, adeno-associated virus, bluetongue virus, hepatitis A virus, human papillomavirus, measles virus, polyoma virus and RNA phage virus, as well as those based on various retroviruses and lentiviruses. For review, see Lechner, et al. (2002) *Intervirology* 45:212-217.

The core protein of hepatitis B virus (HBcAg) is a common VLP used for carrying foreign antigens (see Koletzki et al., (1997) *J Gen Vir* 78:2049-2053). Briefly, HBcAg can be used as a core to construct VLPs that present extended foreign protein segments. The method employs a construct having a linker sequence between the a C-terminally truncated HBcAg and a foreign protein sequence that contains a stop codon. Truncated HBcAg/foreign protein chimera is expressed utilizing a read through mechanism based on the opal TGA-Trp mutation for expression in an *E. coli* suppressor strain. The method described by Koletzki et al. allows for incorporation of long foreign protein sequences into VLPs, allowing for a greater variety of antigens to be carried by the VLP.

The HIV virus Gag protein can be used as an antigen carrier system (see Griffiths et al., (1993) *J. Virol.* 67(6):3191-3198). Griffiths utilized the V3 loop of HIV, which is the principle neutralizing determinant of the HIV envelope. The Gag:V3 fusion proteins assembled in vivo into hybrid Gag particles, designated virus-derived particles (VDPs). The VDPs induce both humoral and cellular responses. As the V3 loop contains a CTL epitope, immunization with Gag:V3 induces a CTL response to the V3 protein portion of the VLP.

A hybrid HIV:Ty VLP can also be used (see Adams et al., (1987) *Nature* 329(3):68-70). The HIV:Ty VLP employs the p1 protein of the yeast transposon Ty. The first 381 amino acids of p1 are sufficient for VLP formation. The HIV:Ty fusion proteins are capable of assembling into VLPs in vivo, as well as inducing an immune response to the HIV antigen carried by the VLP. VLPs using the Ty p1 protein can also contain p1 fused to the whole of an alpha2-interferon, the product of the bovine papilloma virus E1 and E2 genes, and a portion of an influenza hemagglutinin. Each of these Ty fusions formed VLPs and were capable of inducing production of antisera to the non-Ty VLP component.

VLPs can also be designed from variants of the yeast totivirus L-A (see Powilleit et al. (2007) *PLOS One* 2 (5): e415). The Pol gene of the L-A virus can be replaced with an appropriate antigen to induce a specific immune response, demonstrating that yeast VLPs are effective antigen carriers.

Recombinant, nonreplicative parvovirus-like particles can also be used as antigen carriers. (Sedlik, et al. (1997) PNAS 94:7503-7508.) These particles allow the carried antigens into the cytosol so they enter the class 1-restricted immunological pathway, thus stimulating cytotoxic T-lymphocyte (CTL) mediated responses. Sedlik specifically used PPV:VLP, which contained the VP2 capsid protein of the parvovirus and residues 118-132 from the lymphocytic choriomeningitis virus (LCMV) was inserted into the VP2 capsid protein. The PPV:VLP containing LCMV was capable of inducing an immune response to LCMV and elicited immunological protection against lethal viral doses in pre-immunized mice.

VLPs can also comprise replication incompetent influenza that lack the influenza NS2 gene, the gene essential for viral replication. (Watanabe, et al. (1996) *J. Virol.* 76(2):767-773.) These VLPs infect mammalian cells and allow expression of foreign proteins.

Norwalk virus (NV)-based VLPs can also be used as vehicles for immunogen delivery. (Ball, et al. (1999) *Gastroenterology* 117:40-48.) The NV genome has three open reading frames (ORFs 1-3). Recombinant baculovirus expression of ORFs 2 and 3 allows for spontaneous assembly of high yields of recombinant Norwalk virus (rNV) VLPs.

Some conjugates can be formed by linking agents of the invention to at least one T cell epitope. Some T cell epitopes are promiscuous whereas other T cell epitopes are universal. Promiscuous T cell epitopes are capable of enhancing the induction of T cell immunity in a wide variety of subjects displaying various HLA types. In contrast to promiscuous T cell epitopes, universal T cell epitopes are capable of enhancing the induction of T cell immunity in a large percentage, e.g., at least 75%, of subjects displaying various HLA molecules encoded by different HLA-DR alleles.

A large number of naturally occurring T-cell epitopes exist, such as, tetanus toxoid (e.g., the P2 and P30 epitopes), Hepatitis B surface antigen, pertussis, toxoid, measles virus F protein, *Chlamydia trachomatis* major outer membrane protein, diphtheria toxoid, *Plasmodium falciparum* circumsporozoite T, *Plasmodium falciparum* CS antigen, *Schistosoma mansoni* triose phosphate isomerase, *Escherichia coli* TraT, and Influenza virus hemagglutinin (HA). The immunogenic peptides of the invention can also be conjugated to the T-cell epitopes described in Sinigaglia F. et al., *Nature,* 336: 778-780 (1988); Chicz R. M. et al., *J. Exp. Med.,* 178:27-47 (1993); Hammer J. et al., *Cell* 74:197-203 (1993); Falk K. et al., *Immunogenetics,* 39:230-242 (1994); WO 98/23635; and, Southwood S. et al. *J. Immunology,* 160:3363-3373 (1998).

Carriers also include virus-like particles (see US 20040141984).

Fragments are often administered with pharmaceutically acceptable adjuvants. The adjuvant increases the titer of induced antibodies and/or the binding affinity of induced antibodies relative to the situation if the peptide were used alone. A variety of adjuvants can be used in combination with an immunogenic fragment of Aβ, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja *Saponaria* Molina tree found in South America (see Kensil et al., in *Vaccine Design: The Subunit and Adjuvant Approach* (eds. Powell & Newman, Plenum Press, NY, 1995); U.S. Pat. No. 5,057,540), (Aquila BioPharmaceuticals, Framingham, Mass.; now Antigenics, Inc., New York, N.Y.). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Another adjuvant is CpG (WO 98/40100). Adjuvants can be administered as a component of a therapeutic composition with an active agent or can be administered separately, before, concurrently with, or after administration of the therapeutic agent.

A preferred class of adjuvants is aluminum salts (alum), such as alum hydroxide, alum phosphate, alum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™).

Another class of preferred adjuvants is saponin adjuvants, such as Stimulon™ (QS-21, Aquila, Framingham, Mass.) or particles generated therefrom such as ISCOMs (immunostimulating complexes) and ISCOMATRIX. Other adjuvants include RC-529, GM-CSF and Complete Freund's Adjuvant (CFA) and Incomplete Freund's Adjuvant (IFA). Other adjuvants include cytokines, such as interleukins (e.g., IL-1 α and β peptides, IL-2, IL-4, IL-6, IL-12, IL13, and IL-15), macrophage colony stimulating factor (M-CSF), granulocyte-macrophage colony stimulating factor (GM-CSF), tumor necrosis factor (TNF), chemokines, such as MIP1α and β and RANTES. Another class of adjuvants is glycolipid analogues including N-glycosylamides, N-glycosylureas and N-glycosylcarbamates, each of which is substituted in the sugar residue by an amino acid, as immuno-modulators or adjuvants (see U.S. Pat. No. 4,855,283). Heat shock proteins, e.g., HSP70 and HSP90, may also be used as adjuvants.

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, MPL or RC-529 with GM-CSF, and alum, QS-21 and MPL together. Also, Incomplete Freund's adjuvant can be used (Chang et al., *Advanced Drug Delivery Reviews* 32, 173-186 (1998)), optionally in combination with any of alum, QS-21, and MPL and all combinations thereof.

V. Patients Amenable to Treatment

The present regimes are useful for treatment of any disease characterized by amyloid deposits of Aβ in the brain. As well as Alzheimer's disease, such diseases include Down's syndrome, Parkinson's disease, mild-cognitive impairment, and vascular amyloid disease. Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods can also be useful for individuals who have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

Patients amenable to treatment include patients 50 to 87 years of age, patients suffering from mild to moderate Alzheimer's disease, patients having an MMSE score of 14-26, patients having a diagnosis of probable Alzheimer's disease based on Neurological and Communicative Disorders and Stroke-Alzheimer's disease Related Disorders (NINCDS-ADRDA) criteria, and/or patients having an Rosen Modified Hachinski Ischemic score less than or equal to 4. Patients with MRI an scan consistent with the diagnosis of Alzheimer's disease, i.e., that there are no other abnormalities present on the MRI that could be attributed to other diseases, e.g. stroke, traumatic brain injury, arachnoid cysts, tumors, etc are also amendable to treatment.

VI. Treatment Regimes

In prophylactic applications, agents or pharmaceutical compositions or medicaments containing the same are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicaments are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic.

Optionally, antibodies are administered to achieve a mean serum concentration of administered antibody of 0.1-60, 0.4-20, or 1-15 µg/ml in a patient. These ranges bracket the demonstrated effective concentrations in mice and humans allowing some margin for error in measurement and individual patient variation. The serum concentration can be determined by actual measurement or predicted from standard pharmacokinetics (e.g., WinNonline Version 4.0.1 (Pharsight Corporation, Cary, USA)) based on the amount of antibody administered, frequency of administration, route of administration and antibody half-life.

The mean antibody concentration in the serum is optionally within a range of 1-10, 1-5 or 2-4 µg/ml. It is also optional to maintain a maximum serum concentration of the antibody in the patient less than about 28 µg antibody/ml serum for maximizing therapeutic benefit relative to the occurrence of possible side effects, particularly vascular edema. A preferred maximum serum concentration is within a range of about 4-28 µg antibody/ml serum. The combination of maximum serum less than about 28 µg antibody/ml serum and an mean serum concentration of the antibody in the patient is below about 7 mg antibody/ml serum is particularly beneficial. Optionally, the mean concentration is within a range of about 2-7 µg antibody/ml serum.

The concentration of Aβ in plasma following antibody administration changes roughly in parallel with changes of antibody serum concentration. In other words, plasma concentration of Aβ is highest after a dose of antibody and then declines as the concentration of antibody declines between doses. The dose and regime of antibody administration can be varied to obtain a desired level of Aβ in plasma. In such methods, the mean plasma concentration of antibody can be at least 450 pg/ml or for example, within a range of 600-30000 pg/ml or 700-2000 pg/ml or 800-1000 pg/ml.

The preferred dosage ranges for antibodies are from about 0.01 to 5 mg/kg, and more usually 0.1 to 3 mg/kg or 0.15-2 mg/kg or 0.15-1.5 mg/kg, of the host body weight. Subjects can be administered such doses daily, on alternative days, weekly, biweekly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or a month or once every 3 to 6 months.

For intravenous administration, doses of 0.1 mg/kg to 2 mg/kg, and preferably 0.5 mg/kg or 1.5 mg/kg administered intravenously quarterly are suitable. Preferred doses of antibody for monthly intravenous administration occur in the range of 0.1-1.0 mg/kg antibody or preferably 0.5-1.0 mg/kg antibody.

For more frequent dosing, e.g., from weekly to monthly dosing, subcutaneous administration is preferred. Subcutaneous dosing is easier to administer and can reduce maximum serum concentrations relative to intravenous dosing. The doses used for subcutaneous dosing are usually in the range of 0.01 to 0.6 mg/kg or 0.01-0.35 mg/kg, preferably, 0.05-0.25 mg/kg. For weekly or biweekly dosing, the dose is preferably in the range of 0.015-0.2 mg/kg, or 0.05-0.15 mg/kg. For weekly dosing, the dose is preferably 0.05 to 0.07 mg/kg, e.g., about 0.06 mg/kg. For biweekly dosing, the dose is preferably 0.1 to 0.15 mg/kg. For monthly dosing, the dose is preferably 0.1 to 0.3 mg/kg or about 0.2 mg/kg. Monthly dosing includes dosing by the calendar month or lunar month (i.e., every four weeks). Here as elsewhere in the application, dosages expressed in mg/kg can be converted to absolute mass dosages by multiplying by the mass of a typical patient (e.g., 70 or 75 kg) typically rounding to a whole number. Other regimes are described by e.g., PCT/US2007/009499. The dosage and frequency can be varied within these guidelines based on the ApoE status of the patient as discussed above.

The amount of an agent for active administration varies from 1-500 µg per patient and more usually from 5-100 µg per injection for human administration. Exemplary dosages per injection are 3, 10, 30, or 90 µg for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for each immunization of immunogen. The timing of injections can vary significantly from once a day, to once a year, to once a decade. On any given day that a dosage of immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster injections at time intervals, such as 6 week intervals. Another regimen consists of an immunization followed by booster injections 1, 2 and 12 months later. Another regimen entails an injection every two months for life Alternatively, booster injections can be on an irregular basis as indicated by monitoring of immune response. The dosage and frequency can be varied such that antibodies induced by an active agent have mean serum concentrations within a range of 0.1-60, 0.4-20, or 1-15 or 2-7 µg/ml as in passive administration. The dosage and frequency can be varied within these guidelines based on the ApoE status of the patient as discussed above.

VII. Exemplary Regimes Depending on Carrier Status

The invention provides methods of treating non-carrier patients having Alzheimer's disease (e.g., mild or moderate) in which an effective regime of an antibody that specifically binds to an N-terminal epitope of Aβ is administered to such a patient. The antibody can for example bind to an epitope within residues 1-11, 1-7, 1-5, or 3-7 of Aβ. Optionally, the antibody is bapineuzumab. The dosage of the antibody can be within a range of about 0.15 mg/kg to 2 mg/kg administered by intravenous infusion. Optionally, the dosage is about 0.5 mg/kg to about 1 mg/kg The dosage can be administered for example every 8-16 weeks, every 1-14 weeks or every 13 weeks.

The invention also provides methods of reducing cognitive decline in a non-carrier patient having been diagnosed with mild or moderate Alzheimer's disease. The method entails administering an effective regime of an antibody that specifically binds to an N-terminal epitope of Aβ to such a patient. The antibody can for example bind to an epitope within residues 1-11, 1-7, 1-5, or 3-7 of Aβ. Optionally, the antibody is bapineuzumab. The dosage of the antibody can be within a range of about 0.15 mg/kg to 2 mg/kg administered by intravenous infusion. Optionally, the dosage is about 0.5 mg/kg to about 1 mg/kg The dosage can be administered for example every 8-16 weeks, every 1-14 weeks or every 13 weeks. Cognitive decline can be measured by comparing the patient being treated with the cognitive decline in a population of control patients also of non-carrier status and having mild or moderate Alzheimer's disease (e.g., a control population in a clinical trial). Cognitive ability can be measured by scales such as ADAS-COG, NTB, MMSE or CDR-SB. The rate of change in such a scale (points over time) in a patient can be compared with the mean decline in a population of control patients as described above.

The invention also provides methods of reducing brain volume decline in a non-carrier patient having been diagnosed with mild or moderate Alzheimer's disease. The method entails administering an effective regime of an antibody that specifically binds to an N-terminal epitope of Aβ to such a patient. The antibody can for example bind to an epitope within residues 1-11, 1-7, 1-5, or 3-7 of Aβ. Optionally, the antibody is bapineuzumab. The dosage of the antibody can be within a range of about 0.15 mg/kg to 2 mg/kg administered by intravenous infusion. Optionally, the dosage is about 0.5 mg/kg to about 1 mg/kg The dosage can be administered for example every 8-16 weeks, every 1-14 weeks or every 13 weeks. Brain volume can be measured by MRI. Change in brain volume in a patient can be compared with the mean decline in brain volume in a population of control patients also of non-carrier status and having mild or moderate Alzheimer's disease (e.g., a control population in a clinical trial).

The invention also provides methods of treating non-carrier patients having Alzheimer's disease (e.g., mild or moderate) in which a regime of an antibody that specifically binds to an N-terminal epitope of Aβ is administered to such a patient. The regime is effective to maintain a mean serum concentration of the antibody in the range of about 0.1 μg/ml to about 60 μg/ml, optionally 0.4-20 or 1-5 μg/ml. Additionally or alternatively, the regime is administered to maintain a mean plasma concentration of Aβ of 600-3000 pg/ml, 700-2000 pg/ml or 800-100 pg/ml. Optionally, the antibody in such methods is bapineuzumab.

The invention also provides methods of treating a patient who is an ApoE4 carrier and has Alzheimer's disease in which the antibody administered has a constant region mutation that reduces binding to C1q and/or and Fcγ receptor(s). Optionally, the antibody is an antibody that binds to an epitope within an N-terminal region of Aβ. Optionally, the antibody is AAB-003. Optionally, the patients are monitored, e.g., quarterly, by MRI for vasogenic edema. If vasogenic edema develops the frequency or dose can be reduced or eliminated. Vasogenic edema can optionally be treated with a corticosteroid. After resolution of vasogenic edema, administration of treatment can be resumed. Optionally, the dose is increased over time.

The invention also provides methods of treating a patient diagnosed with probable Alzheimer's disease, irrespective of ApoE4 status. In such methods, an effective regime of an antibody that specifically binds to an N-terminal region of Aβ is administered. The antibody has a constant region mutation that reduces binding to C1q and/or and Fcγ receptor relative to an otherwise identical antibody without the mutation. Optionally, the antibody is an antibody that binds to an epitope within an N-terminal region of Aβ. Optionally, the antibody is AAB-003. Optionally, the patients are monitored, e.g., quarterly, by MRI for vasogenic edema. If vasogenic edema develops the frequency or dose can be reduced or eliminated. Vasogenic edema can optionally be treated with a corticosteroid. After resolution of vasogenic edema, administration of treatment can be resumed. Optionally, the dose is increased over time after resolution of vasogenic edema.

The invention provides methods of treating an ApoE carrier patient with Alzheimer disease comprising subcutaneously administering to a patient having the disease an antibody that specifically binds to an N-terminal epitope of Aβ. Optionally, the antibody is administered at a dose of 0.01-0.6 mg/kg and a frequency of between weekly and monthly. Optionally, the antibody is administered at a dose of 0.05-0.5 mg/kg. Optionally, the antibody is administered at a dose of 0.05-0.25 mg/kg. Optionally, the antibody is administered at a dose of 0.015-0.2 mg/kg weekly to biweekly. Optionally, the antibody is administered at a dose of 0.05-0.15 mg/kg weekly to biweekly. Optionally, the antibody is administered at a dose of 0.05-0.07 mg/kg weekly. Optionally, the antibody is administered at a dose of 0.06 mg/kg weekly. Optionally, the antibody is administered at a dose of 0.1 to 0.15 mg/kg biweekly. Optionally, the antibody is administered at a dose of 0.1 to 0.3 mg/kg monthly. Optionally, the antibody is administered at a dose of 0.2 mg/kg monthly.

The invention also provides methods of treating an ApoE4 carrier patient having Alzheimer disease comprising subcutaneously administering to a patient having the disease an antibody that specifically binds to an N-terminal fragment of Aβ, wherein the antibody is administered at a dose of 1-40 mg and a frequency of between weekly and monthly. Optionally, the antibody is administered at a dose of 5-25 mg. Optionally, the antibody is administered at a dose of 2.5-15 mg. Optionally, the antibody is administered at a dose of 1-12 mg weekly to biweekly. Optionally, the antibody is administered at a dose of 2.5-10 mg weekly to biweekly. Optionally, the antibody is administered at a dose of 2.5-5 mg weekly. Optionally, the antibody is administered at a dose of 4-5 mg weekly. Optionally, the antibody is administered at a dose of 7-10 mg biweekly.

VIII. Pharmaceutical Compositions

Agents of the invention are often administered as pharmaceutical compositions comprising an active therapeutic agent, i.e., and a variety of other pharmaceutically acceptable components. See Remington's Pharmaceutical Science (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

Agents are typically administered parenterally. Antibodies are usually administered intravenously or subcutaneously. Agents for inducing an active immune response are usually administered subcutaneously or intramuscularly. For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation, which can be formulated in such a manner as to permit a sustained release of the active ingredient.

Some preferred formulations are described in US 20060193850. A preferred formulation has a pH of about 5.5 to about 6.5, comprises i. at least one Aβ antibody at a concentration of about 1 mg/ml to about 30 mg/ml; ii. mannitol at a concentration of about 4% w/v or NaCl at a concentration of about 150 mM; iii. about 5 mM to about 10 mM histidine or succinate; and iv. 10 mM methionine. Optionally, the formulation also includes polysorbate 80 at a concentration of about 0.001% w/v to about 0.01% w/v. Optionally, the formulation has a pH of about 6.0 to about 6.5 and comprises about 10 mg/ml Aβ antibody, about 10 mM histidine and about 4% w/v mannitol and about 0.005% w/v polysorbate 80 Optionally, the formulation has a pH of about 6.0 to about 6.2 and comprises about 20 mg/ml Aβ antibody, about 10 mM histidine, about 4% w/v mannitol and about 0.005% w/v polysorbate 80. Optionally, the formulation has a pH of about 6.0 to about 6.2 and comprises about 30 mg/ml Aβ antibody, about 10 mM histidine, about 4% w/v mannitol and about 0.005% w/v polysorbate 80.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249: 1527 (1990) and Hanes, Advanced Drug Delivery Reviews 28:97 (1997)). The agents of this invention can be administered in the form of a depot injection or implant preparation, which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

IX. Kits and Labels

The invention provides kits containing an antibody binding to an N-terminal epitope of Aβ. The antibody is typically provided in lyophilized or solution form in a vial, optionally in a single-dose form. The antibody in the vial is typically sterile and manufactured under GMP conditions. The kits can also include diluents, syringes, needles, intravenous or subcutaneous drips and the like. The kits typically contain instructions (e.g., a package insert or label) for use. In some kits, the instructions specify whether the antibody is to be provided to ApoE4 carriers or non-carriers or can be provided to both. The instructions can also specify that the antibody is not to be provided to ApoE4 carriers. In some kits, the instructions can provide information or sources for ApoE testing.

In some kits, the instructions specify results that can be achieved by administering the antibody. The results can include an inhibition of cognitive decline. The instructions can also include a measure of cognitive decline in a control patient (typically a mean value from a population of such patients) for purposes of comparison. Cognitive decline can be measured, by for example, ADAS-COG, NTB, MMSE or CDR-SB Likewise, the instructions can refer to inhibition of decrease in brain volume or inhibition of ventricular volume. The instructions can also include a measure of decrease in brain volume or inhibition of ventricular volume in a control patient (typically a mean value from a population of such patients for purposes of comparison).

In some kits, the instructions specify potential side effects including vasogenic edema. The instructions can also specify a monitoring regime, such as performing MRI at quarterly, six monthly or annual intervals. The instructions can specify different monitoring regimes for ApoE4 non-carriers and carriers as discussed above. The instructions can also specify altered dosing schedules on occurrence and/or resolution of vasogenic edema and treatment measures for vasogenic edema, such as corticosteroids.

The kits can also include instructions for patients for whom treatment is contraindicated such as prior brain injury, CVA, brain tumor, multiple lacunes, venothrombotic disease, anticoagulation (heparin/coumadin) or atrial fibrillation. The kits can also provide instructions for route (e.g., subcutaneous), dosage amount or frequency of dosing.

X. Antibodies with Mutated IgG1 Constant Region

The invention provides a human IgG1 constant region, in which amino acids at positions 234, 235, and 237 (EU numbering) are each alanine, and isolated antibodies or fusion proteins containing such a constant region. Such antibodies include human antibodies, humanized antibodies and chimeric antibodies as described above. Examples of such antibodies include antibodies to Aβ, antibodies to the Lewis Y antigen and the 5T4 tumor antigen, such as described in the Examples. Fusion proteins include the extracellular domains of receptors (e.g., TNF-alpha receptor) linked to a constant region. Methods for fusing or conjugating polypeptides to the constant regions of antibodies are described by, e.g., U.S. Pat. Nos. 5,336,603, 5,622,929, 5,359,046, 5,349,053, 5,447,851, 5,723,125, 5,783,181, 5,908,626, 5,844,095, 5,112,946; EP 0 307 434; EP 0 367 166; EP 0 394 827).

Antibodies or fusion proteins incorporating these mutations can offer advantages of the IgG1 isotype including pharmacokinetics and ease of manufacture, but also have reduced or eliminated effector function relative to an otherwise identical antibody lacking these mutations. Effector function is typically impaired in binding to one or more Fc gamma receptors, binding to C1Q, antibody-dependent cellular cytotoxicity and/or antibody-dependent complement activity. In some antibodies, all of these activities are reduced or eliminated. An activity is considered eliminated if there is no detectable difference beyond experimental error in that activity between an antibody having the above three mutations and an otherwise identical control antibody without the mutations.

Typically, a mutated constant region includes CH1, hinge, CH2 and CH3 domains. However, the CH1 domain is sometimes replaced particularly in fusion proteins with a synthetic linker. Some constant regions contain a full-length IgG1 constant region with the possible exception of a C-terminal lysine residue. Exemplary sequences of a mutated constant region are provided by SEQ ID NOS: 62 and 63. These sequences differ in the 62 contains a C-terminal lysine not present in 63.

The sequences 62 and 63 represent the G1mz allotype of human IgG1. Other examples of allotypes have been provided above. Allotypes are natural polymorphic variations in the human IgG1 constant region that differ between different individuals at the polymorphic position. The G1mz allotype has Glu at position 356 and Met at position 358.

Other allotypic variants of SEQ ID NOS. 62 and 63 are included. Also included are human IgG1 constant regions having alanine residues at positions 234, 235 and 237 any permutation of residues occupying polymorphic positions in natural allotypes.

Mutated IgG1 constant regions having alanine at positions 234, 235 and 237 can have additional mutations present relative to a natural human IgG1 constant region. As an example in which additional mutations can be present, alanine mutations at positions 234, 235 and 237 can be combined with mutations at positions 428 and/or 250 as described in U.S. Pat. No. 7,365,168. Mutations at positions 428 and 250 can result in increased half life. Additional mutations that can be combined with mutations at positions 234, 235 and 237 have been described in Section IV A in connection with antibodies that bind Aβ. Some such constant regions have no additional mutations present. Some such constant regions have no additional mutations present in and around regions of the IgG1 constant region affecting Fc gamma receptor and/or complement binding (e.g., residues 230-240 and 325-325 by EU numbering). The omission of a C-terminal lysine residue by intracellular processing is not considered to be a mutation. Likewise, naturally occurring amino acids occupying polymorphic sites differing between allotypes are considered natural rather than mutant amino acids.

XI. Experimental Models, Assays and Diagnostics

A. Animal Models

Such models include, for example, mice bearing a 717 (APP770 numbering) mutation of APP described by Games et al., supra, and mice bearing a 670/671 (APP770 numbering) Swedish mutation of APP such as described by McConlogue et al., U.S. Pat. No. 5,612,486 and Hsiao et al., *Science*, 274, 99 (1996); Staufenbiel et al., *Proc. Natl. Acad. Sci. USA*, 94:13287-13292 (1997); Sturchler-Pierrat et al., *Proc. Natl. Acad. Sci. USA*, 94:13287-13292 (1997); Borchelt et al., *Neuron*, 19:939-945 (1997)); Richards et al., *J. Neurosci.* 23:8989-9003, 2003; Cheng, Nat. Med. 10(11): 1190-2, 2004 Hwang et al., Exp Neurol. 2004 March Mutations of APP suitable for inclusion in transgenic animals include conversion of the wild-type Val717 (APP770 numbering) codon to a codon for Ile, Phe, Gly, Tyr, Leu, Ala, Pro, Trp, Met, Ser, Thr, Asn, or Gln. A preferred substitution for Val717 is Phe. Another suitable mutation is the arctic mutation E693G (APP 770 numbering). The PSAPP mouse, which has both amyloid precursor protein and presenilin transgenes, is described by Takeuchi et al., American Journal of Pathology. 2000; 157: 331-339. A triple transgenic mouse having amyloid precursor protein, presenilin and tau transgenes is described by LaFerla, (2003), Neuron 39, 409-421. Another useful transgenic mouse has both APP and TGF-β transgenes. Protein encoding sequences in transgenes are in operable linkage with one or more suitable regulatory elements for neural expression. Such elements include the PDGF, prion protein and Thy-1 promoters. Another useful transgenic mouse has an APP transgene with both a Swedish and 717 mutation. Another useful transgenic mouse has an APP transgene with an arctic mutation (E693G).

B. Assays to Detect Amyloid Related Pathologies

Contextual Fear Conditioning Assays.

Contextual fear conditioning (CFC) is a common form of learning that is exceptionally reliable and rapidly acquired in most animals, for example, mammals. Test animals learn to fear a previously neutral stimulus and/or environment because of its association with an aversive experience. (see, e.g., Fanselow, *Anim. Learn. Behav.* 18:264-270 (1990); Wehner et al., *Nature Genet.* 17:331-334. (1997); Caldarone et al., *Nature Genet.* 17:335-337 (1997)).

Contextual fear conditioning is especially useful for determining cognitive function or dysfunction, e.g., as a result of disease or a disorder, such as a neurodegenerative disease or disorder, an Aβ-related disease or disorder, an amyloidogenic disease or disorder, the presence of an unfavorable genetic alteration effecting cognitive function (e.g., genetic mutation, gene disruption, or undesired genotype), and/or the efficacy of an agent, e.g., an Aβ conjugate agent, on cognitive ability. Accordingly, the CFC assay provides a method for independently testing and/or validating the therapeutic effect of agents for preventing or treating a cognitive disease or disorder, and in particular, a disease or disorder affecting one or more regions of the brains, e.g., the hippocampus, subiculum, cingulated cortex, prefrontal cortex, perirhinal cortex, sensory cortex, and medial temporal lobe (see US 2008145373).

C. Phagocytosis Assays to Determine Antibody Effector Function

Antibodies can be screened for clearing an amyloid deposit in an ex vivo assay. A tissue sample from a brain of a patient with Alzheimer's disease or an animal model having characteristic Alzheimer's pathology is contacted with phagocytic cells bearing an Fcγ receptor, such as microglial cells, and the antibody under test in a medium in vitro. The phagocytic cells can be a primary culture or a cell line, such as BV-2, C8-B4, or THP-1. A series of measurements is made of the amount of amyloid deposit in the reaction mixture, starting from a baseline value before the reaction has proceeded, and one or more test values during the reaction. The antigen can be detected by staining, for example, with a fluorescently labelled antibody to Aβ or other component of amyloid plaques. A reduction relative to baseline during the reaction of the amyloid deposits indicates that the antibody under test has clearing activity.

Generally, isotype controls are added to ensure that the appropriate Fc-Fcγ receptor interaction is being observed. Additional controls include use of non-specific antibodies, and/antibodies with a known affinity for the Fγc receptors on the phagocytic cells. Such assays can be carried out with human or non-human tissues and phagocytic cells, and human, non-human, or humanized antibodies.

A variation on the ex vivo phagocytosis assay eliminates the need for an Aβ-containing tissue, although still allowing detection of the interaction between a particular antibody and Fcγ receptors. In this case, the assay relies on a solid matrix which is coated with antibody. The solid matrix is generally in a form that can be engulfed by a phagocytic cell, e.g., a bead or particle on the order of nanometers to several microns in size. The solid matrix can be conjugated to a detectable moiety, e.g., a fluorophore, so that the particle can be traced. Kits and materials for phagocytosis assays of this sort are commercially available, e.g., from Beckman Coulter (Fullerton, Calif.) and Molecular Probes (Eugene, Oreg.). An example of such an assay is provided in the Examples section.

D. Complement Binding Assays

Antibody effector function can also be determined by detecting the ability of an antibody to interact with complement, in particular, the C1q polypeptide (see, e.g., Mansouri et al. (1999) *Infect. Immun.* 67:1461). In the case of Aβ-specific antibody, a solid matrix (e.g., a multiwell plate) can be coated with Aβ, and exposed to antibody, and, in turn, exposed to labelled C1q. Alternatively, C1q can be attached to the matrix, and labelled antibody added. Alternatively, the antibody can be attached to the matrix and exposed to C1q, followed by detection of C1q. Such in vitro binding assays are common in the art and are amenable to modification and optimization as necessary.

E. Diagnostic Methods

Cognitive Function Assessment Tools.

A number of tools exist to quantify the cognition and mental function of dementia patients. These include the NTB, DAD, ADAS, MMSE, CDR-SOB, NINCDS-ADRDA criteria, and the RMHI (Rosen Modified Hachinski Ischemic) score. These tools are generally known in the art.

The NTB (Neuropsychological Test Battery) is composed of nine well-accepted tests of memory and executive function. The test battery is acceptable in the most recent EMEA guidance Patients are generally assessed in the following memory tests periodically: Weschsler Memory Scale Visual Paired Associates; Weschsler Memory Scale Verbal Paired Associates; and Rey Auditory Verbal Learning Test. The Executive function tests include: Wechsler Memory Scale Digit Span; Controlled Word Association Test; and Category Naming Test. This test is sensitive to change in mild AD patients and clinical effects of amyloid lowering agents.

The DAD (Disability Assessment for Dementia) test was developed and validated to measure the functional disability of patients with Alzheimer's disease (Gelinas et al. (1999) *Am J Occup Ther* 53:471-81.) Caregivers answer questions about the patients' ability to perform both instrumental and basic activities of daily living that had been attempted in the preceding two weeks. The proportion of DAD activities successfully completed out of those attempted is then determined and reported as a percentage.

The ADAS-Cog refers to the cognitive portion of the Alzheimer's Disease Assessment Scale (see Rosen, et al. (1984) *Am J Psychiatry* 141:1356-64.) The test consists of eleven tasks that measure disturbances in memory, language, praxis, attention and other cognitive abilities.

The NINCDS-ADRDA (Neurological and Communicative Disorders and Stroke-Alzheimer's disease Related Disorders Assessment) measures eight criteria affected in Alzheimer's: memory, language, perceptual skills, attention, constructive abilities, orientation, problem solving, and functional abilities (McKhann et al. (1984) *Neurology* 34: 939-44)

The MMSE (Mini Mental State Exam), CDR-SOB (Clinical Dementia Rating—Sum of Boxes, and RMHI (Rosen Modified Hachinki Ischemic) score are also known in the art (see, e.g., Folstein et al. (1975) *J Psych Res* 12: 189-198; Morris (1993) *Neurology* 43: 2412-2414; and Rosen et al. (1980) *Ann Neurol.* 17:486-488).

Biomarkers.

Biomarkers for Alzheimer's symptomology in humans can be measured using MRI volumetrics, blood and CSF protein levels, and PET (positron emission topography). For example, biomarkers to support antibody-Aβ engagement include Aβ40 and Aβ42 in the CSF and plasma, and amyloid plaque imaging, e.g., by PET. Biomarkers pointing to disease modification include brain morphology (MRI), CSF tau and phosphotau levels, and again, amyloid plaque imaging.

XII. Use of Tau to Monitor Immunotherapy

Method of immunotherapy involving administering an antibody to Aβ or an agent that induces such an antibody to a patient can be monitored by detecting tau in body fluids. The patient in such and other methods described herein is usually a human amenable to treatment as described above. Tau is a biomarker reported to be elevated in body fluids of Alzheimer's patients relative to the general population. Detection of tau can be performed, for example, in combination with any of the regimes described in the present application.

Monitoring usually involves at least two measurements of tau, one performed before initiation of immunotherapy, and a second after initiation (i.e., during or after immunotherapy). The second measurement is usually performed about 6-18 months after initiating immunotherapy, for example, 10-18 months, or 11-13 months or about a year after initiating immunotherapy. Third and further measurements can also be made after initiation of therapy. Additional measurements are usually made at a frequency between quarterly and every five ears, for example, twice yearly, annually or every two years.

Tau measurements are made on a body fluid, such as blood (e.g., serum or plasma), urine, saliva or preferably, the CSF. Either total tau (t-tau) or phospho-tau (p-tau) or both can be measured. Detection can be by immunoassay, such as an ELISA, with selection of antibodies determining whether total tau or phospho-tau is measured. A level of tau is typically expressed as mass or moles per volume body fluid. Kits for performing ELISA on t-tau or p-tau are commercially available, for example, from Santa Cruz Biotechnology, Inc. or Invitrogen, Inc. Preferred methods for measuring t-tau and p-tau are as described by Blennow, Mol Chem Neuropathol; 26:231-245 (1995) and Vanmechelen, Neurosci Lett; 285:49-52 (2000) (both incorporated by reference in their entirety for their description of tau and phospho-tau assays) respectively as further described in the Examples. Detection of t-tau includes detection of any or all of the natural human isoforms of t-tau found in the CSF or other body fluid. Likewise detection or p-tau includes detection of any or all forms of tau in phosphorylated state naturally occurring in the CSF or other body fluid. The same assay is preferably used in performing multiple determinations of the same analyte on the same patient to facilitate comparisons between different determinations at different times.

In general, a reduction in t-tau or p-tau (or both) in measurement(s) after initiating treatment compared to before initiating treatment indicates a positive response to treatment. A change is considered to be significant if a value determined after initiation of treatment lies outside the value preinitiation±the error in measurement (which can be assessed as one or two standard deviations corresponding to probabilities of significance of about 67 and 95% respectively). Reductions in an individual patient relative to a baseline measurement before initiating treatment of CSF t-tau of more than about 30 pg/ml or p-tau more than about 2.5 pg/ml are likely to be significant at the 95% confidence level. Exemplary changes in t-tau measured 12 months after initiation of treatment in patients showing a positive (i.e., effective) response to treatment are 30-150 or 40-110 pg/ml CSF t-tau. Exemplary changes in p-tau measured 12 months after initiation of treatment are 2-20, 3-17, 5-17 or 6-13 pg/ml CSF.

Changes in t-tau and -p-tau provide an indication of a positive response to treatment and whether the treatment regime needs to be changed. A positive response means at least that the treatment is moving a biomarker in a desired direction and is thus more likely (compared with the situation if the biomarker is not measured or does not change in a desired direction) to achieve a beneficial effect in the patient, such as inhibiting cognitive decline, if it has not already done so. In other words, a positive response is an indication, although not definitive evidence, of an effective regime. Significant changes in t-tau and p-tau may occur before changes in many or even all biomarkers tested, such as FFDG, BBSI, VBSI, CSF Aβ42 and before significant changes in cognitive indexes (including any or all described in the Examples) occur. Significant increases in amyloid deposits including Aβ in the brain may, however, precede changes in t-tau and/or p-tau. Changes in amyloid deposits including Aβ in the brain can be measured by PET scanning as further described in co-pending application 61/308,253 filed Feb. 25, 2010. In some methods, t-tau or p-tau is determined contemporaneously with other markers or cognitive indexes including any mentioned here. In other methods, t-tau or p-tau is measured without contemporaneous measurement of other markers or indexes. Whether or not other markers or indexes are measured, changes in t-tau or p-tau can be used to assess whether an immunotherapy regime has been achieving a positive outcome, and if not, assist in evaluating whether to continue or change the regime.

In general, if monitoring indicates that t-tau or p-tau has decreased relative to before initiation of treatment and/or relative to the last measurement, the regime can be continued. If monitoring indicates that t-tau or p-tau has decreased to a level found in the general population (e.g., within a mean±one or two standard deviations), the regime can be changed from induction to maintenance by decreasing the dose or frequency of the agent administered. If the monitoring indicates that t-tau or p-tau has remained the same within experimental error or has increased relative to before initiation of the regime or the last measurement, a change in regime can be considered. For example, the dose or frequency of administration of immunotherapy can be changed, usually with an increase. Alternatively, the regime can be left as is to determine if further administration and monitoring results in a decrease in t-tau or p-tau. If not, a change of regime can again be considered. If after changing the regime or if the patient is already receiving the maximum recommended dose and frequency of administration, and values of t-tau or p-tau have not decreased over a time period of 1-3 years from initiating immunotherapy, it is likely that the agent being used for immunotherapy is not effective on that particular patient and the regime is terminated. The patient can then be treated with a different immunotherapy agent or receive a non-immunotherapy drug or can receive only palliative care.

Although in an individual patient, determination of a significant change or lack thereof of t-tau or p-tau docs not necessarily signal an immediate change of regime, the association between t-tau or p-tau changes and regime change can be more clearly seen by looking at population of treated patients. In general, a change of regime following measurement of t-tau or p-tau occurs more frequently in patients showing unchanged or increased values of t-tau or p-tau relative to patients showing a decreased level of t-tau or p-tau.

XIII. Inhibition of Soluble-Aβ Induced Synaptotoxicity

Synapses are specialized intercellular junctions between neurons or between neurons and other excitable cells where signals are propagated from one cell to another with high spatial precision and speed. They are the primary sites of intercellular communication in the mammalian nervous system. In general, the basic structure of a synapse consists of a close juxtaposition of specialized regions of the plasma membrane of two neurons, referred to as the presynaptic and postsynaptic neurons, to form a synaptic junction. The presynaptic neuron is the nerve cell transmitting a signal while the postsynaptic neuron is the recipient of the signal. Most neurons in the vertebrate nervous system possess a cell body and two types of cell processes, axons and dendrites. Signals, i.e., action potentials, are initiated and transmitted by the axon while dendrites (and also the cell body) receive inputs via synaptic contacts from other neurons.

The present data show that insoluble, fibrillar Aβ does not bind to synapses whereas soluble-Aβ binds synapses. In particular, soluble-Aβ selectively targets and binds at excitatory synapses. An excitatory synapse is a cell-cell junction at which release of a chemical messenger by one cell causes depolarization of the external membrane of the other cell. An excitatory synapse describes a postsynaptic neuron which has a reversal potential that is more positive than the threshold potential and consequently, in such a synapse, a neurotransmitter increases the probability that an excitatory post synaptic potential will result (i.e., a neuron will fire producing an action potential). Reversal potentials and threshold potentials determine postsynaptic excitation and inhibition. If the reversal potential for a post synaptic potential ("PSP") is more positive than the action potential threshold, the effect of a transmitter is excitatory and produces an excitatory post synaptic potential ("EPSP") and the firing of an action potential by the neuron. If the reversal potential for a post synaptic potential is more negative than the action potential threshold, the transmitter is inhibitory and may generate inhibitory post synaptic potentials (IPSP), thus reducing the likelihood that a synapse will fire an action potential. The general rule for postsynaptic action is: if the reversal potential is more positive than threshold, excitation results; inhibition occurs if the reversal potential is more negative than threshold. See, for example, Chapter 7, NEUROSCIENCE, edited by Dale Purves, Sinauer Associates, Inc., Sunderland, Mass. 1997. By binding to synapses, soluble-Aβ induces reduction of synaptic efficacy and synaptic strength, leading to synaptotoxicity, e.g., synaptic impairment, synaptic dysfunction, synaptic loss, and neurodegeneration. The loss of synapses is often associated with the loss of presynaptic vesicle protein synaptophysin. In some cases, synapse loss is measured by the loss of synaptiphysin. Synaptic loss is an early and invariant feature of Alzheimer's disease the extent of which correlates closely with severity of dementia.

One of synaptic impairments induced by soluble-Aβ is internalization of AMPA receptors. An AMPA receptor is an aggregate of proteins found in some membranes, which allows positive ions to cross the membrane in response to the binding of glutamate or AMPA (DL-α-amino-3-hydroxy-5-methyl-4-isoxazolepropionic acid), but not NMDA. The terms internalization and endocytosis are used interchangeably to refer to a process in which AMPA receptor is drawn into the cell interior. It is believed that AMPA receptor internalization leads to behavioral deficits, such as memory deficits in an animal.

Soluble-Aβ induces spine loss, i.e., dendritic spine density loss. Dendrites are highly branched structure emanating from the cell body of the nerve cells. A dendritic spine is a small membranous protrusion from a neuron's dendrite that serves as a specialized structure for the formation, maintenance, and/or function of synapses. Dendritic spines vary in size and shape. For example, spines can have a bulbous head (the spine head) of varying shape, and a thin neck that connects the head of the spine to the shaft of the dendrite. Spine numbers and shape are regulated by physiological and pathological events. The sites of synaptic contact can be either a dendritic spine head or a dendritic spine shaft. It is believed that dendritic spine loss leads to loss of synapses in an animal.

Soluble-Aβ also induces hyperphosphorylation of Tau protein. Therefore, phospho-tau can serve as a marker for soluble-Aβ induced synaptotoxicity. Accordingly, methods of immunotherapy involving administering an N-terminal specific antibody to Aβ or an agent that induces such an antibody to a patient to treat soluble-Aβ induced synaptotoxicity can be monitored by detecting phospho-tau in body fluids.

The present data show that an N-terminal specific antibody to Aβ (e.g., 3D6 antibody), but not a C-terminal specific antibody to Aβ (e.g., 21 F12 antibody), inhibits soluble-Aβ induced synaptotoxicity. By binding to soluble Aβ, an N-terminal specific antibody to Aβ inhibits the binding of soluble Aβ to neurons, e.g., excitatory synapses. Consequently, an N-terminal specific antibody to Aβ inhibits the soluble-Aβ induced AMPA receptor internalization, soluble-AP induced Tau hyperphosphorylation, and synaptic loss. Administration of an N-terminal specific antibody to Aβ also inhibits behavioral deficits, e.g., memory deficits or contextual fear conditioning deficits. These therapeutic effects were not observed with the use of C-terminal specific antibody to Aβ.

IX. Screening Methods

The invention provides methods of screening an antibody for activity useful in treating Alzheimer's disease, e.g., inhibiting soluble Aβ-induced synaptotoxicity. The activity of an antibody or other agent in inhibiting soluble Aβ-induced synaptotoxicity can be determined by comparing the level of soluble Aβ-induced synaptotoxicity in samples treated with the antibody or other agent with the level of soluble Aβ-induced synaptotoxicity in samples not treated with the antibody or other agent. Relevant soluble Aβ-induced synaptotoxicity to be measured include soluble Aβ-induced synaptic loss, soluble Aβ-induced AMPAR internalization, soluble Aβ-induced spine density loss, soluble Aβ binding to synapses, soluble Aβ-induced tau phosphorylation, and behavioral tests. In addition, determination of soluble Aβ binding to synapses has been described in Lacor P N, et al. *J Neurosci* 24, 10191-200 (2004); Shughrue P J, et al. *Neurobiol Aging* 31, 189-202 (2010). Soluble Aβ-induced synaptic loss can be measured by synaptophysin immunohistochemistry as has been previously demonstrated (Buttini M, et al. (2005). *J Neurosci* 25, 9096-101). Soluble Aβ-induced AMPAR internalization can be measured according to procedures set forth in Hsieh H, et al. *Neuron* 52, 831-43 (2006); Zhao W Q, et al. *J Biol Chem* 285, 7619-32 (2010). Soluble Aβ-induced spine density loss can be characterized using methods discussed in Shughrue P J, et al. *Neurobiol Aging* 31, 189-202 (2010). Similarly, soluble Aβ-induced tau phosphorylation can be determined using methods known in the art (see, e.g., De Felice F G, et al. *Neurobiol Aging* 29, 1334-47 (2008); Blennow, Mol Chem Neuropathol; 26:231-245 (1995) and Vanmechelen, Neurosci Lett; 285:49-52 (2000)). Behavioral tests (e.g., the contextual fear conditioning behavioral assay) have been described previously (sec, e.g., Comery T A, et al. *J Neurosci* 25, 8898-902 (2005)). All references are incorporated by reference in their entirety for their description of soluble Aβ-induced synaptotoxicity assays. The procedures for measuring these soluble Aβ-induced synaptotoxicity are further described in the examples.

Antibodies or other agents can also be screened for activity in inhibiting soluble Aβ-induced synaptotoxicity using the in vitro assay described in Example 17. To screen for activity against soluble Aβ-induced synaptotoxicity, a tissue sample from a brain of a patient with Alzheimer's disease or a transgenic nonhuman animal having characteristic Alzheimer's disease's pathology is contacted with an agent.

Antibodies or other agents can also be screened for activity in inhibiting soluble Aβ-induced synaptotoxicity using the in vivo assay described in Example 17. Briefly, a test antibody is injected into (e.g., parenterally) a transgenic mice that overexpress human Aβ and have soluble Aβ. The transgenic animals used include, e.g., transgenic mice overexpressing human APP (Arendash et al., DNA Cell Biol. 20:737-744, 2001; Hartman et al., J. Neurosci. 22:10083-10087, 2002; Irizarry et al., J. Neurosci. 17:7053-7059, 1997; Murai et al., J Comp Neurol. 392:428-438, 1998; Nakagawa et al., J Comp Neurol. 411:390-398, 1999; Smith et al., Am J. Pathol. 153: 1005-1010, 1998). In one approach, the animals used are PDAPP mice that overexpress a mutant human APP that causes a form of autosomal dominant AD (Games et al., Nature 373:523-527, 1995). In another approach, the animals used are Tg2576 mice (Comery T A, et al. *J Neurosci* 25, 8898-902 (2005)). The test antibody and controls (e.g., irrelevant, iso type-matched control antibodies) are dissolved in a suitable solution (e.g., sterile phosphate-buffered-saline solution) for injection into mice.

EXAMPLES

Example 1

Phase 1 Trial 111 patients with a diagnosis of probable Alzheimer's disease (mild to moderate) were administered the humanized antibody bapineuzumab at doses ranging from 0.15 to 2.0 mg/kg in a multiple ascending dose study (MAD). Antibody was administered by intravenous infusion every thirteen weeks until the dosing regime is complete. Patients were also classified for ApoE4 status. Table 2 shows that eleven patients in the study experienced vasogenic edema detected by MRI. Table 2 also shows symptoms experienced in some of these patients; in other patients the vasogenic edema was asymptomatic. Table 3 shows the risk of vasogenic edema stratified by genotype irrespective of dose. The risk is only 2% in patients lacking an E4 allele but is 35% in patients with two E4 alleles. Table 4 shows the risk of vasogenic edema in only the highest dose group (2 mg/kg). The risk of vasogenic edema for patients with two E4 alleles is 60% and that for patients with one allele is 35%.

Table 5 shows the risk of vasogenic edema at different dosages. The risk of vasogenic edema is very low for all genotypes for doses between 0.15-0.5 mg/ml but starts to become significant for patients with two E4 alleles at a dose of 1 mg/kg and for patients with one E4 allele at 2 mg/kg. These data indicate that the risk of vasogenic edema is dependent on both ApoE genotype and dose and patients.

TABLE 2

| Study | Dose (mg/kg) | Dose # | E4 status | Symptoms |
|---|---|---|---|---|
| SAD | 5 | 1 | ND | — |
| SAD | 5 | 1 | ND | — |
| SAD | 5 | 1 | ND | dizziness, confusion |
| MAD | 0.15 | 2 | 4/4 | abn gait, confusion |
| MAD | 1 | 1 | 4/4 | visual |
| MAD | 1 | 1 | 4/4 | — |
| MAD | 1 | 2 | 3/4 | — |
| MAD | 2 | 1 | 4/4 | — |
| MAD | 2 | 1 | 3/4 | — |
| MAD | 2 | 1 | 4/4 | confusion |
| MAD | 2 | 1 | 3/4 | — |
| MAD | 2 | 1 | 3/4 | HA, lethargy, confusion |
| MAD | 2 | 2 | 3/4 | — |
| PET | 2 | 1 | 3/4 | — |
| MAD | 2 | 3 | 4/4 | — |

TABLE 3

| ApoE4 genotype (alleles) | VE cases genotype/ total VE cases | % of VE cases | VE cases/ patients exposed | % of patients exposed |
|---|---|---|---|---|
| 2 | 6/11 | 55% | 6/17 | 35% |
| 1 | 4/11 | 36% | 4/52 | 8% |
| 0 | 1/11 | 9% | 1/42 | 2% |

TABLE 4

| ApoE$_4$ genotype (alleles) | VE cases genotype/ total VE cases | % of VE cases | VE cases/ patients exposed | % of patients exposed |
|---|---|---|---|---|
| 2 | 3/7 | 43% | 3/5 | 60% |
| 1 | 3/7 | 43% | 3/9 | 33% |
| 0 | 1/7 | 14% | 1/14 | 7% |

TABLE 5

Number of patients (number developing vasogenic edema)

| ApoE4 copy # | 0.15 mg/kg | 0.5 mg/kg | 1.0 mg/kg | 2.0 mg/kg |
|---|---|---|---|---|
| 0 | 13 (0) | 11 (0) | 9 (0) | 14 (1) |
| 1 | 15 (0) | 14 (0) | 14 (1) | 9 (3) |
| 2 | 3 (1) | 4 (0) | 5 (2) | 5 (3) |

Example 2

Phase 2 Trial, Study 201

A randomized double-blind placebo-controlled multiple ascending dose study was conducted on a population of 234 patients randomized from an initial population of 317 screened patients. Patients were assessed for ApoE4 carrier status, but carriers (homozygous and heterozygous) and non-carriers received the same treatment. Inclusion criteria were: probable AD diagnosis; aged 50-85 years; MMSE score 16-26; Rosen Modified Hachinski Ischemic score≤4; Living at home or in a community dwelling with a capable caregiver; MRI consistent with diagnosis of AD; MRI scan of sufficient quality for volumetric analysis; stable doses of medication for treatment of non-excluded conditions; stable doses of AchEIs and/or memantine for 120 days prior to screen. The main exclusion criteria were: current manifestation of a major psychiatric disorder (e.g., major depressive disorder); current systemic illness likely to result in deterioration of the patient's condition; history or evidence of a clinically important auto-immune disease or disorder of the immune system; history of any of the following: clinically evident stroke, clinically important carotid or vertebro-basilar stenosis/ plaque, seizures, cancer within the last 5 years, alcohol/drug dependence within last 2 years, myocardial infarction within the last 2 years, a significant neurologic disease (other than AD) that might affect cognition. Kits of the invention and their accompanying labels or package inserts can provide exclusions for patients meeting any of the above exclusion criteria and any subcombinations thereof.

Four dose levels were employed (0.15, 0.5, 1.0 and 2.0 mg/kg) together with a placebo. 124 patients received bapineuzumab and 110 received a placebo. Of those patients, 122 and 107, respectively, were analyzed for efficacy. Bapineuzumab was supplied as a sterile aqueous solution in 5 ml vials containing: 100 mg of bapineuzumab (20 mg/mL), 10 mM histidine, 10 mM methionine, 4% mannitol, 0.005% polysorbate-80 (vegetable-derived), pH of 6.0. The placebo was supplied in matching vials containing the same constituents except for bapineuzumab. The study medication was diluted in normal saline and administered as a 100 ml intravenous (IV) infusion over ~1 hour The treatment period was for 18 months with 6 intravenous infusions at 13 week intervals. Safety follow-up visits, including MRI scans occurred 6 weeks following each dose. Following the treatment period patients were either monitored with a 1 year safety follow up for continued treatment in open label extension. The primary objective of the trial was to evaluate the safety and tolerability of bapineuzumab in patients with mild to moderate Alzheimer's disease. The primary endpoints for the study were (Alzheimer Disease Assessment Scale-Cognitive Subscale (ADAS-Cog), Disability Assessment Scale for Dementia (DAD) together with safety and tolerability). The ADAS-Cog 12 contains an additional test involving delayed recall of a ten item word list relative to the ADAS-Cog 11. The secondary objective of the study was to evaluate the efficacy of bapineuzumab in patients with mild to moderate Alzheimer's disease. Other end points were neuropsychological test battery (NTB), neuropsychiatric inventory (NPI), clinical dementia rating sum of boxes (CDR-SB), MRI brain volumetrics, and CSF measures.

A summary of the total population, the populations broken down by dosage group and populations broken down by carrier status is provided is the following tables.

TABLE 6

| | Demographics and Patient Characteristics | |
|---|---|---|
| | All Placebo N = 107 | All Bapineuzumab N = 122 |
| Age | 67.9 | 70.1 |
| Gender (% F) | 59.8 | 50.0 |
| Ethnicity (% Caucasian) | 95.3 | 96.7 |
| Years Since Onset | 3.7 | 3.5 |
| ApoE4 (% carrier) | 69.8 | 60.5 |
| Screening MMSE | 20.7 | 20.9 |
| % Cholinesterase or Memantine Use | 96.3 | 95.1 |

TABLE 7

| Bapineuzumab | Avg MMSE | Avg Age | Disease Duration | Disease Severity Mild | Moderate | % APOE Carrier | Con Alz Meds | # of patients Baseline | Wk 78 |
|---|---|---|---|---|---|---|---|---|---|
| 0.15 mg/kg | 20 | 70 | 4 | 29% | 71% | 64% | 100% | 31 | 24 |
| Placebo | 20 | 64 | 4 | 33% | 65% | 46% | 96% | 26 | 17 |
| 0.5 mg/kg | 21 | 71 | 4 | 48% | 51% | 58% | 91% | 33 | 17 |
| Placebo | 21 | 69 | 4 | 43% | 57% | 86% | 93% | 28 | 21 |
| 1.0 mg/kg | 21 | 69 | 3 | 43% | 55% | 69% | 97% | 29 | 25 |
| Placebo | 21 | 69 | 4 | 36% | 69% | 75% | 93% | 26 | 21 |
| 2.0 mg/kg | 2 | 70 | 3 | 63% | 34% | 53% | 90% | 29 | 17 |
| Placebo | 21 | 69 | 3 | 56% | 44% | 70% | 100% | 27 | 22 |

TABLE 7-continued

| Bapineuzumab | Avg MMSE | Avg Age | Disease Duration | Disease Severity Mild | Disease Severity Moderate | % APOE Carrier | Con Alz Meds | # of patients Baseline | # of patients Wk 78 |
|---|---|---|---|---|---|---|---|---|---|
| All Bapineuzumab | 21 | 70 | 4 | 46% | 53% | 61% | 95% | 122 | 83 |
| All Placebo | 21 | 68 | 4 | 42% | 59% | 69% | 96% | 107 | 81 |

TABLE 8

| | Carrier | | Non-carrier | |
|---|---|---|---|---|
| | Placebo N = 74 | Bapineuzumab N = 72 | Placebo N = 32 | Bapineuzumab N = 47 |
| Age | 68.6 | 71.2 | 66.1 | 69.1 |
| Gender (% F) | 59.5 | 48.6 | 62.5 | 51.1 |
| Ethnicity (% Caucasian) | 97.3 | 97.2 | 90.6 | 95.7 |
| Years Since Onset | 3.8 | 3.7 | 3.5 | 3.0 |
| Screening MMSE | 21.0 | 20.6 | 19.8 | 21.4 |
| % Cholinesterase or Memantine Use | 95.9 | 98.6 | 96.9 | 89.4 |

Comparison of the various dosage cohorts with placebo using a linear model of cognitive decline on ADAS-COG and DAD scales did not achieve statistical significance for any of the dosage cohorts or the combined dosage cohorts population.

The data were reanalyzed using a statistical model not assuming linear decline (a) based on all of the patients in whom efficacy was determined and (b) based only on patients who had received all six dosages ("completers") and not including patients who had dropped out for various reasons. The non-linear model is believed to be more accurate because the cognitive abilities do not necessarily decline linearly with time.

The results using the non-linear decline model for all of the patients in whom efficacy was determined (ApoE4 carriers and non-carriers combined) are shown in FIG. 1. MITT (modified intent to treat) analysis was done using the repeated measures model without assumption of linearity. Bars above the X-axis represent a favorable result (i.e., inhibited decline) relative to placebo. Although statistical significance was not obtained, a trend was observed for the combined dosage cohorts using the ADAS-cog and NTB scales ($0.1 \geq p \geq 0.05$).

Figure 2:
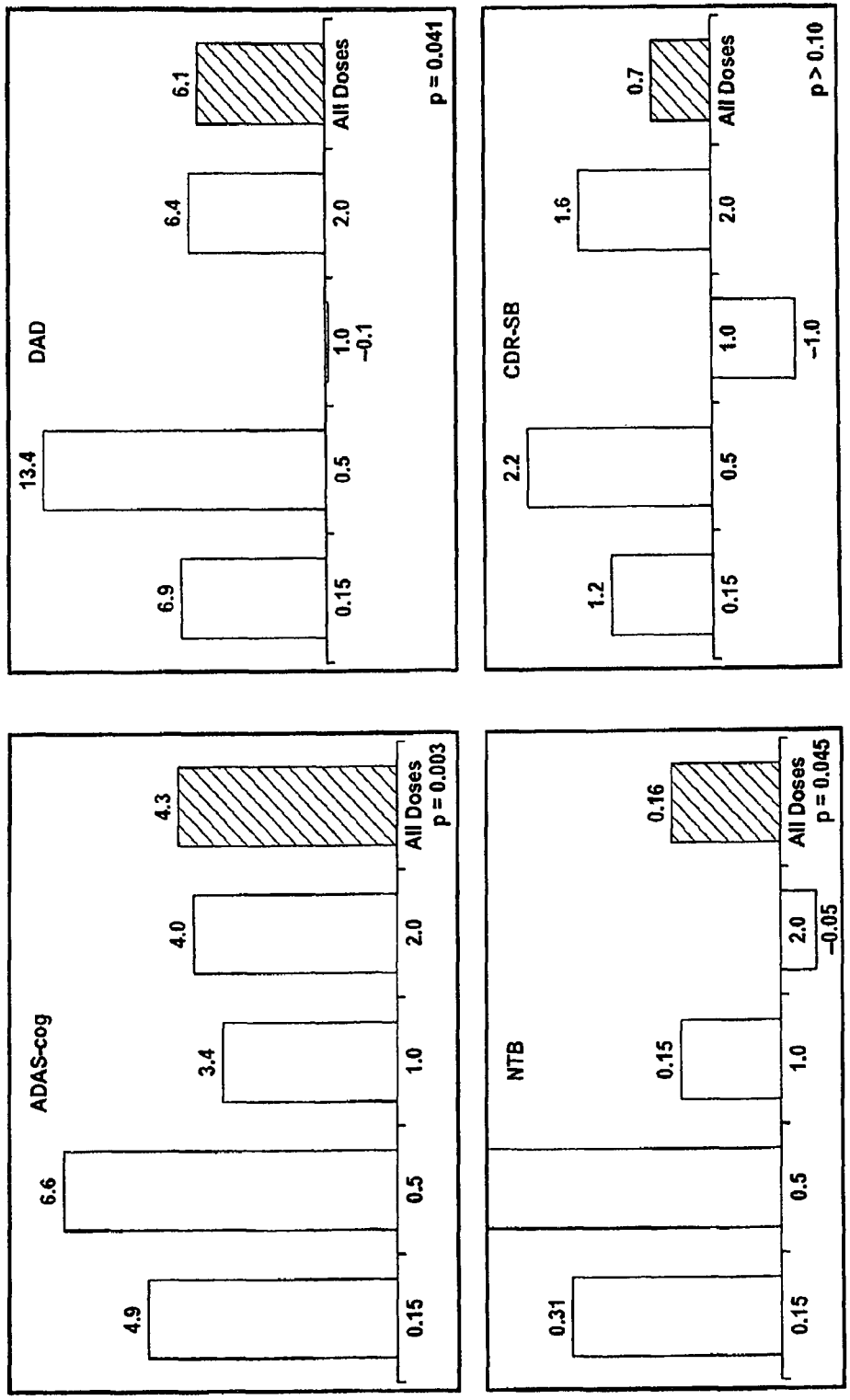
FIG. 2 shows changes in ADAS-Cog, DAD, NTB and CDR-SB in treated patients who completed the trials ("completers") relative to placebo patients using a repeated measures statistical model without assumption of linearity. Bars above zero indicate improvement relative to placebo.

The results for the completer populations (ApoE4 carriers and non-carriers combined) are shown in FIG. 2. Completers were defined as patients who received all 6 infusions and an efficacy assessment at week 78. Bars above the axis indicate improvement relative to placebo. Statistical significance was obtained for the combined dosage cohorts for ADAS-cog and DAD measurements and a positive trend ($0.1 \geq p \geq 0.05$) was found for NTB measurement.

Separate analyses were performed for ApoE4 carriers and non-carriers using the non-linear model and (a) all treated patients in whom efficacy was determined and (b) completers.

Figure 3:
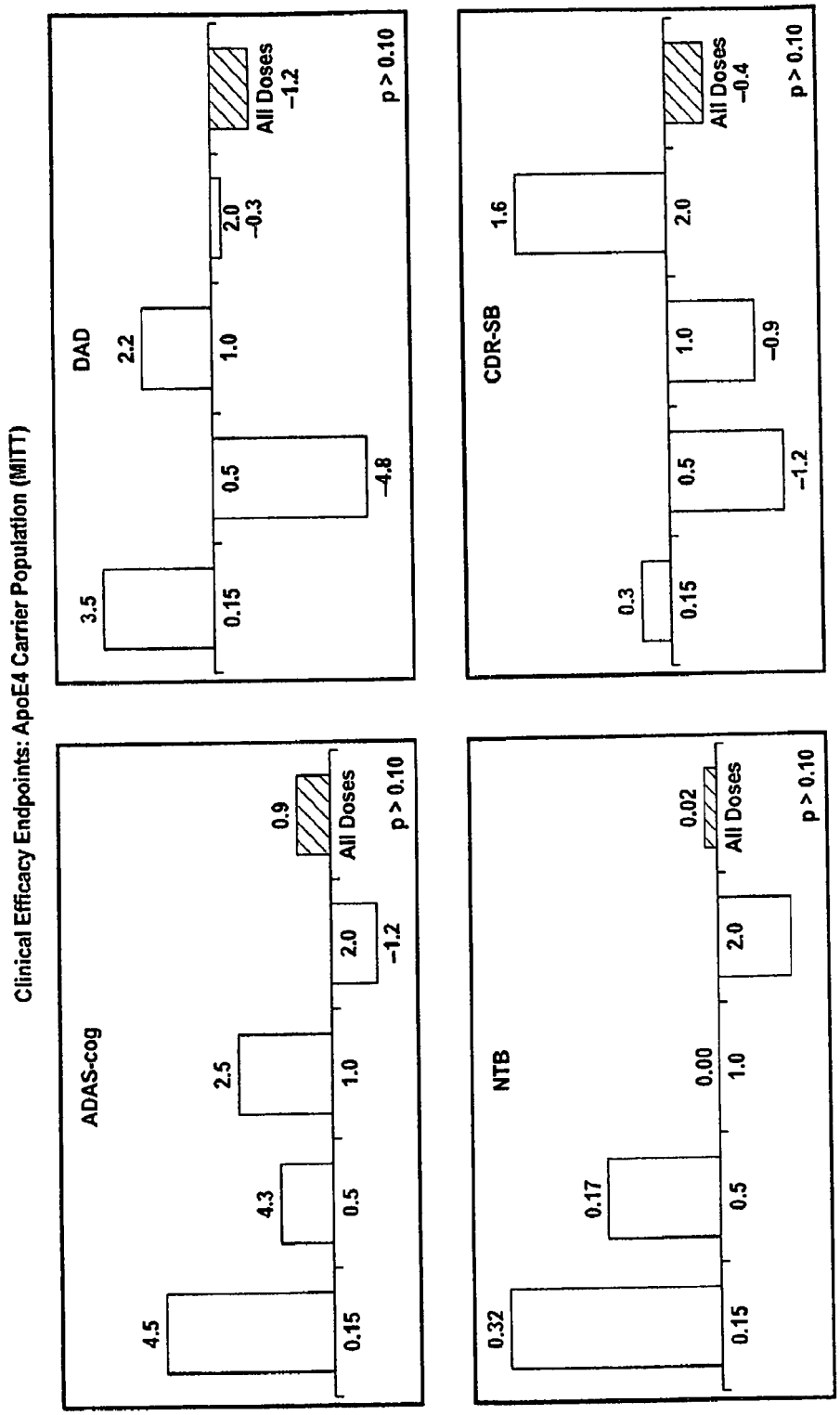
FIG. 3 shows changes in ADAS-Cog, DAD, NTB and CDR-SB in ApoE4 carrier treated patients relative to placebo patients using a repeated measures statistical model without assumption of linearity. Bars above zero indicate improvement relative to placebo.
Figure 4:
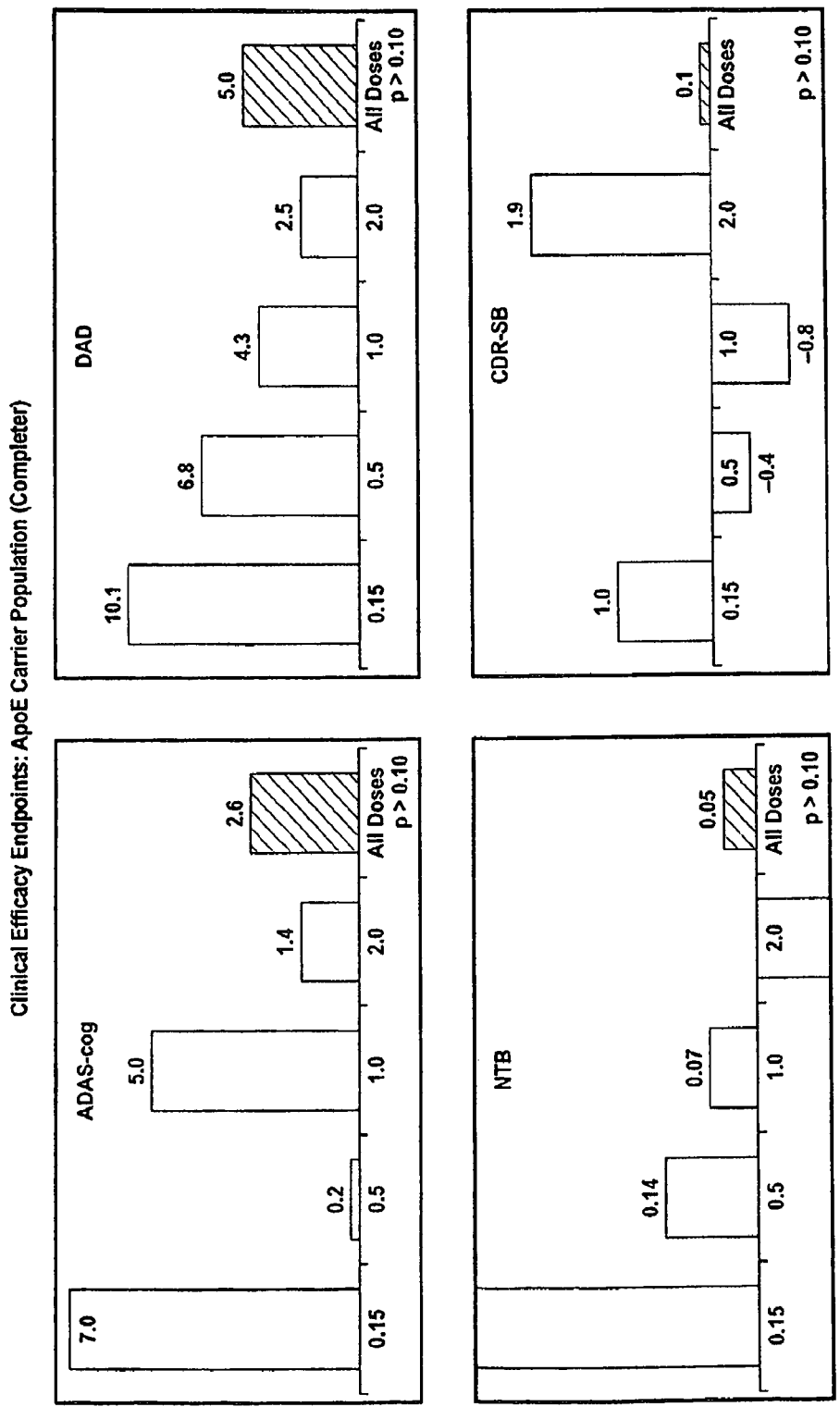
FIG. 4 shows changes in ADAS-Cog, DAD, NTB and CDR-SB in ApoE4 carrier treated patients who completed the trial relative to placebo patients using a repeated measures statistical model without assumption of linearity. Bars above zero indicate improvement relative to placebo.

FIG. 3 shows the results for all ApoE4 carrier patients in which efficacy was measured. Statistical significance was not found for any of the cognitive scales. Again, MITT analysis used repeated measures model without assumption of linearity. FIG. 4 shows the analysis for ApoE4 carrier completers, as defined above. Again, statistical significance was not found by any of the scales (ADAS-cog, DAD, NTB, and CDR-SB). However, favorable directional changes (bars above the axis) were found particularly for the ADAS-cog and DAD measurements.

Figure 5:
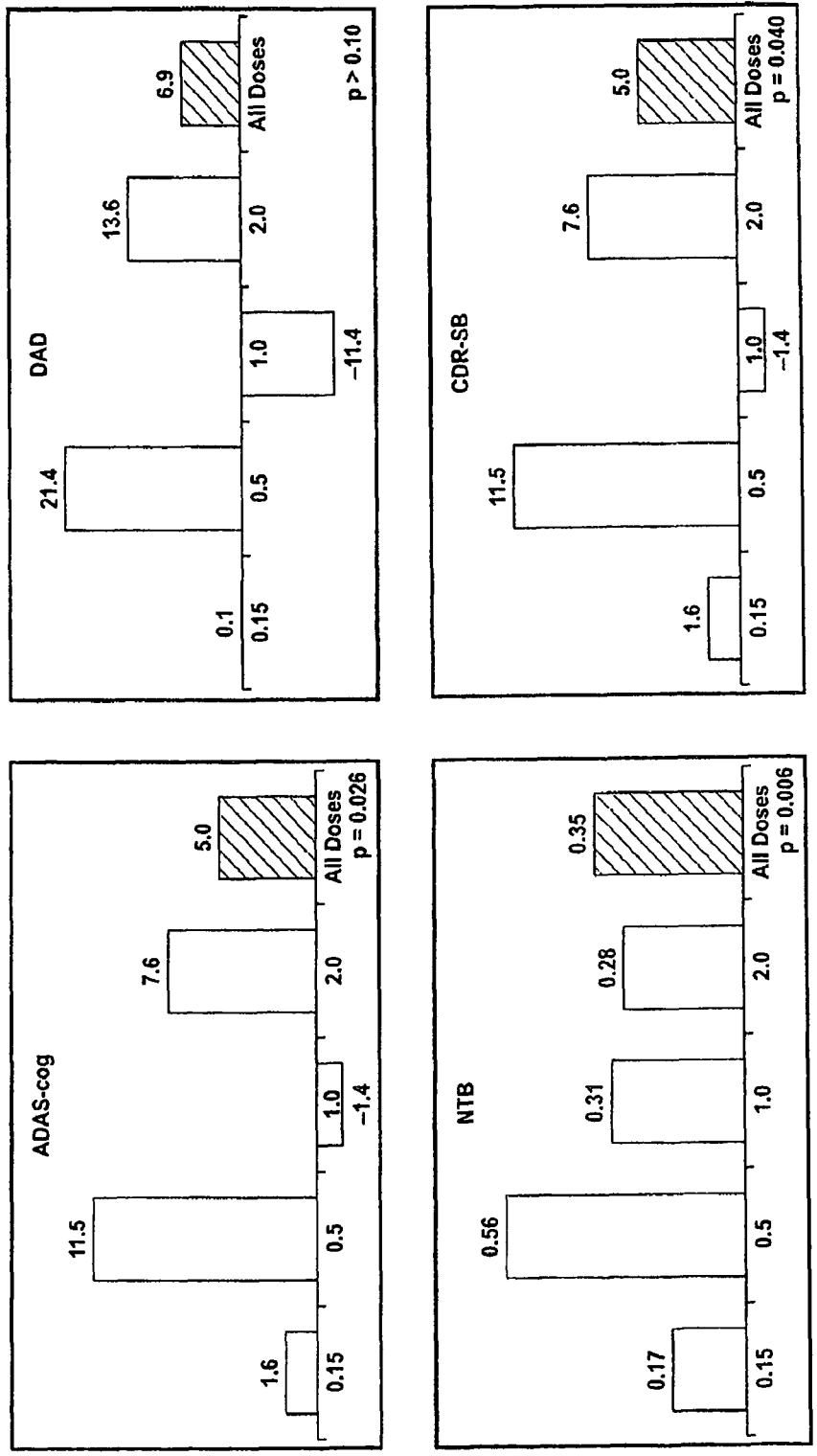
FIG. 5 shows changes in ADAS-Cog, DAD, NTB and CDR-SB in ApoE4 non-carrier treated patients relative to placebo patients using a repeated measures statistical model without assumption of linearity. Bars above zero indicate improvement relative to placebo.
Figure 6:
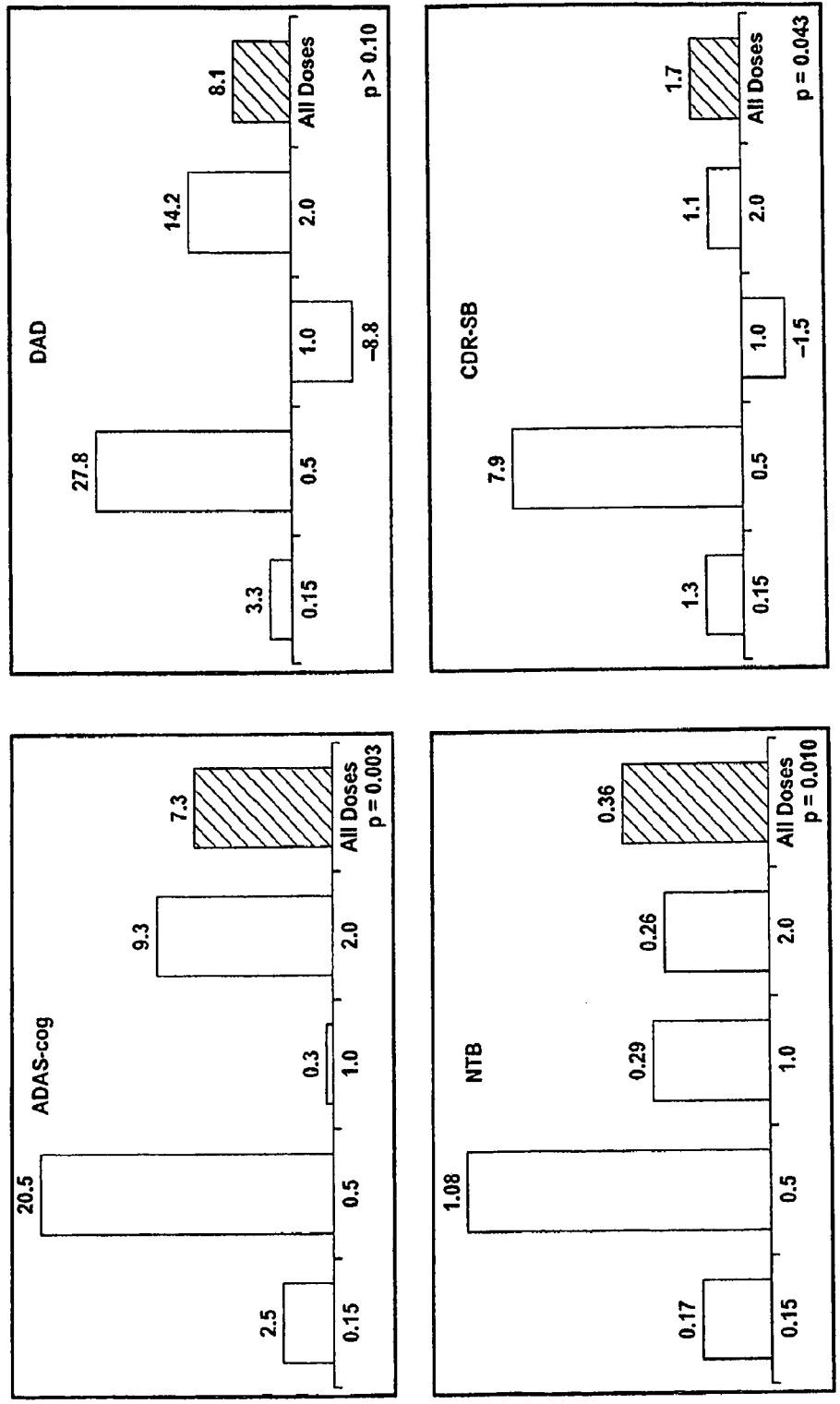
FIG. 6 provides similar information to FIG. 5 except that FIG. 6 shows changes based on the MMSE scale relative to placebo.
Figure 7:
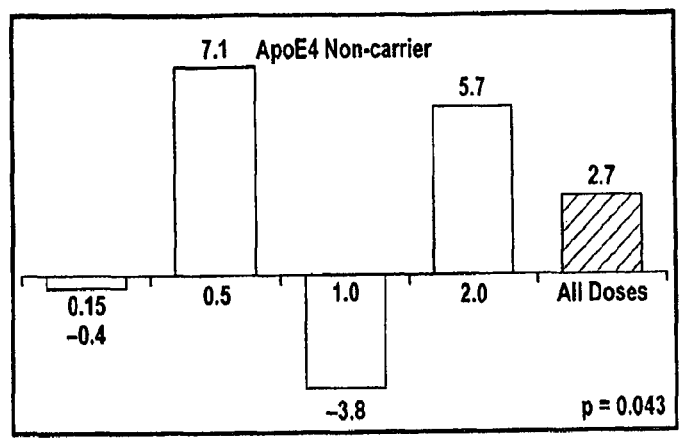
FIG. 7 shows changes in ADAS-Cog, DAD, NTB and CDR-SB in ApoE4 non-carrier treated patients who completed the trial relative to placebo patients using a repeated measures statistical model without assumption of linearity. Bars above zero indicate improvement relative to placebo.
Figure 8:
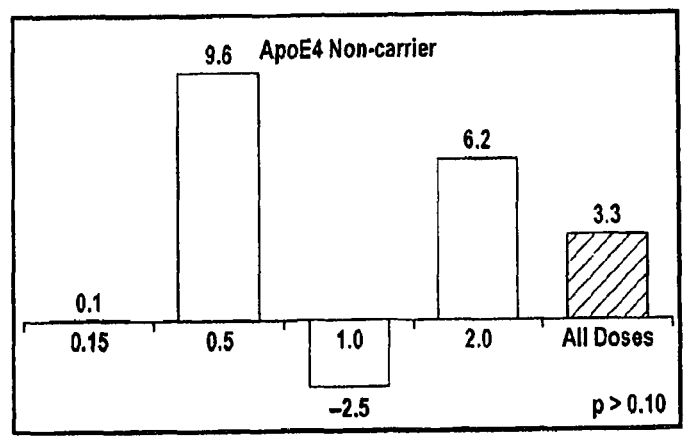
FIG. 8 shows similar information to FIG. 7 except that FIG. 8 shows changed based on the MMSE scale relative to placebo.
Figure 9:
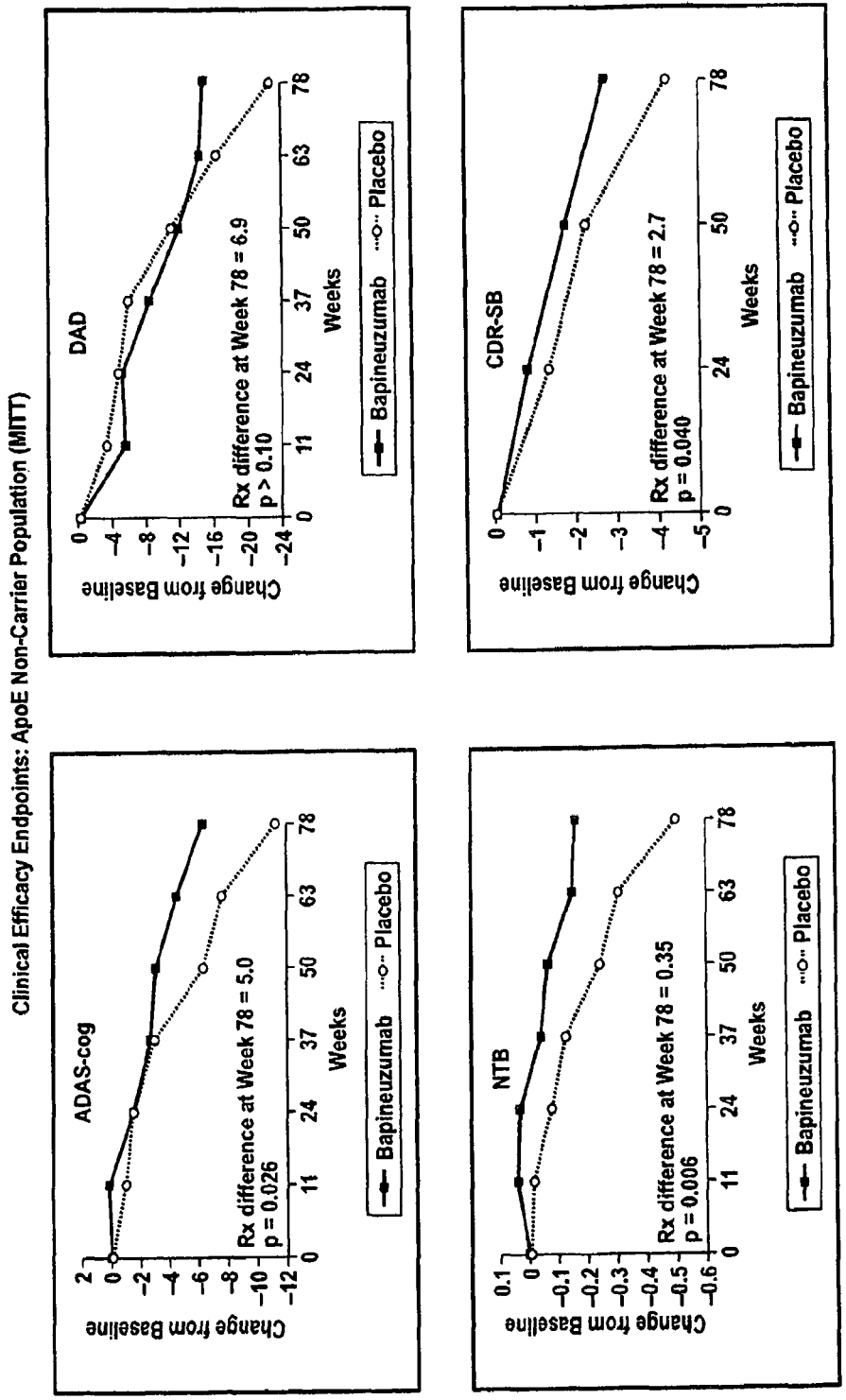
FIG. 9 shows changes in ADAS-cog, DAS, NTB and CDR-SB over time in treated patients compared with placebos in an ApoE4 non-carrier population.

FIGS. 5 and 6 show the results for all ApoE4 non-carrier patients in whom efficacy was measured. Statistical significance was obtained for ADAS-cog, NTB, CDR-SB and MMSE measurements for the combined dosage cohorts. Bars above the axis indicate improvement relative to placebo. FIG. 9 shows time course analysis of these parameters (ADAS-cog, upper left, DAD, upper right, NTB, lower left, CDR-SB, lower right). The decline in cognitive performance for treated patients was less than that of placebo at all time points on the ADAS-cog, NTB and CDR-SB scales. FIGS. 7 and 8 show the analysis for ApoE4 non-carrier completers, as defined above. Statistical significance was again obtained for ADAS-cog, NTB, CDR-SB and MMSE measurements. Again, bars above the axis indicate improvement relative to placebo.

MRI was performed up to seven times per patient during the study six weeks after each infusion. Changes in the brain were assessed by brain volume, ventricular volume, brain boundary shift integral and ventricular boundary shift integral. The boundary shift integral (BSI) as a measure of cerebral volume changes derived from registered repeat three-dimensional magnetic resonance scans. The BSI determines the total volume through which the boundaries of a given cerebral structure have moved and, hence, the volume change, directly from voxel intensities. The ventricular shift integral is a similar measurement of ventricular space changes. Both of these parameters increase as Alzheimer's disease progresses. Thus, inhibition of the increase in these parameters relative to placebo shows a positive (i.e., desired) effect of treatment.

In the total treated population (carriers and non-carriers) no significant differences were found for changes in brain volume measured by brain boundary shift integral or ventricular volume measured by ventricular boundary shift integral over 78 weeks compared with the placebo population.

In the treated non-ApoE4 carrier population brain volume decline was significantly lower than the non-ApoE4 placebo population (mean −10.7 cc; 95% CI: −18.0 to −3.4; p=0.004). The increase in ventricular volume compared to placebo was also reduced but the change did not reach statistical significance. There was no significant change in brain volume compared with the ApoE4 placebo population. However, the ventricular volume increased significantly compared to placebo (mean 2.5 cc; 95% CI: 0.1 to 5.1; p=0.037).

Figure 10:
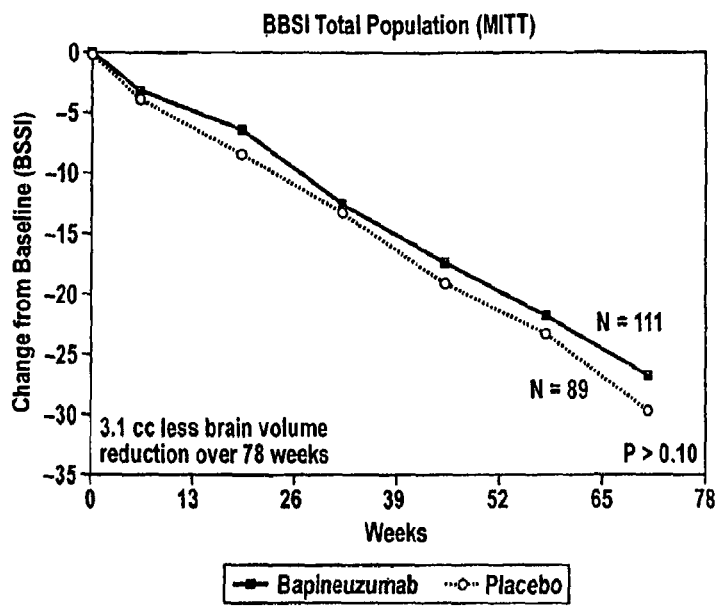
FIGS. 10, 11 and 12 show changes in BBSI in total population (ApoE4 carriers and non-carriers), ApoE4 carriers and ApoE4 non-carriers respectively compared with placebo populations.
Figure 11:
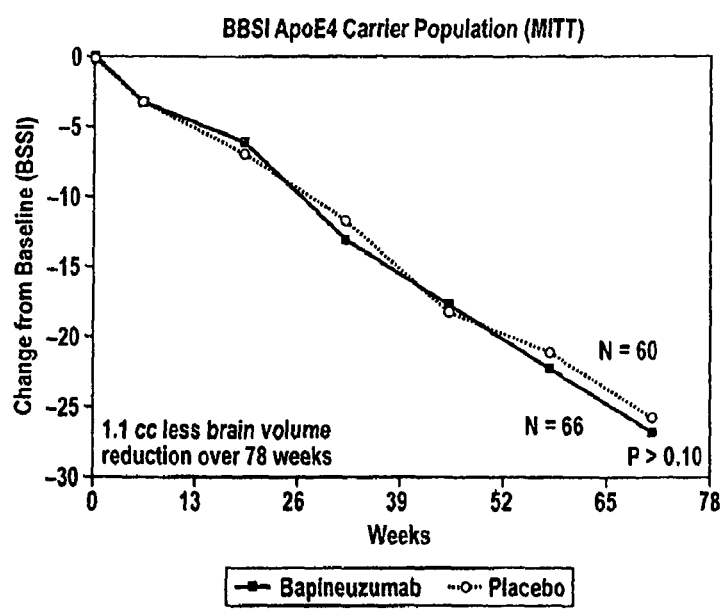
Figure 12:
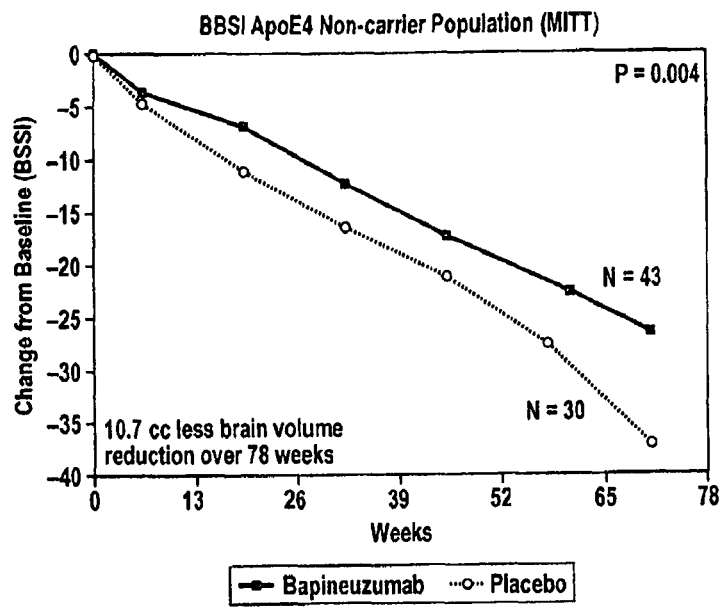

The changes of BBSI in the total population, ApoE4 carrier population and ApoE4 non-carrier population are shown in FIGS. 10-12. FIG. 12 (ApoE4 non-carriers) shows a statistically significant separation between the lines for treated patients and placebo. The change in brain volume was reduced in the treated population relative to placebo at all measured time points. FIG. 10 (combined ApoE4 carriers and non-carriers) shows separation of the lines for treated and placebo patients but the results did not reach statistical significance. FIG. 11 (ApoE4 carriers) shows the lines for treated and placebo patients are virtually superimposed. Analysis used repeated measures model with time as categorical, adjusting for APOE4 carrier status. Baseline was whole brain volume and MMSE stratum.

Figure 13:
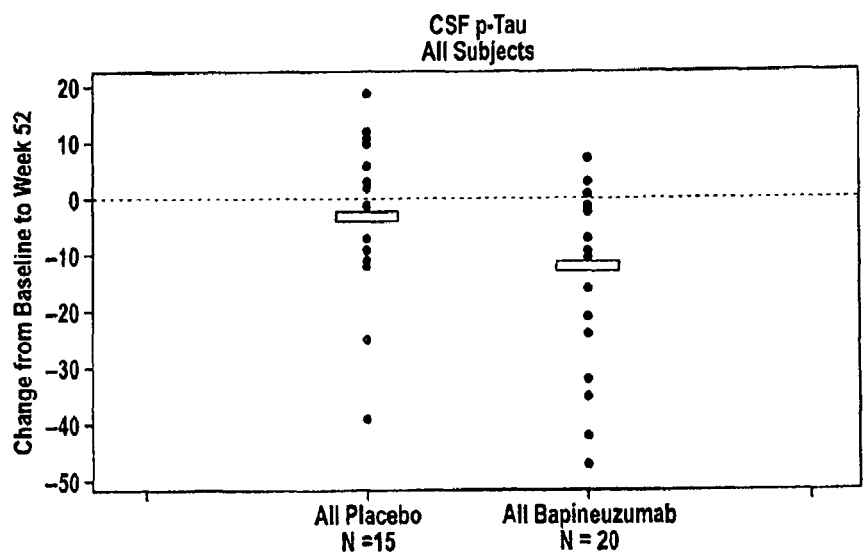
FIG. 13 shows CSF concentration of phospho-tau in treated patients compared with placebo patients (without distinguishing between ApoE4 genotypes).

A trend was observed for reduction in CSF phospho-tau in the bapineuzumab treated patient population relative to the placebo treated population at 52 weeks into the trials (FIG. 13). Phospho-tau is a biomarker associated with Alzheimer's disease. No significant differences were found between CSF levels of tau and Aβ42 between all treated patients and controls. The figure is based on ANCOVA analysis, adjusted for baseline value. One outlier was excluded in the 0.15 mg/kg placebo dose cohort.

Treatment was generally safe and well tolerated. Vasogenic edema (VE) occurred only in bapineuzumab treated patients. VE occurred with greater frequency in ApoE4 carriers (10) than non-carriers (2) and at greater frequency with increasing dose, there being 8, 3, 0 and 1 episodes at doses of 2.0, 1.0, 0.5 and 0.15 mg/kg respectively. All VE episodes occurred after the first or second dose. Most episodes of VE were detected only by MRI and had no detected clinical symptoms. The VE episodes resolved over weeks to months. In one patient, the VE was treated with steroids. Excluding VE, and excluding the 0.15 mg/kg cohort (which contained patients with more advanced disease than other cohorts), serious adverse events were similar between treated and placebo groups. Adverse events were generally mild to moderate, transient, considered unrelated to study drug, occurred in relatively small proportion of patients and did not appear to be dose-related.

Figure 14:
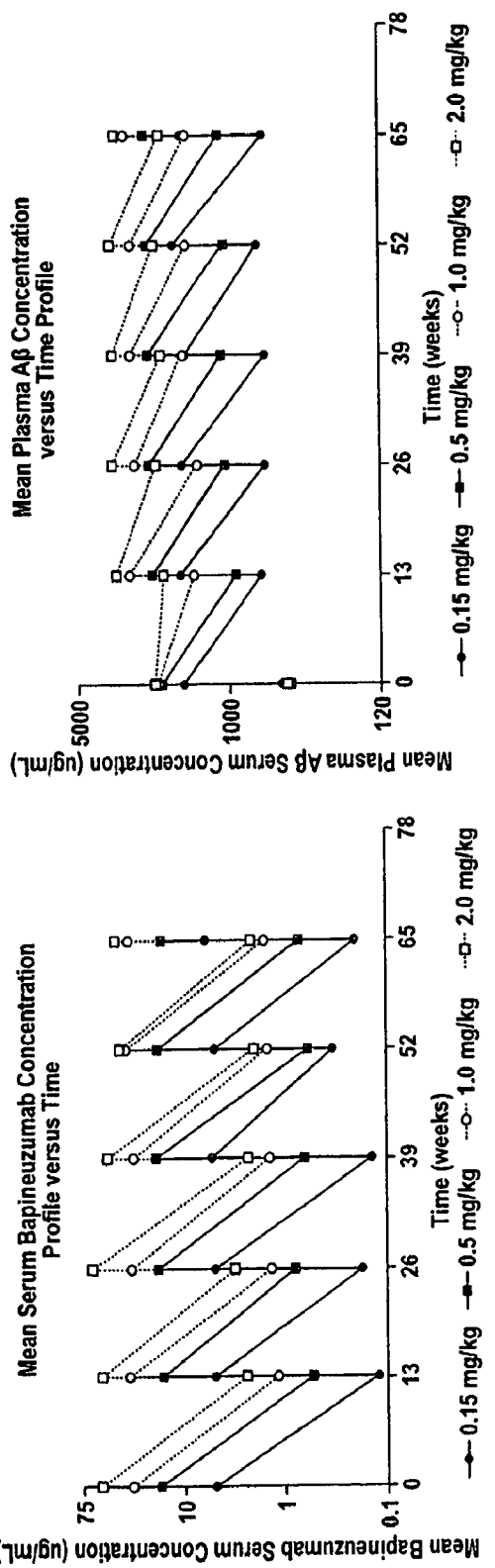
FIG. 14 shows changes in serum concentration of bapineuzuab in serum over time (left) and concentration of Aβ in plasma over time.

Serum concentration of bapineuzumab and plasma concentration of Aβ were measured in treated patients over time for the different dosage cohorts as shown in FIG. 14. The Cmax for serum bapineuzumab ranged from about 3.5-50 μg/ml in the different dosage cohorts from 0.15 mg/kg to 2.0 mg/kg. The profile of mean plasma concentration of Aβ mirrored that of mean serum bapineuzumab with the concentration of plasma Aβ rising on dosing with bapineuzumab and declining as the concentration of bapineuzumab declined. The concentration of plasma Aβ ranged from about 500-3000 pg/ml. The variation of plasma concentration of Aβ between different dosage cohorts showed less variation than the variation between doses. For example, increasing the dose from 0.15 mg/kg to 2 mg/kg increases plasma Aβ by about a factor of 2. The PK parameters after the first infusion of bapineuzumab are summarized in Table 9 below.

4. The trial provides evidence of trends or favorable directional changes in a total population (ApoE4 carriers and non-carriers) and ApoE4-carrier population by some measures. Statistical significance might be shown with larger populations. Alternative treatment regimes in these patients such as discussed above are likely to improve efficacy as discussed above.

5. The trial provides evidence that the treatment is generally safe and well tolerated.

Example 2B

Phase II Clinical Trial 202

The clinical trial was a phase 2, multicenter, randomized, double-blind, placebo-controlled, multiple-ascending dose study. Patients were randomly assigned to receive either intravenous (IV) bapineuzumab or placebo, in one of three dose cohorts (0.5 [A], 1.0 [B], or 2.0 [C] mg/kg). Up to 30 patients were planned for enrollment (10 per dose cohort with patients in each dose cohort [A, B, or C] receiving bapineuzumab or placebo in a 7:3 ratio). Patients who completed the screening phase and met all inclusion criteria were eligible for randomization. 28 patients were enrolled in the study (10 in cohort A, 10 in cohort B and eight in cohort C). The sponsor terminated enrollment in cohort C following the observation of more frequent cerebral vasogenic edema at the 2.0 mg/kg dose in other studies. Randomized patients received study drug as a 1-hour IV infusion every 13 weeks for up to six infusions. Each patient underwent [$^{11}$C]PiB PET, [$^{18}$F]FDG PET, clinical assessments of cognition and function, cerebrospinal fluid (CSF) sampling for Aβ and tau, volumetric and safety magnetic resonance imaging (MRI), and safety evaluations. The final assessment was at week 78.

Patients

Eligible patients were aged 50 to 80 years inclusive and met NINCDS-ADRDA (National Institute of Neurological and Communicative Disorders and Stroke—Alzheimer's Disease and Related Disorders Association [now known as the Alzheimer's Association]) criteria for probable AD. (McKhann, Neurology; 34:939-944 (1984). In addition,

TABLE 9

| Dose (mg/kg) | Cmax (μg/mL) | Cavg (μg/mL) | Cmin (μg/mL) | Tmax (days) | AUCinf (μg · h/mL) | CL/F (mL/hr/kg) | Vz/F (mL/kg) | T½ (days) |
|---|---|---|---|---|---|---|---|---|
| 0.15 | 4.6 | 0.7 | 0.1 ‡ | 0.1 | 1794 | 0.09 | 76.2 | 26.7 |
| 0.5* | 17.7 | 3.0 | 1.1 ‡ | 0.4 | 7165 | 0.07 | 63.7 | 26.4 |
| 1.0 | 28.0 | 5.5 | 1.8 ‡ | 0.1 | 13499 | 0.08 | 75.4 | 28.4 |
| 2.0 | 56.3 | 9.5* | 1.7 ‡ | 0.1 | 21802* | 0.09* | 65.8* | 20.5* |

N = 6 unless otherwise specified;
*n = 5
‡ - trough values of 2nd infusion; all values below limit of quantification for trough of 1st infusion
Abbreviations: Cavg - Average concentration over 13 weeks; Cmin - Minimum concentration ("trough"); Tmax - Time of maximum concentration; AUC inf - Area under Concentration vs. time curve extrapolated to infinity; CLss/F - ratio of the extravascular clearance at steady state (CLss) and extent of bioavailability (F); Vz/F - ratio of apparent volume of distribution at steady state (Vz) and F; t ½ - elimination (or terminal) half-life in days.

Conclusions

1. The trial provides evidence that ApoE4 carriers and non-carriers react differently to immunotherapy.

2. The trial provides evidence that vasogenic edema occurs more frequently in ApoE4 carriers and at higher dosages.

3. The trial provides statistically significant evidence of efficacy in non-ApoE4 carriers and in patients receiving at least 6 doses of bapineuzumab (ApoE4 carriers and non-carriers).

patients were required to have Aβ burden at baseline in the typical range expected for AD patients, defined as [$^{11}$C]PiB PET retention ratios relative to cerebellum in at least three brain regions among the anterior cingulate, posterior cingulate, frontal, temporal, and parietal cortices. Additional inclusion criteria were an MRI consistent with AD, a Mini-Mental State Exam (MMSE) score of 18-26, (Folstein, J Psychiatr Res; 12:189-198 (1975) and a Rosen Modified Hachinski Ischemic score (Rosen, Ann Neurol; 7:486-488 (1980). Patients were excluded for clinically significant neurological disease other than AD; a major psychiatric disorder, history of stroke or seizures, a Hamilton Rating Scale score for Depression>12; (Hamilton, J Neurol Neurosurg Psychiatry; 23:56-62 (1960) current anticonvulsant, antiparkinsonian, anticoagulant, or narcotic medications; recent immunosuppressive or cancer chemotherapy medications; or cognitive enhancers other than acetylcholinesterase inhibitors or memantine at a stable dose for at least 120 days before screening.

[$^{11}$C]PiB PET Methods

Details of the synthesis of [$^{11}$C]PiB and acquisition of PiB PET data have been previously described. Edison et al. Neurology; 68:501-508 (2007). Briefly, all [$^{11}$C]PiB images were acquired using a Siemens ECAT EXACT HR+ scanner after an attenuation scan that preceded an IV bolus of approximately 370 MBq [$^{11}$C]PiB (specific activity≥10 GBq/μmol at injection). The images were acquired in 32 frames over 90 minutes. Cortex:cerebellar ratio images of [$^{11}$C]PiB retention were generated at a single site (Hammersmith Imanet Ltd, GE Healthcare) using data from 60-90 minutes post-injection as previously reported. Edison et al., supra. [$^{11}$C]PiB PET images were co-registered to the individual's MRI, which was normalized into standard Montreal Neurological Institute (MNI) space. A probabilistic brain atlas was used to create a standard template of regions of interest (ROIs) for sampling segmented grey matter regions. (Hammers, et al. Hum Brain Mapp; 19:224-247 (2003). For analysis, six predefined cortical ROIs were included: the anterior cingulate, posterior cingulate, frontal, temporal, parietal, and occipital cortices. The average of all six ROTs was also calculated ([$^{11}$C]PiB average). [$^{11}$C]PiB PET scans were obtained at screening and weeks 20, 45, and 78.

[$^{18}$F]FDG PET, Clinical, CSF and MRI Outcome Measures

Parametric images of regional cerebral glucose metabolism (rCMR$_{glc}$) relative to brainstem were generated from the brain [$^{18}$F]FDG time activity curves between 35-55 minutes after tracer injection. The parametric rCMR$_{glc}$ images were transformed into MNI stereotaxic space, and a probabilistic atlas was used to define six cortical ROIs and their average ([$^{18}$F]FDG average), as for the [$^{11}$C]PiB analysis, at screening and at week 78.

The Alzheimer's Disease Assessment Scale-Cognitive subscale (ADAS-Cog), (Rosen, Am J Psychiatry; 141:1356-1364 (1984); Mohs., Alzheimer Dis Assoc Disord; 11 (Suppl 2):S13-S21 (1997). Disability Assessment for Dementia (DAD), (Gauthier, Int Psychogeriatr; 9 (Suppl 1):163-165 (1997). Neuropsychological Test Battery (NTB), (Harrison, Arch Neurol; 64:1323-1329 (2007) and MMSE (range 0-30) scales were administered approximately every 3 months; the Clinical Dementia Rating-Sum of Boxes (CDR-SB; range 0-18) (Morris J C., Neurology; 43:2412-2414 (1993) and Neuropsychiatric Inventory (NPI) (Cummings, Neurology; 44:2308-2314 (1994) were administered every 6 months. In patients consenting to lumbar puncture, CSF was obtained before treatment and at week 52. CSF biomarkers were measured by sandwich ELISAs for total tau, (Blennow, Mol Chem Neuropathol; 26:231-245 (1995) phospho-tau (P-tau181), (Vanmechelen, Neurosci Lett; 285:49-52 (2000) and Aβ42 (Andreasen, Arch Neurol; 56:673-680 (1999) (with the 4G8 antibody replacing 3D6 to measure Aβ$_{X-42}$). Volumetric and safety MRI scans were performed before treatment, at week 6, and then at 13-week intervals through week 71. Exploratory MRI outcomes included change in whole brain (BBSI) and ventricular volumes (VBSI) from baseline to week 71 as measured by the boundary shift integral (BSI) method. (Fox, Arch Neurol; 57:339-344 (2000).

Statistical Analysis

Primary Analysis

The prespecified primary analysis compared the pooled bapineuzumab and pooled placebo groups at week 78 using a repeated measures model (mixed model for repeated measures, MMRM). The response variable was the change from screening to weeks 20, 45, and 78 in the average [$^{11}$C]PiB cortical:cerebellar retention ratio across the six predefined cortical ROIs. The explanatory variables included treatment group, screening [$^{11}$C]PiB PET value as a continuous covariate, baseline MMSE category (high [22-26] vs low [18-21]), visit week (a categorical factor), and the interaction between treatment and visit week. The covariance matrix was chosen from a prespecified set based on Akaike's information criterion. The primary analysis was a two-sided test of the week 78 least squares mean difference with significance level α=0.05. The analysis included all patients in the modified intent-to-treat (MITT) analysis population, predefined as all randomized patients who received any amount of study drug and who had a screening and at least one valid post-baseline PET scan.

Exploratory Analyses

The six individual [$^{11}$C]PiB PET ROIs were analyzed using the same method as the overall [$^{11}$C]PiB PET average. The change from screening in the [$^{18}$F]FDG PET average was analyzed using analysis of covariance (ANCOVA) with model terms for treatment (pooled bapineuzumab vs pooled placebo), screening value, and baseline MMSE category. MRI and clinical endpoints were analyzed using the same method as [$^{11}$C]PiB PET average, except that the models for BBSI and VBSI included baseline whole brain volume and baseline ventricular volume as covariates, respectively. CSF variables were analyzed using the same ANCOVA approach as [$^{18}$F]FDG PET.

Due to apparent differences between the treated and placebo groups on some baseline assessments (e.g., NTB, CDR-SB, and [$^{11}$C]PiB PET) additional analyses adjusted for these imbalances: the MMRM and ANCOVA analyses described above were repeated without the screening/baseline covariate but with the addition of model terms for baseline NTB, CDR-SB, and [$^{11}$C]PiB average and, in the MMRMs, the corresponding covariate-by-visit interactions. Exploratory analyses were not adjusted for multiple comparisons.

Sample Size

Based on previously reported standardized uptake values, Klunk W E, Engler H, Nordberg A, Wang Y, Bloomqvist G, Holt D P, et al., Ann Neurol; 55 (3) 306-319 (2004)), it was estimated that there would be greater than 97% power to detect a treatment difference of 0.25 in [$^{11}$C]PiB retention between pooled bapineuzumab and pooled placebo in the change from screening to week 78, using a two-sided t-test at the 5% significance level. The study was not powered to evaluate efficacy on clinical or other biomarker outcomes.

Results

Patient Disposition

Of 53 screened patients, 28 were randomized (20 bapineuzumab vs eight placebo; 10 in the 0.5 mg/kg cohort, 10 in the 1.0 mg/kg cohort, and eight in the 2.0 mg/kg cohort). Eight screening failures did not meet the inclusion criteria because of low [$^{11}$C]PiB retention. Fifteen patients failed to meet other inclusion/exclusion criteria, and two did not complete enrollment. All randomized patients received at least one dose of bapineuzumab or placebo (safety population). Among those dosed, 26 (19 bapineuzumab; seven placebo) had a baseline and at least one post-baseline [$^{11}$C]PiB assessment and were included in the MITT population. Eighteen bapineuzumab patients (90.0%) and six placebo (75.0%)

patients were evaluated at week 78. Fifteen bapineuzumab (75.0%) and five (62.5%) placebo patients had [$^{11}$C]PiB assessments at week 78.

Baseline Demographics and Assessments

Baseline characteristics are summarized for the MITT population by treatment group in Table A. Baseline demographics were balanced between treatment groups. The baseline [$^{11}$C]PiB average of all six target regions trended lower for the pooled placebo group compared with the pooled bapineuzumab group (p=0.058). The same pattern held true for some individual ROIs, notably the anterior cingulate (p=0.029), frontal (p=0.040), posterior cingulate (p=0.077), and parietal cortex (p=0.053). Apparent baseline imbalances between the treatment groups were also observed on some of the clinical assessments, with evidence of milder disease (better performance) in the placebo group on the CDR-SB (p=0.007) and the NTB (p=0.040). Seventy-one percent (71.4%) of placebo-treated patients fell into the high MMSE category (22-26) compared with 36.8% of bapineuzumab-treated patients.

[$^{11}$C]PiB PET Results

In the prespecified primary analysis, bapineuzumab-treated patients showed a significant reduction in [$^{11}$C]PiB average retention at week 78 compared with the placebo group (−0.24, p=0.003). A trend (p=0.059) was observed for the treatment-by-time interaction, suggesting that the treatment difference increased over time. Within the bapineuzumab-treated group, a reduction in [$^{11}$C]PiB average retention at week 78 compared with baseline was observed (−0.09, 95% CI −0.157 to −0.019, p=0.014), while the placebo-treated group showed an increase (0.15, 95% CI 0.023 to 0.275, p=0.022).

Exploratory Clinical, [$^{18}$F]FDG, MRI, and CSF Outcomes

Treatment differences varied across the exploratory endpoints (Table B). After adjusting for baseline imbalances on the NTB, CDR-SB, and [$^{11}$C]PiB, treatment differences (p<0.05) were maintained for all PiB PET variables; however, no treatment differences were noted on the clinical, [$^{18}$F]FDG PET, MRI, or CSF endpoints.

TABLE A

Patient demographics and baseline characteristics (MITT population)

| | All bapineuzumab (N = 19) | All placebo (N = 7) | p value |
|---|---|---|---|
| Demographics/baseline characteristics | | | |
| Age, years (mean [SD]) | 67.3 (8.60) | 70.0 (8.81) | 0.481 |
| Gender, n (%) female | 8 (42.1) | 4 (57.1) | 0.665 |
| Race, n (%) white | 19 (100.0) | 7 (100.0) | 1.000 |
| Duration of AD, years (mean [SD]) | 3.4 (2.04) | 3.4 (2.45) | 0.971 |
| MMSE high (22-26), n (%) | 7 (36.8) | 5 (71.4) | 0.190 |
| ApoE4 status, n (%) carrier | 12 (63.2) | 5 (71.4) | 1.000 |
| AChEI or memantine use, n (%) | 19 (100.0) | 7 (100.0) | 1.000 |
| Imaging biomarkers, mean (SD) | | | |
| [$^{11}$C]PiB PET average | 2.06 (0.200) | 1.89 (0.193) | 0.058 |
| Anterior cingulate | 2.38 (0.266) | 2.12 (0.211) | 0.029* |
| Posterior cingulate | 2.37 (0.241) | 2.16 (0.302) | 0.077 |
| Frontal cortex | 2.10 (0.225) | 1.88 (0.207) | 0.040* |
| Temporal cortex | 1.83 (0.209) | 1.72 (0.217) | 0.255 |
| Parietal cortex | 2.03 (0.229) | 1.83 (0.206) | 0.053 |
| Occipital cortex | 1.66 (0.269) | 1.60 (0.202) | 0.620 |
| Whole brain volume (cc) | 1054.26 (104.162) | 1051.67 (149.453) | 0.963 |
| Ventricular volume (cc) | 57.17 (21.648) | 45.98 (41.357) | 0.550 |
| [$^{18}$F]FDG PET average | 1.24 (0.105) | 1.22 (0.080) | 0.645 |
| Clinical efficacy measures, mean (SD) | | | |
| ADAS-cog 11-item | 22.26 (7.649) | 19.19 (5.273) | 0.339 |
| ADAS-cog 12-item | 31.26 (7.075) | 27.33 (6.667) | 0.215 |
| CDR-SB | 5.61 (1.638) | 3.50 (1.500) | 0.007† |
| DAD | 84.38 (11.953) | 93.78 (8.239) | 0.069 |
| MMSE | 21.0 (2.33) | 22.3 (2.69) | 0.243 |
| NTB | −0.149 (0.5416) | 0.478 (0.8321) | 0.040† |
| NPI | 8.1 (8.01) | 5.3 (4.27) | 0.388 |

*p < 0.05; baseline imbalances indicate less [$^{11}$C]PiB uptake in placebo group.

†p < 0.05; imbalances indicate better performance in placebo group.

For continuous variables (represented as mean and SD), p values are calculated based on a two-sample t-test. For categorical variables (represented as counts and percentages), p values are calculated using Fisher's exact test.

AChEI = acetylcholinesterase inhibitor; AD = Alzheimer's disease; ADAS-Cog = Alzheimer's Disease Assessment Scale-Cognitive subscale; ApoE4 = apolipoprotein E4; CDR-SB = Clinical Dementia Rating-Sum of Boxes; DAD = Disability Assessment for Dementia; [$^{18}$F]FDG = 2-fluoro-2-deoxy-D-glucose; MITT = modified intent-to-treat; MMSE = Mini-Mental State Exam; NPI = Neuropsychiatric Inventory; NTB = Neuropsychological Test Battery; PET = positron emission tomography; PiB = Pittsburgh Compound B; [$^{11}$C]PiB average = [$^{11}$C]PiB average of all six cortical regions of interest; SD = standard deviation.

TABLE B

Treatment differences on [$^{11}$C]PiB, clinical, and biomarker endpoints
in prespecified analysis and after adjusting for baseline clinical scores
(NTB, CDR-SB) and [$^{11}$C]PiB average (MITT population)

|  | Prespecified analysis | | Adjusted analysis | |
|---|---|---|---|---|
|  | Treatment difference (95% CI) | p value | Treatment difference (95% CI) | p value |
| PiB endpoints |  |  |  |  |
| [$^{11}$C]PiB average | −0.24 (−0.385, −0.089) | 0.003 | −0.25 (−0.466, −0.034) | 0.025 |
| Anterior cingulate | −0.31 (−0.523, −0.099) | 0.005 | −0.31 (−0.611, −0.017) | 0.039 |
| Posterior cingulate | −0.25 (−0.450, −0.054) | 0.014 | −0.29 (−0.566, −0.016) | 0.039 |
| Frontal cortex | −0.24 (−0.409, −0.073) | 0.006 | −0.25 (−0.489, −0.002) | 0.048 |
| Temporal cortex | −0.21 (−0.332, −0.083) | 0.002 | −0.20 (−0.390, −0.007) | 0.043 |
| Parietal cortex | −0.23 (−0.384, −0.078) | 0.004 | −0.25 (−0.484, −0.016) | 0.037 |
| Occipital cortex | −0.20 (−0.315, −0.086) | 0.001 | −0.20 (−0.388, −0.021) | 0.030 |
| Clinical endpoints |  |  |  |  |
| ADAS-cog 11 | −8.41 (−17.924, 1.113) | 0.081 | −3.49 (−16.862, 9.887) | 0.594 |
| ADAS-cog 12 | −7.62 (−14.963, −0.273) | 0.042 | −3.40 (−13.614, 6.824) | 0.511 |
| DAD | −1.02 (−19.425, 17.387) | 0.910 | 15.20 (−1.777, 32.167) | 0.079 |
| CDR-SB | 0.39 (−2.727, 3.502) | 0.799 | 2.42 (−1.839, 6.681) | 0.251 |
| NTB | −0.12 (−0.735, 0.486) | 0.676 | 0.396 (−0.3235, 1.1145) | 0.266 |
| NPI | −0-52 (−7.975, 6.941) | 0.889 | 5.99 (−4.087, 16.071) | 0.235 |
| MMSE | −3.02 (−7.414, 1.381) | 0.178 | −0.62 (−6.511, 5.272) | 0.836 |
| Biomarker endpoints |  |  |  |  |
| [$^{18}$F]FDG (average) | −0.01 (−0.063, 0.049) | 0.796 | 0.00 (−0.080, 0.080) | 0.992 |
| BBSI | 0.57 (−10.319, 11.460) | 0.914 | −3.32 (−14.465, 7.832) | 0.554 |
| VBSI | 4.87 (−0.643, 10.393) | 0.080 | 3.65 (−1.302, 8.602) | 0.146 |
| CSF Aβ$_{x-42}$ | 52.9 (−316.79, 422.63) | 0.745 | 126.0 (−781.83, 1033.73) | 0.720 |
| CSF tau | −93.5 (−272.69, 85.74) | 0.257 | −165.1 (−542.26, 212.12) | 0.291 |
| CSF p-tau | −5.0 (−25.31, 15.36) | 0.581 | −19.2 (−39.82, 1.35) | 0.060 |

For PiB and clinical endpoints, the prespecified analysis was based on the week 78 treatment difference estimated using least squares means from an MMRM with change from baseline (screening) as the response and with model terms for treatment group with two levels (bapineuzumab and placebo), baseline score, baseline MMSE category, visit week (as a categorical variable), and the visit-by-treatment group interaction. The covariance matrix was chosen from a prespecified set based on Akaike's information criterion. The adjusted analysis removed the baseline covariate and added model terms for baseline NTB, CDR-SB, and [$^{11}$C]PiB average and the corresponding covariate-by-visit interactions. The MMRM analysis incorporates all MITT patients (N=19 for bapineuzumab, N=7 for placebo). For PiB endpoints, negative treatment differences indicate less PiB retention for bapineuzumab; for clinical endpoints, positive treatment differences favor bapineuzumab (due to conventions adopted for calculating change from baseline to represent improvement).

For BBSI and VBSI, the prespecified model was the same, except that estimates are based on week 71 (the final MRI visit), and instead of a baseline covariate, the model for BBSI included whole brain volume and for VBSI included baseline ventricular volume. The adjusted analysis removed these covariates and added model terms for baseline NTB, CDR-SB, and [$^{11}$C]PiB average and the corresponding covariate-by-visit interactions. The MMRM analysis incorporates all MITT patients (N=19 for bapineuzumab, N=7 for placebo). A negative treatment difference for BBSI indicates less brain volume loss in the bapineuzumab group compared with placebo. A positive treatment difference for VBSI indicates a greater ventricular volume increase in the bapineuzumab group compared with placebo.

For [$^{18}$F]FDG (average), the prespecified analysis was based on the week 78 treatment difference estimated using least squares means from an ANCOVA with change from baseline as the response and with model terms for treatment group with two levels (bapineuzumab and placebo), baseline score, and baseline MMSE category. The adjusted analysis removed the baseline covariate and added model terms for baseline NTB, CDR-SB, and [$^{11}$C]PiB average. The analysis is based on available week 78 [$^{18}$F]FDG (average) data (n=17 bapineuzumab, n=5 placebo). A positive treatment difference indicates greater [$^{18}$F]FDG retention compared with baseline for the bapineuzumab group compared with placebo.

For CSF variables, the prespecified analysis was based on the week 52 treatment difference estimated using least squares means from an ANCOVA with change from baseline as the response and with model terms for treatment group with two levels (bapineuzumab and placebo), baseline score, and baseline MMSE category. The adjusted analysis removed the baseline covariate and added model terms for baseline NTB, CDR-SB, and [$^{11}$C]PiB average. The analysis is based on available week 52 CSF data (n=7 bapineuzumab, n=4 placebo). Negative treatment differences for CSF tau and p-tau indicate greater reduction at week 52 relative to baseline in the bapineuzumab group compared with placebo. Positive treatment differences for CSF Aβ$_{X-42}$ indicate an increase relative to baseline in the bapineuzumab group compared with placebo.

ADAS-Cog=Alzheimer's Disease Assessment Scale-Cognitive subscale; ANCOVA=analysis of covariance; BBSI=brain boundary shift integral; CDR-SB=Clinical Dementia Rating-Sum of Boxes; CI=confidence interval, CSF=cerebrospinal fluid; DAD=Disability Assessment for Dementia; [$^{18}$F]FDG=2-fluoro-2-deoxy-D-glucose; MITT=modified intent-to-treat; MMRM=mixed model for repeated measures, MMSE=Mini-Mental State Exam; NPI=Neuropsychiatric Inventory;

NTB=Neuropsychological Test Battery; PiB=Pittsburgh Compound B; [11C]PiB average=[11C]PiB average of all six cortical regions of interest; VBSI=ventricular boundary shift integral.

Example 2C

Combined Analysis of Phospho and Total Tau in Clinical Trials 201 and 202

Study 201 enrolled 35 cases (20 bapinezumab, 15 placebo) in the CSF substudy and Study 202 11 cases (7 bapineuzumab and 4 placebo). CSF was collected at baseline and two weeks after the Week 52 infusion.
Results
Phospho Tau (P-Tau)
Study 201 showed a trend (p=0.0564) towards a decrease in CSF P-tau in bapineuzumab (−12.16±3.01 pg/mL) compared with placebo (−3.05±3.48 pg/mL) treated cases. In Study 202, a trend (p=0.06) was seen in the adjusted analysis. When combining data from both studies, a statistically significant decrease (p=0.0270) was found in bapineuzumab (−9.49±2.74 pg/mL) compared with placebo (−0.51±3.26 pg/mL) treated cases.
Total Tau (T-Tau)
Difference in CSF T-tau either in Study 201 (p=0.2063) or Study 202 (p=0.1723) did not reach a trend (p≤0.1). However, when data from both studies were combined, a trend (p=0.0856) for a decrease in CSF T-tau was found in bapineuzumab treated cases (−73.31±32.73 pg/mL) compared with placebo (+9.79±38.95 pg/mL) in the change from baseline to month 12 values.

Example 3

Clinical Study of Subcutaneous Administration of Bapineuzumab in Alzheimer's Patients Subcutaneous injections are generally easier to administer, which can be a consideration for patients with impaired mental function and coordination, or caregivers administering to an uncooperative patient. It is also easier to do at home, which is less upsetting to the patient, as well as less expensive. Finally, subcutaneous administration usually results in a lower peak concentration of the composition (Cmax) in the patient's system than intravenous. The reduced peak can reduce the likelihood of vasogenic edema.

For these reasons, a clinical study was designed for subcutaneous administration of bapineuzumab. The primary endpoints for the initial study are safety and bioavailability. Once these are established for subcutaneous administration, the cognitive tests described above will be administered to determine efficacy.

Under the initial regime, bapineuzumab is administered subcutaneously to patients every 13 weeks for 24 months, for a total of 9 doses. All patients receive a dose of 0.5 mg/kg. Patients are screened and periodically monitored as described in the above examples, e.g., for blood levels of the antibody, heart function, and vasogenic edema.

Example 4

Design of Specific Mouse and Human Antibodies

Variants of humanized and mouse 3D6 antibodies differing in isotype and or constant region mutations were constructed to test effects of reducing effector function on amyloid deposit clearing, cognitive function and microhemorrhaging. Mice treated with antibodies to Aβ proteins often exhibit signs of microhemorrhage in cerebral vessels, which is one factor that my be related to the vasogenic edema observed in human patients undergoing similar treatment.

Figure 15:
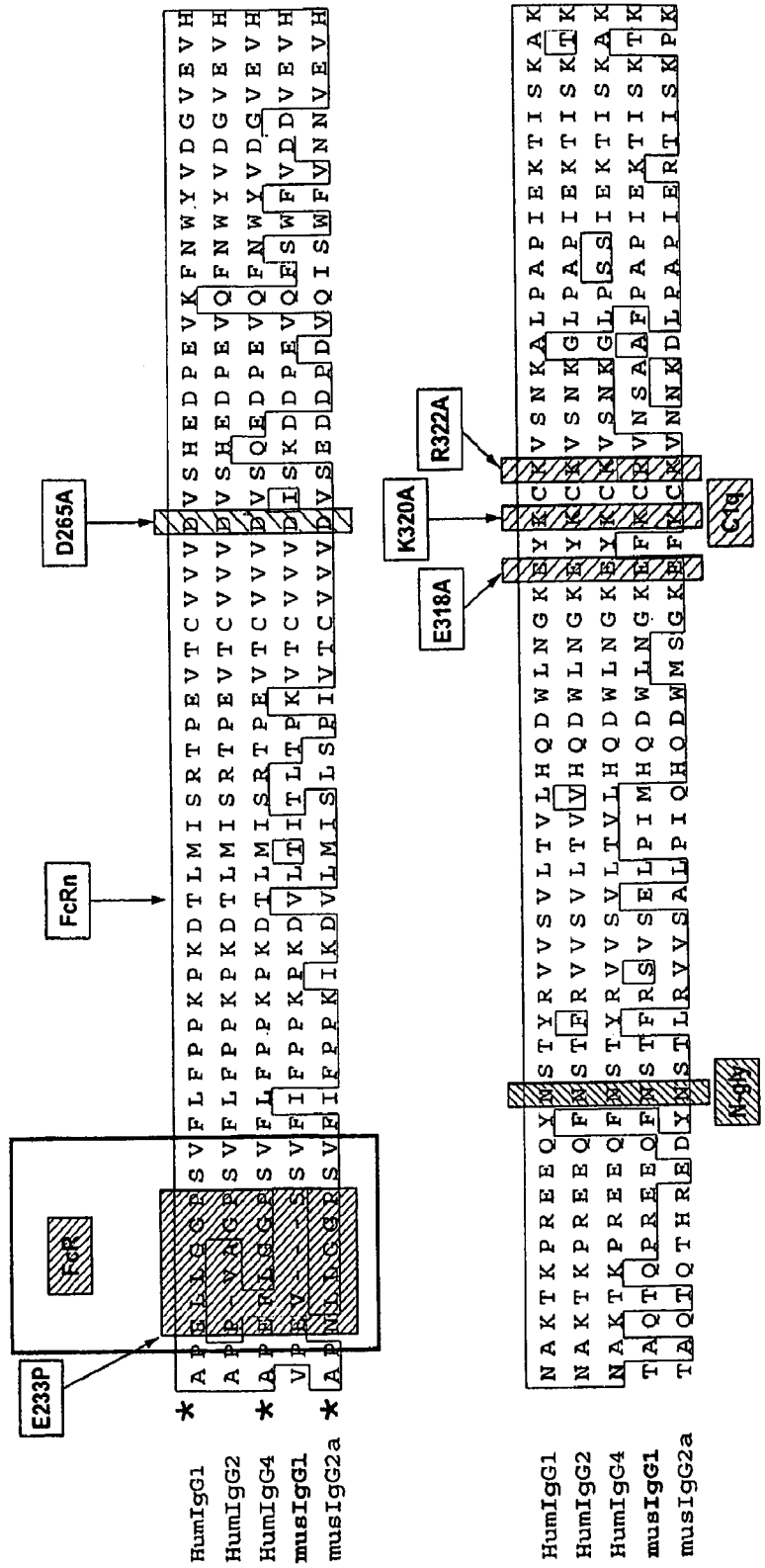
FIG. 15 shows an alignment of the CH2 domains of human IgG1 (SEQ ID NO: 95), IgG2 (SEQ ID NO: 96), and IgG4 (SEQ ID NO: 97) with mouse IgG1 (SEQ ID NO: 98) and IgG2a (SEQ ID NO: 99).

An alignment of the CH2 domains of human IgG1, IgG2, and IgG4 with mouse IgG1 and IgG2a are shown in FIG. 15. The alignment highlights the residues responsible for FcR and C1q binding. The C1q binding motif is conserved across species and isotypes. The FcR binding motif is conserved in human IgG1, IgG4, and murine IgG2a.

The following table discloses the particular modifications made to the CH2 region of the heavy chain. The amino acid numbering is by the EU system. The format is wildtype residue, position, mutant residue.

TABLE 10

3D6 Derivative Antibodies

| 3D6 Derivative Antibody | Isotype (species) | Mutated Residues |
|---|---|---|
| Bapineuzumab Control AAB-001 | IgG1 (human) | — |
| Humanized 3D6 2m (FcγR) | IgG1 (human) | L234A/G237A (EU numbering) |
| Humanized 3D6 3m (FcγR) AAB-003 | IgG1 (human) | L234A/L235A/G237A (EU numbering) |
| Humanized 3D6 1m (hinge region) | IgG4 (human) | S241P (Kabat numbering) |
| 3D6 Control | IgG1 (mouse) | — |
| 3D6 1m (FcγR) | IgG1 (mouse) | E233P |
| 3D6 3m (C1q) | IgG1 (mouse) | E318A/K320A/R322A |
| 3D6 4m (C1q) | IgG1 (mouse) | E318A/K320A/R322A/E233P |
| 3D6 Control | IgG2a (mouse) | — |
| 3D6 1m (FcγR) | IgG2a (mouse) | D265A |
| 3D6 4m (FcγR, C1q) | IgG2a (mouse) | L235A/E318A/K320A/K322A |

The epitope-binding regions of 3D6 derivative antibodies are the same, and the kinetics of Aβ binding are comparable. Table 11 discloses the kinetics of the Fc receptor binding to the 3D6 derivative antibodies listed in Table 10. These values were generated as follows.

For the humanized 3D6 derivative antibodies, the following assay conditions were used. A Biacore 3000 and CM5 chip coated with penta-His (SEQ ID NO: 93) antibody (Qiagen, Cat #34660) was used in combination with His-tagged domains of human FcγRI, FcγRII, and FcγRIII (R&D Systems, Cat #1257-Fc, 1330-CD, 1597-Fe). Each receptor was separately captured in one flow cell of the sensor chip by the penta-His (SEQ ID NO: 93) antibody. A solution of the antibody to be tested was injected to enable measurements of association and dissociation rates to the captured receptor. After measurements were completed, the receptors and experimental antibodies were removed by injection of buffer at pH2.5. The flow cell was then ready for the next cycle. Each cycle was carried out in duplicate, and the same conditions (e.g., concentrations, flow rates, and timing) were used for each sample.

As indicated by the values in Table 11, bapineuzumab (unmodified Fc region) bound to all of the human FcγR receptors with relatively high affinity. $K_D$ for FcγRI was in the nm range, while $K_D$ for FcγRII and III were in the μm range. For the latter two, the sensorgrams showed typical fast-on, fast-off kinetics. IgG4 isotype had similar binding to FcγRI, but did not bind FcγRIII, as expected. The two IgG1 derivatives, Hu 3D6 2m and 3m, did not show detectable binding to either FcγRI or FcγRIII.

For the mouse 3D6 derivative antibodies, similar methods were used to determine binding to mouse FcγRI, II, and III. FcγRI and III are activating receptors, while FcγRII is generally considered to be inhibitory. The antibodies tested were 3D6 IgG2a, 3D6 IgG1, and the IgG1 mutants, 3D6 1m, 3m and 4m. Results are expressed as a relative percentage of 3D6 IgG2a binding. As shown in Table 11, 3D6 IgG2a was the only antibody with detectable FcγRI binding ability. 3D6 IgG1 and the 3D6 3m IgG1 had similar FcγRII and III binding profiles.

TABLE 11

Fc Receptor Binding Ability of 3D6 Antibodies

| 3D6 Derivative | Relative Binding Capability* (%) | | |
|---|---|---|---|
|  | Human FcγRI** | Human FcγRII** | Human FcγRIII** |
| Bapineuzumab Control | 100 | 100 | 100 |
| Humanized 3D6 1m | 85-95 | 40-50 | 0 |
| Humanized 3D6 2m | 0 | 40-50 | 0 |
| Humanized 3D6 3m AAB-003 | 0 | 8-12 | 0 |
|  | Mouse FcγRI** | Mouse FcγRII** | Mouse FcγRIII** |
| 3D6 Control IgG2a | 100*** | 100 | 100 |
| 3D6 Control IgG1 | 0 | 180 | 70 |
| 3D6 1m IgG1 | 0 | 15 | 10 |
| 3D6 3m IgG1 | 0 | 180 | 70 |
| 3D6 4m IgG1 | 0 | 25 | 15 |

*Defined as the amount of binding in (RU) relative to that of IgG2a control at the steady state
**The mFcγRI and mFcγRIII are activating receptors, mFcγRII is an inhibitory receptor. Another potent activating receptor, mFcγRIV, is not commercially available.
***A steady-state binding was not reached. Kinetic fitting led to an estimate of $K_D$ in the nanomolar range.

The above results show that that the Hu 3D6 3m (AAB-003) antibody has the most reduced Fc gamma receptor binding of the three tested. Of those tested, the 3D6 1m IgG1 mouse mutant antibody was the most similar to AAB-003, in that its FcγR binding was reduced to near 10% of normal.

Example 5

Mouse Studies of 3D6 Derivative Antibodies

Study Design

One-year old PDAPP mice were exposed to a 6 month treatment paradigm with control or the 3D6 derivative antibodies described in Table 10. The negative control was a mouse IgG2a antibody to an irrelevant, non-amyloid epitope. The mice were injected IP with 3 mg/kg of the indicated antibody each week.

Serum antibody concentrations were tested over the course of the study by ELISA. Levels were comparable in all groups. After six months, the mice were sacrificed and perfused. Brain sections and tissues were prepared according to known methods (Johnson-Wood et al. (1997) *Proc. Natl. Acad. Sci., USA* 94:1550-55).

Amyloid burden was measured in the cortex and hippocampus of transgenic mice. Results in Table 12A and 12B are indicated as percentage reduction of area with amyloid (p values indicate significant difference compared to IgG2a control antibody).

TABLE 12A

Cortical Amyloid Burden (% reduction)

|  | Control IgG2a | 3D6 Control IgG2a | 3D6 Control IgG1 | 3D6 1m IgG1 (FcγR) | 3D6 3m IgG1 (C1q) |
|---|---|---|---|---|---|
| Median % Area | 6.25076 | 0.757259 | 1.24205 | 2.06056 | 1.50084 |
| Range | 0.069-17.073 | 0-9.646 | 0-17.799 | 0-24.531 | 0-17.069 |
| % Change | — | 88 | 80 | 67 | 76 |
| Control IgG2a |  | $p < 0.0001$ | $p < 0.0001$ | $p < 0.003$ | $p < 0.0001$ |
| % Change 3D6 IgG1 | — | — | — | 165.9 | 120.8 |
| Number | 32 | 34 | 36 | 36 | 34 |

TABLE 12B

Hippocampal Amyloid Burden (% reduction)

|  | Control IgG2a | 3D6 Control IgG2a | 3D6 Control IgG1 | 3D6 1m IgG1 (FcγR) | 3D6 3m IgG1 (C1q) |
|---|---|---|---|---|---|
| Median % Area | 20.36 | 8.462 | 12.29 | 12.18 | 8.435 |
| Range | 4.707-35.79 | 1.467-17.59 | 0.2449-18.61 | 0-26.99 | 0.8445-18.61 |
| % Change | — | 58 | 40 | 40 | 59 |
| Control IgG2a |  | $p < 0.0001$ | $p < 0.0001$ | $p < 0.0001$ | $p < 0.0001$ |
| % Change 3D6 IgG1 | — | — | — | 0.895 | 31.4 |
| number | 34 | 34 | 37 | 37 | 34 |

The above results indicate that all of the 3D6 antibodies (IgG2a, IgG1 and mutants) significantly reduced amyloid burden relative to negative controls. Differences between the tested antibodies were not statistically significant.

The effect of the 3D6 derivative antibodies was then tested on vascular amyloid ratings. Table 13 shows the number of mice with the indicated vascular amyloid rating and the percentage of animals with a rating of 4 or greater (p values indicate significant difference compared to 3D6 IgG2a antibody).

TABLE 13

| | % of Mice Having Vascular Amyloid | | |
|---|---|---|---|
| | None-little (0-3) | Moderate (4+) | Percentage with moderate rating |
| Control IgG2a | 11 | 24 | 69 |
| | | | $p < 0.0001$ |
| 3D6 Control IgG2a | 27 | 7 | 21 |
| 3D6 Control IgG1 | 12 | 25 | 68 |
| | | | $p < 0.0001$ |
| 3D6 1m (FcγR) IgG1 | 15 | 21 | 58 |
| | | | $p < 0.0016$ |
| 3D6 3m (C1q) IgG1 | 20 | 17 | 46 |
| | | | <0.0434 |

The above data show that the positive control 3D6 IgG2a significantly reduced vascular amyloid relative to the irrelevant IgG2a antibody. The reduction with 3D6 IgG2a was also statistically significant relative to that with 3D6 IgG1, 3D6 1 m IgG1 and 3D6 3 m IgG1. Differences between 3D6 IgG1, 3D6 1 m IgG1 and 3D6 3 m IgG1 and control IgG2a were not statistically significant.

To determine whether the 3D6 antibody derivatives cause microhemorrhage in mice, hemosiderin levels, a marker for microhemorrhage, were examined in brain sections of mice treated with 3 mg/kg antibody. Staining was carried out with 2% potassium ferrocyanide in 2% hydrochloric acid, followed by a counterstain in a 1% neutral red solution. Table 14 indicates the percentage and absolute number of mice with the indicated level of hemosiderin staining. The results demonstrate that 3D6 1m IgG1 (FcγR) and 3D6 3m IgG1 (C1q), which are shown above to be effective in clearing amyloid plaques, reduce microhemorrhage levels relative to 3D6 IgG2a. Differences between 3D6 IgG1, 3D6 1 m IgG1 and 3D6 3m IgG1 did not reach statistical significance, although the difference between 3D6 1m IgG1 and 3D6 IgG1 showed a trend. (p values indicate significant difference compared to 3D6 IgG2a antibody).

TABLE 14

| | Microhemorrhage level: | | | |
|---|---|---|---|---|
| | 0 | 1 | 2 | 3 |
| Control IgG2a | 68% (23) | 32% (11) | 0% (0) | 0% (0) |
| $p < 0.0001$ | | | | |
| 3D6 Control IgG2a | 9% (3) | 42% (14) | 27% (9) | 21% (7) |
| 3D6 Control IgG1 | 38% (14) | 46% (17) | 3% (1) | 13% (5) |
| $p < 0.0023$ | | | | |
| 3D6 1m IgG1 (FcγR) | 51% (19) | 49% (18) | 0% (0) | 0% (0) |
| $p < 0.0007$ | | | | |
| 3D6 3m IgG1 (C1q) | 53% (19) | 42% (15) | 0% (0) | 5% (2) |
| $p < 0.0001$ | | | | |

Example 6

Phagocytosis Assays

Materials and Methods

Ex vivo plaque phagocytosis assays: Frozen brain sections from PDAPP mice were pre-incubated with 3D6 IgG1 and the effector function mutants described in Table 10 (3D6 1m (FcγRI) and 3D6 3m (C1q), both mouse IgG1 isotype). 3D6 IgG2a was used as a positive control and irrelevant IgG1 and IgG2a antibodies were used as isotype controls. Sections were treated with 0.3 or 3 µg/ml antibody for 30 minutes prior to addition of mouse microglia, at 5% $CO_2$ at 37 C. The co-cultures were extracted the next day. Remaining Aβ was measured by ELISA (266 antibody for capture, and 3D6-B for reporter) to assess Aβ clearance.

Phagocytosis of murine IgG2a derivatives was tested. These experiments included: 3D6 IgG2a (positive control); non-specific IgG2a (negative control); 3D61m (FcγRI, IgG2a isotype); and 3D6 4m (FcγRI/C1q) antibodies. Conditions were similar to those described above.

Non-plaque phagocytosis was additionally determined for humanized 3D6 (Hu 3D6 IgG1) and the effector mutants described in Table 10 (Hu 3D6 2m IgG1, Hu 3D6 3m IgG1, and Hu 3D6 1m IgG4). The negative control was an irrelevant human IgG1 antibody. Assay and detection conditions were otherwise the same.

In vitro assays: For the mouse antibody assays of fluorescently conjugated bead phagocytosis, 10 µM FluoroSphere particles ($5 \times 10^6$) were opsonized with 1 mg/ml of mouse F(ab'2), 3D6 IgG2a, 3D6 IgG1, or the 3D6 FcγR mutant for 2 hrs at RT with rotation. Following 2 hrs, beads were washed with 1 ml of PBS 3 times to remove unbound IgG. Opsonized particles were added (1:10) to mouse microglia for the murine 3D6 Ig2a (3D62a) experiments. Beads were incubated with the cells for 90 min at 37 C. Unbound particles were then washed away with PBS. Cells were stained with DiffQuick for 30 sec for each stain and phagocytosis was visualized by light microscopy. Controls for this assay were un-opsonized beads (unlabelled) (to detect non-specific engulfment) and pre-treatment with human Fc-fragments (3D62a+FC)(to block FcγRI).

For humanized antibody assays, conditions and detection were the same. However, the antibodies were: no antibody (unlabelled; negative control), irrelevant human IgG1 (Human IgG1; positive control), Hu 3D6 IgG1, Hu 3D6 2m IgG1, Hu 3D6 3m IgG1, and Hu 3D6 1m IgG4. The phagocytic cells were human THP-1 cells (differentiated with PMA).

Results

Figure 16:
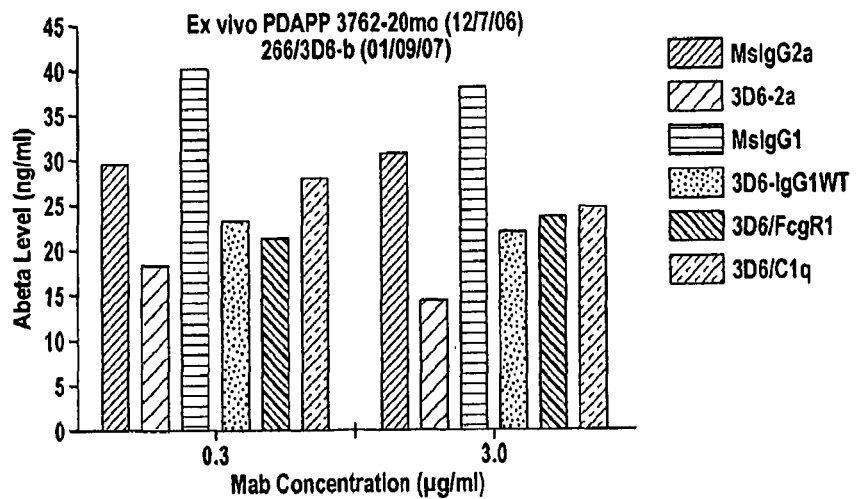
FIG. 16 shows Aβ plaque clearance by mouse microglia of murine 3D6 IgG1 derivatives. MsIgG1 and MsIgG2a are murine antibodies against irrelevant antigens. The 3D6 antibodies have the variable region described herein. 3D6/FcγR1 indicates the single E233P mutant in the Fc binding region of the IgG1 constant region. 3D6/C1q indicates the triple mutant in the C1q binding region. See, e.g., Example 6 and Table 10.

Ex vivo plaque phagocytosis assays: The murine 3D6 IgG1 antibody and its effector mutants (3D6 1m (FcγRI) and 3D6 3m (C1q)) were assayed to assess their ability to facilitate amyloid clearance (see FIG. 16). The 3D6 IgG2a antibody stimulated more robust clearance than 3D6 IgG1, 3D6 1m (FcγRI) and 3D6 3m (C1q). Stimulation of phagocytosis by 3D6 IgG1, 3D6 1m (FcγRI) and 3D6 3m (C1q) was greater than the negative control. Mutations to the Fc domain of 3D6 IgG1 do not appear to significantly dampen its ability to stimulate clearance in the ex vivo clearance assay.

Figure 17A:
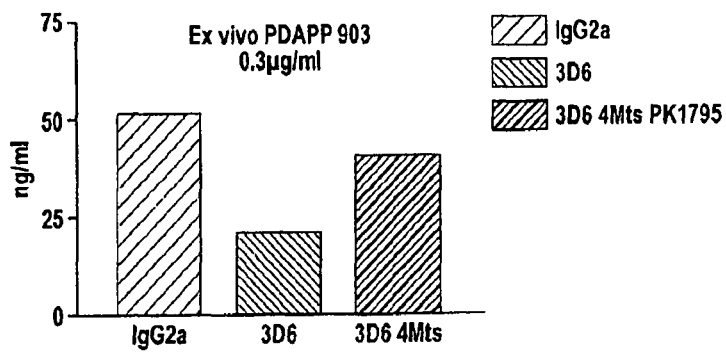
FIGS. 17A & B show Aβ plaque clearance by mouse microglia of murine 3D6 IgG2a derivatives. IgG2a is a murine antibody against an irrelevant antigen. The remaining antibodies and conditions are described, e.g., in Example 6 and Table 10.
Figure 17B:
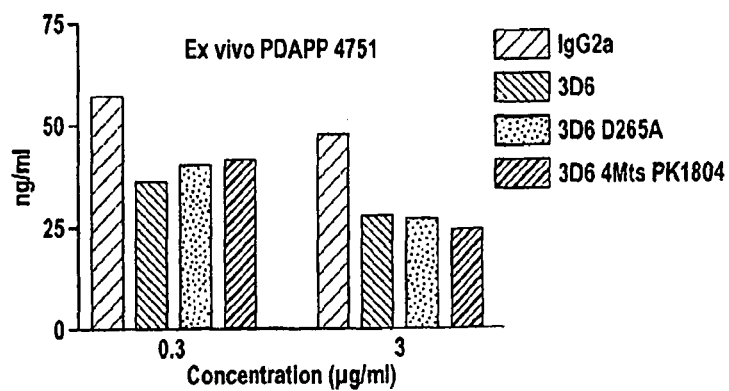

For the IgG2a 3D6 derivatives, the mutants stimulated clearance equivalent to wild-type 3D6 IgG2a and to a greater degree relative to an irrelevant IgG2 isotype matched control (see FIGS. 17A & B). Thus, neither of the mutants completely inhibited Aβ phagocytosis.

Figure 18:
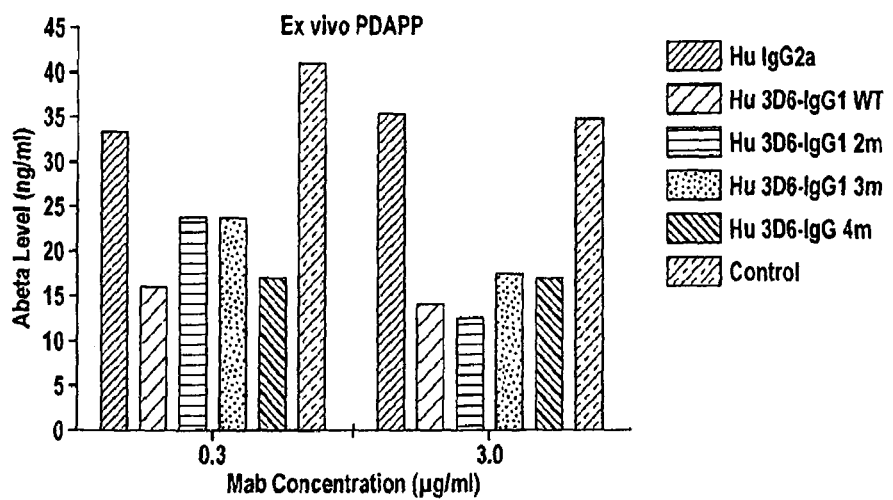
FIG. 18 shows Aβ plaque clearance by mouse microglia of humanized 3D6 derivatives (AAB). The antibodies and conditions are described e.g., in Example 6 and Table 10.

In the humanized antibody assays, mutations to the effector region of the Hu 3D6 IgG1 retained significant clearing activity relative to the negative control. Hu 3D6 IgG1 stimulated clearance in the ex vivo Aβ plaque clearance assay, and the effector region mutants had moderately impaired function. Hu 3D6 IgG4 induced phagocytosis to the same extent as Hu 3D6 IgG1, and mutation to the IgG4 hinge region of 3D6 did not appear to change its effector function (see FIG. 18).

Figure 19:
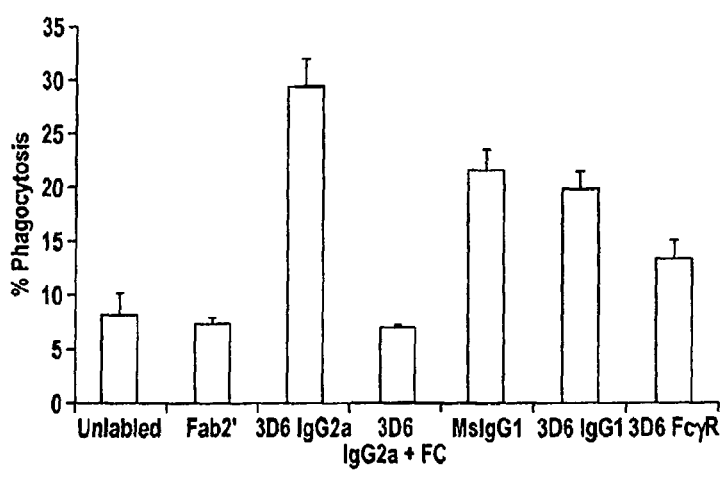
FIG. 19 shows results of an in vitro assay measuring engulfment of murine IgG-coated beads by mouse microglial cells. Conditions are described in Example 6.

In vitro bead phagocytosis assays: To determine if the ex vivo results were specific for Aβ clearance and whether the Fc mutation in the 3D6 IgG1 altered its effector function, non-specific Fc-mediated bead phagocytosis assays were performed. In the mouse antibody bead phagocytosis assay, the 3D6 IgG2a isotype antibody mediated more efficient phagocytosis than 3D6 IgG1 (see FIG. 19). The Fc mutation in 3D6 IgG1 did not significantly diminish the ability to stimulate phagocytosis, as compared to the positive control 3D6 IgG2a, indicating that the Fc mutation in 3D6 IgG1 was moderately effective in reducing phagocytosis.

Figure 20:
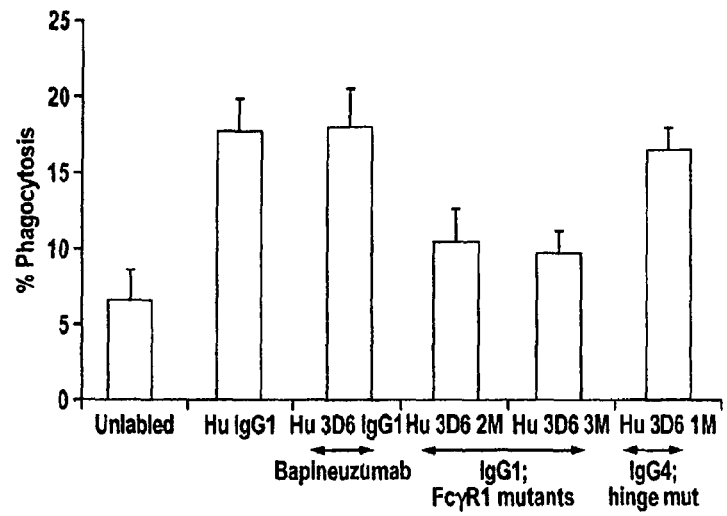
FIG. 20 shows a similar assay using the indicated humanized antibodies. Conditions are described in Example 6.

In the humanized antibody assay, the effect of the Fc mutation seen in the ex vivo plaque phagocytosis assay was verified on Fc-mediated bead phagocytosis. Again, the mutations in the Fc portion of humanized 3D6 diminished its ability to mediate phagocytosis of fluorescent beads and there was no significant difference between the 2m and 3m mutants. Again, the theoretically ineffective IgG4 isotype mediated removal to the same extent as the IgG1 isotype (see FIG. 20). Mutation to the IgG4 hinge region of 3D6 does not appear to change its effector function.

Example 7

C1q Binding Ability of Humanized 3D6 Derivatives

The humanized 3D6 derivatives were tested for ability to bind C1q and induce a complement response. A standard C1q dilution series protocol was followed, as described below. Similar protocols are described, e.g., in Idusogie et al. (2000) *J. Immunol.* 164: 4178-4184.

Figure 21:
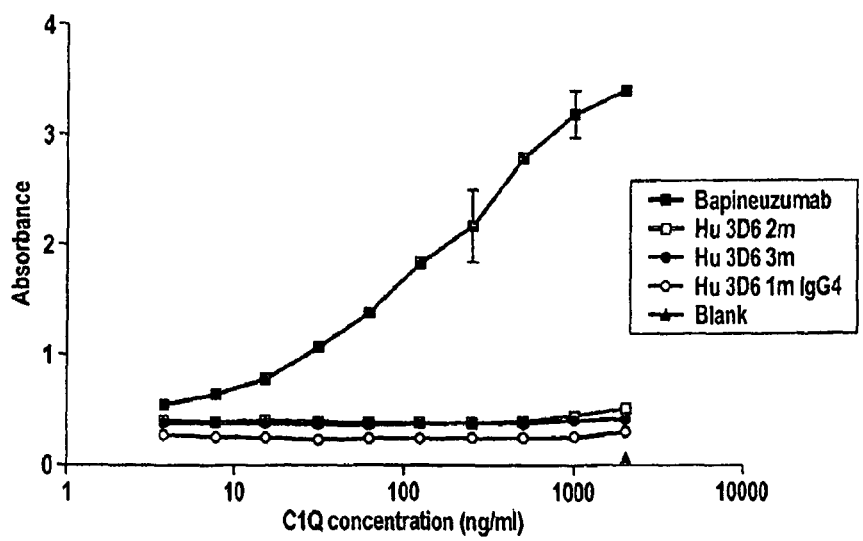
FIG. 21 shows results of an ELISA assay measuring C1q binding by the indicated humanized antibodies. See Example 7.

Purified Aβ was coated on to ELISA plates and exposed to one of the following humanized 3D6 antibodies at the concentrations indicated in FIG. 21: Hu 3D6 2m (IgG1), Hu 3D6 3m (IgG1), Hu 3D6 1m (IgG4), and unmodified Hu 3D6 (IgG1). The ELISA plates were washed and then blocked with 0.02% Casein solution in PBS for 3 to 24 hours with slow agitation. The blocking solution was removed with another step of washing.

Next, purified human C1q (191391, MP Biomedicals) was added to the ELISA plates, with 2 ug C1q/ml assay buffer starting the 2× dilution series. C1q was allowed to bind for 2 hours with agitation. Following another wash step, 1000 well anti-C1q antibody (Rb anti human C1q FITC conjugated cat #F010 DBS (dbiosys.com)) used at 1:200 was added for 1 hour with agitation. Results were compared to a blank with no anti-C1q antibody.

As shown in FIG. 21, the humanized 3D6 derivative antibodies did not significantly interact with C1q. This is in contrast to bapineuzumab, which does not have mutations in the Fc region.

The derivative antibodies were tested for ability to induce complement-mediated lysis of HEK 293 cells expressing Aβ on the surface. A standard $^{51}$Cr release assay was used, as described in Phillips et al. (2000) *Cancer Res.* 60:6977-84; Aprile et al. (1981) *Clin. Exp. Immunol.* 46:565-76.

The target cells were HEK293 cells (ATCC, CRL-1573) that expressed a fusion protein with the Aβ epitope detected by 3D6 (DAEFR (SEQ ID NO: 94)) on the surface. The Aβ-containing sequence was inserted into the pDisplay vector (Invitrogen). The pDisplay vector was altered to remove the HA tag and instead start with the Aβ-containing peptide after leader sequence. A stable pool of HEK 293 was moved forward to the ADCC assay.

For labeling, $10^7$ cells were suspended in 2 ml RPMI 10% FCS and added 250uCi of $^{51}$Cr (NEN catalog #NEZ-030; sodium$^{51}$chromate in saline). Cells were incubated for 1 hour at 37 C with occasional agitation. At the end of the incubation, 10 ml RPMI with 10% FCS was added. Cells were spun down so the supernatant could be removed, and resuspended in 10 ml RPMI containing 10% FCS. Cells were again incubated, at room temperature for 1.5 hours with occasional agitation, to allow excess $^{51}$Cr to bleed from the cells. Target cells were washed 3 times with 10 ml RPMI, and a final time in 10 ml RPMI containing 10% FCS. Cells were resuspended in RPMI with 10% FCS to a concentration of $10^6$ cells/ml.

Effector cells were collected from human blood. Briefly, blood was diluted 1:1 with PBS and layered over Ficoll (Sigma Histopaque 1077). The column was spun for 20 min, 1200×g, with no brake at 20 C. Cells at the interface were collected; washed once with 2-3 volumes PBS, and twice with RPMI containing 10% FCS. NK enrichment is detected with antibodies to CD3 and CD56.

Effector cells and target cells were added to 96 well plates at a ratio of 25:1 (effector:target) in a total volume of 200 μl. The following control samples were included: Spontaneous lysis (containing target cells with no effectors) and Total lysis (leave wells empty) was included. The cells were incubated for 5 hours at 37 C. Just before harvest, 100 μl 0.1% Triton X-100 was added to the Total lysis sample to release $^{51}$Cr. The reactions were harvested onto filter units with a Skatron harvester (Molecular Devices) and total $^{51}$Cr was detected.

To calculate % lysis, the average cpm and standard deviation was determined for each sample. The % Maximum $^{51}$Cr Release is determined with the following formula:

$$(\text{Experimental}-\text{Spontaneous})\times 100(\text{Total}-\text{Spontaneous})$$

Figure 22:
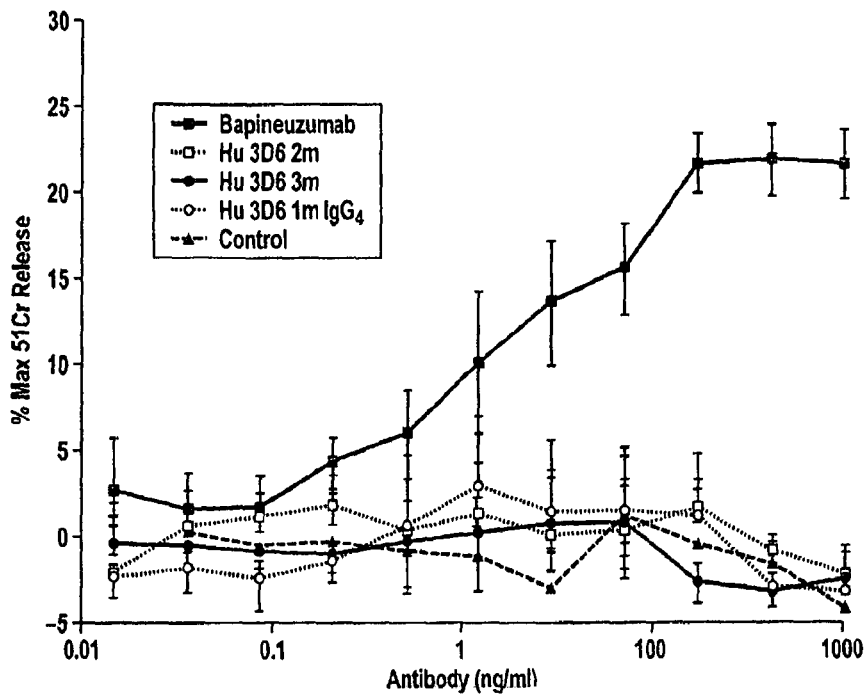
FIG. 22 shows the results of an antibody dependent complement cytotoxicity assay using the indicated humanized antibodies. Results are expressed as described in Example 7.

Consistent with the results of the C1q binding assay, the humanized 3D6 effector function mutant derivative antibodies were not effective at inducing complement lysis of the Aβ-expressing HEK 293 cells (see FIG. 22).

Example 8

ELISA Assay Measuring C1q Binding Ability of Murine 3D6 Derivatives

Materials and Methods

A 96-well fluorescent plate was coated with 1, 3, or 6 μg/ml of various antibodies in 100 μl well coating buffer overnight at 4 C. After coating, plates were washed and blocked with 200 μl. Casein Elisa Block for 1 hr at RT. Plates were washed and 100 μl of 2 μg/ml human C1q in diluent buffer was added for 2 hrs at RT. After 2 hrs, plates were washed and FITC-labelled rabbit anti-C1q (1:1000) was added for 1 hr. Plates were washed twice and read at 494/517 on the fluorescent plate reader in PBS. The following mouse antibody samples were tested: IgG2a, IgG2b, 3D6 IgG2a, IgG1, 3D6 IgG1, and the 3D6 IgG1 C1q mutant.

Results

Figure 23:
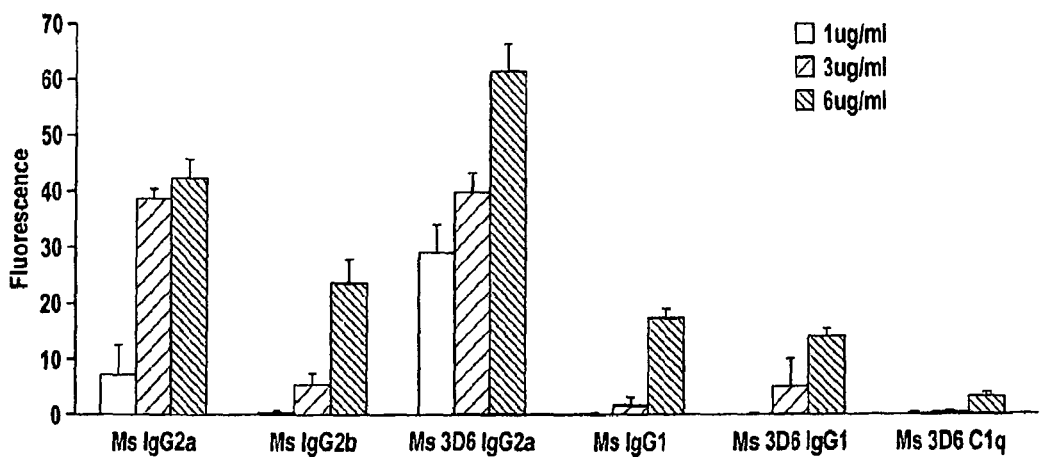
FIG. 23 shows results of an ELISA assay measuring C1q binding by the indicated murine antibodies. See Example 8.

The highest level of C1q binding was observed for IgG2a and 3D6 IgG2a (see FIG. 23). C1q binding to IgG1 and 3D6 IgG1 was significantly lower than IgG2a. The mutation in 3D6 IgG1 C1q binding domain suppressed this binding further.

Example 9

Contextual Fear Conditioning (CFC) Assay

Tg2576 transgenic mice and wild-type littermate controls were individually housed for at least 2 weeks prior to any testing and allowed ad libitum access to food and water. CFC occurred in operant chambers (Med Associates, Inc.) constructed from aluminum sidewalls and PLEXIGLAS ceiling, door and rear wall. Each chamber was equipped with a floor through which a foot shock could be administered. In addition, each chamber had 2 stimulus lights, one house light and a solenoid. Lighting, the footshock (US) and the solenoid (CS) were all controlled by a PC running MED-PC software. Chambers were located in a sound isolated room in the presence of red light.

Mice (n=8-12/genotype/treatment) were trained and tested on two consecutive days. The Training Phase consisted of placing mice in the operant chambers, illuminating both the stimulus and house lights and allowing them to explore for 2 minutes. At the end of the two minutes, a footshock (US; 1.5 mAmp) was administered for 2 seconds. This procedure was repeated and 30 seconds after the second foot shock the mice were removed from the chambers and returned to their home cages.

Twenty hours after training, animals were returned to the chambers in which they had previously been trained. Freezing behavior, in the same environment in which they had received the shock ("Context"), was then recorded using time sampling in 10 seconds bins for 5 minutes (30 sample points). Freezing was defined as the lack of movement except that required for respiration. At the end of the 5 minute Context test mice were returned to their home cages.

Approximately 20-week old wild-type mice and Tg2576 transgenic mice were administered a single dose of treatment antibody by intraperitoneal injection at 24 hours prior to the training phase of the CFC. Treatment antibodies were: (i) non-specific IgG1 antibody; (ii) Hu 3D6 3m (FcγR) (also called AAB-003); and (iii) bapineuzumab (also called AAB-001).

Figure 24:
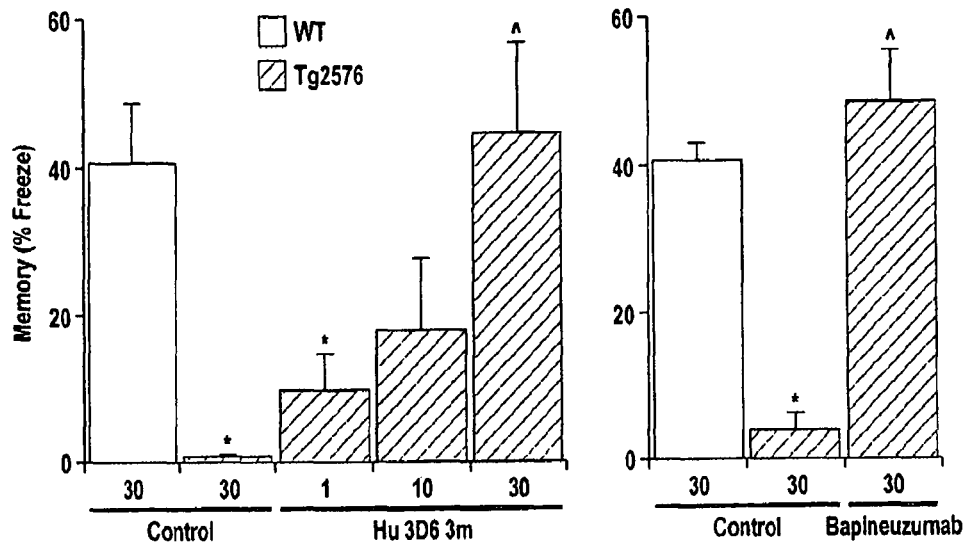
FIGS. 24-25 show the results of a contextual fear assay in mice treated with the indicated humanized antibodies. Results are compared between wild type and Tg2576 mice, as described in Example 9.

FIG. 24 demonstrates the results. Control-treated wild type mice showed about 40% freeze, while in comparison, control-treated transgenic mice exhibited a severe deficit in contextual memory. When administered at 30 mg/kg, the Hu 3D6 3m antibody restored cognitive function to wild type levels. Furthermore, the effector function mutant had the same effect on contextual memory as the parent antibody, bapineuzumab.

Figure 25:
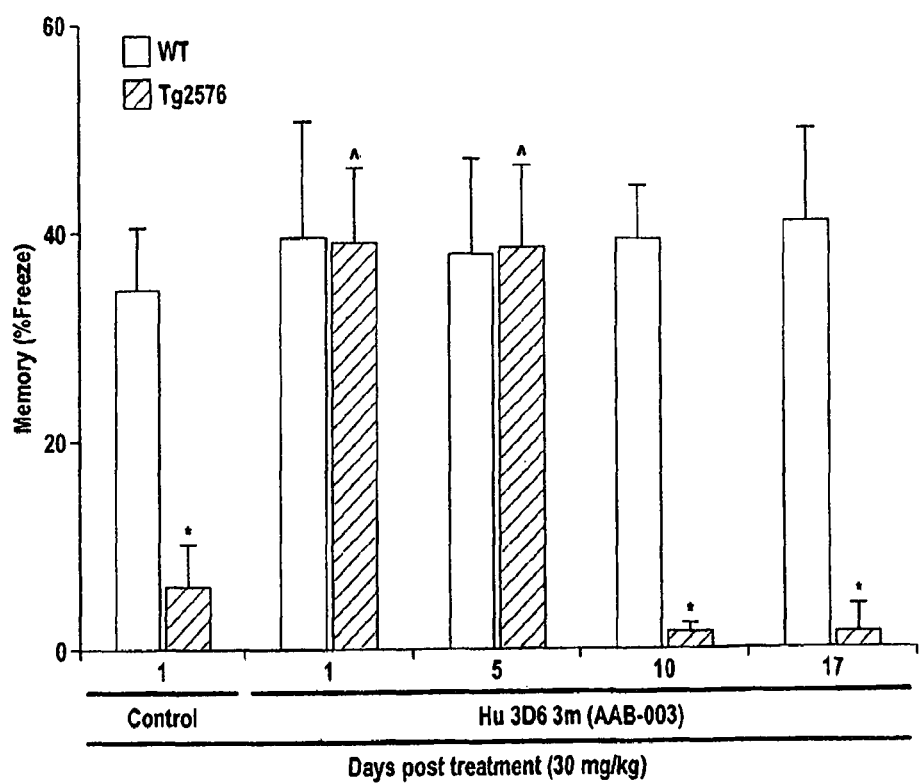

The effect of the Hu 3D6 3m antibody on contextual memory was observed over time. FIG. 25 illustrates that treatment with 30 mg/kg Hu 3D6 3m antibody provided wild type levels of cognition at least 5 days post-administration.

In summary, the above examples show that Hu 3D6 3m results in similar cognition improvements as bapineuzumab. This is despite the fact that the derivative antibody does not significantly bind to Fc receptors or C1q, or induce phagocytosis or ADCC activity.

Example 10

Mouse Studies with 3D6 4m (FcγR/C1q) IgG2a and Hu 3D6 3m IgG1 (AAB-003)

Study Design

One-year old PDAPP mice are exposed to a 6 month treatment paradigm with control; 3D6 4m (FcγR/C1q) IgG2a; or Hu 3D6 3m IgG1 (see Table 10). Negative controls include a mouse IgG2a antibody and a human IgG1 antibody to an irrelevant, non-amyloid epitope. Positive controls include 3D6 IgG2a and Hu 3D6 IgG1. The mice are split into dosage cohorts and injected IP at weekly intervals with 3, 30, or 300 mg/kg of the indicated antibody. Experimental conditions are as described in Example 5.

After 6 months, the mice are sacrificed and brain tissue harvested as described above. Tissues are examined for cortical and hippocampal Aβ and amyloid burden, vascular amyloid, and microhemorrhage.

Example 11

Cynomolgus Monkey Studies with Hu 3D6 3m IgG1 (AAB-003)

Study Design

Cynomolgus monkeys are treated with Hu 3D6 3m IgG1 (AAB-003). The negative control includes a human IgG1 antibody to an irrelevant, non-amyloid epitope. The positive control include Hu 3D6 IgG1 (Bapineuzumab). Monkeys are split into dosage cohorts receiving either 15, 50, or 150 mg/kg of the indicated antibody. Each cohort is further split into IV and SC administration groups.

Monkeys are injected weekly for 13 weeks, with a 2 month observation period. At the end of the study, the monkeys are sacrificed and brain tissue harvested. Tissues are examined for cortical and hippocampal Aβ and amyloid burden, vascular amyloid, and microhemorrhage.

Example 12

Single Ascending Dose (SAD) Study in Humans of Hu 3D6 3m (AAB-003) Antibody

Mild to moderate Alzheimer's patients, including ApoE4 carriers and non-carriers, are divided into cohorts for intravenous (IV) or subcutaneous (SC) injection with AAB-003 antibody. The cohorts are given a single dose with a 12 month follow up, and monitored throughout by an independent safety monitoring committee.

The goal of the study is to increase the exposure equivalent to at least 5 mg/kg of intravenous Bapineuzumab (unless signs of vasogenic edema are observed). At this dose of Bapincuzumab, VE was observed in 3 of 10 patients.

The SC cohorts include at least two subcutaneous dosage levels. These patients are be observed for bioavailability of the antibody and linearity thereof.

All patients are screened (e.g., for ApoE status) and monitored as described in Example 1. For all cohorts, safety monitoring includes MRI monitoring. MRI results are compared to those from the Bapineuzumab study described in the above examples. Efficacy is measured by cognitive metrics (e.g., NTB, DAD, ADAS-Cog,); plasma Aβ levels; CSF levels of amyloid, tau, and phosphotau; and amyloid imaging.

Certain biomarkers are tracked in each patient during the study. Biomarkers to support Aβ binding by the antibody include Aβ40 and Aβ42 in the CSF and plasma, and amyloid plaque imaging, e.g., by PET. Biomarkers pointing to disease modification include MRI, CSF tau and phosphotau levels, and again, amyloid plaque imaging.

Example 13

Pharmacokinetic Profiles of Hu 3D6 3m (AAB-003) in Tg2576 and Wild Type Mice Tg2576 transgenic mice and wild type controls were dosed with AAB-003 subcutaneously (SC) or intraperitoneally (IP)

to determine bioavailability of the antibody. The profile was typical for therapeutic antibody.

AAB-003 was eliminated slowly, with a $T_{1/2}$ of 66-160 hours. There was low volume distribution (71-96) and good exposure (as measured by AUC).

Some differences between the wild type and transgenic mice were apparent. For example, wild type mice had higher AUC and $T_{1/2}$. The transgenic mice had slightly higher levels of anti-AAB-003 antibodies.

Example 14

Pharmacokinetic Profiles of Hu 3D6 3m (AAB-003) in Cynomolgus Monkeys 10 mg/kg Hu 3D6 3m or bapineuzumab were administered intravenously (IV) to cynomolgus monkeys (3 animals/antibody treatment) to compare the pharmacokinetic profiles and determine whether the effector function mutation had any effect. The results were comparable between the two antibodies, and typical for therapeutic antibodies in general. There was low clearance (0.16±0.06 ml/hr/kg), small volume of distribution (~62 ml/kg), and long elimination half-life (309±226 hours). One of the three animals tested positive for antibodies against AAB-003.

The same antibody doses were administered subcutaneously (SC). Bioavailability was good, approximating 69%, and the half-life ranged from 21-445 hours. Two of the three animals tested positive for antibodies against AAB-003.

Example 15

Effect of Fc Mutations on the Effector Function of an Anti-Lewis Y Antibody

To determine the effect of mutations in the low hinge region of human IgG1 on the effector function of antibodies with different antigen specificity, we designed antibodies to the Lewis Y (LeY) antigen. LeY is a type 2 blood group related difucosylated oligosaccharide that is mainly expressed in epithelial cancers, including breast, pancreas, colon, ovary, gastric, and lung. LeY does not appear to be expressed on tumors of neuroectodermal or mesodermal origin.

The anti-LeY Ab02 antibody was generated with one of three heavy chain constant regions: (i) wild type human IgG1; (ii) wild type human IgG4; and (iii) human IgG1 with two effector region mutations, L234A and G237A (see SEQ ID NOs:50 and 51). IgG4 has been shown to have reduced effector function in other systems.

Figure 26:
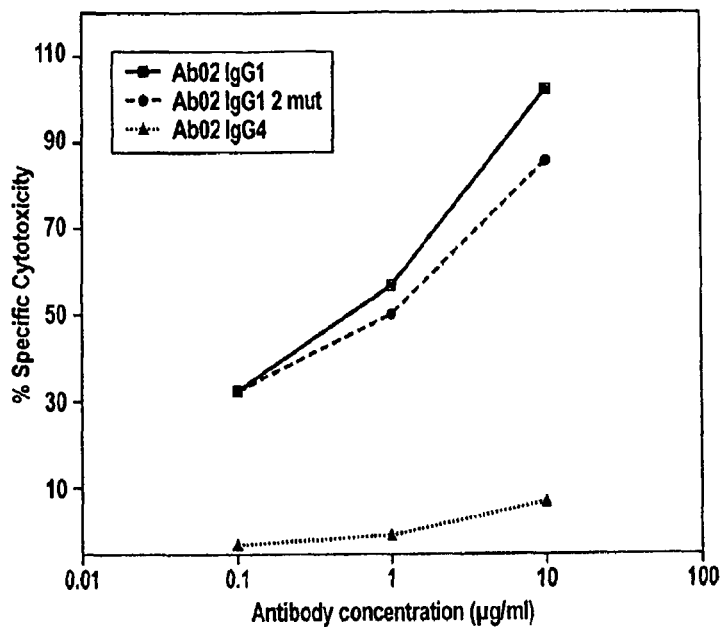
FIG. 26 shows the results of the ADCC activities of anti-Lewis Y Ab02 antibodies. See Example 15.

For the ADCC (antibody-dependent complement cytotoxicity) assay, LeY-overexpressing N87 human gastric adenocarcinoma cells were used as target cells, and freshly isolated human PBMC were used as effector cells. Effector and target cells were plated at a ratio of 50:1 in 96 well plates. Antibody was applied at varying concentrations (0.1, 1 and 10 µg/ml) in triplicate with medium, effector and target cell controls, and antibody controls. The ADCC activities of anti-Lewis Y Ab02 versions are presented in FIG. 26.

For the CDC (complement dependent cytotoxicity) assay, LeY positive tumor cells (A431 LeY) were plated in 96 well plates with varying amount of antibody (0.1, 1 and 10 µg/ml) Diluted human complement (1:100), was added to each well. Tests were done in triplicate at a final volume of 100 µl/ml with medium, cells alone, and antibody and complement controls. After 4 hours incubation at 37 C, plates were removed and equilibrated to 22 C.

Figure 27:
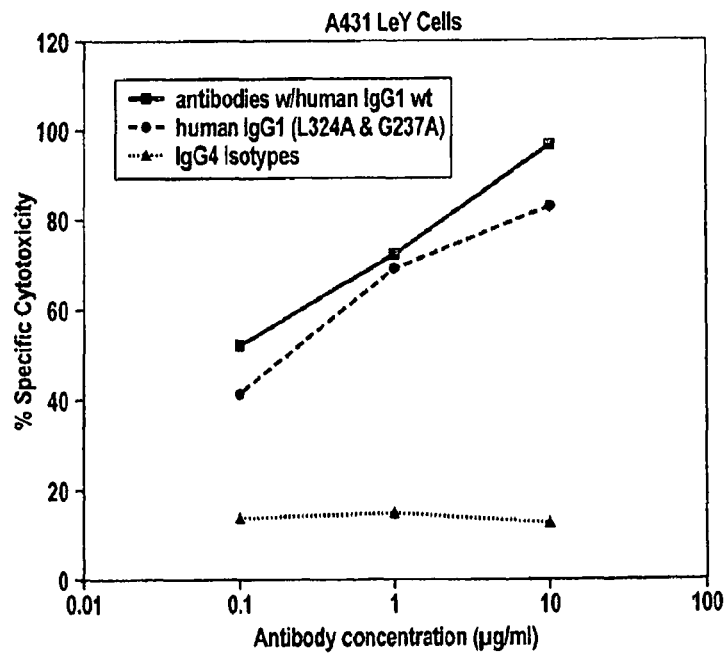
FIG. 27 shows the results of the CDC (complement dependent cytotoxicity) activities of anti-Lewis Y Ab02 antibodies. See Example 15.

An equal volume of CytoTox-One™ was added to each well, and incubated for 10 minutes at 22 C. As a positive control, 2 µl of lysis buffer per well (in triplicate) was added to generate a maximum LDH (lactate dehydrogenase) release in control wells. The enzymatic reaction was stopped by adding 50 µl of stop solution. The resulting fluorescence was recorded with an excitation wavelength of 560 nm and an emission wavelength of 590 nm. The % of complement-related cell lysis was calculated as % of total LDH release (FIG. 27).

In spite of the L234A and G237A mutations in IgG1, the mutant antibody fully retained its capacity to mediate both ADCC and CDC against Lewis Y expressing tumor cells, as compared to wild type IgG1.

Example 16

Effect of Fc Mutations on the Effector Function of Anti-5T4 Antibody

To investigate further the effect of Fc mutations in human IgG1 on the effector function of antibodies with different antigen specificity, we designed antibodies to the oncofetal protein 5T4. 5T4 is a tumor-associated protein displayed on the cell membrane of various carcinomas, and is a promising target for anti-tumor vaccine development and for antibody directed therapies.

The anti-5T4 antibody was generated with different combinations of mutations in the heavy chain constant region. The heavy chains used were: (i) wild type human IgG1; (ii) wild type human IgG4; (iii) human IgG1, L234A and L235A; (iv) human IgG1, L234A and G237A; (v) human IgG1, L235A and G237A; and (vi) human IgG1 with three effector region mutations, L234A, L235A, and G237A (see SEQ ID NOs:62 and 63).

Human breast carcinoma cell line MDAMB435, stably transfected with 5T4 antigen, was used for the ADCC and CDC assays. The ADCC assay of anti-5T4 antibodies was as described in Example 15, using freshly isolated human PBMC as effector cells at an effector:target cell ratio 50:1. MDAMB435-Neo transfected cells were used as a negative control. The results of ADCC activity (maximum specific cytotoxicity at the antibody concentration 10 ug/ml) are summarized in Table 15.

TABLE 15

ADCC activity of anti-5T4 antibodies against 5T4 positive and negative human breast carcinoma cell line MDAMB435

| Antibody | MDAMB345-5T4 % specific cytotoxicity | MDAMB-Neo % specific cytotoxicity |
| --- | --- | --- |
| 5T4-IgG1wt | 81 | 3 |
| 5T4-IgG1 L234A/G237A | 78 | 2 |
| 5T4-IgG1 L234A/L235A | 15 | 2 |
| 5T4-IgG1 L235A/G237A | 27 | 2 |
| 5T4-IgG1 L234A/L235A/G237A | 2 | 2 |
| 5T4-IgG1 N297A | 5 | 3 |
| 5T4-IgG4 | 2 | 2 |

To evaluate an effect of Fc mutations on the complement induced cytotoxicity, human breast carcinoma MDAMB435-

5T4 cells were incubated with diluted human complement as described in the Example 15. The results of CDC assays are presented in the Table 16.

TABLE 16

CDC activity of anti-5T4 antibodies against 5T4 positive and negative human breast carcinoma cell line MDAMB435

| Antibody | MDAMB345-5T4 % specific cytotoxicity | MDAMB-Neo % specific cytotoxicity |
|---|---|---|
| 5T4-IgG1wt | 90 | 2 |
| 5T4-IgG1 L234A/G237A | 72 | 2 |
| 5T4-IgG1 L3234A/L235A | 5 | 2 |
| 5T4-IgG1 L235A/G237A | 19 | 2 |
| 5T4-IgG1 L234A/L235A/G237A | 1 | 1 |
| 5T4-IgG1 N297A | 1 | 1 |
| 5T4-IgG4 | 1 | 1 |

The introduction of two mutations in the low hinge region of human IgG1 in any of the combinations tried (L234A/L235; L234A/G237A; L235A/G237A) only partially reduced ADCC and CDC activity with L235A/G237A showing the higher residual effector function capabilities. However, anti-5T4 antibody with three mutations in the IgG1 low hinge region (L234A/L235A/G237A) demonstrated completely abolished ADCC and CDC activities.

Conclusions

The Examples provide a number of comparisons of Fc region mutant antibodies with different antigen specificities. Example 6 describes an ADCC assay using Aβ-specific antibodies with IgG1 Fc mutations at either L234A and G237A (double mutant), or L234, L235A, and G237A (triple mutant). Both the double and triple mutants had significantly reduced function (see FIG. 22). Example 15 describes ADCC and CDC assays using LeY-specific antibodies with IgG1 mutations at L234A and G237A. In this case, the mutant antibody retained effector function (see FIGS. 26 and 27). Finally, Example 16 compares IgG1 Fc mutants of 5T4-specific antibodies. Each of the double mutants (L234A/L235; L234A/G237A; L235A/G237A) retained more effector activity than the triple mutant (L234A/L235A/G237A) (see Tables 15 and 16). The effector activity of the L234A/L235 double mutant, however, was reduced to nearly the same level as that of the triple mutant.

The above results demonstrate that the effect of the hinge-region mutations can depend on a number of factors, including target antigen density on the cell surface. However, the data indicate that disruptions at all three positions are necessary to eliminate effector activity.

Example 17

Neutralization of Synaptotoxic Soluble Aβ Species with the N-Terminal Anti-Aβ Antibody 3D6

Several anti-amyloid beta (Aβ) antibodies are under evaluation for the treatment of Alzheimer's disease (AD). Clinical studies using the N-terminal directed anti-Aβ antibody bapineuzumab have demonstrated reduced PET signals using the Pittsburg-B label and reduced levels of total and phosphorylated tau protein in the cerebrospinal fluid of treated AD patients. Preclinical studies using 3D6 (the murine form of bapineuzumab) have demonstrated resolution of Aβ plaque burden, vascular Aβ burden, neuritic dystrophy, and preservation of synaptic density in the PDAPP mouse model. Despite the robust literature describing bapineuzumab and 3D6 effects on insoluble forms of Aβ there are relatively few reports that have evaluated the interaction of this antibody with soluble Aβ species. In the current report, we demonstrated that 3D6 binds to soluble, synaptotoxic assemblies of $A\beta_{1-42}$ and prevented multiple downstream functional consequences in rat hippocampal neurons such as changes in glutamate AMPA receptor trafficking, AD-type tau phosphorylation, and loss of dendritic spines. In vivo, we further demonstrated that 3D6 prevented synaptic loss and acutely reversed the behavioral deficit in the contextual fear conditioning task in transgenic mouse models of AD, two endpoints known to be linked to toxic soluble Aβ moieties. By contrast, the C-terminal anti-Aβ antibody 21F12 was ineffective on all in vitro and in vivo endpoints analyzed. The current study demonstrates that passive immunotherapy with an N-terminal directed anti-Aβ antibody interacts with soluble Aβ and neutralize several measures of synaptotoxicity. These results, taken with prior studies, suggest that N-terminal anti-Aβ antibodies effectively interact with both soluble and insoluble forms of Aβ and are therefore useful for testing the Aβ hypothesis of AD.

We performed studies to evaluate the ability of 3D6 to interact with soluble synaptotoxic forms of the Aβ peptide and directly compare these effects with the actions of the Aβ42 specific C-terminal directed mAb 21F12. In vitro, we characterized the ability of 3D6 and 21F12 to interact with and inhibit the binding of soluble Aβ to neurons using rat hippocampal primary neuronal cultures (Lacor P N, et al. *J Neurosci* 24, 10191-200 (2004); Shughrue P J, et al. *Neurobiol Aging* 31, 189-202 (2010)). In this same preparation we evaluated the ability of 3D6 to reduce physiological changes known to be caused by soluble synaptotoxic Aβ such as reduction of spine density (Shughrue P J, et al. *Neurobiol Aging* 31, 189-202 (2010)), trafficking of the AMPA subunit GluR2 (Hsieh H, et al. *Neuron* 52, 831-43 (2006); Zhao W Q, et al. *J Biol Chem* 285, 7619-32 (2010)) and phosphorylation of tau protein (De Felice F G, et al. *Neurobiol Aging* 29, 1334-47 (2008)). Using the PDAPP mouse model we evaluated the ability of 3D6 and 21F12 to preserve synapses as measured by synaptophysin immunohistochemistry as has been previously demonstrated (Buttini M, et al. (2005). *J Neurosci* 25, 9096-101) and further evaluated the effect of treatment using these antibodies on a behavioral pharmacodynamic endpoint sensitive to soluble synaptotoxic Aβ (i.e., the contextual fear conditioning behavioral assay using the Tg2576 mouse model (Comery T A, et al. *J Neurosci* 25, 8898-902 (2005)).

Results

Binding of the N-Terminal Antibody 3D6 to Soluble Aβ Species.

To investigate the binding characteristics of soluble Aβ species to neurons, we utilized a known preparation of synthetic $A\beta_{1-42}$ peptide enriched in synaptotoxic oligomeric species and devoid of insoluble material (Lambert M P, et al. *J Neurochem* 79, 595-605 (2001)). For purposes of clarity, we refer to soluble synaptotoxic forms of Aβ herein as a general term so as to avoid any confusion surrounding the absolute sizing of a relevant Aβ species and/or selection of the abundant terminology that currently exists in the literature [e.g., oligomers, dimers, Aβ*56, globulomers, ADDLs, soluble protofibrils, etc.; see e.g. (Catalano S M, et al. *Curr Top Med*

Chem 6, 597-608 (2006))]. The "relevant" species of soluble Aβ is a debated subject in the field, further confused by the fact that the same aggregation state of this peptide may be determined to be different sizes dependent on the analytical method used (Hepler R W, et al. *Biochemistry* 45, 15157-67 (2006)).

We monitored the interaction of soluble Aβ with the surface of rat hippocampal neurons maintained for 3-4 weeks in vitro by quantitative immunocytochemical analysis. These neuronal-enriched cultures produce highly differentiated neurons with extensive synaptic input. The detection of Aβ binding to neurons was performed with fluorescently-tagged 3D6, a rabbit polyclonal anti-Aβ antibody or, when using solutions from biotinlated Aβ$_{1-42}$ peptide, fluorescent streptavidin (Shughrue P J, et al. *Neurobiol Aging* 31, 189-202 (2010)). The pattern of distribution of Aβ on the surface of neurons was indistinguishable among the different methods of detection. Consistent with previous reports (Zhao W Q, et al. *J Biol Chem* 285, 7619-32 (2010)), we find that soluble Aβ applied to hippocampal cultures selectively binds to the surface of a subpopulation of hippocampal neurons (~80% of neurons in the present studies), and distributes in a punctuate pattern that is primarily restricted to excitatory synapses (FIG. 28), evidenced by the extensive colocalization between Aβ, the presynaptic glutamatergic marker VGluT1 and postsynaptic spine marker drebrin. The characteristic synaptic binding was absent when insoluble, fibrillar Aβ was applied to cultures. The results demonstrate that the 3D6 antibody can bind to soluble Aβ species that are selectively targeted and bound at excitatory synapses.

Figure 28:
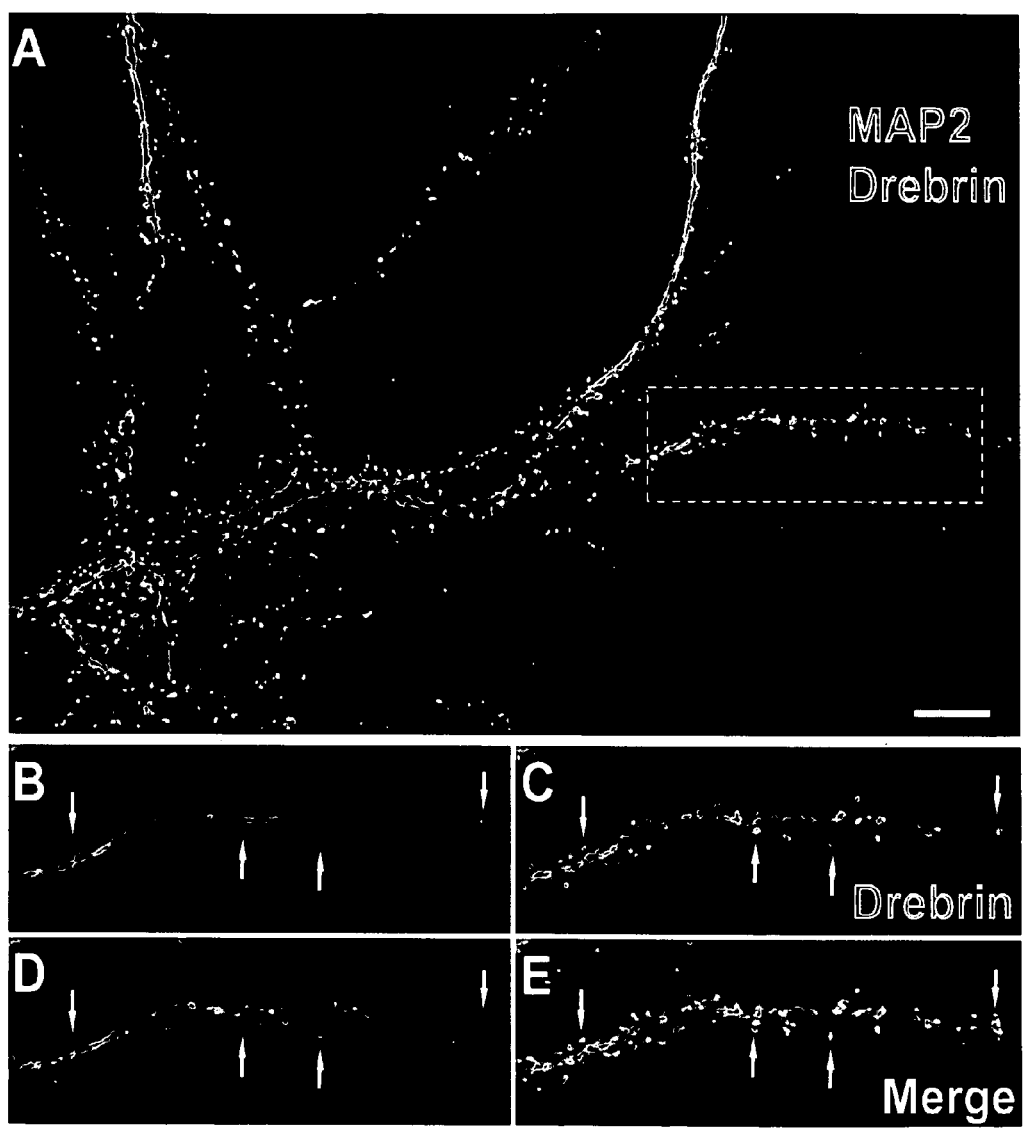
FIG. 28 shows soluble Aβ species bind to excitatory synapses on hippocampal neurons. Differentiated hippocampal neurons treated with soluble Aβ preparations (500 nM, 15 min.) and stained with fluorescently tagged 3D6 mAb for Aβ (A, B, E) and co-stained for MAP2 for dendrites (A-E), drebrin for spines (C.E), and vesicular glutamate transporter 1 (VGluT1) for glutamatergic presynaptic terminals (D,E). Aβ-positive clusters are found on soma and dendrites, almost exclusively restricted to excitatory synapses (arrows). Scale bar, 20 μm.
Figure 29:
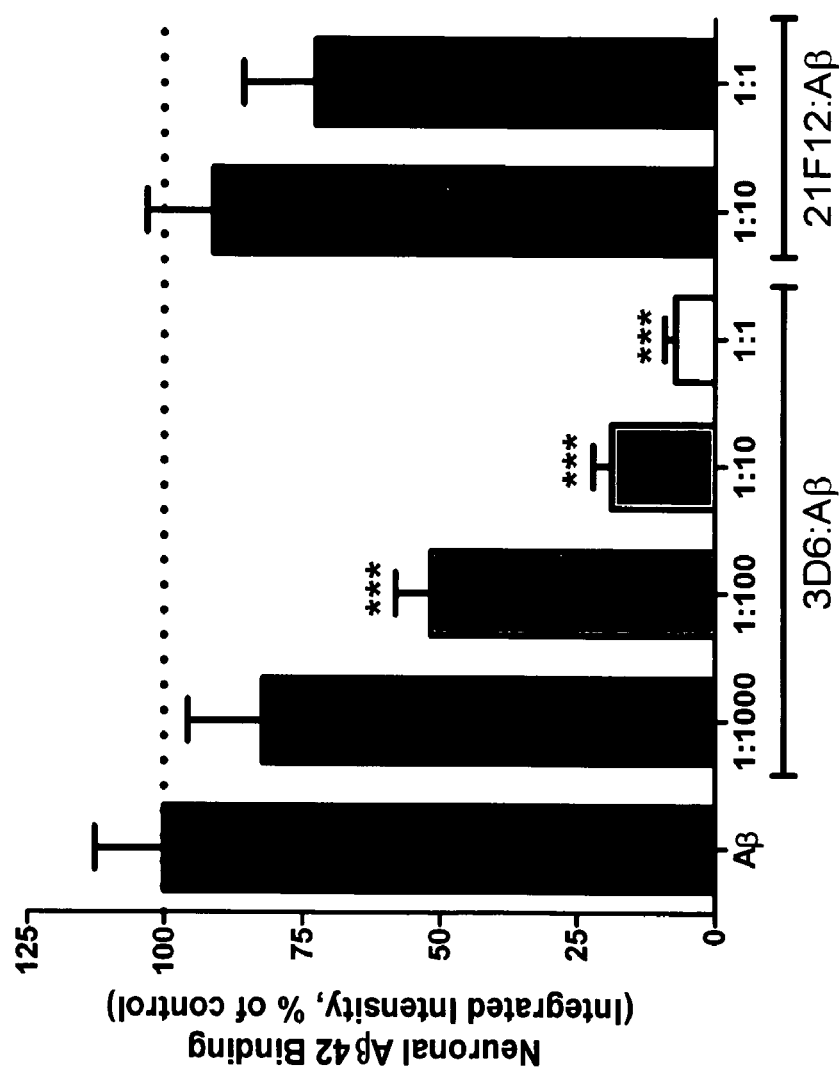
FIG. 29 shows 3D6 mAb blocks the binding of soluble Aβ species to rat hippocampal neurons. Quantification of binding of soluble Aβ to neurons in the presence or not of anti-Aβ mAbs. 3D6, but not 21F12, showed a concentration-dependent blockage of Aβ binding to neurons. The data were normalized by control levels (Aβ-only) and values represent the means±SEMs of results from 14-53 optical fields (>2 neurons/field), pooled from 4-6 independent experiments/cultures. Statistical differences were determined by ANOVA; ***P<0.001 with respect to Aβ-only group.

The N-terminal mAb 3D6 blocks the binding of soluble Aβ to hippocampal neurons. To assess the ability of 3D6 to neutralize soluble Aβ binding we pre-incubated the antibody with soluble biotin-Aβ prior to application to hippocampal neurons and detected binding using fluorescent-streptavidin. The antibody 21F12, which binds to the C-terminal of Aβ (amino acids 34-42) and shows equivalent avidity for immobilized aggregated Aβ as 3D6 (Bard F, et al. *Nat Med* 6, 916-9 (2000)), served as a control. We found that 3D6 (30 min, 37° C.) effectively blocked the binding of soluble Aβ to synapses in a concentration-dependent manner (FIG. 29). The effect was detected at molar 3D6:Aβ ratios as low as 1:100 (P<0.001), and reached complete blockade of binding at equimolar ratios (P>0.05 comparing to background values). The antibody 21F12 was ineffective in blocking Aβ binding (P>0.05) at the ratios tested. The results of these studies suggest that 3D6, but not 21F12, sequesters and prevents the interaction of Aβ with neurons (FIG. 28).

Figure 30:
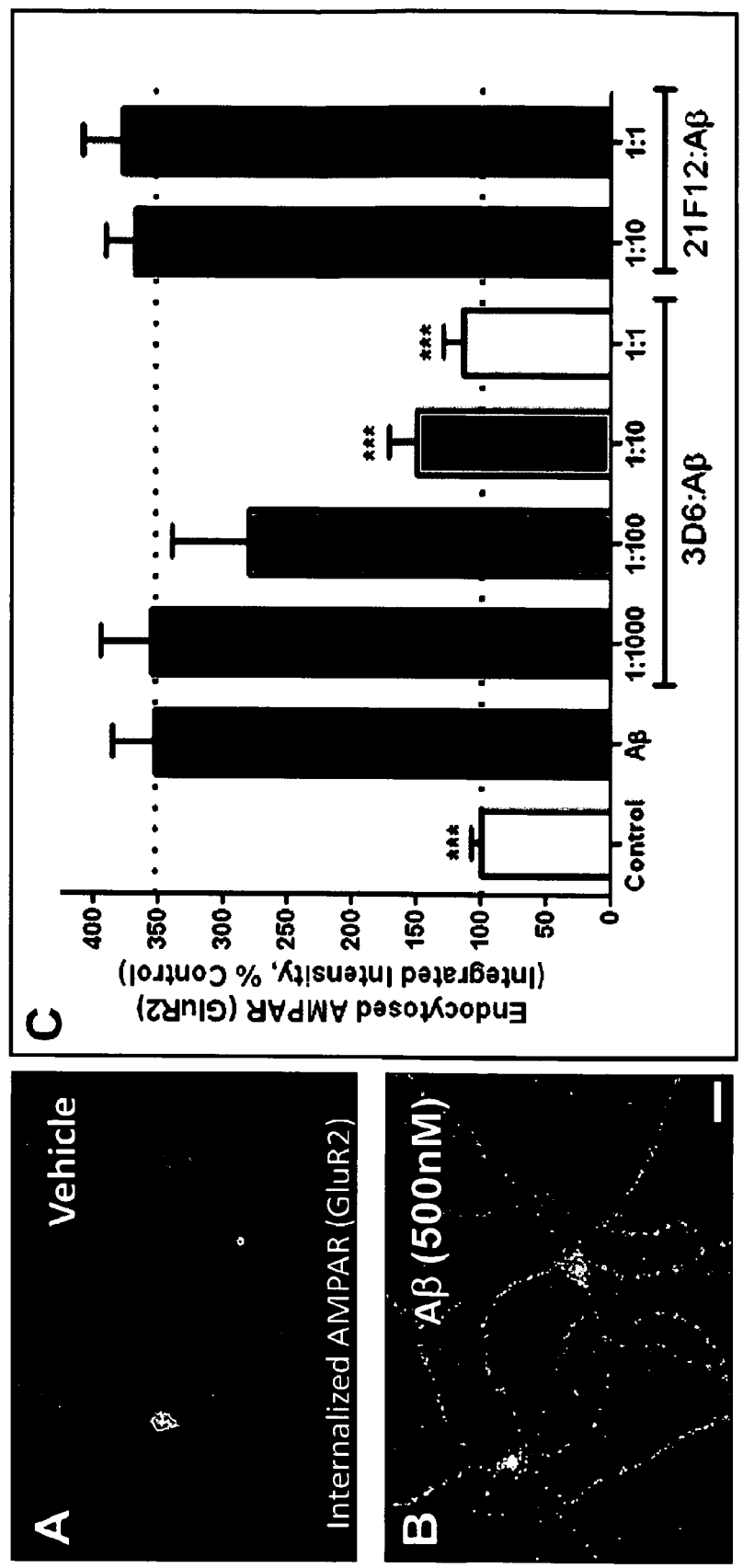
FIG. 30 shows 3D6 mAb blocks the Aβ-induced AMPA receptor endocytosis. (A,B) Representative images of untreated cells showing low levels of AMPAR internalization under basal conditions (A), whereas cells treated with Aβ (B) demonstrate significant staining for AMPARs internalized from the plasma membrane. (C) Quantification of AMPAR internalization in neurons treated with soluble Aβ in the presence or not of anti-Aβ mAbs. 3D6, but not 12F12 shows concentration-dependent blockage of soluble Aβ-induced AMPAR internalization. The data were normalized by control levels (vehicle control) and values represent the means±SEMs of results from 15 optical fields (>2 neurons/field), pooled from 3 independent experiments/cultures. Statistical differences were determined by ANOVA; ***P<0.001 with respect to Aβ-only group. Scale bar, 10 μm.
Figure 31:
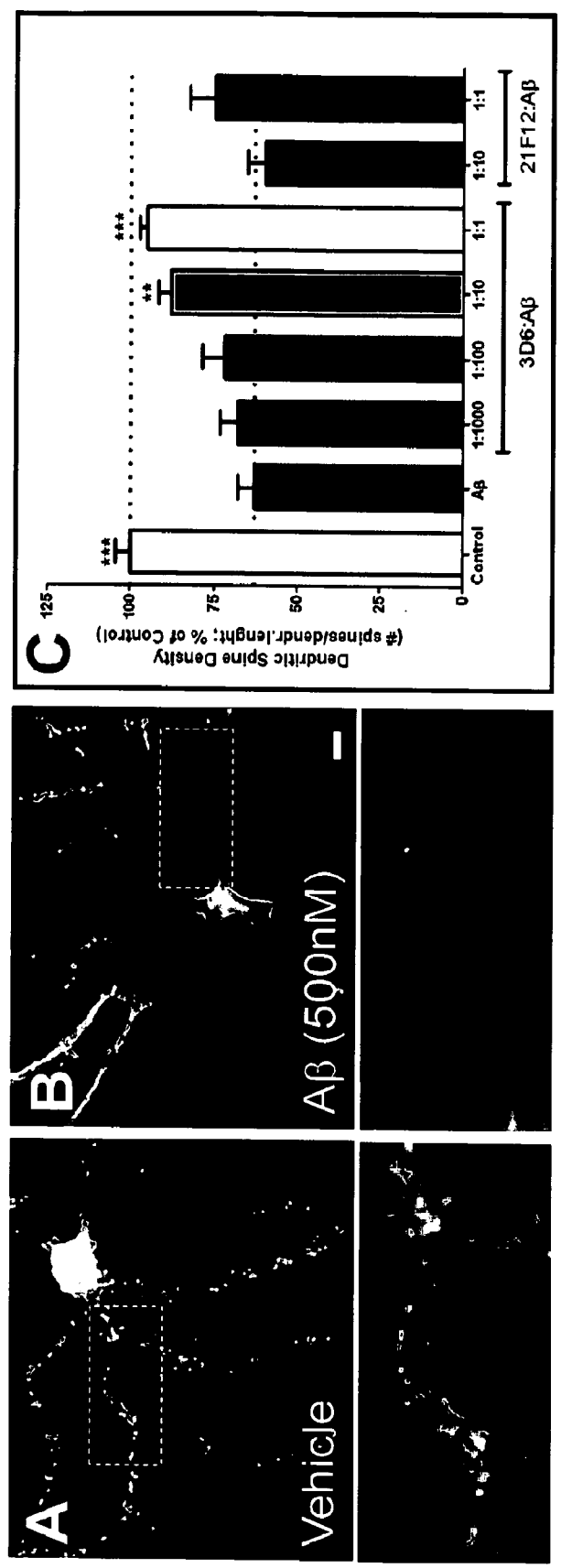
FIG. 31 shows 3D6 mAb blocks the Aβ-induced loss of dendritic spines. (A,B) Representative images showing soluble Aβ-induced (500 nM, 24 h) spine loss in hippocampal neurons, visualized by spinophilin immunostaining. (C) Quantification of spine density in neurons treated with soluble Aβ in the presence or not of anti-Aβ mAbs. 3D6, but not 21F12 shows a concentration-dependent blockage of the soluble Aβ-induced loss of spine. The data were normalized by control levels (vehicle control) and values represent the means±SEMs of results from 15-20 optical fields (>2 neurons/field), pooled from 3 independent experiments/cultures.

The N-terminal mAb 3D6 blocks soluble Aβ-induced internalization of AMPA receptors and loss of dendritic spines. Once bound to neurons, soluble Aβ assemblies engage signaling pathways resulting in the endocytosis of synaptic AMPA receptor proteins, leading to synaptic impairment and loss (Hsieh H, et al. *Neuron* 52, 831-43 (2006)). Since 3D6 treatment neutralizes soluble Aβ species and prevents their binding to synapses (see above), we hypothesized that such administration would similarly protect against downstream, Aβ-induced synaptic changes. To evaluate this possibility we carried out two independent studies. First, we determined whether 3D6 was capable of inhibiting the Aβ-induced internalization of AMPA receptors in rat hippocampal neurons. We used a previously described technique (Zhao W Q, et al. *J Biol Chem* 285, 7619-32 (2010); Carroll R C, et al. *Proc Natl Acad Sci USA* 96, 14112-7 (1999)) which involved staining surface AMPARs with an antibody to the AMPAR subunit GluR2. Following Aβ treatment, surface-bound antibodies were stripped so that only internalized AMPARs were visualized (details in Methods). Treatment of cultures with Aβ (500 nM for 15 min) caused significant internalization of AMPARs (FIG. 30A, B). These effects were restricted to somatic and dendritic areas of most hippocampal neurons. 3D6 (30 min, 37° C.) blocked Aβ-induced increases in receptor internalization in a concentration-dependent manner (FIG. 30C). The antibody 21F12 was ineffective in preventing this effect. The application of the antibodies alone to neurons did not cause significant changes in AMPAR endocytosis relative to that observed in untreated cells (97.4±5.1% of untreated control, n=3). In a second set of studies, we examined the effects of 3D6 on Aβ-induced changes in dendritic spine structure. A 24 h treatment of hippocampal cultures with 500 nM soluble Aβ caused a significant decrease in spine density when compared to control untreated cultures (FIG. 31A, B). Preincubation of soluble Aβ solutions with 3D6 prior to addition to neurons prevented the loss of spines in a dose-dependent manner (FIG. 30C). The protection against spine loss was not observed in 21F12 treated samples.

The N-terminal anti-Aβ mAb 3D6 blocks soluble Aβ-induced tau hyperphosphorylation in rat hippocampal neurons. We next carried out an investigation of the effects of 3D6 against soluble Aβ-induced tau hyperphosphorylation in hippocampal neurons. We specifically evaluated phosphorylation of the tau protein at the Ser$^{202}$ and Thr$^{205}$ sites using the AT8 antibody, which has been used to detect hyperphosphorylated tau in cerebrospinal fluid from AD patients. Consistent with previous reports (De Felice F G, et al. Neurobiol Aging 29, 1334-47 (2008)) we observed that 1 μM of soluble Aβ produced an increase in the immunofluorescence associated with phosphorylation of tau protein (p-Tau) over the period of 8 hours (FIG. 32A, B). Preincubation of Aβ with 3D6 completely blocked the Aβ-induced p-Tau in a concentration-dependent manner, while the 21F12 antibody had no significant effect (FIG. 32C).

The N-terminal anti-Aβ mAb 3D6 acutely reverses CFC deficit in Tg2576 mice. Transgenic mice that overexpress the Swedish mutation of human amyloid precursor protein (hAPPswe; Tg2576) exhibit age-dependent memory deficits in a Pavlovian fear-conditioning paradigm, the contextual fear conditioning (CFC). Deficits in CFC precede plaque deposition in the Tg2576 mouse model and can be acutely reversed by inhibitors of Aβ production (Comery T A, et al. *J Neurosci* 25, 8898-902 (2005)), suggesting that soluble Aβ is primarily responsible for the observed deficits. To determine whether 3D6 targets and neutralizes soluble Aβ species in vivo, we examined CFC in Tg2576 mice following passive immunization. As shown in FIG. 33, CFC is impaired in Tg2576 mice relative to wild-type mice. As with other N-terminal anti-Aβ mAbs (Basi G S, et al. *J Biol Chem* 285, 3417-27 (2010)) administration of 3D6 24 h prior to the training session resulted in complete reversal of the behavioral deficit (p>0.05, comparing to wild-type; FIG. 33A). The antibody 21 F12, on the other hand, was ineffective in this paradigm (FIG. 33B).

The N-Terminal Anti-Aβ mAb 3D6 Prevents Synaptic Loss in PDAPP Mice.

We next investigated whether the protective properties of 3D6 against soluble Aβ-induced changes in synaptic integrity in vitro would also be observed in vivo following chronic administration. PDAPP mice were immunized with either 3D6 or 21F12 for 6 months and the synaptophysin levels were quantified by immunofluorescence as previously described (Buttini M, et al. (2005). *J Neurosci* 25, 9096-101). Immunization with 3D6, but not 21F12, prevented the synaptic loss in PDAPP mice (FIG. 34).

The Aβ cascade is hypothesized to play a critical role in Alzheimer's disease. These present studies provide the first comprehensive comparison of an N-terminally directed and C-terminally directed anti-Aβ antibody on in vitro and in vivo endpoints sensitive to soluble Aβ. Our results demonstrate that 3D6 interacts with and neutralizes the binding of Aβ to neurons and thereby prevents the soluble Aβ induced aberrant trafficking of AMPA receptors, synaptic spine downregulation and tau phosphorylation. The effects of 3D6 were potent, with disruption of soluble Aβ binding noted at antibody:Aβ ratios as high as 1:100. These results are consistent with those previously reported by Shankar et al. (Shankar G M, et al. *Nat Med* 14, 837-42 (2008)), where 3D6 reversed impairments in LTP induced by AD brain homogenates, and by Spires-Jones (Spires-Jones T L, et al. *Neurobiol Dis* 33, 213-20 (2009)), where 3D6 acutely (1 h) rescued the disruption in dendritic spine plasticity observed in PDAPP mouse brains. In both Shankar and Spires-Jones studies, it was assumed that soluble Aβ was the relevant component promoting changes in synaptic function and form. The current studies demonstrating a direct interaction of 3D6 and soluble Aβ on synaptic endpoints support this interpretation. The changes in p-Tau are consistent with reports of decreased total tau and p-Tau in the CSF of patients treated with bapineuzumab (Blennow et al., Nature Reviews Neurology 6, 131-144 (2010)).

In an effort to understand if the effects observed in vitro were relevant to in vivo endpoints, we evaluated the effect of 3D6 and 21F12 treatment on two in vivo pharmacodynamic endpoints sensitive to soluble Aβ. The first evaluation used the contextual fear conditioning (CFC) test. Tg2576 hAPP expressing mice are deficient in CFC, an effect that is evident before plaque formation and sensitive to reductions in Aβ production (Comery T A, et al. *J Neurosci* 25, 8898-902 (2005)). 3D6, but not 21 F12, treatment completely reversed the deficits in Tg2576 mice following a single administration. A second in vivo evaluation examined the quantitation of synapses using synaptophysin immunoreactivy in the PDAPP mouse model. Since the loss of synaptophysin immunoreactivity in PDAPP mice is found throughout the brain and is not restricted to areas proximal to plaque these deficits are believed to be caused by increased soluble Aβ. Consistent with prior reports (Buttini M, et al. (2005). *J Neurosci* 25, 9096-101), repeated administration of 3D6, but not 21F12, demonstrated a protective effect on this endpoint. These in vivo studies collectively suggest that the effects observed in the present experiments in vitro are also relevant in vivo.

In order to understand the degree to which any putative anti-Aβ clinical therapeutic tests the Aβ hypothesis of AD, it is critical to fully understand the interaction of these antibodies with all forms of Aβ. This understanding, if widely applied across all antibody candidates in clinical development could allow for a rationale interpretation of the relative importance of soluble and insoluble species to clinical efficacy endpoints in AD patients.

Materials and Methods
Preparation of Soluble Aβ Solutions.
Synthetic, soluble Aβ solutions were prepared using previously described methods (Lambert M P, et al. *J Neurochem* 79, 595-605 (2001)). Briefly, HFIP films from synthetic Aβ$_{1-42}$ peptide (American Peptide, CA) were dissolved in cold Neurobasal Media without phenol red (Invitrogen) to a final concentration of 100 µM. Following an overnight incubation at 4° C., the samples were centrifuged for 15 min at 14,000×g at 4° C. to remove insoluble material, and supernatant stored until use at 4° C. Biotinylated Aβ solutions were prepared using the same method as above from N-terminal biotinylated Aβ1-42 peptide (American Peptide). Due to the heterogeneity in Aβ assembling states in this preparation (Hepler et al., 2006), we refer to the molar concentrations of Aβ based on the starting Aβ$_{1-42}$ peptide.

Anti-Aβ and Control Antibodies.
The monoclonal antibodies 3D6, 21F12, and TY1115 were obtained as previously described (Bard F, et al. *Nat Med* 6, 916-9 (2000)).

Hippocampal Neuronal Cultures.
Hippocampal neurons were isolated from prenatal rat hippocampi (embryonic day 18) and cultured in antibiotic free NbActiv4 media (both from BrainBits, Springfield, Ill.) at 37° C. in an atmosphere of 5% $CO_2$, 9% O2 and on substrates coated with poly-lysine. Half of the medium was replaced every 3-4 days. The obtained cultures resulted in a population enriched in large pyramidal neurons. Cells were used for the experiments after ~21-28 days in vitro.

Aβ Binding.
For Aβ binding assays, hippocampal cultures were incubated live with 500 nM soluble Aβ or biotin-Aβ preparations for 15 min at 37° C. in Neurobasal media without phenol red (Invitrogen). After a series of washes, the cells were fixed in 4% paraformaldehyde and detection of Aβ performed with fluorescently tagged 3D6 (Alexa-647, Invitrogen), polyclonal rabbit anti-Aβ$_{1-42}$ antibody (Millipore). When using biotin-conjugated Aβ, streptavidin-647 (Invitrogen) was applied for detection. For colocalization assays, cells were further permeabilized with 0.1% Triton X-100 and incubated with primary antibodies for 24 h at room temperature. These included a mouse anti-drebrin (Enzo Life Sciences), a rabbit anti-spinophilin (Millipore Corporation), a guinea-pig anti VGluT1 (Millipore Corporation), and a chicken anti-MAP2 (Abeam). After labeling, the cultures were washed in PBS and detection performed after incubation with appropriate secondary antibodies conjugated to Alexa fluorophores (Invitrogen).

Receptor Internalization.
For AMPA receptor internalization assays, hippocampal neurons were pre-incubated live with anti-GluR2 antibody (Millipore) on ice for 30 min and then treated with 500 nM soluble Aβ preparation or respective vehicle for 15 minutes at 37° C. to induce receptor internalization. Prior do addition to neurons, soluble Aβ was pre-incubated with 3D6, 21F12 or vehicle (PBS) 30 min at 37° C. prior to addition to cultures. The remaining surface-bound antibodies were removed by using acidic stripping buffer (0.5M NaCl/0.2M acetic acid) on ice for 3 min., and cells were then fixed in 4% paraformaldehyde and permeabilized with 0.1% Triton X-100. The internalized receptors were visualized after incubation with secondary antibodies conjugated to Alexa fluorophores (Invitrogen).

Tau Phosphorylation.
For phospho-tau assays, hippocampal neurons were incubated with 1 µM of soluble Aβ preparation for 8 hours at 37° C. Immunostaining for p-Tau with AT8 antibody (Termo Scientific) was performed following the same immunocytochemical procedures described above for other antibodies. The effects of preincubation with anti-Aβ antibodies were assessed in cultures with evident increase in AT8 immunostaining between vehicle and soluble Aβ-treated groups (~2/3 of the cultures).

Image Acquisition and Quantification.
Digital images of fluorescently labeled cells were collected using either laser scanning confocal microscope (Leica, SPE) or Cellomics ArrayScan automated imaging system (Thermo Scientific). Typically, 3-5 optical fields/group/experiment were randomly sampled by software. Fields containing fewer than 2 neurons were discarded. Spine density was reported as the number of manually-counted spines, visualized by combination of two image channels, drebrin and spinophilin, and divided by dendrite segment length (5-100 μm away from soma). Images were analyzed with MetaMorph imaging system (Molecular Devices).

Behavioral Testing in the Contextual Fear Conditioning (CFC) Assay. Heterozygous male Tg2576 mice expressing human amyloid precursor protein with the Swedish mutation or littermate wild-type mice at 20 weeks of age were trained and tested in operant chambers controlled by Med-PC software (Med-Associates, Inc., Burlington, Vt.) on two consecutive days in the contextual fear conditioning (CFC) paradigm as previously described (Buttini M, et al. (2005). *J Neurosci* 25, 9096-101; Hepler R W, et al. *Biochemistry* 45, 15157-67 (2006)). Purified antibodies were administered parenterally by IP injection of 30 mg/kg dissolved in PBS, 24 h prior to the training session on the first day. Freezing scores for each animal were converted to percent freezing for each portion of the test. Memory for the context (Contextual memory) for each animal was obtained by subtracting freezing score in the novel condition (a measure of basal activity) from that observed in the context.

Synaptophysin.

Purified antibodies dissolved in PBS were administered parenterally by IP injection of 3 mg/kg/week for 6 months. Control PDAPP mice received equivalent injections of an irrelevant isotyped-matched antibody (TY11/15). At the end of all treatments, mice were sacrificed and perfused transcardially with PBS. The brains were quickly removed and fixed for 48 h in phosphate-buffered 4% paraformaldehyde before being processed for immunohistochemistry. Forty-micrometer free-floating sections were immunostained with anti-synaptophysion antibody (clone SY38; Dako, Carpenteria, Calif.) and FITC-labeled secondary antibody following a standard protocol. Immunolabeled brain sections were imaged with a laser scanning confocal microscope and synaptophysin levels were assessed in the frontal neocortex, as described previously (Buttini M, et al. (2005). *J Neurosci* 25, 9096-101).

Statistical Analysis.

For statistical analysis, differences among groups were examined with by one-way ANOVA, followed by Dunnett post hoc test for comparison of individual group means. A criterion for statistical confidence of $P<0.05$ was adopted.

Spine Density.

For spine counting assays, hippocampal cultures were incubated with 500 nM of soluble Aβ preparation for 24 hours at 37° C. Prior do addition to neurons, soluble Aβ was pre-incubated with 3D6, 21F12 or vehicle (PBS) 30 min at 37° C. Cells were fixed in 4% paraformaldehyde and permeabilized with 0.1% Triton X-100 and spined detected by staining for drebrin and spinophylin (Millipore). Spine density was reported as the number of manually-counted spines, visualized by combination of two image channels, drebrin and spinophilin, and divided by dendrite segment length (5-100 μm away from soma).

The above examples are illustrative only and do not define the invention; other variants will be readily apparent to those of ordinary skill in the art. The scope of the invention is encompassed by the claims of any patent(s) issuing herefrom. The scope of the invention should, therefore, be determined not with reference to the above description, but instead should be determined with reference to the issued claims along with their full scope of equivalents. All publications, references, accession numbers, and patent documents cited in this application are incorporated by reference in their entirety for all purposes to the same extent as if each individual publication or patent document were so individually denoted.

What is claimed is:

1. A method of treating, reducing the risk, lessening the severity or delaying outset of an amyloidogenic disease characterized by amyloid deposits of Aβ in the brain in a population of patients, comprising:
   administering different regimes to different patients in the population depending on the number of alleles of ApoE4 present in the patients; wherein at least one of the regimes comprises administering an antibody to Aβ to a patient;
   wherein response to treatment of patients receiving the antibody to Aβ is monitored by determining CSF levels of phospho or total tau before and after initiating a regime involving administration of the antibody, a reduction after initiating the regime in a patient providing an indication the regime is effective in the patient.

2. The method of claim 1, wherein a first regime comprises administering an antibody to Aβ to a patient and a second regime lacks an antibody to Aβ or an agent that induces an antibody to Aβ and the first regime is administered to patients having zero copies of an ApoE4 allele and the second regime is administered to patients having one or two copies of an ApoE4 allele.

3. The method of claim 1, wherein the different regimes comprise first and second regimes each comprising administering an antibody to Aβ; and the second regime differs from the first regime in at least one of (i)-(vi) below:
   (i) the dose of the antibody is reduced;
   (ii) the frequency of administration of the antibody is reduced;
   (iii) the capacity of the antibody to induce a clearing response to amyloid deposits is reduced;
   (iv) the mean serum concentration of the antibody is reduced;
   (v) the maximum serum concentration of the antibody is reduced;
   (vi) the time of initiation of treatment relative to disease progression is earlier;
   whereby the first and second regimes are administered such that at least one of (a), (b) and (c) occurs:
   (a) the second regime is administered in patients having two copies of an ApoE4 allele and the first regime in patients having zero copies of an ApoE4 allele;
   (b) the second regime is administered in patients having one copy of an ApoE4 allele and the first regime in patients having zero copies of an ApoE4 allele; and/or
   (c) the second regime is administered in patients having two copies of an ApoE4 allele and the first regime is administered to patients having one copy of an ApoE4 allele.

4. The method of claim 1, wherein a first regime comprises administering a first antibody to Aβ and the second regime comprises administering a second antibody to Aβ and the second antibody has reduced binding to an Fcγ receptor and/or C1q relative to the first antibody, and the first antibody is administered to patients having zero copies of an ApoE4 allele and the second antibody is administered to patients having one or two copies of an ApoE4 allele.

5. The method of claim 4, wherein the second antibody has one or more mutations in the constant region that reduce binding to the Fcγ receptor and/or C1q, the mutations not being present in the first antibody.

6. The method of claim 4, wherein the first antibody is bapineuzumab and the second antibody is an L234A, L235A, G237A variant of bapineuzumab.

7. The method of claim 1, wherein a first regime comprises administering a first antibody to Aβ and a second regime comprises administering a second antibody to Aβ, the first antibody being of human IgG1 isotype and the second antibody of human IgG4 isotype, and the first antibody is administered to patients having zero copies of an ApoE4 allele and the second antibody is administered to patients having one or two copies of an ApoE4 allele.

8. The method of claim 1, further comprising performing an assay to determine which alleles of ApoE are present in the patient.

9. The method of claim 1, wherein the dose of the antibody and/or the frequency of administration of the antibody and/or the capacity of the antibody to induce a clearing response to amyloid deposits is reduced in (a) patients having two ApoE4 alleles relative to patients having one ApoE4 allele; and/or (b) patients having one copy of an ApoE4 allele relative to patients having zero copies of an ApoE4 allele, and/or (c) patients having two copies of an ApoE4 allele relative to patients having one copy of an ApoE4 allele.

10. The method of claim 1, wherein the patients in the population having one or two ApoE4 alleles are administered a lower dosage of an agent than patients having zero ApoE4 alleles until vasogenic edema has appeared and resolved, and the same dosage of the agent thereafter as patients having zero ApoE4 alleles.

11. The method of claim 1, wherein the patients in the population having one or two ApoE4 alleles are administered a lower frequency of an agent than the patients having zero ApoE4 alleles until vasogenic edema has appeared and resolved, and the same frequency of the agent as patients with zero ApoE4 alleles thereafter.

12. The method of claim 1, further comprising monitoring at least some of the patients in the population for vasogenic edema.

13. The method of claim 1, wherein patients with one or two ApoE4 alleles are administered humanized 266 antibody and patients with zero ApoE4 alleles are administered bapineuzumab.

14. The method of claim 1, wherein the subject is suspected of, or already suffering Alzheimer's disease.

15. The method of claim 1, wherein the subject is asymptomatic but has a known genetic risk of Alzheimer's disease.

16. The method of claim 1, wherein the antibody is bapineuzumab.

* * * * *